United States Patent [19]
Arimilli et al.

[11] Patent Number: 5,922,695
[45] Date of Patent: Jul. 13, 1999

[54] ANTIVIRAL PHOSPHONOMETHYOXY NUCLEOTIDE ANALOGS HAVING INCREASED ORAL BIOAVARILABILITY

[75] Inventors: Murty N. Arimilli, Fremont; Kenneth C. Cundy, Belmont, both of Calif.; Joseph P. Dougherty, New York, N.Y.; Choung U. Kim, San Carlos; Reza Oliyai, Foster City, both of Calif.; Valentino J. Stella, Lawrence, Kans.

[73] Assignee: Gilead Sciences, Inc., Foster City, Calif.

[21] Appl. No.: 08/900,746

[22] Filed: Jul. 25, 1997

Related U.S. Application Data

[60] Provisional application No. 60/022,708, Jul. 26, 1996.
[51] Int. Cl.$^6$ .................. A61K 31/675; C07F 9/6512; C07F 9/6561
[52] U.S. Cl. .................. 514/81; 514/86; 544/243; 544/244; 546/23
[58] Field of Search ................. 514/81, 86; 544/243, 544/244; 546/23

[56] References Cited

U.S. PATENT DOCUMENTS

| | | |
|---|---|---|
| 3,524,846 | 8/1970 | Moffatt et al. . |
| 4,476,248 | 10/1984 | Gordon et al. . |
| 4,816,570 | 3/1989 | Farquhar ................................ 536/27 |
| 4,968,788 | 11/1990 | Farquhar ................................ 536/27 |
| 5,142,051 | 8/1992 | Holy et al. ............................ 544/244 |
| 5,177,064 | 1/1993 | Bodor . |
| 5,208,221 | 5/1993 | Kim et al. ............................. 514/81 |
| 5,386,030 | 1/1995 | Kim et al. ............................ 544/243 |
| 5,506,347 | 4/1996 | Erion et al. . |
| 5,512,596 | 4/1996 | Kim et al. ............................. 514/568 |
| 5,514,798 | 5/1996 | Bischofberger et al. . |
| 5,618,964 | 4/1997 | Cheng et al. . |

FOREIGN PATENT DOCUMENTS

| | | |
|---|---|---|
| 0 269 947 A1 | 6/1988 | European Pat. Off. . |
| 0 369 409 A1 | 5/1990 | European Pat. Off. . |
| 0 481 214 A1 | 4/1992 | European Pat. Off. . |
| 0 632 048 A1 | 6/1994 | European Pat. Off. . |
| 0 647 649 A1 | 4/1995 | European Pat. Off. . |
| 41 38 584 | 5/1993 | Germany . |
| WO 88/05438 | 7/1988 | WIPO . |
| WO 91/19721 | 12/1991 | WIPO . |
| WO 92/01698 | 2/1992 | WIPO . |
| WO 92/09611 | 6/1992 | WIPO . |
| WO 92/13869 | 8/1992 | WIPO . |
| WO 94/03466 | 2/1994 | WIPO . |
| WO 94/03467 | 2/1994 | WIPO . |
| WO 95/07919 | 3/1995 | WIPO . |
| WO 95/07920 | 3/1995 | WIPO . |
| WO 96/18605 | 6/1996 | WIPO . |

OTHER PUBLICATIONS

Ikeda et al., "Studies on Prodrugs. III. A Convenient and Practical Preparation of Ampicillin Prodrugs", 32:4316–4322, Chem Pharm Bull, 1984.

Jones et al., "Minireview: nucleotide prodrugs", 27:1–17, Antiviral Res, 1995.

Krise et al, "Prodrugs of phosphates, phosphonates, and phosphinates", 19:287–310, Advanced Drug Delivery Reviews, May 22, 1996.

Landgrebe, John A., "Crystallization and Filtration", 3rd edition, pp. 65–77, Theory and Practice in the Organic Laboratory, 1982.

Starrett et al., "Synthesis, Oral Bioavailability Determination, and in Vitro Evaluation of Prodrugs of the Antiviral Agent 9–[2–(Phosphonomethoxy)eth]adenine (PMEA)", 37:1857–1864, J Med Chem, 1994.

Isai et al., "Effects of (R)–9–(2–Phosphonylmethoxypropy)adenine Monotherapy on Chronic SIV Infection in Macaques", 13(8):707–712, AIDS Res & Hum Retro, 1997.

Isai et al., "Prevention of SIV Infection in Macaques by (R)–9–(2–Phosphonylmethoxypropyl)adenine", 270:1197–1199, Science, Nov. 17, 1995.

Arimilli et al., "Synthesis, in vitro biological evaluation and oral bioavailability of 9–[2–(phosphonomethoxy)propyl]adenine (PMPA) prodrugs", 8(6):557–567, Antiviral Chem & Chemo, 1997.

Arimilli et al., "Orally Bioavailable Acyclic Nucleoside Phosphonate Prodrugs: Adefovir Dipivoxil and Bis(POC)PMPA", vol. 3 (accepted for publication), ADV Antiviral Drug Design, 1988.

Shaw et al., "Metabolism and Pharmacokinetics of Novel Oral Prodrugs of 9–[(R)–2–(phosphonomethoxy)propyl]adenine (PMPA) in Dogs", 14(12):1824–1829, Pharm Res, 1997.

Alexander et al., "Investigation of (Oxodioxolenyl)methyl Carbamates as Nonchiral Bioreversible Prodrug Moieties for Chiral Amines", 39:480–486, J Med Chem, 1996.

(List continued on next page.)

*Primary Examiner*—Michael G. Ambrose
*Attorney, Agent, or Firm*—Daryl D. Muenchau

[57] ABSTRACT

Novel compounds are provided that comprise esters of antiviral phosphonomethoxy nucleotide analogs with carbonates and/or carbamates having the structure —OC(R$^2$)$_2$OC(O)X(R)$_a$, wherein R$^2$ independently is H, C$_1$–C$_{12}$ alkyl, aryl, alkenyl, alkynyl, alkyenylaryl, alkynylaryl, alkaryl, arylalkynyl, arylalkenyl or arylalkyl which is unsubstituted or is substituted with halo, azido, nitro or OR$^3$ in which R$^3$ is C$_1$–C12 alkyl; X is N or O; R is independently H, C$_1$–C$_{12}$ alkyl, aryl, alkenyl, alkynyl, alkyenylaryl, alkynylaryl, alkaryl, arylalkynyl, arylalkenyl or arylalkyl which is unsubstituted or is substituted with halo, azido, nitro, —O—, —N=, —NR$^4$—, —N(R$^4$)$_2$— or OR$^3$, R$^4$ independently is —H or C$_1$–C$_8$ alkyl, provided that at least one R is not H; and a is 1 or 2, with the proviso that when a is 2 and X is N, (a) two R groups can be taken together to form a carbocycle or oxygen-containing heterocycle, or (b) one R additionally can be OR$^3$. The compounds are useful as intermediates for the preparation of antiviral compounds or oligonucleotides, or are useful for administration directly to patients for antiviral therapy or prophylaxis. Embodiments are particularly useful when administered orally.

31 Claims, No Drawings

OTHER PUBLICATIONS

Benzaria et al., "New Prodrugs of 9-(2-Phosphonomethoxyethyl) Adenine [PMEA]: Synthesis and Stability Studies", 14(3–5):563–565, Nucls & Nuclt, 1995.

Cannon, Joseph G. (Reviewer), "The Chemistry of the Carbonyl Group", vol. II, Edited by Saul Patai, Book Review, Sep. 1966.

Davidsen et al, "N-(Acyloxyalkyl)pyridinium Salts as Soluble Prodrugs of a Potent Platelete Activating Factor Antagonist", 37(26):4423–4429, J Med Chem, Dec. 23, 1994.

Engel, R., "Phosphonates as Analogues of Natural Phosphates", 77(3):349–367, Chem Rev, 1977.

Farquhar et al, "Biologically Reversible Phosphate–Protective Groups", 72:324–325, J Pharm Sci, 1983.

Flaherty et al., "Synthesis and Selective Monoamine Oxidase B–Inhibiting Properties of 1–Methyl–1,2,3, 6–tetrahydropryrid–4–yl Carbamate Derivatives: Potential Prodrugs of (R)–and (S)–Nordeprenyl", 39:4759–4761, J Med Chem, 1996.

Folkmann et al., "Acyloxymethyl Carbonochloridates. New Intermediates in Prodrug Synthesis", pp. 1159–1166, Synthesis, Dec. 1990.

Hammer et al., "Ether, Carbonate and Urethane Deoxynucleoside Derivatives as Prodrugs", 50:609–622, Acta Chemica Scandinavia, 1996.

Ikeda et al., "Studies on Prodrugs. III. A Convenient and Practical Preparation of Ampicillin Prodrugs", 32:4316–4322, Chem Pharm Bull, 1984.

Iyer et al., "Synthesis of Acyloxyalkyl Acylphosphonates as Potential Prodrugs of the Antiviral, Trisodium Phosphonoformate (Foscarnet Sodium)", 30(51):7141:7144, Tet Lett, 1989.

Lindahl et al., "Synthesis of an Acyloxymethyl Prodrug of the Inositol Phosphate Alpha–Trinositol", 15(5):549–554, J Carbohydrate Chemistry, 1996.

Maillard et al., "Adenosine Receptor Prodrugs: Synthesis and Biological Activity of Derivatives of Potent, A1–Selective Agonists", 83(1):46–53, J Pharm Sci, Jan. 1994.

Myerson, Allan S. (editor), "Solutions and Solution Properties", pp. 1–165, Handbook of Industrial Crystallization, 1993.

Naesens et al., "Antiretroviral Activity and Pharmacokinetics in Mice of Oral Bis(Pivaloyloxymethyl)– 9–(2–Phosphonylmethoxyethyl)Adenine, the Bis(Pivaloyloxymethyl)Ester Prodrug of 9–(2–Phosphonylmethoxyethl)Adenine", 40(1):22–28, Antimicro AG & Chemo, Jan. 1996.

Robinson et al., "Discovery of the Hemifumarate and (alpha–L–Alanyloxy)methyl Ether as Prodrugs of an Antirheumatic Oxindole: Prodrugs for the Enolic OH Group", 39:10–18, J Med Chem, 1996.

Safadi et al, "Phosphoryloxymethyl Carbamates and Carbonates—Novel Water–Soluble Prodrugs for Amines and Hindered Alcohols", 10(9):1350–1355, Pharm Res, 1993.

Sakamoto et al, "Studies on Prodrugs. II. Preparation and Characterization of (5–Substituted 2–Oxo–1, 3–dioxolen–4–yl)methyl Esters of Ampicillin", 32(6):2241–2248, Chem Pharm Bull, Aug. 19, 1983.

Samara et al., "Pharmacokinetic Analysis of Diethylcarbonate Prodrugs of Ibuprofen and Naproxen", 16:201–210, Biopharmaceutics & Drug Disposition, 1995.

Srinivas et al., "Metabolism and In Vitro Antiretroviral Activities of Bis(Pivaloyloxymethyl) Prodrugs of Acyclic Nucleoside Phosphonates", 37(10:2247–2250, Antimicro AG & Chemo, Oct.–1993.

Srivastva et al, "Bioreversible Phosphate Protective Groups: Synthesis and Stability of Model Acyloxymethyl Phosphates", 12:118–129, Bioorg Chem, 1984.

Starrett et al, "Synthesis and in vitro evaluation of a phosphonate prodrug: bis(pivaloyloxymethyl) 9–(2–phosphonylmethoxyethyl)adenine", 19:267–273, Antiviral Res, 1992.

Sueoka et al., "Pharmacokinetics of Alkoxycarbonyloxy Ester Prodrugs of PMPA in Dogs", Abstract, American Association of Pharmaceutical Science, Western Regional Meeting, Apr. 24–25, 1997.

Sueoka et al., "Pharmacokinetics of Alkoxycarbonyloxy Ester Prodrugs of PMPA in Dogs", Poster, American Association of Pharmaceutical Science, Western Regional Meeting, Apr. 24–25, 1997.

Weller et al., "Orally Active Fibrinogen Receptor Antagonists. 2. Amidoximes a Prodrugs of Amidines", 39:3139–3147, J Med Chem, Dec. 20, 1995.

ANTIVIRAL PHOSPHONOMETHYOXY NUCLEOTIDE ANALOGS HAVING INCREASED ORAL BIOAVARILABILITY

CROSS REFERENCED TO RELATED APPLICATIONS

This application is a continuation-in-part of U.S. Provisional Patent Application Serial No. 60/022,708, filed Jul. 26, 1996, which is incorporated herein by reference in its entirety.

BACKGROUND OF THE INVENTION

The present invention relates to intermediates for phosphonomethoxy nucleotide analogs, in particular intermediates suitable for use in the efficient oral delivery of such analogs.

Such analogs per se and various technologies for oral delivery of these and other therapeutic compounds are known. See WO 91/19721, WO 94/03467, WO 94/03466, WO 92/13869, U.S. Pat. Nos. 5,208,221, 5,124,051, DE 41 38 584 A1, WO 94/10539, WO 94/10467, WO 96/18605, WO 95/07920, WO 95 79/07919, WO 92/09611, WO 92/01698, WO 91/19721, WO 88/05438, EP 0 632 048, EP 0 481 214, EP 0 369 409, EP 0 269 947, U.S. Pat. Nos. 3,524,846 and 5,386,030, Engel *Chem. Rev.* 77:349–367 1977, Farquhar et al., *J. Pharm. Sci.* 72:324–325 1983, Starrett et al., *Antiviral Res.* 19:267–273 1992, Safadi et al., *Pharmaceutical Research* 10(9):1350–1355 1993, Sakamoto et al., *Chem. Pharm. Bull.* 32(6):2241–2248 1984, and Davidsen et al., *J. Med. Chem.* 37(26):4423–4429 1994.

SUMMARY OF THE INVENTION

In accordance with this invention, compounds are provided having formula (1a)

(1a)

wherein Z is independently —OC($R^2$)$_2$OC(O)X(R)$_a$, an ester, an amidate or —H, but at least one Z is —OC($R^2$)$_2$OC(O)X(R)$_a$;

A is the residue of an antiviral phosphonomethoxy nucleotide analog;

X is N or O;

$R^2$ independently is —H, $C_1$–$C_{12}$ alkyl, $C_5$–$C_{12}$ aryl, $C_2$–$C_{12}$ alkenyl, $C_2$–$C_{12}$ alkynyl, $C_7$–$C_{12}$ alkenylaryl, $C_7$–$C_{12}$ alkynylaryl, or $C_6$–$C_{12}$ alkaryl, any one of which is unsubstituted or is substituted with 1 or 2 halo, cyano, azido, nitro or —$OR^3$ in which $R^3$ is $C_1$–$C_{12}$ alkyl, $C_2$–$C_{12}$ alkenyl, $C_2$–$C_{12}$ alkynyl or $C_5$–$C_{12}$ aryl;

R independently is —H, $C_1$–$C_{12}$ alkyl, $C_5$–$C_{12}$ aryl, $C_2$–$C_{12}$ alkenyl, $C_2$–$C_{12}$ alkynyl, $C_7$–$C_{12}$ alkyenylaryl, $C_7$–$C_{12}$ alkynylaryl, or $C_6$–$C_{12}$ alkaryl, any one of which is unsubstituted or is substituted with 1 or 2 halo, cyano, azido, nitro, —N($R^4$)$_2$ or —$OR^3$, where $R^4$ independently is —H or $C_1$–$C_8$ alkyl, provided that at least one R is not H; and a is 1 when X is O, or 1 or 2 when X is N;

with the proviso that when a is 2 and X is N, (a) two N-linked R groups can be taken together to form a carbocycle or oxygen-containing heterocycle, (b) one N-linked R additionally can be —$OR^3$ or (c) both N-linked R groups can be —H;

and the salts, hydrates, tautomers and solvates thereof.

Further embodiments of the compounds of this invention are compounds of formula (1)

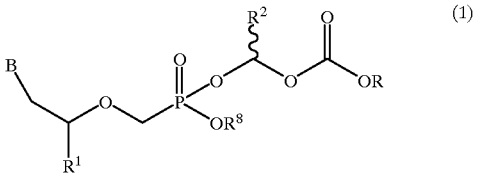
(1)

wherein B is guanin-9-yl, adenin-9-yl, 2,6-diaminopurin-9-yl, 2-aminopurin-9-yl or their 1-deaza, 3-deaza, or 8-aza analogs, or B is cytosin-1-yl;

R is independently —H, $C_1$–$C_{12}$ alkyl, $C_5$–$C_{12}$ aryl, $C_2$–$C_{12}$ alkenyl, $C_2$–$C_{12}$ alkynyl, $C_7$–$C_{12}$ alkenylaryl, $C_7$–$C_{12}$ alkynylaryl, or $C_6$–$C_{12}$ alkaryl, any one of which is unsubstituted or is substituted with 1 or 2 halo, cyano, azido, nitro, or —$OR^3$ in which $R^3$ is $C_1$–$C_{12}$ alkyl, $C_2$–$C_{12}$ alkenyl, $C_2$–$C_{12}$ alkynyl or $C_5$–$C_{12}$ aryl;

$R^1$ is hydrogen, —$CH_3$, —$CH_2OH$, —$CH_2F$, —$CH=CH_2$, or —$CH_2N_3$, or $R^1$ and $R^8$ are joined to form —$CH_2$—;

$R^2$ independently is hydrogen or $C_1$–$C_6$ alkyl; and $R^8$ is hydrogen or —$CHR^2$—O—C(O)—OR, or $R^8$ is joined with $R^1$ to form —$CH_2$—;

and the salts, hydrates, tautomers and solvates thereof.

Other embodiments comprise orally administering to a patient infected with virus or at risk for viral infection a therapeutically effective amount of a compound of formulas (1a) or (1).

Other embodiments of this invention include a method for preparing a compound of formula (1a) which comprises reacting the diacid of a phosphonomethoxy nucleotide analog with LC($R^2$)$_2$OC(O)X(R)$_a$ wherein L is a leaving group.

In particular embodiments of this invention, a method for preparing a compound of formula (1) is provided which comprises reacting a compound of formula (4)

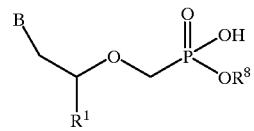
(4)

with LC($R^2$)$_2$OC(O)X(R)$_a$.

DETAILED DESCRIPTION OF THE INVENTION

The abbreviations NMP, DMF and DMPU mean, respectively, N-methylpyrrolidinone, dimethylformamide and N,N'-dimethylpropyleneurea.

Heterocycle means aromatic and nonaromatic ringed moieties. Heterocyclic moieties typically comprise one ring or two fused rings, where the ring(s) is 5- or 6-membered and typically contains 1 or 2 noncarbon atoms such as oxygen, nitrogen or sulfur, usually oxygen or nitrogen.

"Alkyl" as used herein, unless stated to the contrary is $C_1$–$C_{12}$ hydrocarbon containing 1, 2, 3, 4, 5, 6, 7, 8, 9, 10, 11 or 12 carbon atoms in the form of normal, secondary, tertiary or cyclic structures. Examples are —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$CH_2CH_2CH_2CH_2CH_3$, —$CH(CH_3)CH_2CH_2CH_3$, —$CH(CH_2CH_3)_2$, —$C(CH_3)_2CH_2CH_3$, —$CH(CH_3)CH(CH_3)_2$, —$CH_2CH_2CH(CH_3)_2$, —$CH_2CH(CH_3)CH_2CH_3$, —$CH_2C(CH_3)_3$, —$CH_2CH_2CH_2CH_2CH_2CH_3$, —$CH(CH_3)$ CH$_2$CH$_2$CH$_2$CH$_3$, —CH(CH$_2$CH$_3$)(CH$_2$CH$_2$CH$_3$), —C(CH$_3$)$_2$CH$_2$CH$_2$CH$_3$, —CH(CH$_3$)CH(CH$_3$)CH$_2$CH$_3$, —CH(CH$_3$)CH$_2$CH(CH$_3$)$_2$, —C(CH$_3$)(CH$_2$CH$_3$)$_2$, —CH(CH$_2$CH$_3$)CH(CH$_3$)$_2$, —C(CH$_3$)$_2$CH(CH$_3$)$_2$, —CH(CH$_3$)C(CH$_3$)$_3$, cyclopropyl, cyclobutyl, cyclopropylmethyl, cyclopentyl, cyclobutylmethyl, 1-cyclopropyl-1-ethyl, 2-cyclopropyl-1-ethyl, cyclohexyl, cyclopentylmethyl, 1-cyclobutyl-1-ethyl, 2-cyclobutyl-1-ethyl, 1-cyclopropyl-1-propyl, 2-cyclopropyl-1-propyl, 3-cyclopropyl-1-propyl, 2-cyclopropyl-2-propyl, and 1-cyclopropyl-2-propyl.

"Alkenyl" as used herein, unless stated to the contrary, is C$_1$–C$_{12}$ hydrocarbon containing normal, secondary, tertiary or cyclic structures. Examples are —CH=CH$_2$, —CH=CHCH$_3$, —CH$_2$CH=CH$_2$, —C(=CH$_2$)(CH$_3$), —CH=CHCH$_2$CH$_3$, —CH$_2$CH=CHCH$_3$, —CH$_2$CH$_2$CH=CH$_2$, —CH=C(CH$_3$)$_2$, —CH$_2$C(=CH$_2$)(CH$_3$), —C(=CH$_2$)CH$_2$CH$_3$, —C(CH$_3$)=CHCH$_3$, —CH(CH$_3$)CH=CH$_2$, —C=CHCH$_2$CH$_2$CH$_3$, —CHCH=CHCH$_2$CH$_3$, —CHCH$_2$CH=CHCH$_3$, —CHCH$_2$CH$_2$CH=CH$_2$, —C(=CH$_2$)CH$_2$CH$_2$CH$_3$, —C(CH$_3$)=CH$_2$CH$_2$CH$_3$, —CH(CH$_3$)CH=CHCH$_3$, —CH(CH$_3$)CH$_2$CH=CH$_2$, —CH$_2$CH=C(CH$_3$)$_2$, 1-cyclopent-1-enyl, 1-cyclopent-2-enyl, 1-cyclopent-3-enyl, 1-cyclohex-1-enyl, 1-cyclohex-2-enyl, and 1-cyclohex-3-enyl.

"alkynyl" as used herein, unless stated to the contrary, is C$_1$–C$_{12}$ hydrocarbon containing normal, secondary, tertiary or cyclic structures. Examples are —CCH, —CCCH$_3$, —CH$_2$CCH, —CCCH$_2$CH$_3$, —CH$_2$CCCH$_3$, —CH$_2$CH$_2$CCH, CH(CH$_3$)CCH, —CCCH$_2$CH$_2$CH$_3$, —CH$_2$CCCH$_2$CH$_3$, —CH$_2$CH$_2$CCCH$_3$ and —CH$_2$CH$_2$CH$_2$CCH.

Salt(s) include those derived by combination of appropriate anions such as inorganic or organic acids. Suitable acids include those having sufficient acidity to form a stable salt, preferably acids or low toxicity. For example, one may form invention salts from acid addition of certain organic and inorganic acids, e.g., HF, HCl, HBr, HI, H$_2$SO$_4$, H$_3$PO$_4$, or from organic sulfonic acids, organic carboxylic acids to basic centers, typically amines. Exemplary organic sulfonic acids include C$_{6-16}$ aryl sulfonic acids, C$_{6-16}$ heteroaryl sulfonic acids and C$_{1-16}$ alkyl sulfonic acids such as phenyl, a-naphthyl, b-naphthyl, (S)-camphor, methyl, ethyl, n-propyl, i-propyl, n-butyl, s-butyl, i-butyl, t-butyl, pentyl and hexyl sulfonic acids. Exemplary organic carboxylic acids include C$_{1-16}$ alkyl, C$_{6-16}$ aryl carboxylic acids and C$_{4-16}$ heteroaryl carboxylic acids such as acetic, glycolic, lactic, pyruvic, malonic, glutaric, tartaric, citric, fumaric, succinic, malic, maleic, hydroxymaleic, benzoic, hydroxybenzoic, phenylacetic, cinnamic, salicylic and 2-phenoxybenzoic. Salts also include the invention compound salts with one or more amino acids. Many amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine. Salts are usually biologically compatible or pharmaceutically acceptable or non-toxic, particularly for mammalian cells. Salts that are biologically toxic are generally used with synthetic intermediates of invention compounds. The salts of invention compounds may be crystalline or noncrystalline.

A is the residue of a phosphonomethoxy nucleotide analog. The parental compounds have the structure AOCH$_2$P(O)(OH)$_2$. They are well known and have demonstrated antiviral activity. Per se, they are not part of this invention.

In general, A has the structure BQ wherein B is a purine or pyrimidine base or the aza and/or deaza analogs thereof and Q is a cyclic or acyclic aglycon. B is linked to Q through the purine 9 or pyrimidine 1 positions. Examples of these analogs can be found in U.S. Pat. Nos. 4,659,825, 4,724,233, 5,142,051 and 5,130,427, EP 369,409, EP 398,231, EP 494,370, EP 454,427, EP 270,885, EP 269,947, EP 452,935, WO 93/07157, WO 94/03467, and WO96/23801. Typically, A will have the structure BCH$_2$CH(CH$_3$)— or BCH$_2$CH$_2$—.

The designation "a" is an integer of 1 or 2. If X is N then a is 2 and one R is usually H and the other is not H. If X is O then a is 1.

B generally is guanin-9-yl, adenin-9-yl, 2,6-diaminopurin-9-yl, 2-aminopurin-9-yl or their 1-deaza, 3-deaza, or 8-aza analogs, or B is cytosin-1-yl. Ordinarily, B is adenin-9-yl or 2,6-diaminopurin-9-yl. In formula (1a) compounds, one Z optionally comprises an ester or an amidate. Suitable esters or amidates have been described, e.g., WO 95/07920. Exemplary esters are phenyl, benzyl, o-ethoxyphenyl, p-ethoxyphenyl, 2-pyridyl, 3-pyridyl, 4-pyridyl, N-ethylmorpholino, C$_1$–C$_8$ O-alkyl and C$_1$–C$_8$ NH-alkyl. However, every compound of the invention will contain at least one —C(R$^2$)$_2$OC(O)X(R)$_a$ moiety.

R$^2$ independently is —H, C$_1$–C$_{12}$ alkyl, C$_5$–C$_{12}$ aryl, C$_2$–C$_{12}$ alkenyl, C$_2$–C$_{12}$ alkynyl, C$_7$–C$_{12}$ alkenylaryl, C$_7$–C$_{12}$ alkynylaryl, or C$_6$–C$_{12}$ alkaryl, any one of which is unsubstituted or substituted with 1 or 2 halo, cyano, azido, nitro or —OR$^3$ in which R$^3$ is C$_1$–C$_{12}$ alkyl, C$_2$–C$_{12}$ alkenyl, C$_2$–C$_{12}$ alkynyl or C$_5$–C$_{12}$ aryl. R$^2$ is usually H or C$_1$–C$_6$ alkyl, and typically only one R$^2$ is other than H. In most embodiments R$^2$ is H in both instances. The carbon atom to which R$^2$ is bonded is capable of chiral substitution, in which case R$^2$ is in the (R), (S) or racemic configuration. In most embodiments, if R$^2$ is other than H the compounds of this invention are chirally enriched or pure at this site. In general, however, manufacturing is somewhat less expensive if chirality at the R$^2$ carbon can be avoided. Thus, R$^2$ is H when it is desired to help minimize the cost of synthesis.

X is O or N, typically O. The carbamates (where X=N) tend to be more stable in biological environments than the carbonates. When X is O then a is 1.

R independently is —H, C$_1$–C$_{12}$ alkyl, C$_5$–C$_{12}$ aryl, C$_2$–C$_{12}$ alkenyl, C$_2$–C$_{12}$ alkynyl, C$_7$–C$_{12}$ alkyenylaryl, C$_7$–C$_{12}$ alkynylaryl, or C$_6$–C$_{12}$ alkaryl, any one of which is unsubstituted or is substituted with 1 or 2 halo, cyano, azido, nitro, —N(R$^4$)$_2$ or —OR$^3$, where R$^4$ independently is —H or C$_1$–C$_8$ alkyl, provided that at least one R is not H. In general, R is C$_1$–C$_6$ secondary or normal alkyl which is unsubstituted or substituted with OR$^3$. When X is N then a is 2. In the latter case one R is usually other than H. Alternatively, two N-linked R groups are joined to form a carbocycle or O-containing heterocycle, typically containing 3 to 5 carbon atoms in the ring. When R is unsaturated, but not aryl, the site of unsaturation is not critical and is in the Z or E configuration. The alkenyl chains of naturally occurring unsaturated fatty acids would be suitable as R groups, for example. R also includes cycloalkenyl or cycloalkynyl containing 1 or 2 unsaturated bonds, typically 1 unsaturated bond. When R is unsaturated, usually it is alkenyl or alkynyl without aryl substitution.

If R is substituted with halo, cyano, azido, nitro or OR$^3$, typically R will contain 1 of these substituents. If substituted with 2 of these substituents, they are same or different. Generally, substituents found on R are OR$^3$. An exemplary R group containing an OR$^3$ substituent is —CH$_2$C(CH$_2$OCH$_3$)(CH$_3$)$_2$.

When R contains an aryl group, the aryl group generally is bonded directly to X or is linked to X by methylene or ethylene. The aryl group may contain —N= or —O— as a ring atom. In general, the aryl group contains 5 or 6 carbons. If substituted, the aryl moiety is substituted with halo or $OR^3$ in the ortho, meta or para positions, with $R^3$ in this instance being typically $C_1$–$C_3$. Aryl groups containing 5 carbons are typically 2-, 3- or 4-pyridyl. In general, only one substituent group will be found on the aryl moiety if it is substituted at all. Exemplary aromatic and nonaromatic heterocyclic groups as used herein includes by way of example and not limitation the heterocycles described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960).

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, b-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, of 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or b-carboline. Still more typically, nitrogen bonded heterocycles include 1-aziridyl, 1-azetedyl, 1-pyrrolyl, 1-imidazolyl, 1-pyrazolyl, and 1-piperidinyl.

R includes the structure —$C_2$–$C_6R^5C_2$–$C_6$— where each $C_2$–$C_6$ independently is a 2, 3, 4, 5 or 6 carbon linear, branched or cyclic alkyl moiety, e.g., ethylene, ethyl, propylene, propyl, isopropylene, isopropyl, cyclohexyl, etc., and $R^5$ is —O— or —$NR^6$— where $R^6$ is linear, branched or cyclic alkyl having 1, 2, 3, 4, 5 or 6 carbon atoms.

Embodiments include compounds where $R^4$ is —H or —$CH_3$.

R includes the structure —$C_2$–$C_{12}R^9$, where each $C_2$–$C_{12}$ independently is a 2, 3, 4, 5, 6, 7, 8, 9, 10, 11 or 12 carbon linear, branched or cyclic alkyl moiety, and $R^9$ is N-morpholino

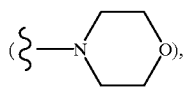

N-piperidino, 2-pyridyl, 3-pyridyl or 4-pyridyl.

R also includes —$C(CH_2(X_{0-1}R^7)_3$, —$CH[C(CH_2(X)_{0-1}R^7)_3]_2$ and —$CH_2(C(X)_{0-1}R^7)_3$, where $R^7$ is 1, 2, 3, 4, 5 or 6 carbon linear, branched or cyclic alkyl or $R^7$ is 5 or 6 carbon aryl. In these embodiments, one or two X are typically present, usually 1, X is usually oxygen and $R^7$ is typically methyl, ethyl, isopropyl, propyl or butyl, usually methyl.

R usually is phenyl, methyl, ethyl, 1-propyl, 2-propyl, n-butyl, i-butyl, t-butyl, pentyl or 3-pentyl.

$R^1$ is a substituent found in prior art phosphonomethoxy nucleotide analogs. $R^1$ typically is any of hydrogen, —$CH_3$, —$CH_2OH$, —$CH_2F$, —CH=$CH_2$, —$CH_2N_3$ or $R^1$ and $R^8$ are joined to form —$CH_2$—. $R^1$ is usually H or methyl. If $R^1$ and $R^8$ are joined to form methylene, B typically is cytosin-1-yl.

$R^3$ is $C_1$–$C_{12}$ alkyl, but typically is $C_1$–$C_6$ alkyl.

Compounds of structure (1) typically are those in which B is adenin-9-yl, $R^1$ is methyl or H, $R^8$ is —$CHR^2$—O—C(O)—OR and R, $R^2$ and $R^3$ are as set forth above.

The compounds of this invention are optionally enriched or resolved at the carbon atom chiral center linked to $R^1$ in accordance with prior findings associating optimal antiviral activity with the configuration at this site. Thus, where $R^1$ is methyl the compounds will be in (R) configuration at this center and will be substantially free of the (S) enantiomer.

Other embodiments include structure (10) and (11) compounds where R and each $R^2$ are independently chosen and $R^2$ is $C_1$–$C_6$ alkyl

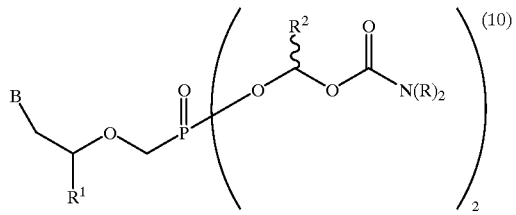

-continued

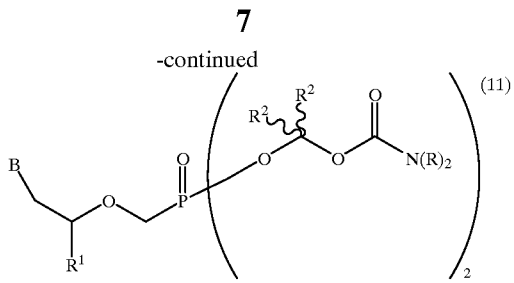

(11)

Exemplary embodiments include the compounds named in Table B. Each compound in Table B is depicted as a compound having the formula (8)

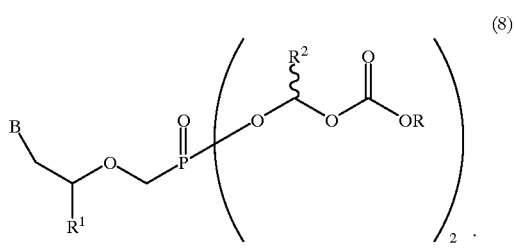

(8)

Compounds named in Table B are designated by numbers assigned to B, R, $R^1$ and $R^2$ according to the following convention, $B.R.R^1.R^2$, using the numbered structures depicted in Table A. Thus, the compound named 1.2.3.4 specifies adenin-9-yl at B, —$CH_2CH_3$ at both R groups, —$CH_2OH$ at $R^1$ and —$(CH_2)_2CH_3$ at both $R^2$ groups.

TABLE A

| | B | | $R^1$ |
|---|---|---|---|
| 1 | adenin-9-yl | 1 | —$CH_3$ |
| 2 | guanin-9-yl | 2 | —H |
| 3 | 2,6-diaminopurin-9-yl | 3 | —$CH_2OH$ |
| 4 | 2-aminopurin-9-yl | 4 | —$CH_2F$ |
| 5 | cytosin-1-yl | 5 | —CH=$CH_2$ |
| | | 6 | —$CH_2N_3$ |

| | R | | $R^2$ |
|---|---|---|---|
| 1 | —$CH_3$ | 1 | —H |
| 2 | —$C_2H_5$ | 2 | —$CH_3$ |
| 3 | —$(CH_2)_2CH_3$ | 3 | —$C_2H_5$ |
| 4 | —$CH(CH_3)_2$ | 4 | —$(CH_2)_2CH_3$ |
| 5 | —$(CH_2)_3CH_3$ | 5 | —$CH(CH_3)_2$ |
| 6 | —$CH_2CH(CH_3)_2$ | 6 | —$(CH_2)_3CH_3$ |
| 7 | —$CH(CH_3)CH_2CH_3$ | 7 | —$CH_2CH(CH_3)_2$ |
| 8 | —$C(CH_3)_3$ | 8 | —$C(CH_3)_3$ |
| 9 | —$(CH_2)_4CH_3$ | 9 | —$(CH_2)_4CH_3$ |
| 10 | —$CH(CH_3)CH_2CH_2CH_3$ | 10 | —$(CH_2)_5CH_3$ |
| 11 | —$CH(CH_2CH_3)_2$ | | |
| 12 | —$C(CH_3)_2CH_2CH_3$ | | |
| 13 | —$CH(CH_3)CH(CH_3)_2$ | | |
| 14 | —$CH_2CH_2CH(CH_3)_2$ | | |
| 15 | —$CH_2CH(CH_3)CH_2CH_3$ | | |
| 16 | —$CH_2CH_2CH_2CH_2CH_2CH_3$ | | |
| 17 | —$CH(CH_3)CH_2CH_2CH_2CH_3$ | | |
| 18 | —$CH(CH_2CH_3)CH_2CH_2CH_3$ | | |
| 19 | —$C(CH_3)_2CH_2CH_2CH_3$ | | |
| 20 | —$CH(CH_3)CH(CH_3)CH_2CH_3$ | | |
| 21 | —$CH(CH_3)CH_2CH(CH_3)_2$ | | |
| 22 | —$C(CH_3)(CH_2CH_3)_2$ | | |
| 23 | —$CH(CH_2CH_3)CH(CH_3)_2$ | | |
| 24 | —$CH_2C_6H_5$ | | |
| 25 | —$C_6H_5$ | | |

TABLE B

| | | | | | | | | | | | |
|---|---|---|---|---|---|---|---|---|---|---|---|
| 1.1.1.1 | 1.1.1.2 | 1.1.1.3 | 1.1.1.4 | 1.1.1.5 | 1.1.1.6 | 1.1.1.7 | 1.1.1.8 | 1.1.1.9 | 1.1.1.10 | 1.1.2.1 | 1.1.2.2 | 1.1.2.3 |
| 1.1.2.4 | 1.1.2.5 | 1.1.2.6 | 1.1.2.7 | 1.1.2.8 | 1.1.2.9 | 1.1.2.10 | 1.1.3.1 | 1.1.3.2 | 1.1.3.3 | 1.1.3.4 | 1.1.3.5 | 1.1.3.6 |
| 1.1.3.7 | 1.1.3.8 | 1.1.3.9 | 1.1.3.10 | 1.1.4.1 | 1.1.4.2 | 1.1.4.3 | 1.1.4.4 | 1.1.4.5 | 1.1.4.6 | 1.1.4.7 | 1.1.4.8 | 1.1.4.9 |
| 1.1.4.10 | 1.1.5.1 | 1.1.5.2 | 1.1.5.3 | 1.1.5.4 | 1.1.5.5 | 1.1.5.6 | 1.1.5.7 | 1.1.5.8 | 1.1.5.9 | 1.1.5.10 | 1.1.6.1 | 1.1.6.2 |
| 1.1.6.3 | 1.1.6.4 | 1.1.6.5 | 1.1.6.6 | 1.1.6.7 | 1.1.6.8 | 1.1.6.9 | 1.1.6.10 | 1.2.1.1 | 1.2.1.2 | 1.2.1.3 | 1.2.1.4 | 1.2.1.5 |
| 1.2.1.6 | 1.2.1.7 | 1.2.1.8 | 1.2.1.9 | 1.2.1.10 | 1.2.2.1 | 1.2.2.2 | 1.2.2.3 | 1.2.2.4 | 1.2.2.5 | 1.2.2.6 | 1.2.2.7 | 1.2.2.8 |
| 1.2.2.9 | 1.2.2.10 | 1.2.3.1 | 1.2.3.2 | 1.2.3.3 | 1.2.3.4 | 1.2.3.5 | 1.2.3.6 | 1.2.3.7 | 1.2.3.8 | 1.2.3.9 | 1.2.3.10 | 1.2.4.1 |
| 1.2.4.2 | 1.2.4.3 | 1.2.4.4 | 1.2.4.5 | 1.2.4.6 | 1.2.4.7 | 1.2.4.8 | 1.2.4.9 | 1.2.4.10 | 1.2.5.1 | 1.2.5.2 | 1.2.5.3 | 1.2.5.4 |
| 1.2.5.5 | 1.2.5.6 | 1.2.5.7 | 1.2.5.8 | 1.2.5.9 | 1.2.5.10 | 1.2.6.1 | 1.2.6.2 | 1.2.6.3 | 1.2.6.4 | 1.2.6.5 | 1.2.6.6 | 1.2.6.7 |
| 1.2.6.8 | 1.2.6.9 | 1.2.6.10 | 1.3.1.1 | 1.3.1.2 | 1.3.1.3 | 1.3.1.4 | 1.3.1.5 | 1.3.1.6 | 1.3.1.7 | 1.3.1.8 | 1.3.1.9 | 1.3.1.10 |
| 1.3.2.1 | 1.3.2.2 | 1.3.2.3 | 1.3.2.4 | 1.3.2.5 | 1.3.2.6 | 1.3.2.7 | 1.3.2.8 | 1.3.2.9 | 1.3.2.10 | 1.3.3.1 | 1.3.3.2 | 1.3.3.3 |
| 1.3.3.4 | 1.3.3.5 | 1.3.3.6 | 1.3.3.7 | 1.3.3.8 | 1.3.3.9 | 1.3.3.10 | 1.3.4.1 | 1.3.4.2 | 1.3.4.3 | 1.3.4.4 | 1.3.4.5 | 1.3.4.6 |
| 1.3.4.7 | 1.3.4.8 | 1.3.4.9 | 1.3.4.10 | 1.3.5.1 | 1.3.5.2 | 1.3.5.3 | 1.3.5.4 | 1.3.5.5 | 1.3.5.6 | 1.3.5.7 | 1.3.5.8 | 1.3.5.9 |
| 1.3.5.10 | 1.3.6.1 | 1.3.6.2 | 1.3.6.3 | 1.3.6.4 | 1.3.6.5 | 1.3.6.6 | 1.3.6.7 | 1.3.6.8 | 1.3.6.9 | 1.3.6.10 | 1.4.1.1 | 1.4.1.2 |
| 1.4.1.3 | 1.4.1.4 | 1.4.1.5 | 1.4.1.6 | 1.4.1.7 | 1.4.1.8 | 1.4.1.9 | 1.4.1.10 | 1.4.2.1 | 1.4.2.2 | 1.4.2.3 | 1.4.2.4 | 1.4.2.5 |
| 1.4.2.6 | 1.4.2.7 | 1.4.2.8 | 1.4.2.9 | 1.4.2.10 | 1.4.3.1 | 1.4.3.2 | 1.4.3.3 | 1.4.3.4 | 1.4.3.5 | 1.4.3.6 | 1.4.3.7 | 1.4.3.8 |
| 1.4.3.9 | 1.4.3.10 | 1.4.4.1 | 1.4.4.2 | 1.4.4.3 | 1.4.4.4 | 1.4.4.5 | 1.4.4.6 | 1.4.4.7 | 1.4.4.8 | 1.4.4.9 | 1.4.4.10 | 1.4.5.1 |
| 1.4.5.2 | 1.4.5.3 | 1.4.5.4 | 1.4.5.5 | 1.4.5.6 | 1.4.5.7 | 1.4.5.8 | 1.4.5.9 | 1.4.5.10 | 1.4.6.1 | 1.4.6.2 | 1.4.6.3 | 1.4.6.4 |
| 1.4.6.5 | 1.4.6.6 | 1.4.6.7 | 1.4.6.8 | 1.4.6.9 | 1.4.6.10 | 1.5.1.1 | 1.5.1.2 | 1.5.1.3 | 1.5.1.4 | 1.5.1.5 | 1.5.1.6 | 1.5.1.7 |
| 1.5.1.8 | 1.5.1.9 | 1.5.1.10 | 1.5.2.1 | 1.5.2.2 | 1.5.2.3 | 1.5.2.4 | 1.5.2.5 | 1.5.2.6 | 1.5.2.7 | 1.5.2.8 | 1.5.2.9 | 1.5.2.10 |
| 1.5.3.1 | 1.5.3.2 | 1.5.3.3 | 1.5.3.4 | 1.5.3.5 | 1.5.3.6 | 1.5.3.7 | 1.5.3.8 | 1.5.3.9 | 1.5.3.10 | 1.5.4.1 | 1.5.4.2 | 1.5.4.3 |
| 1.5.4.4 | 1.5.4.5 | 1.5.4.6 | 1.5.4.7 | 1.5.4.8 | 1.5.4.9 | 1.5.4.10 | 1.5.5.1 | 1.5.5.2 | 1.5.5.3 | 1.5.5.4 | 1.5.5.5 | 1.5.5.6 |
| 1.5.5.7 | 1.5.5.8 | 1.5.5.9 | 1.5.5.10 | 1.5.6.1 | 1.5.6.2 | 1.5.6.3 | 1.5.6.4 | 1.5.6.5 | 1.5.6.6 | 1.5.6.7 | 1.5.6.8 | 1.5.6.9 |
| 1.5.6.10 | 1.6.1.1 | 1.6.1.2 | 1.6.1.3 | 1.6.1.4 | 1.6.1.5 | 1.6.1.6 | 1.6.1.7 | 1.6.1.8 | 1.6.1.9 | 1.6.1.10 | 1.6.2.1 | 1.6.2.2 |
| 1.6.2.3 | 1.6.2.4 | 1.6.2.5 | 1.6.2.6 | 1.6.2.7 | 1.6.2.8 | 1.6.2.9 | 1.6.2.10 | 1.6.3.1 | 1.6.3.2 | 1.6.3.3 | 1.6.3.4 | 1.6.3.5 |
| 1.6.3.6 | 1.6.3.7 | 1.6.3.8 | 1.6.3.9 | 1.6.3.10 | 1.6.4.1 | 1.6.4.2 | 1.6.4.3 | 1.6.4.4 | 1.6.4.5 | 1.6.4.6 | 1.6.4.7 | 1.6.4.8 |
| 1.6.4.9 | 1.6.4.10 | 1.6.5.1 | 1.6.5.2 | 1.6.5.3 | 1.6.5.4 | 1.6.5.5 | 1.6.5.6 | 1.6.5.7 | 1.6.5.8 | 1.6.5.9 | 1.6.5.10 | 1.6.6.1 |
| 1.6.6.2 | 1.6.6.3 | 1.6.6.4 | 1.6.6.5 | 1.6.6.6 | 1.6.6.7 | 1.6.6.8 | 1.6.6.9 | 1.6.6.10 | 1.7.1.1 | 1.7.1.2 | 1.7.1.3 | 1.7.1.4 |
| 1.7.1.5 | 1.7.1.6 | 1.7.1.7 | 1.7.1.8 | 1.7.1.9 | 1.7.1.10 | 1.7.2.1 | 1.7.2.2 | 1.7.2.3 | 1.7.2.4 | 1.7.2.5 | 1.7.2.6 | 1.7.2.7 |
| 1.7.2.8 | 1.7.2.9 | 1.7.2.10 | 1.7.3.1 | 1.7.3.2 | 1.7.3.3 | 1.7.3.4 | 1.7.3.5 | 1.7.3.6 | 1.7.3.7 | 1.7.3.8 | 1.7.3.9 | 1.7.3.10 |
| 1.7.4.1 | 1.7.4.2 | 1.7.4.3 | 1.7.4.4 | 1.7.4.5 | 1.7.4.6 | 1.7.4.7 | 1.7.4.8 | 1.7.4.9 | 1.7.4.10 | 1.7.5.1 | 1.7.5.2 | 1.7.5.3 |
| 1.7.5.4 | 1.7.5.5 | 1.7.5.6 | 1.7.5.7 | 1.7.5.8 | 1.7.5.9 | 1.7.5.10 | 1.7.6.1 | 1.7.6.2 | 1.7.6.3 | 1.7.6.4 | 1.7.6.5 | 1.7.6.6 |
| 1.7.6.7 | 1.7.6.8 | 1.7.6.9 | 1.7.6.10 | 1.8.1.1 | 1.8.1.2 | 1.8.1.3 | 1.8.1.4 | 1.8.1.5 | 1.8.1.6 | 1.8.1.7 | 1.8.1.8 | 1.8.1.9 |
| 1.8.1.10 | 1.8.2.1 | 1.8.2.2 | 1.8.2.3 | 1.8.2.4 | 1.8.2.5 | 1.8.2.6 | 1.8.2.7 | 1.8.2.8 | 1.8.2.9 | 1.8.2.10 | 1.8.3.1 | 1.8.3.2 |
| 1.8.3.3 | 1.8.3.4 | 1.8.3.5 | 1.8.3.6 | 1.8.3.7 | 1.8.3.8 | 1.8.3.9 | 1.8.3.10 | 1.8.4.1 | 1.8.4.2 | 1.8.4.3 | 1.8.4.4 | 1.8.4.5 |
| 1.8.4.6 | 1.8.4.7 | 1.8.4.8 | 1.8.4.9 | 1.8.4.10 | 1.8.5.1 | 1.8.5.2 | 1.8.5.3 | 1.8.5.4 | 1.8.5.5 | 1.8.5.6 | 1.8.5.7 | 1.8.5.8 |

TABLE B-continued

| | | | | | | | | | | | |
|---|---|---|---|---|---|---|---|---|---|---|---|
| 1.8.5.9 | 1.8.5.10 | 1.8.6.1 | 1.8.6.2 | 1.8.6.3 | 1.8.6.4 | 1.8.6.5 | 1.8.6.6 | 1.8.6.7 | 1.8.6.8 | 1.8.6.9 | 1.8.6.10 1.9.1.1 |
| 1.9.1.2 | 1.9.1.3 | 1.9.1.4 | 1.9.1.5 | 1.9.1.6 | 1.9.1.7 | 1.9.1.8 | 1.9.1.9 | 1.9.1.10 | 1.9.2.1 | 1.9.2.2 | 1.9.2.3 1.9.2.4 |
| 1.9.2.5 | 1.9.2.6 | 1.9.2.7 | 1.9.2.8 | 1.9.2.9 | 1.9.2.10 | 1.9.3.1 | 1.9.3.2 | 1.9.3.3 | 1.9.3.4 | 1.9.3.5 | 1.9.3.6 1.9.3.7 |
| 1.9.3.8 | 1.9.3.9 | 1.9.3.10 | 1.9.4.1 | 1.9.4.2 | 1.9.4.3 | 1.9.4.4 | 1.9.4.5 | 1.9.4.6 | 1.9.4.7 | 1.9.4.8 | 1.9.4.9 1.9.4.10 |
| 1.9.5.1 | 1.9.5.2 | 1.9.5.3 | 1.9.5.4 | 1.9.5.5 | 1.9.5.6 | 1.9.5.7 | 1.9.5.8 | 1.9.5.9 | 1.9.5.10 | 1.9.6.1 | 1.9.6.2 1.9.6.3 |
| 1.9.6.4 | 1.9.6.5 | 1.9.6.6 | 1.9.6.7 | 1.9.6.8 | 1.9.6.9 | 1.9.6.10 | 1.10.1.1 | 1.10.1.2 | 1.10.1.3 | 1.10.1.4 | 1.10.1.5 |
| 1.10.1.6 | 1.10.1.7 | 1.10.1.8 | 1.10.1.9 | 1.10.1.10 | 1.10.2.1 | 1.10.2.2 | 1.10.2.3 | 1.10.2.4 | 1.10.2.5 | 1.10.2.6 | |
| 1.10.2.7 | 1.10.2.8 | 1.10.2.9 | 1.10.2.10 | 1.10.3.1 | 1.10.3.2 | 1.10.3.3 | 1.10.3.4 | 1.10.3.5 | 1.10.3.6 | 1.10.3.7 | |
| 1.10.3.8 | 1.10.3.9 | 1.10.3.10 | 1.10.4.1 | 1.10.4.2 | 1.10.4.3 | 1.10.4.4 | 1.10.4.5 | 1.10.4.6 | 1.10.4.7 | 1.10.4.8 | |
| 1.10.4.9 | 1.10.4.10 | 1.10.5.1 | 1.10.5.2 | 1.10.5.3 | 1.10.5.4 | 1.10.5.5 | 1.10.5.6 | 1.10.5.7 | 1.10.5.8 | 1.10.5.9 | |
| 1.10.5.10 | 1.10.6.1 | 1.10.6.2 | 1.10.6.3 | 1.10.6.4 | 1.10.6.5 | 1.10.6.6 | 1.10.6.7 | 1.10.6.8 | 1.10.6.9 | 1.10.6.10 | |
| 1.11.1.1 | 1.11.1.2 | 1.11.1.3 | 1.11.1.4 | 1.11.1.5 | 1.11.1.6 | 1.11.1.7 | 1.11.1.8 | 1.11.1.9 | 1.11.1.10 | 1.11.2.1 | |
| 1.11.2.2 | 1.11.2.3 | 1.11.2.4 | 1.11.2.5 | 1.11.2.6 | 1.11.2.7 | 1.11.2.8 | 1.11.2.9 | 1.11.2.10 | 1.11.3.1 | 1.11.3.2 | |
| 1.11.3.3 | 1.11.3.4 | 1.11.3.5 | 1.11.3.6 | 1.11.3.7 | 1.11.3.8 | 1.11.3.9 | 1.11.3.10 | 1.11.4.1 | 1.11.4.2 | 1.11.4.3 | |
| 1.11.4.4 | 1.11.4.5 | 1.11.4.6 | 1.11.4.7 | 1.11.4.8 | 1.11.4.9 | 1.11.4.10 | 1.11.5.1 | 1.11.5.2 | 1.11.5.3 | 1.11.5.4 | |
| 1.11.5.5 | 1.11.5.6 | 1.11.5.7 | 1.11.5.8 | 1.11.5.9 | 1.11.5.10 | 1.11.6.1 | 1.11.6.2 | 1.11.6.3 | 1.11.6.4 | 1.11.6.5 | |
| 1.11.6.6 | 1.11.6.7 | 1.11.6.8 | 1.11.6.9 | 1.11.6.10 | 1.12.1.1 | 1.12.1.2 | 1.12.1.3 | 1.12.1.4 | 1.12.1.5 | 1.12.1.6 | |
| 1.12.1.7 | 1.12.1.8 | 1.12.1.9 | 1.12.1.10 | 1.12.2.1 | 1.12.2.2 | 1.12.2.3 | 1.12.2.4 | 1.12.2.5 | 1.12.2.6 | 1.12.2.7 | |
| 1.12.2.8 | 1.12.2.9 | 1.12.2.10 | 1.12.3.1 | 1.12.3.2 | 1.12.3.3 | 1.12.3.4 | 1.12.3.5 | 1.12.3.6 | 1.12.3.7 | 1.12.3.8 | |
| 1.12.3.9 | 1.12.3.10 | 1.12.4.1 | 1.12.4.2 | 1.12.4.3 | 1.12.4.4 | 1.12.4.5 | 1.12.4.6 | 1.12.4.7 | 1.12.4.8 | 1.12.4.9 | |
| 1.12.4.10 | 1.12.5.1 | 1.12.5.2 | 1.12.5.3 | 1.12.5.4 | 1.12.5.5 | 1.12.5.6 | 1.12.5.7 | 1.12.5.8 | 1.12.5.9 | 1.12.5.10 | |
| 1.12.6.1 | 1.12.6.2 | 1.12.6.3 | 1.12.6.4 | 1.12.6.5 | 1.12.6.6 | 1.12.6.7 | 1.12.6.8 | 1.12.6.9 | 1.12.6.10 | 1.13.1.1 | |
| 1.13.1.2 | 1.13.1.3 | 1.13.1.4 | 1.13.1.5 | 1.13.1.6 | 1.13.1.7 | 1.13.1.8 | 1.13.1.9 | 1.13.1.10 | 1.13.2.1 | 1.13.2.2 | |
| 1.13.2.3 | 1.13.2.4 | 1.13.2.5 | 1.13.2.6 | 1.13.2.7 | 1.13.2.8 | 1.13.2.9 | 1.13.2.10 | 1.13.3.1 | 1.13.3.2 | 1.13.3.3 | |
| 1.13.3.4 | 1.13.3.5 | 1.13.3.6 | 1.13.3.7 | 1.13.3.8 | 1.13.3.9 | 1.13.3.10 | 1.13.4.1 | 1.13.4.2 | 1.13.4.3 | 1.13.4.4 | |
| 1.13.4.5 | 1.13.4.6 | 1.13.4.7 | 1.13.4.8 | 1.13.4.9 | 1.13.4.10 | 1.13.5.1 | 1.13.5.2 | 1.13.5.3 | 1.13.5.4 | 1.13.5.5 | |
| 1.13.5.6 | 1.13.5.7 | 1.13.5.8 | 1.13.5.9 | 1.13.5.10 | 1.13.6.1 | 1.13.6.2 | 1.13.6.3 | 1.13.6.4 | 1.13.6.5 | 1.13.6.6 | |
| 1.13.6.7 | 1.13.6.8 | 1.13.6.9 | 1.13.6.10 | 1.14.1.1 | 1.14.1.2 | 1.14.1.3 | 1.14.1.4 | 1.14.1.5 | 1.14.1.6 | 1.14.1.7 | |
| 1.14.1.8 | 1.14.1.9 | 1.14.1.10 | 1.14.2.1 | 1.14.2.2 | 1.14.2.3 | 1.14.2.4 | 1.14.2.5 | 1.14.2.6 | 1.14.2.7 | 1.14.2.8 | |
| 1.14.2.9 | 1.14.2.10 | 1.14.3.1 | 1.14.3.2 | 1.14.3.3 | 1.14.3.4 | 1.14.3.5 | 1.14.3.6 | 1.14.3.7 | 1.14.3.8 | 1.14.3.9 | |
| 1.14.3.10 | 1.14.4.1 | 1.14.4.2 | 1.14.4.3 | 1.14.4.4 | 1.14.4.5 | 1.14.4.6 | 1.14.4.7 | 1.14.4.8 | 1.14.4.9 | 1.14.4.10 | |
| 1.14.5.1 | 1.14.5.2 | 1.14.5.3 | 1.14.5.4 | 1.14.5.5 | 1.14.5.6 | 1.14.5.7 | 1.14.5.8 | 1.14.5.9 | 1.14.5.10 | 1.14.6.1 | |
| 1.14.6.2 | 1.14.6.3 | 1.14.6.4 | 1.14.6.5 | 1.14.6.6 | 1.14.6.7 | 1.14.6.8 | 1.14.6.9 | 1.14.6.10 | 1.15.1.1 | 1.15.1.2 | |
| 1.15.1.3 | 1.15.1.4 | 1.15.1.5 | 1.15.1.6 | 1.15.1.7 | 1.15.1.8 | 1.15.1.9 | 1.15.1.10 | 1.15.2.1 | 1.15.2.2 | 1.15.2.3 | |
| 1.15.2.4 | 1.15.2.5 | 1.15.2.6 | 1.15.2.7 | 1.15.2.8 | 1.15.2.9 | 1.15.2.10 | 1.15.3.1 | 1.15.3.2 | 1.15.3.3 | 1.15.3.4 | |
| 1.15.3.5 | 1.15.3.6 | 1.15.3.7 | 1.15.3.8 | 1.15.3.9 | 1.15.3.10 | 1.15.4.1 | 1.15.4.2 | 1.15.4.3 | 1.15.4.4 | 1.15.4.5 | |
| 1.15.4.6 | 1.15.4.7 | 1.15.4.8 | 1.15.4.9 | 1.15.4.10 | 1.15.5.1 | 1.15.5.2 | 1.15.5.3 | 1.15.5.4 | 1.15.5.5 | 1.15.5.6 | |
| 1.15.5.7 | 1.15.5.8 | 1.15.5.9 | 1.15.5.10 | 1.15.6.1 | 1.15.6.2 | 1.15.6.3 | 1.15.6.4 | 1.15.6.5 | 1.15.6.6 | 1.15.6.7 | |
| 1.15.6.8 | 1.15.6.9 | 1.15.6.10 | 1.16.1.1 | 1.16.1.2 | 1.16.1.3 | 1.16.1.4 | 1.16.1.5 | 1.16.1.6 | 1.16.1.7 | 1.16.1.8 | |
| 1.16.1.9 | 1.16.1.10 | 1.16.2.1 | 1.16.2.2 | 1.16.2.3 | 1.16.2.4 | 1.16.2.5 | 1.16.2.6 | 1.16.2.7 | 1.16.2.8 | 1.16.2.9 | |
| 1.16.2.10 | 1.16.3.1 | 1.16.3.2 | 1.16.3.3 | 1.16.3.4 | 1.16.3.5 | 1.16.3.6 | 1.16.3.7 | 1.16.3.8 | 1.16.3.9 | 1.16.3.10 | |
| 1.16.4.1 | 1.16.4.2 | 1.16.4.3 | 1.16.4.4 | 1.16.4.5 | 1.16.4.6 | 1.16.4.7 | 1.16.4.8 | 1.16.4.9 | 1.16.4.10 | 1.16.5.1 | |
| 1.16.5.2 | 1.16.5.3 | 1.16.5.4 | 1.16.5.5 | 1.16.5.6 | 1.16.5.7 | 1.16.5.8 | 1.16.5.9 | 1.16.5.10 | 1.16.6.1 | 1.16.6.2 | |
| 1.16.6.3 | 1.16.6.4 | 1.16.6.5 | 1.16.6.6 | 1.16.6.7 | 1.16.6.8 | 1.16.6.9 | 1.16.6.10 | 1.17.1.1 | 1.17.1.2 | 1.17.1.3 | |
| 1.17.1.4 | 1.17.1.5 | 1.17.1.6 | 1.17.1.7 | 1.17.1.8 | 1.17.1.9 | 1.17.1.10 | 1.17.2.1 | 1.17.2.2 | 1.17.2.3 | 1.17.2.4 | |
| 1.17.2.5 | 1.17.2.6 | 1.17.2.7 | 1.17.2.8 | 1.17.2.9 | 1.17.2.10 | 1.17.3.1 | 1.17.3.2 | 1.17.3.3 | 1.17.3.4 | 1.17.3.5 | |
| 1.17.3.6 | 1.17.3.7 | 1.17.3.8 | 1.17.3.9 | 1.17.3.10 | 1.17.4.1 | 1.17.4.2 | 1.17.4.3 | 1.17.4.4 | 1.17.4.5 | 1.17.4.6 | |
| 1.17.4.7 | 1.17.4.8 | 1.17.4.9 | 1.17.4.10 | 1.17.5.1 | 1.17.5.2 | 1.17.5.3 | 1.17.5.4 | 1.17.5.5 | 1.17.5.6 | 1.17.5.7 | |
| 1.17.5.8 | 1.17.5.9 | 1.17.5.10 | 1.17.6.1 | 1.17.6.2 | 1.17.6.3 | 1.17.6.4 | 1.17.6.5 | 1.17.6.6 | 1.17.6.7 | 1.17.6.8 | |
| 1.17.6.9 | 1.17.6.10 | 1.18.1.1 | 1.18.1.2 | 1.18.1.3 | 1.18.1.4 | 1.18.1.5 | 1.18.1.6 | 1.18.1.7 | 1.18.1.8 | 1.18.1.9 | |
| 1.18.1.10 | 1.18.2.1 | 1.18.2.2 | 1.18.2.3 | 1.18.2.4 | 1.18.2.5 | 1.18.2.6 | 1.18.2.7 | 1.18.2.8 | 1.18.2.9 | 1.18.2.10 | |
| 1.18.3.1 | 1.18.3.2 | 1.18.3.3 | 1.18.3.4 | 1.18.3.5 | 1.18.3.6 | 1.18.3.7 | 1.18.3.8 | 1.18.3.9 | 1.18.3.10 | 1.18.4.1 | |
| 1.18.4.2 | 1.18.4.3 | 1.18.4.4 | 1.18.4.5 | 1.18.4.6 | 1.18.4.7 | 1.18.4.8 | 1.18.4.9 | 1.18.4.10 | 1.18.5.1 | 1.18.5.2 | |
| 1.18.5.3 | 1.18.5.4 | 1.18.5.5 | 1.18.5.6 | 1.18.5.7 | 1.18.5.8 | 1.18.5.9 | 1.18.5.10 | 1.18.6.1 | 1.18.6.2 | 1.18.6.3 | |
| 1.18.6.4 | 1.18.6.5 | 1.18.6.6 | 1.18.6.7 | 1.18.6.8 | 1.18.6.9 | 1.18.6.10 | 1.19.1.1 | 1.19.1.2 | 1.19.1.3 | 1.19.1.4 | |
| 1.19.1.5 | 1.19.1.6 | 1.19.1.7 | 1.19.1.8 | 1.19.1.9 | 1.19.1.10 | 1.19.2.1 | 1.19.2.2 | 1.19.2.3 | 1.19.2.4 | 1.19.2.5 | |
| 1.19.2.6 | 1.19.2.7 | 1.19.2.8 | 1.19.2.9 | 1.19.2.10 | 1.19.3.1 | 1.19.3.2 | 1.19.3.3 | 1.19.3.4 | 1.19.3.5 | 1.19.3.6 | |
| 1.19.3.7 | 1.19.3.8 | 1.19.3.9 | 1.19.3.10 | 1.19.4.1 | 1.19.4.2 | 1.19.4.3 | 1.19.4.4 | 1.19.4.5 | 1.19.4.6 | 1.19.4.7 | |
| 1.19.4.8 | 1.19.4.9 | 1.19.4.10 | 1.19.5.1 | 1.19.5.2 | 1.19.5.3 | 1.19.5.4 | 1.19.5.5 | 1.19.5.6 | 1.19.5.7 | 1.19.5.8 | |
| 1.19.5.9 | 1.19.5.10 | 1.19.6.1 | 1.19.6.2 | 1.19.6.3 | 1.19.6.4 | 1.19.6.5 | 1.19.6.6 | 1.19.6.7 | 1.19.6.8 | 1.19.6.9 | |
| 1.19.6.10 | 1.20.1.1 | 1.20.1.2 | 1.20.1.3 | 1.20.1.4 | 1.20.1.5 | 1.20.1.6 | 1.20.1.7 | 1.20.1.8 | 1.20.1.9 | 1.20.1.10 | |
| 1.20.2.1 | 1.20.2.2 | 1.20.2.3 | 1.20.2.4 | 1.20.2.5 | 1.20.2.6 | 1.20.2.7 | 1.20.2.8 | 1.20.2.9 | 1.20.2.10 | 1.20.3.1 | |
| 1.20.3.2 | 1.20.3.3 | 1.20.3.4 | 1.20.3.5 | 1.20.3.6 | 1.20.3.7 | 1.20.3.8 | 1.20.3.9 | 1.20.3.10 | 1.20.4.1 | 1.20.4.2 | |
| 1.20.4.3 | 1.20.4.4 | 1.20.4.5 | 1.20.4.6 | 1.20.4.7 | 1.20.4.8 | 1.20.4.9 | 1.20.4.10 | 1.20.5.1 | 1.20.5.2 | 1.20.5.3 | |
| 1.20.5.4 | 1.20.5.5 | 1.20.5.6 | 1.20.5.7 | 1.20.5.8 | 1.20.5.9 | 1.20.5.10 | 1.20.6.1 | 1.20.6.2 | 1.20.6.3 | 1.20.6.4 | |
| 1.20.6.5 | 1.20.6.6 | 1.20.6.7 | 1.20.6.8 | 1.20.6.9 | 1.20.6.10 | 1.21.1.1 | 1.21.1.2 | 1.21.1.3 | 1.21.1.4 | 1.21.1.5 | |
| 1.21.1.6 | 1.21.1.7 | 1.21.1.8 | 1.21.1.9 | 1.21.1.10 | 1.21.2.1 | 1.21.2.2 | 1.21.2.3 | 1.21.2.4 | 1.21.2.5 | 1.21.2.6 | |
| 1.21.2.7 | 1.21.2.8 | 1.21.2.9 | 1.21.2.10 | 1.21.3.1 | 1.21.3.2 | 1.21.3.3 | 1.21.3.4 | 1.21.3.5 | 1.21.3.6 | 1.21.3.7 | |
| 1.21.3.8 | 1.21.3.9 | 1.21.3.10 | 1.21.4.1 | 1.21.4.2 | 1.21.4.3 | 1.21.4.4 | 1.21.4.5 | 1.21.4.6 | 1.21.4.7 | 1.21.4.8 | |
| 1.21.4.9 | 1.21.4.10 | 1.21.5.1 | 1.21.5.2 | 1.21.5.3 | 1.21.5.4 | 1.21.5.5 | 1.21.5.6 | 1.21.5.7 | 1.21.5.8 | 1.21.5.9 | |
| 1.21.5.10 | 1.21.6.1 | 1.21.6.2 | 1.21.6.3 | 1.21.6.4 | 1.21.6.5 | 1.21.6.6 | 1.21.6.7 | 1.21.6.8 | 1.21.6.9 | 1.21.6.10 | |
| 1.22.1.1 | 1.22.1.2 | 1.22.1.3 | 1.22.1.4 | 1.22.1.5 | 1.22.1.6 | 1.22.1.7 | 1.22.1.8 | 1.22.1.9 | 1.22.1.10 | 1.22.2.1 | |
| 1.22.2.2 | 1.22.2.3 | 1.22.2.4 | 1.22.2.5 | 1.22.2.6 | 1.22.2.7 | 1.22.2.8 | 1.22.2.9 | 1.22.2.10 | 1.22.3.1 | 1.22.3.2 | |
| 1.22.3.3 | 1.22.3.4 | 1.22.3.5 | 1.22.3.6 | 1.22.3.7 | 1.22.3.8 | 1.22.3.9 | 1.22.3.10 | 1.22.4.1 | 1.22.4.2 | 1.22.4.3 | |
| 1.22.4.4 | 1.22.4.5 | 1.22.4.6 | 1.22.4.7 | 1.22.4.8 | 1.22.4.9 | 1.22.4.10 | 1.22.5.1 | 1.22.5.2 | 1.22.5.3 | 1.22.5.4 | |
| 1.22.5.5 | 1.22.5.6 | 1.22.5.7 | 1.22.5.8 | 1.22.5.9 | 1.22.5.10 | 1.22.6.1 | 1.22.6.2 | 1.22.6.3 | 1.22.6.4 | 1.22.6.5 | |
| 1.22.6.6 | 1.22.6.7 | 1.22.6.8 | 1.22.6.9 | 1.22.6.10 | 1.23.1.1 | 1.23.1.2 | 1.23.1.3 | 1.23.1.4 | 1.23.1.5 | 1.23.1.6 | |
| 1.23.1.7 | 1.23.1.8 | 1.23.1.9 | 1.23.1.10 | 1.23.2.1 | 1.23.2.2 | 1.23.2.3 | 1.23.2.4 | 1.23.2.5 | 1.23.2.6 | 1.23.2.7 | |
| 1.23.2.8 | 1.23.2.9 | 1.23.2.10 | 1.23.3.1 | 1.23.3.2 | 1.23.3.3 | 1.23.3.4 | 1.23.3.5 | 1.23.3.6 | 1.23.3.7 | 1.23.3.8 | |

TABLE B-continued

| | | | | | | | | | | | |
|---|---|---|---|---|---|---|---|---|---|---|---|
| 1.23.3.9 | 1.23.3.10 | 1.23.4.1 | 1.23.4.2 | 1.23.4.3 | 1.23.4.4 | 1.23.4.5 | 1.23.4.6 | 1.23.4.7 | 1.23.4.8 | 1.23.4.9 | |
| 1.23.4.10 | 1.23.5.1 | 1.23.5.2 | 1.23.5.3 | 1.23.5.4 | 1.23.5.5 | 1.23.5.6 | 1.23.5.7 | 1.23.5.8 | 1.23.5.9 | 1.23.5.10 | |
| 1.23.6.1 | 1.23.6.2 | 1.23.6.3 | 1.23.6.4 | 1.23.6.5 | 1.23.6.6 | 1.23.6.7 | 1.23.6.8 | 1.23.6.9 | 1.23.6.10 | 1.24.1.1 | |
| 1.24.1.2 | 1.24.1.3 | 1.24.1.4 | 1.24.1.5 | 1.24.1.6 | 1.24.1.7 | 1.24.1.8 | 1.24.1.9 | 1.24.1.10 | 1.24.2.1 | 1.24.2.2 | |
| 1.24.2.3 | 1.24.2.4 | 1.24.2.5 | 1.24.2.6 | 1.24.2.7 | 1.24.2.8 | 1.24.2.9 | 1.24.2.10 | 1.24.3.1 | 1.24.3.2 | 1.24.3.3 | |
| 1.24.3.4 | 1.24.3.5 | 1.24.3.6 | 1.24.3.7 | 1.24.3.8 | 1.24.3.9 | 1.24.3.10 | 1.24.4.1 | 1.24.4.2 | 1.24.4.3 | 1.24.4.4 | |
| 1.24.4.5 | 1.24.4.6 | 1.24.4.7 | 1.24.4.8 | 1.24.4.9 | 1.24.4.10 | 1.24.5.1 | 1.24.5.2 | 1.24.5.3 | 1.24.5.4 | 1.24.5.5 | |
| 1.24.5.6 | 1.24.5.7 | 1.24.5.8 | 1.24.5.9 | 1.24.5.10 | 1.24.6.1 | 1.24.6.2 | 1.24.6.3 | 1.24.6.4 | 1.24.6.5 | 1.24.6.6 | |
| 1.24.6.7 | 1.24.6.8 | 1.24.6.9 | 1.24.6.10 | 1.25.1.1 | 1.25.1.2 | 1.25.1.3 | 1.25.1.4 | 1.25.1.5 | 1.25.1.6 | 1.25.1.7 | |
| 1.25.1.8 | 1.25.1.9 | 1.25.1.10 | 1.25.2.1 | 1.25.2.2 | 1.25.2.3 | 1.25.2.4 | 1.25.2.5 | 1.25.2.6 | 1.25.2.7 | 1.25.2.8 | |
| 1.25.2.9 | 1.25.2.10 | 1.25.3.1 | 1.25.3.2 | 1.25.3.3 | 1.25.3.4 | 1.25.3.5 | 1.25.3.6 | 1.25.3.7 | 1.25.3.8 | 1.25.3.9 | |
| 1.25.3.10 | 1.25.4.1 | 1.25.4.2 | 1.25.4.3 | 1.25.4.4 | 1.25.4.5 | 1.25.4.6 | 1.25.4.7 | 1.25.4.8 | 1.25.4.9 | 1.25.4.10 | |
| 1.25.5.1 | 1.25.5.2 | 1.25.5.3 | 1.25.5.4 | 1.25.5.5 | 1.25.5.6 | 1.25.5.7 | 1.25.5.8 | 1.25.5.9 | 1.25.5.10 | 1.25.6.1 | |
| 1.25.6.2 | 1.25.6.3 | 1.25.6.4 | 1.25.6.5 | 1.25.6.6 | 1.25.6.7 | 1.25.6.8 | 1.25.6.9 | 1.25.6.10 | 2.1.1.1 | 2.1.1.2 | 2.1.1.3 |
| 2.1.1.4 | 2.1.1.5 | 2.1.1.6 | 2.1.1.7 | 2.1.1.8 | 2.1.1.9 | 2.1.1.10 | 2.1.2.1 | 2.1.2.2 | 2.1.2.3 | 2.1.2.4 | 2.1.2.5 | 2.1.2.6 |
| 2.1.2.7 | 2.1.2.8 | 2.1.2.9 | 2.1.2.10 | 2.1.3.1 | 2.1.3.2 | 2.1.3.3 | 2.1.3.4 | 2.1.3.5 | 2.1.3.6 | 2.1.3.7 | 2.1.3.8 | 2.1.3.9 |
| 2.1.3.10 | 2.1.4.1 | 2.1.4.2 | 2.1.4.3 | 2.1.4.4 | 2.1.4.5 | 2.1.4.6 | 2.1.4.7 | 2.1.4.8 | 2.1.4.9 | 2.1.4.10 | 2.1.5.1 | 2.1.5.2 |
| 2.1.5.3 | 2.1.5.4 | 2.1.5.5 | 2.1.5.6 | 2.1.5.7 | 2.1.5.8 | 2.1.5.9 | 2.1.5.10 | 2.1.6.1 | 2.1.6.2 | 2.1.6.3 | 2.1.6.4 | 2.1.6.5 |
| 2.1.6.6 | 2.1.6.7 | 2.1.6.8 | 2.1.6.9 | 2.1.6.10 | 2.2.1.1 | 2.2.1.2 | 2.2.1.3 | 2.2.1.4 | 2.2.1.5 | 2.2.1.6 | 2.2.1.7 | 2.2.1.8 |
| 2.2.1.9 | 2.2.1.10 | 2.2.2.1 | 2.2.2.2 | 2.2.2.3 | 2.2.2.4 | 2.2.2.5 | 2.2.2.6 | 2.2.2.7 | 2.2.2.8 | 2.2.2.9 | 2.2.2.10 | 2.2.3.1 |
| 2.2.3.2 | 2.2.3.3 | 2.2.3.4 | 2.2.3.5 | 2.2.3.6 | 2.2.3.7 | 2.2.3.8 | 2.2.3.9 | 2.2.3.10 | 2.2.4.1 | 2.2.4.2 | 2.2.4.3 | 2.2.4.4 |
| 2.2.4.5 | 2.2.4.6 | 2.2.4.7 | 2.2.4.8 | 2.2.4.9 | 2.2.4.10 | 2.2.5.1 | 2.2.5.2 | 2.2.5.3 | 2.2.5.4 | 2.2.5.5 | 2.2.5.6 | 2.2.5.7 |
| 2.2.5.8 | 2.2.5.9 | 2.2.5.10 | 2.2.6.1 | 2.2.6.2 | 2.2.6.3 | 2.2.6.4 | 2.2.6.5 | 2.2.6.6 | 2.2.6.7 | 2.2.6.8 | 2.2.6.9 | 2.2.6.10 |
| 2.3.1.1 | 2.3.1.2 | 2.3.1.3 | 2.3.1.4 | 2.3.1.5 | 2.3.1.6 | 2.3.1.7 | 2.3.1.8 | 2.3.1.9 | 2.3.1.10 | 2.3.2.1 | 2.3.2.2 | 2.3.2.3 |
| 2.3.2.4 | 2.3.2.5 | 2.3.2.6 | 2.3.2.7 | 2.3.2.8 | 2.3.2.9 | 2.3.2.10 | 2.3.3.1 | 2.3.3.2 | 2.3.3.3 | 2.3.3.4 | 2.3.3.5 | 2.3.3.6 |
| 2.3.3.7 | 2.3.3.8 | 2.3.3.9 | 2.3.3.10 | 2.3.4.1 | 2.3.4.2 | 2.3.4.3 | 2.3.4.4 | 2.3.4.5 | 2.3.4.6 | 2.3.4.7 | 2.3.4.8 | 2.3.4.9 |
| 2.3.4.10 | 2.3.5.1 | 2.3.5.2 | 2.3.5.3 | 2.3.5.4 | 2.3.5.5 | 2.3.5.6 | 2.3.5.7 | 2.3.5.8 | 2.3.5.9 | 2.3.5.10 | 2.3.6.1 | 2.3.6.2 |
| 2.3.6.3 | 2.3.6.4 | 2.3.6.5 | 2.3.6.6 | 2.3.6.7 | 2.3.6.8 | 2.3.6.9 | 2.3.6.10 | 2.4.1.1 | 2.4.1.2 | 2.4.1.3 | 2.4.1.4 | 2.4.1.5 |
| 2.4.1.6 | 2.4.1.7 | 2.4.1.8 | 2.4.1.9 | 2.4.1.10 | 2.4.2.1 | 2.4.2.2 | 2.4.2.3 | 2.4.2.4 | 2.4.2.5 | 2.4.2.6 | 2.4.2.7 | 2.4.2.8 |
| 2.4.2.9 | 2.4.2.10 | 2.4.3.1 | 1.4.3.2 | 2.4.3.3 | 2.4.3.4 | 2.4.3.5 | 2.4.3.6 | 2.4.3.7 | 2.4.3.8 | 2.4.3.9 | 1.4.3.10 | 2.4.4.1 |
| 2.4.4.2 | 2.4.4.3 | 2.4.4.4 | 2.4.4.5 | 2.4.4.6 | 2.4.4.7 | 2.4.4.8 | 2.4.4.9 | 2.4.4.10 | 2.4.5.1 | 2.4.5.2 | 2.4.5.3 | 2.4.5.4 |
| 2.4.5.5 | 2.4.5.6 | 2.4.5.7 | 2.4.5.8 | 2.4.5.9 | 2.4.5.10 | 2.4.6.1 | 2.4.6.2 | 2.4.6.3 | 2.4.6.4 | 2.4.6.5 | 2.4.6.6 | 2.4.6.7 |
| 2.4.6.8 | 2.4.6.9 | 2.4.6.10 | 2.5.1.1 | 2.5.1.2 | 2.5.1.3 | 2.5.1.4 | 2.5.1.5 | 2.5.1.6 | 2.5.1.7 | 2.5.1.8 | 2.5.1.9 | 2.5.1.10 |
| 2.5.2.1 | 2.5.2.2 | 2.5.2.3 | 2.5.2.4 | 2.5.2.5 | 2.5.2.6 | 2.5.2.7 | 2.5.2.8 | 2.5.2.9 | 2.5.2.10 | 2.5.3.1 | 2.5.3.2 | 2.5.3.3 |
| 2.5.3.4 | 2.5.3.5 | 2.5.3.6 | 2.5.3.7 | 2.5.3.8 | 2.5.3.9 | 2.5.3.10 | 2.5.4.1 | 2.5.4.2 | 2.5.4.3 | 2.5.4.4 | 2.5.4.5 | 2.5.4.6 |
| 2.5.4.7 | 2.5.4.8 | 2.5.4.9 | 2.5.4.10 | 2.5.5.1 | 2.5.5.2 | 2.5.5.3 | 2.5.5.4 | 2.5.5.5 | 2.5.5.6 | 2.5.5.7 | 2.5.5.8 | 2.5.5.9 |
| 2.5.5.10 | 2.5.6.1 | 2.5.6.2 | 2.5.6.3 | 2.5.6.4 | 2.5.6.5 | 2.5.6.6 | 2.5.6.7 | 2.5.6.8 | 2.5.6.9 | 2.5.6.10 | 2.6.1.1 | 2.6.1.2 |
| 2.6.1.3 | 2.6.1.4 | 2.6.1.5 | 2.6.1.6 | 2.6.1.7 | 2.6.1.8 | 2.6.1.9 | 1.6.1.10 | 2.6.2.1 | 2.6.2.2 | 2.6.2.3 | 2.6.2.4 | 2.6.2.5 |
| 2.6.2.6 | 2.6.2.7 | 2.6.2.8 | 2.6.2.9 | 2.6.2.10 | 2.6.3.1 | 2.6.3.2 | 2.6.3.3 | 2.6.3.4 | 2.6.3.5 | 2.6.3.6 | 2.6.3.7 | 2.6.3.8 |
| 2.6.3.9 | 2.6.3.10 | 2.6.4.1 | 2.6.4.2 | 2.6.4.3 | 2.6.4.4 | 2.6.4.5 | 2.6.4.6 | 2.6.4.7 | 2.6.4.8 | 2.6.4.9 | 2.6.4.10 | 2.6.5.1 |
| 2.6.5.2 | 2.6.5.3 | 2.6.5.4 | 2.6.5.5 | 2.6.5.6 | 2.6.5.7 | 2.6.5.8 | 2.6.5.9 | 2.6.5.10 | 2.6.6.1 | 2.6.6.2 | 2.6.6.3 | 2.6.6.4 |
| 2.6.6.5 | 2.6.6.6 | 2.6.6.7 | 2.6.6.8 | 2.6.6.9 | 2.6.6.10 | 2.7.1.1 | 2.7.1.2 | 2.7.1.3 | 2.7.1.4 | 2.7.1.5 | 2.7.1.6 | 2.7.1.7 |
| 2.7.1.8 | 2.7.1.9 | 2.7.1.10 | 2.7.2.1 | 2.7.2.2 | 2.7.2.3 | 2.7.2.4 | 2.7.2.5 | 2.7.2.6 | 2.7.2.7 | 2.7.2.8 | 2.7.2.9 | 2.7.2.10 |
| 2.7.3.1 | 2.7.3.2 | 2.7.3.3 | 2.7.3.4 | 2.7.3.5 | 2.7.3.6 | 2.7.3.7 | 2.7.3.8 | 2.7.3.9 | 2.7.3.10 | 2.7.4.1 | 2.7.4.2 | 2.7.4.3 |
| 2.7.4.4 | 2.7.4.5 | 2.7.4.6 | 2.7.4.7 | 2.7.4.8 | 2.7.4.9 | 2.7.4.10 | 2.7.5.1 | 2.7.5.2 | 2.7.5.3 | 2.7.5.4 | 2.7.5.5 | 2.7.5.6 |
| 2.7.5.7 | 2.7.5.8 | 2.7.5.9 | 2.7.5.10 | 2.7.6.1 | 2.7.6.2 | 2.7.6.3 | 2.7.6.4 | 2.7.6.5 | 2.7.6.6 | 2.7.6.7 | 2.7.6.8 | 2.7.6.9 |
| 2.7.6.10 | 2.8.1.1 | 2.8.1.2 | 2.8.1.3 | 2.8.1.4 | 2.8.1.5 | 2.8.1.6 | 2.8.1.7 | 2.8.1.8 | 2.8.1.9 | 2.8.1.10 | 2.8.2.1 | 2.8.2.2 |
| 2.8.2.3 | 2.8.2.4 | 2.8.2.5 | 2.8.2.6 | 2.8.2.7 | 2.8.2.8 | 2.8.2.9 | 2.8.2.10 | 2.8.3.1 | 2.8.3.2 | 2.8.3.3 | 2.8.3.4 | 2.8.3.5 |
| 2.8.3.6 | 2.8.3.7 | 2.8.3.8 | 2.8.3.9 | 2.8.3.10 | 2.8.4.1 | 2.8.4.2 | 2.8.4.3 | 2.8.4.4 | 2.8.4.5 | 2.8.4.6 | 2.8.4.7 | 2.8.4.8 |
| 2.8.4.9 | 2.8.4.10 | 2.8.5.1 | 2.8.5.2 | 2.8.5.3 | 2.8.5.4 | 2.8.5.5 | 2.8.5.6 | 2.8.5.7 | 2.8.5.8 | 2.8.5.9 | 2.8.5.10 | 2.8.6.1 |
| 2.8.6.2 | 2.8.6.3 | 2.8.6.4 | 2.8.6.5 | 2.8.6.6 | 2.8.6.7 | 2.8.6.8 | 2.8.6.9 | 2.8.6.10 | 2.9.1.1 | 2.9.1.2 | 2.9.1.3 | 2.9.1.4 |
| 2.9.1.5 | 2.9.1.6 | 2.9.1.7 | 2.9.1.8 | 2.9.1.9 | 2.9.1.10 | 2.9.2.1 | 2.9.2.2 | 2.9.2.3 | 2.9.2.4 | 2.9.2.5 | 2.9.2.6 | 2.9.2.7 |
| 2.9.2.8 | 2.9.2.9 | 2.9.2.10 | 2.9.3.1 | 2.9.3.2 | 2.9.3.3 | 2.9.3.4 | 2.9.3.5 | 2.9.3.6 | 2.9.3.7 | 2.9.3.8 | 2.9.3.9 | 2.9.3.10 |
| 2.9.4.1 | 2.9.4.2 | 2.9.4.3 | 2.9.4.4 | 2.9.4.5 | 2.9.4.6 | 2.9.4.7 | 2.9.4.8 | 2.9.4.9 | 2.9.4.10 | 2.9.5.1 | 2.9.5.2 | 2.9.5.3 |
| 2.9.5.4 | 2.9.5.5 | 2.9.5.6 | 2.9.5.7 | 2.9.5.8 | 2.9.5.9 | 2.9.5.10 | 2.9.6.1 | 2.9.6.2 | 2.9.6.3 | 2.9.6.4 | 2.9.6.5 | 2.9.6.6 |
| 2.9.6.7 | 2.9.6.8 | 2.9.6.9 | 2.9.6.10 | 2.10.1.1 | 2.10.1.2 | 2.10.1.3 | 2.10.1.4 | 2.10.1.5 | 2.10.1.6 | 2.10.1.7 | 2.10.1.8 | |
| 2.10.1.9 | 2.10.1.10 | 2.10.2.1 | 2.10.2.2 | 2.10.2.3 | 2.10.2.4 | 2.10.2.5 | 2.10.2.6 | 2.10.2.7 | 2.10.2.8 | 2.10.2.9 | | |
| 2.10.2.10 | 2.10.3.1 | 2.10.3.2 | 2.10.3.3 | 2.10.3.4 | 2.10.3.5 | 2.10.3.6 | 2.10.3.7 | 2.10.3.8 | 2.10.3.9 | 2.10.3.10 | | |
| 2.10.4.1 | 2.10.4.2 | 2.10.4.3 | 2.10.4.4 | 2.10.4.5 | 2.10.4.6 | 2.10.4.7 | 2.10.4.8 | 2.10.4.9 | 2.10.4.10 | 2.10.5.1 | | |
| 2.10.5.2 | 2.10.5.3 | 2.10.5.4 | 2.10.5.5 | 2.10.5.6 | 2.10.5.7 | 2.10.5.8 | 2.10.5.9 | 2.10.5.10 | 2.10.6.1 | 2.10.6.2 | | |
| 2.10.6.3 | 2.10.6.4 | 2.10.6.5 | 2.10.6.6 | 2.10.6.7 | 2.10.6.8 | 2.10.6.9 | 2.10.6.10 | 2.11.1.1 | 2.11.1.2 | 2.11.1.3 | | |
| 2.11.1.4 | 2.11.1.5 | 2.11.1.6 | 2.11.1.7 | 2.11.1.8 | 2.11.1.9 | 2.11.1.10 | 2.11.2.1 | 2.11.2.2 | 2.11.2.3 | 2.11.2.4 | | |
| 2.11.2.5 | 2.11.2.6 | 2.11.2.7 | 2.11.2.8 | 2.11.2.9 | 2.11.2.10 | 2.11.3.1 | 2.11.3.2 | 2.11.3.3 | 2.11.3.4 | 2.11.3.5 | | |
| 2.11.3.6 | 2.11.3.7 | 2.11.3.8 | 2.11.3.9 | 2.11.3.10 | 2.11.4.1 | 2.11.4.2 | 2.11.4.3 | 2.11.4.4 | 2.11.4.5 | 2.11.4.6 | | |
| 2.11.4.7 | 2.11.4.8 | 2.11.4.9 | 2.11.4.10 | 2.11.5.1 | 2.11.5.2 | 2.11.5.3 | 2.11.5.4 | 2.11.5.5 | 2.11.5.6 | 2.11.5.7 | | |
| 2.11.5.8 | 2.11.5.9 | 2.11.5.10 | 2.11.6.1 | 2.11.6.2 | 2.11.6.3 | 2.11.6.4 | 2.11.6.5 | 2.11.6.6 | 2.11.6.7 | 2.11.6.8 | | |
| 2.11.6.9 | 2.11.6.10 | 2.12.1.1 | 2.12.1.2 | 2.12.1.3 | 2.12.1.4 | 2.12.1.5 | 2.12.1.6 | 2.12.1.7 | 2.12.1.8 | 2.12.1.9 | | |
| 2.12.1.10 | 2.12.2.1 | 2.12.2.2 | 2.12.2.3 | 2.12.2.4 | 2.12.2.5 | 2.12.2.6 | 2.12.2.7 | 2.12.2.8 | 2.12.2.9 | 2.12.2.10 | | |
| 2.12.3.1 | 2.12.3.2 | 2.12.3.3 | 2.12.3.4 | 2.12.3.5 | 2.12.3.6 | 2.12.3.7 | 2.12.3.8 | 2.12.3.9 | 2.12.3.10 | 2.12.4.1 | | |
| 2.12.4.2 | 2.12.4.3 | 2.12.4.4 | 2.12.4.5 | 2.12.4.6 | 2.12.4.7 | 2.12.4.8 | 2.12.4.9 | 2.12.4.10 | 2.12.5.1 | 2.12.5.2 | | |
| 2.12.5.3 | 2.12.5.4 | 2.12.5.5 | 2.12.5.6 | 2.12.5.7 | 2.12.5.8 | 2.12.5.9 | 2.12.5.10 | 2.12.6.1 | 2.12.6.2 | 2.12.6.3 | | |
| 2.12.6.4 | 2.12.6.5 | 2.12.6.6 | 2.12.6.7 | 2.12.6.8 | 2.12.6.9 | 2.12.6.10 | 2.13.1.1 | 2.13.1.2 | 2.13.1.3 | 2.13.1.4 | | |
| 2.13.1.5 | 2.13.1.6 | 2.13.1.7 | 2.13.1.8 | 2.13.1.9 | 2.13.1.10 | 2.13.2.1 | 2.13.2.2 | 2.13.2.3 | 2.13.2.4 | 2.13.2.5 | | |
| 2.13.2.6 | 2.13.2.7 | 2.13.2.8 | 2.13.2.9 | 2.13.2.10 | 2.13.3.1 | 2.13.3.2 | 2.13.3.3 | 2.13.3.4 | 2.13.3.5 | 2.13.3.6 | | |
| 2.13.3.7 | 2.13.3.8 | 2.13.3.9 | 2.13.3.10 | 2.13.4.1 | 2.13.4.2 | 2.13.4.3 | 2.13.4.4 | 2.13.4.5 | 2.13.4.6 | 2.13.4.7 | | |
| 2.13.4.8 | 2.13.4.9 | 2.13.4.10 | 2.13.5.1 | 2.13.5.2 | 2.13.5.3 | 2.13.5.4 | 2.13.5.5 | 2.13.5.6 | 2.13.5.7 | 2.13.5.8 | | |
| 2.13.5.9 | 2.13.5.10 | 2.13.6.1 | 2.13.6.2 | 2.13.6.3 | 2.13.6.4 | 2.13.6.5 | 2.13.6.6 | 2.13.6.7 | 2.13.6.8 | 2.13.6.9 | | |
| 2.13.6.10 | 2.14.1.1 | 2.14.1.2 | 2.14.1.3 | 2.14.1.4 | 2.14.1.5 | 2.14.1.6 | 2.14.1.7 | 2.14.1.8 | 2.14.1.9 | 2.14.1.10 | | |
| 2.14.2.1 | 2.14.2.2 | 2.14.2.3 | 2.14.2.4 | 2.14.2.5 | 2.14.2.6 | 2.14.2.7 | 2.14.2.8 | 2.14.2.9 | 2.14.2.10 | 2.14.3.1 | | |

TABLE B-continued

| | | | | | | | | | | | |
|---|---|---|---|---|---|---|---|---|---|---|---|
| 2.14.3.2 | 2.14.3.3 | 2.14.3.4 | 2.14.3.5 | 2.14.3.6 | 2.14.3.7 | 2.14.3.8 | 2.14.3.9 | 2.14.3.10 | 2.14.4.1 | 2.14.4.2 | |
| 2.14.4.3 | 2.14.4.4 | 2.14.4.5 | 2.14.4.6 | 2.14.4.7 | 2.14.4.8 | 2.14.4.9 | 2.14.4.10 | 2.14.5.1 | 2.14.5.2 | 2.14.5.3 | |
| 2.14.5.4 | 2.14.5.5 | 2.14.5.6 | 2.14.5.7 | 2.14.5.8 | 2.14.5.9 | 2.14.5.10 | 2.14.6.1 | 2.14.6.2 | 2.14.6.3 | 2.14.6.4 | |
| 2.14.6.5 | 2.14.6.6 | 2.14.6.7 | 2.14.6.8 | 2.14.6.9 | 2.14.6.10 | 2.15.1.1 | 2.15.1.2 | 2.15.1.3 | 2.15.1.4 | 2.15.1.5 | |
| 2.15.1.6 | 2.15.1.7 | 2.15.1.8 | 2.15.1.9 | 2.15.1.10 | 2.15.2.1 | 2.15.2.2 | 2.15.2.3 | 2.15.2.4 | 2.15.2.5 | 2.15.2.6 | |
| 2.15.2.7 | 2.15.2.8 | 2.15.2.9 | 2.15.2.10 | 2.15.3.1 | 2.15.3.2 | 2.15.3.3 | 2.15.3.4 | 2.15.3.5 | 2.15.3.6 | 2.15.3.7 | |
| 2.15.3.8 | 2.15.3.9 | 2.15.3.10 | 2.15.4.1 | 2.15.4.2 | 2.15.4.3 | 2.15.4.4 | 2.15.4.5 | 2.15.4.6 | 2.15.4.7 | 2.15.4.8 | |
| 2.15.4.9 | 2.15.4.10 | 2.15.5.1 | 2.15.5.2 | 2.15.5.3 | 2.15.5.4 | 2.15.5.5 | 2.15.5.6 | 2.15.5.7 | 2.15.5.8 | 2.15.5.9 | |
| 2.15.5.10 | 2.15.6.1 | 2.15.6.2 | 2.15.6.3 | 2.15.6.4 | 2.15.6.5 | 2.15.6.6 | 2.15.6.7 | 2.15.6.8 | 2.15.6.9 | 2.15.6.10 | |
| 2.16.1.1 | 2.16.1.2 | 2.16.1.3 | 2.16.1.4 | 2.16.1.5 | 2.16.1.6 | 2.16.1.7 | 2.16.1.8 | 2.16.1.9 | 2.16.1.10 | 2.16.2.1 | |
| 2.16.2.2 | 2.16.2.3 | 2.16.2.4 | 2.16.2.5 | 2.16.2.6 | 2.16.2.7 | 2.16.2.8 | 2.16.2.9 | 2.16.2.10 | 2.16.3.1 | 2.16.3.2 | |
| 2.16.3.3 | 2.16.3.4 | 2.16.3.5 | 2.16.3.6 | 2.16.3.7 | 2.16.3.8 | 2.16.3.9 | 2.16.3.10 | 2.16.4.1 | 2.16.4.2 | 2.16.4.3 | |
| 2.16.4.4 | 2.16.4.5 | 2.16.4.6 | 2.16.4.7 | 2.16.4.8 | 2.16.4.9 | 2.16.4.10 | 2.16.5.1 | 2.16.5.2 | 2.16.5.3 | 2.16.5.4 | |
| 2.16.5.5 | 2.16.5.6 | 2.16.5.7 | 2.16.5.8 | 2.16.5.9 | 2.16.5.10 | 2.16.6.1 | 2.16.6.2 | 2.16.6.3 | 2.16.6.4 | 2.16.6.5 | |
| 2.16.6.6 | 2.16.6.7 | 2.16.6.8 | 2.16.6.9 | 2.16.6.10 | 2.17.1.1 | 2.17.1.2 | 2.17.1.3 | 2.17.1.4 | 2.17.1.5 | 2.17.1.6 | |
| 2.17.1.7 | 2.17.1.8 | 2.17.1.9 | 2.17.1.10 | 2.17.2.1 | 2.17.2.2 | 2.17.2.3 | 2.17.2.4 | 2.17.2.5 | 2.17.2.6 | 2.17.2.7 | |
| 2.17.2.8 | 2.17.2.9 | 2.17.2.10 | 2.17.3.1 | 2.17.3.2 | 2.17.3.3 | 2.17.3.4 | 2.17.3.5 | 2.17.3.6 | 2.17.3.7 | 2.17.3.8 | |
| 2.17.3.9 | 2.17.3.10 | 2.17.4.1 | 2.17.4.2 | 2.17.4.3 | 2.17.4.4 | 2.17.4.5 | 2.17.4.6 | 2.17.4.7 | 2.17.4.8 | 2.17.4.9 | |
| 2.17.4.10 | 2.17.5.1 | 2.17.5.2 | 2.17.5.3 | 2.17.5.4 | 2.17.5.5 | 2.17.5.6 | 2.17.5.7 | 2.17.5.8 | 2.17.5.9 | 2.17.5.10 | |
| 2.17.6.1 | 2.17.6.2 | 2.17.6.3 | 2.17.6.4 | 2.17.6.5 | 2.17.6.6 | 2.17.6.7 | 2.17.6.8 | 2.17.6.9 | 2.17.6.10 | 2.18.1.1 | |
| 2.18.1.2 | 2.18.1.3 | 2.18.1.4 | 2.18.1.5 | 2.18.1.6 | 2.18.1.7 | 2.18.1.8 | 2.18.1.9 | 2.18.1.10 | 2.18.2.1 | 2.18.2.2 | |
| 2.18.2.3 | 2.18.2.4 | 2.18.2.5 | 2.18.2.6 | 2.18.2.7 | 2.18.2.8 | 2.18.2.9 | 2.18.2.10 | 2.18.3.1 | 2.18.3.2 | 2.18.3.3 | |
| 2.18.3.4 | 2.18.3.5 | 2.18.3.6 | 2.18.3.7 | 2.18.3.8 | 2.18.3.9 | 2.18.3.10 | 2.18.4.1 | 2.18.4.2 | 2.18.4.3 | 2.18.4.4 | |
| 2.18.4.5 | 2.18.4.6 | 2.18.4.7 | 2.18.4.8 | 2.18.4.9 | 2.18.4.10 | 2.18.5.1 | 2.18.5.2 | 2.18.5.3 | 2.18.5.4 | 2.18.5.5 | |
| 2.18.5.6 | 2.18.5.7 | 2.18.5.8 | 2.18.5.9 | 2.18.5.10 | 2.18.6.1 | 2.18.6.2 | 2.18.6.3 | 2.18.6.4 | 2.18.6.5 | 2.18.6.6 | |
| 2.18.6.7 | 2.18.6.8 | 2.18.6.9 | 2.18.6.10 | 2.19.1.1 | 2.19.1.2 | 2.19.1.3 | 2.19.1.4 | 2.19.1.5 | 2.19.1.6 | 2.19.1.7 | |
| 2.19.1.8 | 2.19.1.9 | 2.19.1.10 | 2.19.2.1 | 2.19.2.2 | 2.19.2.3 | 2.19.2.4 | 2.19.2.5 | 2.19.2.6 | 2.19.2.7 | 2.19.2.8 | |
| 2.19.2.9 | 2.19.2.10 | 2.19.3.1 | 2.19.3.2 | 2.19.3.3 | 2.19.3.4 | 2.19.3.5 | 2.19.3.6 | 2.19.3.7 | 2.19.3.8 | 2.19.3.9 | |
| 2.19.3.10 | 2.19.4.1 | 2.19.4.2 | 2.19.4.3 | 2.19.4.4 | 2.19.4.5 | 2.19.4.6 | 2.19.4.7 | 2.19.4.8 | 2.19.4.9 | 2.19.4.10 | |
| 2.19.5.1 | 2.19.5.2 | 2.19.5.3 | 2.19.5.4 | 2.19.5.5 | 2.19.5.6 | 2.19.5.7 | 2.19.5.8 | 2.19.5.9 | 2.19.5.10 | 2.19.6.1 | |
| 2.19.6.2 | 2.19.6.3 | 2.19.6.4 | 2.19.6.5 | 2.19.6.6 | 2.19.6.7 | 2.19.6.8 | 2.19.6.9 | 2.19.6.10 | 2.20.1.1 | 2.20.1.2 | |
| 2.20.1.3 | 2.20.1.4 | 2.20.1.5 | 2.20.1.6 | 2.20.1.7 | 2.20.1.8 | 2.20.1.9 | 2.20.1.10 | 2.20.2.1 | 2.20.2.2 | 2.20.2.3 | |
| 2.20.2.4 | 2.20.2.5 | 2.20.2.6 | 2.20.2.7 | 2.20.2.8 | 2.20.2.9 | 2.20.2.10 | 2.20.3.1 | 2.20.3.2 | 2.20.3.3 | 2.20.3.4 | |
| 2.20.3.5 | 2.20.3.6 | 2.20.3.7 | 2.20.3.8 | 2.20.3.9 | 2.20.3.10 | 2.20.4.1 | 2.20.4.2 | 2.20.4.3 | 2.20.4.4 | 2.20.4.5 | |
| 2.20.4.6 | 2.20.4.7 | 2.20.4.8 | 2.20.4.9 | 2.20.4.10 | 2.20.5.1 | 2.20.5.2 | 2.20.5.3 | 2.20.5.4 | 2.20.5.5 | 2.20.5.6 | |
| 2.20.5.7 | 2.20.5.8 | 2.20.5.9 | 2.20.5.10 | 2.20.6.1 | 2.20.6.2 | 2.20.6.3 | 2.20.6.4 | 2.20.6.5 | 2.20.6.6 | 2.20.6.7 | |
| 2.20.6.8 | 2.20.6.9 | 2.20.6.10 | 2.21.1.1 | 2.21.1.2 | 2.21.1.3 | 2.21.1.4 | 2.21.1.5 | 2.21.1.6 | 2.21.1.7 | 2.21.1.8 | |
| 2.21.1.9 | 2.21.1.10 | 2.21.2.1 | 2.21.2.2 | 2.21.2.3 | 2.21.2.4 | 2.21.2.5 | 2.21.2.6 | 2.21.2.7 | 2.21.2.8 | 2.21.2.9 | |
| 2.21.2.10 | 2.21.3.1 | 2.21.3.2 | 2.21.3.3 | 2.21.3.4 | 2.21.3.5 | 2.21.3.6 | 2.21.3.7 | 2.21.3.8 | 2.21.3.9 | 2.21.3.10 | |
| 2.21.4.1 | 2.21.4.2 | 2.21.4.3 | 2.21.4.4 | 2.21.4.5 | 2.21.4.6 | 2.21.4.7 | 2.21.4.8 | 2.21.4.9 | 2.21.4.10 | 2.21.5.1 | |
| 2.21.5.2 | 2.21.5.3 | 2.21.5.4 | 2.21.5.5 | 2.21.5.6 | 2.21.5.7 | 2.21.5.8 | 2.21.5.9 | 2.21.5.10 | 2.21.6.1 | 2.21.6.2 | |
| 2.21.6.3 | 2.21.6.4 | 2.21.6.5 | 2.21.6.6 | 2.21.6.7 | 2.21.6.8 | 2.21.6.9 | 2.21.6.10 | 2.22.1.1 | 2.22.1.2 | 2.22.1.3 | |
| 2.22.1.4 | 2.22.1.5 | 2.22.1.6 | 2.22.1.7 | 2.22.1.8 | 2.22.1.9 | 2.22.1.10 | 2.22.2.1 | 2.22.2.2 | 2.22.2.3 | 2.22.2.4 | |
| 2.22.2.5 | 2.22.2.6 | 2.22.2.7 | 2.22.2.8 | 2.22.2.9 | 2.22.2.10 | 2.22.3.1 | 2.22.3.2 | 2.22.3.3 | 2.22.3.4 | 2.22.3.5 | |
| 2.22.3.6 | 2.22.3.7 | 2.22.3.8 | 2.22.3.9 | 2.22.3.10 | 2.22.4.1 | 2.22.4.2 | 2.22.4.3 | 2.22.4.4 | 2.22.4.5 | 2.22.4.6 | |
| 2.22.4.7 | 2.22.4.8 | 2.22.4.9 | 2.22.4.10 | 2.22.5.1 | 2.22.5.2 | 2.22.5.3 | 2.22.5.4 | 2.22.5.5 | 2.22.5.6 | 2.22.5.7 | |
| 2.22.5.8 | 2.22.5.9 | 2.22.5.10 | 2.22.6.1 | 2.22.6.2 | 2.22.6.3 | 2.22.6.4 | 2.22.6.5 | 2.22.6.6 | 2.22.6.7 | 2.22.6.8 | |
| 2.22.6.9 | 2.22.6.10 | 2.23.1.1 | 2.23.1.2 | 2.23.1.3 | 2.23.1.4 | 2.23.1.5 | 2.23.1.6 | 2.23.1.7 | 2.23.1.8 | 2.23.1.9 | |
| 2.23.1.10 | 2.23.2.1 | 2.23.2.2 | 2.23.2.3 | 2.23.2.4 | 2.23.2.5 | 2.23.2.6 | 2.23.2.7 | 2.23.2.8 | 2.23.2.9 | 2.23.2.10 | |
| 2.23.3.1 | 2.23.3.2 | 2.23.3.3 | 2.23.3.4 | 2.23.3.5 | 2.23.3.6 | 2.23.3.7 | 2.23.3.8 | 2.23.3.9 | 2.23.3.10 | 2.23.4.1 | |
| 2.23.4.2 | 2.23.4.3 | 2.23.4.4 | 2.23.4.5 | 2.23.4.6 | 2.23.4.7 | 2.23.4.8 | 2.23.4.9 | 2.23.4.10 | 2.23.5.1 | 2.23.5.2 | |
| 2.23.5.3 | 2.23.5.4 | 2.23.5.5 | 2.23.5.6 | 2.23.5.7 | 2.23.5.8 | 2.23.5.9 | 2.23.5.10 | 2.23.6.1 | 2.23.6.2 | 2.23.6.3 | |
| 2.23.6.4 | 2.23.6.5 | 2.23.6.6 | 2.23.6.7 | 2.23.6.8 | 2.23.6.9 | 2.23.6.10 | 2.24.1.1 | 2.24.1.2 | 2.24.1.3 | 2.24.1.4 | |
| 2.24.1.5 | 2.24.1.6 | 2.24.1.7 | 2.24.1.8 | 2.24.1.9 | 2.24.1.10 | 2.24.2.1 | 2.24.2.2 | 2.24.2.3 | 2.24.2.4 | 2.24.2.5 | |
| 2.24.2.6 | 2.24.2.7 | 2.24.2.8 | 2.24.2.9 | 2.24.2.10 | 2.24.3.1 | 2.24.3.2 | 2.24.3.3 | 2.24.3.4 | 2.24.3.5 | 2.24.3.6 | |
| 2.24.3.7 | 2.24.3.8 | 2.24.3.9 | 2.24.3.10 | 2.24.4.1 | 2.24.4.2 | 2.24.4.3 | 2.24.4.4 | 2.24.4.5 | 2.24.4.6 | 2.24.4.7 | |
| 2.24.4.8 | 2.24.4.9 | 2.24.4.10 | 2.24.5.1 | 2.24.5.2 | 2.24.5.3 | 2.24.5.4 | 2.24.5.5 | 2.24.5.6 | 2.24.5.7 | 2.24.5.8 | |
| 2.24.5.9 | 2.24.5.10 | 2.24.6.1 | 2.24.6.2 | 2.24.6.3 | 2.24.6.4 | 2.24.6.5 | 2.24.6.6 | 2.24.6.7 | 2.24.6.8 | 2.24.6.9 | |
| 2.24.6.10 | 2.25.1.1 | 2.25.1.2 | 2.25.1.3 | 2.25.1.4 | 2.25.1.5 | 2.25.1.6 | 2.25.1.7 | 2.25.1.8 | 2.25.1.9 | 2.25.1.10 | |
| 2.25.2.1 | 2.25.2.2 | 2.25.2.3 | 2.25.2.4 | 2.25.2.5 | 2.25.2.6 | 2.25.2.7 | 2.25.2.8 | 2.25.2.9 | 2.25.2.10 | 2.25.3.1 | |
| 2.25.3.2 | 2.25.3.3 | 2.25.3.4 | 2.25.3.5 | 2.25.3.6 | 2.25.3.7 | 2.25.3.8 | 2.25.3.9 | 2.25.3.10 | 2.25.4.1 | 2.25.4.2 | |
| 2.25.4.3 | 2.25.4.4 | 2.25.4.5 | 2.25.4.6 | 2.25.4.7 | 2.25.4.8 | 2.25.4.9 | 2.25.4.10 | 2.25.5.1 | 2.25.5.2 | 2.25.5.3 | |
| 2.25.5.4 | 2.25.5.5 | 2.25.5.6 | 2.25.5.7 | 2.25.5.8 | 2.25.5.9 | 2.25.5.10 | 2.25.6.1 | 2.25.6.2 | 2.25.6.3 | 2.25.6.4 | |
| 2.25.6.5 | 2.25.6.6 | 2.25.6.7 | 2.25.6.8 | 2.25.6.9 | 2.25.6.10 | 3.1.1.1 | 3.1.1.2 | 3.1.1.3 | 2.1.1.4 | 3.1.1.5 | 3.1.1.6 |
| 3.1.1.7 | 3.1.1.8 | 3.1.1.9 | 3.1.1.10 | 3.1.2.1 | 3.1.2.2 | 3.1.2.3 | 3.1.2.4 | 3.1.2.5 | 3.1.2.6 | 3.1.2.7 | 3.1.2.8 | 3.1.2.9 |
| 3.1.2.10 | 3.1.3.1 | 3.1.3.2 | 3.1.3.3 | 3.1.3.4 | 3.1.3.5 | 3.1.3.6 | 3.1.3.7 | 3.1.3.8 | 3.1.3.9 | 3.1.3.10 | 3.1.4.1 | 3.1.4.2 |
| 3.1.4.3 | 3.1.4.4 | 3.1.4.5 | 3.1.4.6 | 3.1.4.7 | 3.1.4.8 | 3.1.4.9 | 3.1.4.10 | 3.1.5.1 | 3.1.5.2 | 3.1.5.3 | 3.1.5.4 | 3.1.5.5 |
| 3.1.5.6 | 3.1.5.7 | 3.1.5.8 | 3.1.5.9 | 3.1.5.10 | 3.1.6.1 | 3.1.6.2 | 3.1.6.3 | 3.1.6.4 | 3.1.6.5 | 3.1.6.6 | 3.1.6.7 | 3.1.6.8 |
| 3.1.6.9 | 3.1.6.10 | 3.2.1.1 | 3.2.1.2 | 3.2.1.3 | 3.2.1.4 | 3.2.1.5 | 3.2.1.6 | 3.2.1.7 | 3.2.1.8 | 3.2.1.9 | 3.2.1.10 | 3.2.2.1 |
| 3.2.2.2 | 3.2.2.3 | 3.2.2.4 | 3.2.2.5 | 3.2.2.6 | 3.2.2.7 | 3.2.2.8 | 3.2.2.9 | 3.2.2.10 | 3.2.3.1 | 3.2.3.2 | 3.2.3.3 | 3.2.3.4 |
| 3.2.3.5 | 3.2.3.6 | 3.2.3.7 | 3.2.3.8 | 3.2.3.9 | 3.2.3.10 | 3.2.4.1 | 3.2.4.2 | 3.2.4.3 | 3.2.4.4 | 3.2.4.5 | 3.2.4.6 | 3.2.4.7 |
| 3.2.4.8 | 3.2.4.9 | 3.2.4.10 | 3.2.5.1 | 3.2.5.2 | 3.2.5.3 | 3.2.5.4 | 3.2.5.5 | 3.2.5.6 | 3.2.5.7 | 3.2.5.8 | 3.2.5.9 | 3.2.5.10 |
| 3.2.6.1 | 3.2.6.2 | 3.2.6.3 | 3.2.6.4 | 3.2.6.5 | 3.2.6.6 | 3.2.6.7 | 3.2.6.8 | 3.2.6.9 | 3.2.6.10 | 3.3.1.1 | 3.3.1.2 | 3.3.1.3 |
| 3.3.1.4 | 3.3.1.5 | 3.3.1.6 | 3.3.1.7 | 3.3.1.8 | 3.3.1.9 | 3.3.1.10 | 3.3.2.1 | 3.3.2.2 | 3.3.2.3 | 3.3.2.4 | 3.3.2.5 | 3.3.2.6 |
| 3.3.2.7 | 3.3.2.8 | 3.3.2.9 | 3.3.2.10 | 3.3.3.1 | 3.3.3.2 | 3.3.3.3 | 3.3.3.4 | 3.3.3.5 | 3.3.3.6 | 3.3.3.7 | 3.3.3.8 | 3.3.3.9 |
| 3.3.3.10 | 3.3.4.1 | 3.3.4.2 | 3.3.4.3 | 3.3.4.4 | 3.3.4.5 | 3.3.4.6 | 3.3.4.7 | 3.3.4.8 | 3.3.4.9 | 3.3.4.10 | 3.3.5.1 | 3.3.5.2 |
| 3.3.5.3 | 3.3.5.4 | 3.3.5.5 | 3.3.5.6 | 3.3.5.7 | 3.3.5.8 | 3.3.5.9 | 3.3.5.10 | 3.3.6.1 | 3.3.6.2 | 3.3.6.3 | 3.3.6.4 | 3.3.6.5 |
| 3.3.6.6 | 3.3.6.7 | 3.3.6.8 | 3.3.6.9 | 3.3.6.10 | 3.4.1.1 | 3.4.1.2 | 3.4.1.3 | 3.4.1.4 | 3.4.1.5 | 3.4.1.6 | 3.4.1.7 | 3.4.1.8 |
| 3.4.1.9 | 3.4.1.10 | 3.4.2.1 | 3.4.2.2 | 3.4.2.3 | 3.4.2.4 | 3.4.2.5 | 3.4.2.6 | 3.4.2.7 | 3.4.2.8 | 3.4.2.9 | 3.4.2.10 | 3.4.3.1 |

TABLE B-continued

| | | | | | | | | | | | | |
|---|---|---|---|---|---|---|---|---|---|---|---|---|
| 3.4.3.2 | 3.4.3.3 | 3.4.3.4 | 3.4.3.5 | 3.4.3.6 | 3.4.3.7 | 3.4.3.8 | 3.4.3.9 | 3.4.3.10 | 3.4.4.1 | 3.4.4.2 | 3.4.4.3 | 3.4.4.4 |
| 3.4.4.5 | 3.4.4.6 | 3.4.4.7 | 3.4.4.8 | 3.4.4.9 | 3.4.4.10 | 3.4.5.1 | 3.4.5.2 | 3.4.5.3 | 3.4.5.4 | 3.4.5.5 | 3.4.5.6 | 3.4.5.7 |
| 3.4.5.8 | 3.4.5.9 | 3.4.5.10 | 3.4.6.1 | 3.4.6.2 | 3.4.6.3 | 3.4.6.4 | 3.4.6.5 | 3.4.6.6 | 3.4.6.7 | 3.4.6.8 | 3.4.6.9 | 3.4.6.10 |
| 3.5.1.1 | 3.5.1.2 | 3.5.1.3 | 3.5.1.4 | 3.5.1.5 | 3.5.1.6 | 3.5.1.7 | 3.5.1.8 | 3.5.1.9 | 3.5.1.10 | 3.5.2.1 | 3.5.2.2 | 3.5.2.3 |
| 3.5.2.4 | 3.5.2.5 | 3.5.2.6 | 3.5.2.7 | 3.5.2.8 | 3.5.2.9 | 3.5.2.10 | 3.5.3.1 | 3.5.3.2 | 3.5.3.3 | 3.5.3.4 | 3.5.3.5 | 3.5.3.6 |
| 3.5.3.7 | 3.5.3.8 | 3.5.3.9 | 3.5.3.10 | 3.5.4.1 | 3.5.4.2 | 3.5.4.3 | 3.5.4.4 | 3.5.4.5 | 3.5.4.6 | 3.5.4.7 | 3.5.4.8 | 3.5.4.9 |
| 3.5.4.10 | 3.5.5.1 | 3.5.5.2 | 3.5.5.3 | 3.5.5.4 | 3.5.5.5 | 3.5.5.6 | 3.5.5.7 | 3.5.5.8 | 3.5.5.9 | 3.5.5.10 | 3.5.6.1 | 3.5.6.2 |
| 3.5.6.3 | 3.5.6.4 | 3.5.6.5 | 3.5.6.6 | 3.5.6.7 | 3.5.6.8 | 3.5.6.9 | 3.5.6.10 | 3.6.1.1 | 3.6.1.2 | 3.6.1.3 | 3.6.1.4 | 3.6.1.5 |
| 3.6.1.6 | 3.6.1.7 | 3.6.1.8 | 3.6.1.9 | 3.6.1.10 | 3.6.2.1 | 3.6.2.2 | 3.6.2.3 | 3.6.2.4 | 3.6.2.5 | 3.6.2.6 | 3.6.2.7 | 3.6.2.8 |
| 3.6.2.9 | 3.6.2.10 | 3.6.3.1 | 3.6.3.2 | 3.6.3.3 | 3.6.3.4 | 3.6.3.5 | 3.6.3.6 | 3.6.3.7 | 3.6.3.8 | 3.6.3.9 | 3.6.3.10 | 3.6.4.1 |
| 3.6.4.2 | 3.6.4.3 | 3.6.4.4 | 3.6.4.5 | 3.6.4.6 | 3.6.4.7 | 3.6.4.8 | 3.6.4.9 | 3.6.4.10 | 3.6.5.1 | 3.6.5.2 | 3.6.5.3 | 3.6.5.4 |
| 3.6.5.5 | 3.6.5.6 | 3.6.5.7 | 3.6.5.8 | 3.6.5.9 | 3.6.5.10 | 3.6.6.1 | 3.6.6.2 | 3.6.6.3 | 3.6.6.4 | 3.6.6.5 | 3.6.6.6 | 3.6.6.7 |
| 3.6.6.8 | 3.6.6.9 | 3.6.6.10 | 3.7.1.1 | 3.7.1.2 | 3.7.1.3 | 3.7.1.4 | 3.7.1.5 | 3.7.1.6 | 3.7.1.7 | 3.7.1.8 | 3.7.1.9 | 3.7.1.10 |
| 3.7.2.1 | 3.7.2.2 | 3.7.2.3 | 3.7.2.4 | 3.7.2.5 | 3.7.2.6 | 3.7.2.7 | 3.7.2.8 | 3.7.2.9 | 3.7.2.10 | 3.7.3.1 | 3.7.3.2 | 3.7.3.3 |
| 3.7.3.4 | 3.7.3.5 | 3.7.3.6 | 3.7.3.7 | 3.7.3.8 | 3.7.3.9 | 3.7.3.10 | 3.7.4.1 | 3.7.4.2 | 3.7.4.3 | 3.7.4.4 | 3.7.4.5 | 3.7.4.6 |
| 3.7.4.7 | 3.7.4.8 | 3.7.4.9 | 3.7.4.10 | 3.7.5.1 | 3.7.5.2 | 3.7.5.3 | 3.7.5.4 | 3.7.5.5 | 3.7.5.6 | 3.7.5.7 | 3.7.5.8 | 3.7.5.9 |
| 3.7.5.10 | 3.7.6.1 | 3.7.6.2 | 3.7.6.3 | 3.7.6.4 | 3.7.6.5 | 3.7.6.6 | 3.7.6.7 | 3.7.6.8 | 3.7.6.9 | 3.7.6.10 | 3.8.1.1 | 3.8.1.2 |
| 3.8.1.3 | 3.8.1.4 | 3.8.1.5 | 3.8.1.6 | 3.8.1.7 | 3.8.1.8 | 3.8.1.9 | 3.8.1.10 | 3.8.2.1 | 3.8.2.2 | 3.8.2.3 | 3.8.2.4 | 3.8.2.5 |
| 3.8.2.6 | 3.8.2.7 | 3.8.2.8 | 3.8.2.9 | 3.8.2.10 | 3.8.3.1 | 3.8.3.2 | 3.8.3.3 | 3.8.3.4 | 3.8.3.5 | 3.8.3.6 | 3.8.3.7 | 3.8.3.8 |
| 3.8.3.9 | 3.8.3.10 | 3.8.4.1 | 3.8.4.2 | 3.8.4.3 | 3.8.4.4 | 3.8.4.5 | 3.8.4.6 | 3.8.4.7 | 3.8.4.8 | 3.8.4.9 | 3.8.4.10 | 3.8.5.1 |
| 3.8.5.2 | 3.8.5.3 | 3.8.5.4 | 3.8.5.5 | 3.8.5.6 | 3.8.5.7 | 3.8.5.8 | 3.8.5.9 | 3.8.5.10 | 3.8.6.1 | 3.8.6.2 | 3.8.6.3 | 3.8.6.4 |
| 3.8.6.5 | 3.8.6.6 | 3.8.6.7 | 3.8.6.8 | 3.8.6.9 | 3.8.6.10 | 3.9.1.1 | 3.9.1.2 | 3.9.1.3 | 3.9.1.4 | 3.9.1.5 | 3.9.1.6 | 3.9.1.7 |
| 3.9.1.8 | 3.9.1.9 | 3.9.1.10 | 3.9.2.1 | 3.9.2.2 | 3.9.2.3 | 3.9.2.4 | 3.9.2.5 | 3.9.2.6 | 3.9.2.7 | 3.9.2.8 | 3.9.2.9 | 3.9.2.10 |
| 3.9.3.1 | 3.9.3.2 | 3.9.3.3 | 3.9.3.4 | 3.9.3.5 | 3.9.3.6 | 3.9.3.7 | 3.9.3.8 | 3.9.3.9 | 3.9.3.10 | 3.9.4.1 | 3.9.4.2 | 3.9.4.3 |
| 3.9.4.4 | 3.9.4.5 | 3.9.4.6 | 3.9.4.7 | 3.9.4.8 | 3.9.4.9 | 3.9.4.10 | 3.9.5.1 | 3.9.5.2 | 3.9.5.3 | 3.9.5.4 | 3.9.5.5 | 3.9.5.6 |
| 3.9.5.7 | 3.9.5.8 | 3.9.5.9 | 3.9.5.10 | 3.9.6.1 | 3.9.6.2 | 3.9.6.3 | 3.9.6.4 | 3.9.6.5 | 3.9.6.6 | 3.9.6.7 | 3.9.6.8 | 3.9.6.9 |
| 3.9.6.10 | 3.10.1.1 | 3.10.1.2 | 3.10.1.3 | 3.10.1.4 | 3.10.1.5 | 3.10.1.6 | 3.10.1.7 | 3.10.1.8 | 3.10.1.9 | 3.10.1.10 | | |
| 3.10.2.1 | 3.10.2.2 | 3.10.2.3 | 3.10.2.4 | 3.10.2.5 | 3.10.2.6 | 3.10.2.7 | 3.10.2.8 | 3.10.2.9 | 3.10.2.10 | 3.10.3.1 | | |
| 3.10.3.2 | 3.10.3.3 | 3.10.3.4 | 3.10.3.5 | 3.10.3.6 | 3.10.3.7 | 3.10.3.8 | 3.10.3.9 | 3.10.3.10 | 3.10.4.1 | 3.10.4.2 | | |
| 3.10.4.3 | 3.10.4.4 | 3.10.4.5 | 3.10.4.6 | 3.10.4.7 | 3.10.4.8 | 3.10.4.9 | 3.10.4.10 | 3.10.5.1 | 3.10.5.2 | 3.10.5.3 | | |
| 3.10.5.4 | 3.10.5.5 | 3.10.5.6 | 3.10.5.7 | 3.10.5.8 | 3.10.5.9 | 3.10.5.10 | 3.10.6.1 | 3.10.6.2 | 3.10.6.3 | 3.10.6.4 | | |
| 3.10.6.5 | 3.10.6.6 | 3.10.6.7 | 3.10.6.8 | 3.10.6.9 | 3.10.6.10 | 3.11.1.1 | 3.11.1.2 | 3.11.1.3 | 3.11.1.4 | 3.11.1.5 | | |
| 3.11.1.6 | 3.11.1.7 | 3.11.1.8 | 3.11.1.9 | 3.11.1.10 | 3.11.2.1 | 3.11.2.2 | 3.11.2.3 | 3.11.2.4 | 3.11.2.5 | 3.11.2.6 | | |
| 3.11.2.7 | 3.11.2.8 | 3.11.2.9 | 3.11.2.10 | 3.11.3.1 | 3.11.3.2 | 3.11.3.3 | 3.11.3.4 | 3.11.3.5 | 3.11.3.6 | 3.11.3.7 | | |
| 3.11.3.8 | 3.11.3.9 | 3.11.3.10 | 3.11.4.1 | 3.11.4.2 | 3.11.4.3 | 3.11.4.4 | 3.11.4.5 | 3.11.4.6 | 3.11.4.7 | 3.11.4.8 | | |
| 3.11.4.9 | 3.11.4.10 | 3.11.5.1 | 3.11.5.2 | 3.11.5.3 | 3.11.5.4 | 3.11.5.5 | 3.11.5.6 | 3.11.5.7 | 3.11.5.8 | 3.11.5.9 | | |
| 3.11.5.10 | 3.11.6.1 | 3.11.6.2 | 3.11.6.3 | 3.11.6.4 | 3.11.6.5 | 3.11.6.6 | 3.11.6.7 | 3.11.6.8 | 3.11.6.9 | 3.11.6.10 | | |
| 3.12.1.1 | 3.12.1.2 | 3.12.1.3 | 3.12.1.4 | 3.12.1.5 | 3.12.1.6 | 3.12.1.7 | 3.12.1.8 | 3.12.1.9 | 3.12.1.10 | 3.12.2.1 | | |
| 3.12.2.2 | 3.12.2.3 | 3.12.2.4 | 3.12.2.5 | 3.12.2.6 | 3.12.2.7 | 3.12.2.8 | 3.12.2.9 | 3.12.2.10 | 3.12.3.1 | 3.12.3.2 | | |
| 3.12.3.3 | 3.12.3.4 | 3.12.3.5 | 3.12.3.6 | 3.12.3.7 | 3.12.3.8 | 3.12.3.9 | 3.12.3.10 | 3.12.4.1 | 3.12.4.2 | 3.12.4.3 | | |
| 3.12.4.4 | 3.12.4.5 | 3.12.4.6 | 3.12.4.7 | 3.12.4.8 | 3.12.4.9 | 3.12.4.10 | 3.12.5.1 | 3.12.5.2 | 3.12.5.3 | 3.12.5.4 | | |
| 3.12.5.5 | 3.12.5.6 | 3.12.5.7 | 3.12.5.8 | 3.12.5.9 | 3.12.5.10 | 3.12.6.1 | 3.12.6.2 | 3.12.6.3 | 3.12.6.4 | 3.12.6.5 | | |
| 3.12.6.6 | 3.12.6.7 | 3.12.6.8 | 3.12.6.9 | 3.12.6.10 | 3.13.1.1 | 3.13.1.2 | 3.13.1.3 | 3.13.1.4 | 3.13.1.5 | 3.13.1.6 | | |
| 3.13.1.7 | 3.13.1.8 | 3.13.1.9 | 3.13.1.10 | 3.13.2.1 | 3.13.2.2 | 3.13.2.3 | 3.13.2.4 | 3.13.2.5 | 3.13.2.6 | 3.13.2.7 | | |
| 3.13.2.8 | 3.13.2.9 | 3.13.2.10 | 3.13.3.1 | 3.13.3.2 | 3.13.3.3 | 3.13.3.4 | 3.13.3.5 | 3.13.3.6 | 3.13.3.7 | 3.13.3.8 | | |
| 3.13.3.9 | 3.13.3.10 | 3.13.4.1 | 3.13.4.2 | 3.13.4.3 | 3.13.4.4 | 3.13.4.5 | 3.13.4.6 | 3.13.4.7 | 3.13.4.8 | 3.13.4.9 | | |
| 3.13.4.10 | 3.13.5.1 | 3.13.5.2 | 3.13.5.3 | 3.13.5.4 | 3.13.5.5 | 3.13.5.6 | 3.13.5.7 | 3.13.5.8 | 3.13.5.9 | 3.13.5.10 | | |
| 3.13.6.1 | 3.13.6.2 | 3.13.6.3 | 3.13.6.4 | 3.13.6.5 | 3.13.6.6 | 3.13.6.7 | 3.13.6.8 | 3.13.6.9 | 3.13.6.10 | 3.14.1.1 | | |
| 3.14.1.2 | 3.14.1.3 | 3.14.1.4 | 3.14.1.5 | 3.14.1.6 | 3.14.1.7 | 3.14.1.8 | 3.14.1.9 | 3.14.1.10 | 3.14.2.1 | 3.14.2.2 | | |
| 3.14.2.3 | 3.14.2.4 | 3.14.2.5 | 3.14.2.6 | 3.14.2.7 | 3.14.2.8 | 3.14.2.9 | 3.14.2.10 | 3.14.3.1 | 3.14.3.2 | 3.14.3.3 | | |
| 3.14.3.4 | 3.14.3.5 | 3.14.3.6 | 3.14.3.7 | 3.14.3.8 | 3.14.3.9 | 3.14.3.10 | 3.14.4.1 | 3.14.4.2 | 3.14.4.3 | 3.14.4.4 | | |
| 3.14.4.5 | 3.14.4.6 | 3.14.4.7 | 3.14.4.8 | 3.14.4.9 | 3.14.4.10 | 3.14.5.1 | 3.14.5.2 | 3.14.5.3 | 3.14.5.4 | 3.14.5.5 | | |
| 3.14.5.6 | 3.14.5.7 | 3.14.5.8 | 3.14.5.9 | 3.14.5.10 | 3.14.6.1 | 3.14.6.2 | 3.14.6.3 | 3.14.6.4 | 3.14.6.5 | 3.14.6.6 | | |
| 3.14.6.7 | 3.14.6.8 | 3.14.6.9 | 3.14.6.10 | 3.15.1.1 | 3.15.1.2 | 3.15.1.3 | 3.15.1.4 | 3.15.1.5 | 3.15.1.6 | 3.15.1.7 | | |
| 3.15.1.8 | 3.15.1.9 | 3.15.1.10 | 3.15.2.1 | 3.15.2.2 | 3.15.2.3 | 3.15.2.4 | 3.15.2.5 | 3.15.2.6 | 3.15.2.7 | 3.15.2.8 | | |
| 3.15.2.9 | 3.15.2.10 | 3.15.3.1 | 3.15.3.2 | 3.15.3.3 | 3.15.3.4 | 3.15.3.5 | 3.15.3.6 | 3.15.3.7 | 3.15.3.8 | 3.15.3.9 | | |
| 3.15.3.10 | 3.15.4.1 | 3.15.4.2 | 3.15.4.3 | 3.15.4.4 | 3.15.4.5 | 3.15.4.6 | 3.15.4.7 | 3.15.4.8 | 3.15.4.9 | 3.15.4.10 | | |
| 3.15.5.1 | 3.15.5.2 | 3.15.5.3 | 3.15.5.4 | 3.15.5.5 | 3.15.5.6 | 3.15.5.7 | 3.15.5.8 | 3.15.5.9 | 3.15.5.10 | 3.15.6.1 | | |
| 3.15.6.2 | 3.15.6.3 | 3.15.6.4 | 3.15.6.5 | 3.15.6.6 | 3.15.6.7 | 3.15.6.8 | 3.15.6.9 | 3.15.6.10 | 3.16.1.1 | 3.16.1.2 | | |
| 3.16.1.3 | 3.16.1.4 | 3.16.1.5 | 3.16.1.6 | 3.16.1.7 | 3.16.1.8 | 3.16.1.9 | 3.16.1.10 | 3.16.2.1 | 3.16.2.2 | 3.16.2.3 | | |
| 3.16.2.4 | 3.16.2.5 | 3.16.2.6 | 3.16.2.7 | 3.16.2.8 | 3.16.2.9 | 3.16.2.10 | 3.16.3.1 | 3.16.3.2 | 3.16.3.3 | 3.16.3.4 | | |
| 3.16.3.5 | 3.16.3.6 | 3.16.3.7 | 3.16.3.8 | 3.16.3.9 | 3.16.3.10 | 3.16.4.1 | 3.16.4.2 | 3.16.4.3 | 3.16.4.4 | 3.16.4.5 | | |
| 3.16.4.6 | 3.16.4.7 | 3.16.4.8 | 3.16.4.9 | 3.16.4.10 | 3.16.5.1 | 3.16.5.2 | 3.16.5.3 | 3.16.5.4 | 3.16.5.5 | 3.16.5.6 | | |
| 3.16.5.7 | 3.16.5.8 | 3.16.5.9 | 3.16.5.10 | 3.16.6.1 | 3.16.6.2 | 3.16.6.3 | 3.16.6.4 | 3.16.6.5 | 3.16.6.6 | 3.16.6.7 | | |
| 3.16.6.8 | 3.16.6.9 | 3.16.6.10 | 3.17.1.1 | 3.17.1.2 | 3.17.1.3 | 3.17.1.4 | 3.17.1.5 | 3.17.1.6 | 3.17.1.7 | 3.17.1.8 | | |
| 3.17.1.9 | 3.17.1.10 | 3.17.2.1 | 3.17.2.2 | 3.17.2.3 | 3.17.2.4 | 3.17.2.5 | 3.17.2.6 | 3.17.2.7 | 3.17.2.8 | 3.17.2.9 | | |
| 3.17.2.10 | 3.17.3.1 | 3.17.3.2 | 3.17.3.3 | 3.17.3.4 | 3.17.3.5 | 3.17.3.6 | 3.17.3.7 | 3.17.3.8 | 3.17.3.9 | 3.17.3.10 | | |
| 3.17.4.1 | 3.17.4.2 | 3.17.4.3 | 3.17.4.4 | 3.17.4.5 | 3.17.4.6 | 3.17.4.7 | 3.17.4.8 | 3.17.4.9 | 3.17.4.10 | 3.17.5.1 | | |
| 3.17.5.2 | 3.17.5.3 | 3.17.5.4 | 3.17.5.5 | 3.17.5.6 | 3.17.5.7 | 3.17.5.8 | 3.17.5.9 | 3.17.5.10 | 3.17.6.1 | 3.17.6.2 | | |
| 3.17.6.3 | 3.17.6.4 | 3.17.6.5 | 3.17.6.6 | 3.17.6.7 | 3.17.6.8 | 3.17.6.9 | 3.17.6.10 | 3.18.1.1 | 3.18.1.2 | 3.18.1.3 | | |
| 3.18.1.4 | 3.18.1.5 | 3.18.1.6 | 3.18.1.7 | 3.18.1.8 | 3.18.1.9 | 3.18.1.10 | 3.18.2.1 | 3.18.2.2 | 3.18.2.3 | 3.18.2.4 | | |
| 3.18.2.5 | 3.18.2.6 | 3.18.2.7 | 3.18.2.8 | 3.18.2.9 | 3.18.2.10 | 3.18.3.1 | 3.18.3.2 | 3.18.3.3 | 3.18.3.4 | 3.18.3.5 | | |
| 3.18.3.6 | 3.18.3.7 | 3.18.3.8 | 3.18.3.9 | 3.18.3.10 | 3.18.4.1 | 3.18.4.2 | 3.18.4.3 | 3.18.4.4 | 3.18.4.5 | 3.18.4.6 | | |
| 3.18.4.7 | 3.18.4.8 | 3.18.4.9 | 3.18.4.10 | 3.18.5.1 | 3.18.5.2 | 3.18.5.3 | 3.18.5.4 | 3.18.5.5 | 3.18.5.6 | 3.18.5.7 | | |
| 3.18.5.8 | 3.18.5.9 | 3.18.5.10 | 3.18.6.1 | 3.18.6.2 | 3.18.6.3 | 3.18.6.4 | 3.18.6.5 | 3.18.6.6 | 3.18.6.7 | 3.18.6.8 | | |
| 3.18.6.9 | 3.18.6.10 | 3.19.1.1 | 3.19.1.2 | 3.19.1.3 | 3.19.1.4 | 3.19.1.5 | 3.19.1.6 | 3.19.1.7 | 3.19.1.8 | 3.19.1.9 | | |
| 3.19.1.10 | 3.19.2.1 | 3.19.2.2 | 3.19.2.3 | 3.19.2.4 | 3.19.2.5 | 3.19.2.6 | 3.19.2.7 | 3.19.2.8 | 3.19.2.9 | 3.19.2.10 | | |
| 3.19.3.1 | 3.19.3.2 | 3.19.3.3 | 3.19.3.4 | 3.19.3.5 | 3.19.3.6 | 3.19.3.7 | 3.19.3.8 | 3.19.3.9 | 3.19.3.10 | 3.19.4.1 | | |
| 3.19.4.2 | 3.19.4.3 | 3.19.4.4 | 3.19.4.5 | 3.19.4.6 | 3.19.4.7 | 3.19.4.8 | 3.19.4.9 | 3.19.4.10 | 3.19.5.1 | 3.19.5.2 | | |

TABLE B-continued

| | | | | | | | | | | | |
|---|---|---|---|---|---|---|---|---|---|---|---|
| 3.19.5.3 | 3.19.5.4 | 3.19.5.5 | 3.19.5.6 | 3.19.5.7 | 3.19.5.8 | 3.19.5.9 | 3.19.5.10 | 3.19.6.1 | 3.19.6.2 | 3.19.6.3 | |
| 3.19.6.4 | 3.19.6.5 | 3.19.6.6 | 3.19.6.7 | 3.19.6.8 | 3.19.6.9 | 3.19.6.10 | 3.20.1.1 | 3.20.1.2 | 3.20.1.3 | 3.20.1.4 | |
| 3.20.1.5 | 3.20.1.6 | 3.20.1.7 | 3.20.1.8 | 3.20.1.9 | 3.20.1.10 | 3.20.2.1 | 3.20.2.2 | 3.20.2.3 | 3.20.2.4 | 3.20.2.5 | |
| 3.20.2.6 | 3.20.2.7 | 3.20.2.8 | 3.20.2.9 | 3.20.2.10 | 3.20.3.1 | 3.20.3.2 | 3.20.3.3 | 3.20.3.4 | 3.20.3.5 | 3.20.3.6 | |
| 3.20.3.7 | 3.20.3.8 | 3.20.3.9 | 3.20.3.10 | 3.20.4.1 | 3.20.4.2 | 3.20.4.3 | 3.20.4.4 | 3.20.4.5 | 3.20.4.6 | 3.20.4.7 | |
| 3.20.4.8 | 3.20.4.9 | 3.20.4.10 | 3.20.5.1 | 3.20.5.2 | 3.20.5.3 | 3.20.5.4 | 3.20.5.5 | 3.20.5.6 | 3.20.5.7 | 3.20.5.8 | |
| 3.20.5.9 | 3.20.5.10 | 3.20.6.1 | 3.20.6.2 | 3.20.6.3 | 3.20.6.4 | 3.20.6.5 | 3.20.6.6 | 3.20.6.7 | 3.20.6.8 | 3.20.6.9 | |
| 3.20.6.10 | 3.21.1.1 | 3.21.1.2 | 3.21.1.3 | 3.21.1.4 | 3.21.1.5 | 3.21.1.6 | 3.21.1.7 | 3.21.1.8 | 3.21.1.9 | 3.21.1.10 | |
| 3.21.2.1 | 3.21.2.2 | 3.21.2.3 | 3.21.2.4 | 3.21.2.5 | 3.21.2.6 | 3.21.2.7 | 3.21.2.8 | 3.21.2.9 | 3.21.2.10 | 3.21.3.1 | |
| 3.21.3.2 | 3.21.3.3 | 3.21.3.4 | 3.21.3.5 | 3.21.3.6 | 3.21.3.7 | 3.21.3.8 | 3.21.3.9 | 3.21.3.10 | 3.21.4.1 | 3.21.4.2 | |
| 3.21.4.3 | 3.21.4.4 | 3.21.4.5 | 3.21.4.6 | 3.21.4.7 | 3.21.4.8 | 3.21.4.9 | 3.21.4.10 | 3.21.5.1 | 3.21.5.2 | 3.21.5.3 | |
| 3.21.5.4 | 3.21.5.5 | 3.21.5.6 | 3.21.5.7 | 3.21.5.8 | 3.21.5.9 | 3.21.5.10 | 3.21.6.1 | 3.21.6.2 | 3.21.6.3 | 3.21.6.4 | |
| 3.21.6.5 | 3.21.6.6 | 3.21.6.7 | 3.21.6.8 | 3.21.6.9 | 3.21.6.10 | 3.22.1.1 | 3.22.1.2 | 3.22.1.3 | 3.22.1.4 | 3.22.1.5 | |
| 3.22.1.6 | 3.22.1.7 | 3.22.1.8 | 3.22.1.9 | 3.22.1.10 | 3.22.2.1 | 3.22.2.2 | 3.22.2.3 | 3.22.2.4 | 3.22.2.5 | 3.22.2.6 | |
| 3.22.2.7 | 3.22.2.8 | 3.22.2.9 | 3.22.2.10 | 3.22.3.1 | 3.22.3.2 | 3.22.3.3 | 3.22.3.4 | 3.22.3.5 | 3.22.3.6 | 3.22.3.7 | |
| 3.22.3.8 | 3.22.3.9 | 3.22.3.10 | 3.22.4.1 | 3.22.4.2 | 3.22.4.3 | 3.22.4.4 | 3.22.4.5 | 3.22.4.6 | 3.22.4.7 | 3.22.4.8 | |
| 3.22.4.9 | 3.22.4.10 | 3.22.5.1 | 3.22.5.2 | 3.22.5.3 | 3.22.5.4 | 3.22.5.5 | 3.22.5.6 | 3.22.5.7 | 3.22.5.8 | 3.22.5.9 | |
| 3.22.5.10 | 3.22.6.1 | 3.22.6.2 | 3.22.6.3 | 3.22.6.4 | 3.22.6.5 | 3.22.6.6 | 3.22.6.7 | 3.22.6.8 | 3.22.6.9 | 3.22.6.10 | |
| 3.23.1.1 | 3.23.1.2 | 3.23.1.3 | 3.23.1.4 | 3.23.1.5 | 3.23.1.6 | 3.23.1.7 | 3.23.1.8 | 3.23.1.9 | 3.23.1.10 | 3.23.2.1 | |
| 3.23.2.2 | 3.23.2.3 | 3.23.2.4 | 3.23.2.5 | 3.23.2.6 | 3.23.2.7 | 3.23.2.8 | 3.23.2.9 | 3.23.2.10 | 3.23.3.1 | 3.23.3.2 | |
| 3.23.3.3 | 3.23.3.4 | 3.23.3.5 | 3.23.3.6 | 3.23.3.7 | 3.23.3.8 | 3.23.3.9 | 3.23.3.10 | 3.23.4.1 | 3.23.4.2 | 3.23.4.3 | |
| 3.23.4.4 | 3.23.4.5 | 3.23.4.6 | 3.23.4.7 | 3.23.4.8 | 3.23.4.9 | 3.23.4.10 | 3.23.5.1 | 3.23.5.2 | 3.23.5.3 | 3.23.5.4 | |
| 3.23.5.5 | 3.23.5.6 | 3.23.5.7 | 3.23.5.8 | 3.23.5.9 | 3.23.5.10 | 3.23.6.1 | 3.23.6.2 | 3.23.6.3 | 3.23.6.4 | 3.23.6.5 | |
| 3.23.6.6 | 3.23.6.7 | 3.23.6.8 | 3.23.6.9 | 3.23.6.10 | 3.24.1.1 | 3.24.1.2 | 3.24.1.3 | 3.24.1.4 | 3.24.1.5 | 3.24.1.6 | |
| 3.24.1.7 | 3.24.1.8 | 3.24.1.9 | 3.24.1.10 | 3.24.2.1 | 3.24.2.2 | 3.24.2.3 | 3.24.2.4 | 3.24.2.5 | 3.24.2.6 | 3.24.2.7 | |
| 3.24.2.8 | 3.24.2.9 | 3.24.2.10 | 3.24.3.1 | 3.24.3.2 | 3.24.3.3 | 3.24.3.4 | 3.24.3.5 | 3.24.3.6 | 3.24.3.7 | 3.24.3.8 | |
| 3.24.3.9 | 3.24.3.10 | 3.24.4.1 | 3.24.4.2 | 3.24.4.3 | 3.24.4.4 | 2.24.4.5 | 3.24.4.6 | 3.24.4.7 | 3.24.4.8 | 3.24.4.9 | |
| 3.24.4.10 | 3.24.5.1 | 3.24.5.2 | 3.24.5.3 | 3.24.5.4 | 3.24.5.5 | 3.24.5.6 | 3.24.5.7 | 3.24.5.8 | 3.24.5.9 | 3.24.5.10 | |
| 3.24.6.1 | 3.24.6.2 | 3.24.6.3 | 3.24.6.4 | 3.24.6.5 | 3.24.6.6 | 3.24.6.7 | 3.24.6.8 | 3.24.6.9 | 3.24.6.10 | 3.25.1.1 | |
| 3.25.1.2 | 3.25.1.3 | 3.25.1.4 | 3.25.1.5 | 3.25.1.6 | 3.25.1.7 | 3.25.1.8 | 3.25.1.9 | 3.25.1.10 | 3.25.2.1 | 3.25.2.2 | |
| 3.25.2.3 | 3.25.2.4 | 3.25.2.5 | 3.25.2.6 | 3.25.2.7 | 3.25.2.8 | 3.25.2.9 | 3.25.2.10 | 3.25.3.1 | 3.25.3.2 | 3.25.3.3 | |
| 3.25.3.4 | 3.25.3.5 | 3.25.3.6 | 3.25.3.7 | 3.25.3.8 | 3.25.3.9 | 3.25.3.10 | 3.25.4.1 | 3.25.4.2 | 3.25.4.3 | 3.25.4.4 | |
| 3.25.4.5 | 3.25.4.6 | 3.25.4.7 | 3.25.4.8 | 3.25.4.9 | 3.25.4.10 | 3.25.5.1 | 3.25.5.2 | 3.25.5.3 | 3.25.5.4 | 3.25.5.5 | |
| 3.25.5.6 | 3.25.5.7 | 3.25.5.8 | 3.25.5.9 | 3.25.5.10 | 3.25.6.1 | 3.25.6.2 | 3.25.6.3 | 3.25.6.4 | 3.25.6.5 | 3.25.6.6 | |
| 3.25.6.7 | 3.25.6.8 | 3.25.6.9 | 3.25.6.10 | 4.1.1.1 | 4.1.1.2 | 4.1.1.3 | 2.1.1.4 | 4.1.1.5 | 4.1.1.6 | 4.1.1.7 | 4.1.1.8 | 4.1.1.9 |
| 4.1.1.10 | 4.1.2.1 | 4.1.2.2 | 4.1.2.3 | 4.1.2.4 | 4.1.2.5 | 4.1.2.6 | 4.1.2.7 | 4.1.2.8 | 4.1.2.9 | 4.1.2.10 | 4.1.3.1 | 4.1.3.2 |
| 4.1.3.3 | 4.1.3.4 | 4.1.3.5 | 4.1.3.6 | 4.1.3.7 | 4.1.3.8 | 4.1.3.9 | 4.1.3.10 | 4.1.4.1 | 4.1.4.2 | 4.1.4.3 | 4.1.4.4 | 4.1.4.5 |
| 4.1.4.6 | 4.1.4.7 | 4.1.4.8 | 4.1.4.9 | 4.1.4.10 | 4.1.5.1 | 4.1.5.2 | 4.1.5.3 | 4.1.5.4 | 4.1.5.5 | 4.1.5.6 | 4.1.5.7 | 4.1.5.8 |
| 4.1.5.9 | 4.1.5.10 | 4.1.6.1 | 4.1.6.2 | 4.1.6.3 | 4.1.6.4 | 4.1.6.5 | 4.1.6.6 | 4.1.6.7 | 4.1.6.8 | 4.1.6.9 | 4.1.6.10 | 4.2.1.1 |
| 4.2.1.2 | 4.2.1.3 | 4.2.1.4 | 4.2.1.5 | 4.2.1.6 | 4.2.1.7 | 4.2.1.8 | 4.2.1.9 | 4.2.1.10 | 4.2.2.1 | 4.2.2.2 | 4.2.2.3 | 4.2.2.4 |
| 4.2.2.5 | 4.2.2.6 | 4.2.2.7 | 4.2.2.8 | 4.2.2.9 | 4.2.2.10 | 4.2.3.1 | 4.2.3.2 | 4.2.3.3 | 4.2.3.4 | 4.2.3.5 | 4.2.3.6 | 4.2.3.7 |
| 4.2.3.8 | 4.2.3.9 | 4.2.3.10 | 4.2.4.1 | 4.2.4.2 | 4.2.4.3 | 4.2.4.4 | 4.2.4.5 | 4.2.4.6 | 4.2.4.7 | 4.2.4.8 | 4.2.4.9 | 4.2.4.10 |
| 4.2.5.1 | 4.2.5.2 | 4.2.5.3 | 4.2.5.4 | 4.2.5.5 | 4.2.5.6 | 4.2.5.7 | 4.2.5.8 | 4.2.5.9 | 4.2.5.10 | 4.2.6.1 | 4.2.6.2 | 4.2.6.3 |
| 4.2.6.4 | 4.2.6.5 | 4.2.6.6 | 4.2.6.7 | 4.2.6.8 | 4.2.6.9 | 4.2.6.10 | 4.3.1.1 | 4.3.1.2 | 4.3.1.3 | 4.3.1.4 | 4.3.1.5 | 4.3.1.6 |
| 4.3.1.7 | 4.3.1.8 | 4.3.1.9 | 4.3.1.10 | 4.3.2.1 | 4.3.2.2 | 4.3.2.3 | 4.3.2.4 | 4.3.2.5 | 4.3.2.6 | 4.3.2.7 | 4.3.2.8 | 4.3.2.9 |
| 4.3.2.10 | 4.3.3.1 | 4.3.3.2 | 4.3.3.3 | 4.3.3.4 | 4.3.3.5 | 4.3.3.6 | 4.3.3.7 | 4.3.3.8 | 4.3.3.9 | 4.3.3.10 | 4.3.4.1 | 4.3.4.2 |
| 4.3.4.3 | 4.3.4.4 | 4.3.4.5 | 4.3.4.6 | 4.3.4.7 | 4.3.4.8 | 4.3.4.9 | 4.3.4.10 | 4.3.5.1 | 4.3.5.2 | 4.3.5.3 | 4.3.5.4 | 4.3.5.5 |
| 4.3.5.6 | 4.3.5.7 | 4.3.5.8 | 4.3.5.9 | 4.3.5.10 | 4.3.6.1 | 4.3.6.2 | 4.3.6.3 | 4.3.6.4 | 4.3.6.5 | 4.3.6.6 | 4.3.6.7 | 4.3.6.8 |
| 4.3.6.9 | 4.3.6.10 | 4.4.1.1 | 4.4.1.2 | 4.4.1.3 | 4.4.1.4 | 4.4.1.5 | 4.4.1.6 | 4.4.1.7 | 4.4.1.8 | 4.4.1.9 | 4.4.1.10 | 4.4.2.1 |
| 4.4.2.2 | 4.4.2.3 | 4.4.2.4 | 4.4.2.5 | 4.4.2.6 | 4.4.2.7 | 4.4.2.8 | 4.4.2.9 | 4.4.2.10 | 4.4.3.1 | 4.4.3.2 | 4.4.3.3 | 4.4.3.4 |
| 4.4.3.5 | 4.4.3.6 | 4.4.3.7 | 4.4.3.8 | 4.4.3.9 | 4.4.3.10 | 4.4.4.1 | 4.4.4.2 | 4.4.4.3 | 4.4.4.4 | 4.4.4.5 | 4.4.4.6 | 4.4.4.7 |
| 4.4.4.8 | 4.4.4.9 | 4.4.4.10 | 4.4.5.1 | 4.4.5.2 | 4.4.5.3 | 4.4.5.4 | 4.4.5.5 | 4.4.5.6 | 4.4.5.7 | 4.4.5.8 | 4.4.5.9 | 4.4.5.10 |
| 4.4.6.1 | 4.4.6.2 | 4.4.6.3 | 4.4.6.4 | 4.4.6.5 | 4.4.6.6 | 4.4.6.7 | 4.4.6.8 | 4.4.6.9 | 4.4.6.10 | 4.5.1.1 | 4.5.1.2 | 4.5.1.3 |
| 4.5.1.4 | 4.5.1.5 | 4.5.1.6 | 4.5.1.7 | 4.5.1.8 | 4.5.1.9 | 4.5.1.10 | 4.5.2.1 | 4.5.2.2 | 4.5.2.3 | 4.5.2.4 | 4.5.2.5 | 4.5.2.6 |
| 4.5.2.7 | 4.5.2.8 | 4.5.2.9 | 4.5.2.10 | 4.5.3.1 | 4.5.3.2 | 4.5.3.3 | 4.5.3.4 | 4.5.3.5 | 4.5.3.6 | 4.5.3.7 | 4.5.3.8 | 4.5.3.9 |
| 4.5.3.10 | 4.5.4.1 | 4.5.4.2 | 4.5.4.3 | 4.5.4.4 | 4.5.4.5 | 4.5.4.6 | 4.5.4.7 | 4.5.4.8 | 4.5.4.9 | 4.5.4.10 | 4.5.5.1 | 4.5.5.2 |
| 4.5.5.3 | 4.5.5.4 | 4.5.5.5 | 4.5.5.6 | 4.5.5.7 | 4.5.5.8 | 4.5.5.9 | 4.5.5.10 | 4.5.6.1 | 4.5.6.2 | 4.5.6.3 | 4.5.6.4 | 4.5.6.5 |
| 4.5.6.6 | 4.5.6.7 | 4.5.6.8 | 4.5.6.9 | 4.5.6.10 | 4.6.1.1 | 4.6.1.2 | 4.6.1.3 | 4.6.1.4 | 4.6.1.5 | 4.6.1.6 | 4.6.1.7 | 4.6.1.8 |
| 4.6.1.9 | 4.6.1.10 | 4.6.2.1 | 4.6.2.2 | 4.6.2.3 | 4.6.2.4 | 4.6.2.5 | 4.6.2.6 | 4.6.2.7 | 4.6.2.8 | 4.6.2.9 | 4.6.2.10 | 4.6.3.1 |
| 4.6.3.2 | 4.6.3.3 | 4.6.3.4 | 4.6.3.5 | 4.6.3.6 | 4.6.3.7 | 4.6.3.8 | 4.6.3.9 | 4.6.3.10 | 4.6.4.1 | 4.6.4.2 | 4.6.4.3 | 4.6.4.4 |
| 4.6.4.5 | 4.6.4.6 | 4.6.4.7 | 4.6.4.8 | 4.6.4.9 | 4.6.4.10 | 4.6.5.1 | 4.6.5.2 | 4.6.5.3 | 4.6.5.4 | 4.6.5.5 | 4.6.5.6 | 4.6.5.7 |
| 4.6.5.8 | 4.6.5.9 | 4.6.5.10 | 4.6.6.1 | 4.6.6.2 | 4.6.6.3 | 4.6.6.4 | 4.6.6.5 | 4.6.6.6 | 4.6.6.7 | 4.6.6.8 | 4.6.6.9 | 4.6.6.10 |
| 4.7.1.1 | 4.7.1.2 | 4.7.1.3 | 4.7.1.4 | 4.7.1.5 | 4.7.1.6 | 4.7.1.7 | 4.7.1.8 | 4.7.1.9 | 4.7.1.10 | 4.7.2.1 | 4.7.2.2 | 4.7.2.3 |
| 4.7.2.4 | 4.7.2.5 | 4.7.2.6 | 4.7.2.7 | 4.7.2.8 | 4.7.2.9 | 4.7.2.10 | 4.7.3.1 | 4.7.3.2 | 4.7.3.3 | 4.7.3.4 | 4.7.3.5 | 4.7.3.6 |
| 4.7.3.7 | 4.7.3.8 | 4.7.3.9 | 4.7.3.10 | 4.7.4.1 | 4.7.4.2 | 4.7.4.3 | 4.7.4.4 | 4.7.4.5 | 4.7.4.6 | 4.7.4.7 | 4.7.4.8 | 4.7.4.9 |
| 4.7.4.10 | 4.7.5.1 | 4.7.5.2 | 4.7.5.3 | 4.7.5.4 | 4.7.5.5 | 4.7.5.6 | 4.7.5.7 | 4.7.5.8 | 4.7.5.9 | 4.7.5.10 | 4.7.6.1 | 4.7.6.2 |
| 4.7.6.3 | 4.7.6.4 | 4.7.6.5 | 4.7.6.6 | 4.7.6.7 | 4.7.6.8 | 4.7.6.9 | 4.7.6.10 | 4.8.1.1 | 4.8.1.2 | 4.8.1.3 | 4.8.1.4 | 4.8.1.5 |
| 4.8.1.6 | 4.8.1.7 | 4.8.1.8 | 4.8.1.9 | 4.8.1.10 | 4.8.2.1 | 4.8.2.2 | 4.8.2.3 | 4.8.2.4 | 4.8.2.5 | 4.8.2.6 | 4.8.2.7 | 4.8.2.8 |
| 4.8.2.9 | 4.8.2.10 | 4.8.3.1 | 4.8.3.2 | 4.8.3.3 | 4.8.3.4 | 4.8.3.5 | 4.8.3.6 | 4.8.3.7 | 4.8.3.8 | 4.8.3.9 | 4.8.3.10 | 4.8.4.1 |
| 4.8.4.2 | 4.8.4.3 | 4.8.4.4 | 4.8.4.5 | 4.8.4.6 | 4.8.4.7 | 4.8.4.8 | 4.8.4.9 | 4.8.4.10 | 4.8.5.1 | 4.8.5.2 | 4.8.5.3 | 4.8.5.4 |
| 4.8.5.5 | 4.8.5.6 | 4.8.5.7 | 4.8.5.8 | 4.8.5.9 | 4.8.5.10 | 4.8.6.1 | 4.8.6.2 | 4.8.6.3 | 4.8.6.4 | 4.8.6.5 | 4.8.6.6 | 4.8.6.7 |
| 4.8.6.8 | 4.8.6.9 | 4.8.6.10 | 4.9.1.1 | 4.9.1.2 | 4.9.1.3 | 4.9.1.4 | 4.9.1.5 | 4.9.1.6 | 4.9.1.7 | 4.9.1.8 | 4.9.1.9 | 4.9.1.10 |
| 4.9.2.1 | 4.9.2.2 | 4.9.2.3 | 4.9.2.4 | 4.9.2.5 | 4.9.2.6 | 4.9.2.7 | 4.9.2.8 | 4.9.2.9 | 4.9.2.10 | 4.9.3.1 | 4.9.3.2 | 4.9.3.3 |
| 4.9.3.4 | 4.9.3.5 | 4.9.3.6 | 4.9.3.7 | 4.9.3.8 | 4.9.3.9 | 4.9.3.10 | 4.9.4.1 | 4.9.4.2 | 4.9.4.3 | 4.9.4.4 | 4.9.4.5 | 4.9.4.6 |
| 4.9.4.7 | 4.9.4.8 | 4.9.4.9 | 4.9.4.10 | 4.9.5.1 | 4.9.5.2 | 4.9.5.3 | 4.9.5.4 | 4.9.5.5 | 4.9.5.6 | 4.9.5.7 | 4.9.5.8 | 4.9.5.9 |
| 4.9.5.10 | 4.9.6.1 | 4.9.6.2 | 4.9.6.3 | 4.9.6.4 | 4.9.6.5 | 4.9.6.6 | 4.9.6.7 | 4.9.6.8 | 4.9.6.9 | 4.9.6.10 | 4.10.1.1 | 4.10.1.2 |
| 4.10.1.3 | 4.10.1.4 | 4.10.1.5 | 4.10.1.6 | 4.10.1.7 | 4.10.1.8 | 4.10.1.9 | 4.10.1.10 | 4.10.2.1 | 4.10.2.2 | 4.10.2.3 | | |
| 4.10.2.4 | 4.10.2.5 | 4.10.2.6 | 4.10.2.7 | 4.10.2.8 | 4.10.2.9 | 4.10.2.10 | 4.10.3.1 | 4.10.3.2 | 4.10.3.3 | 4.10.3.4 | | |
| 4.10.3.5 | 4.10.3.6 | 4.10.3.7 | 4.10.3.8 | 4.10.3.9 | 4.10.3.10 | 4.10.4.1 | 4.10.4.2 | 4.10.4.3 | 4.10.4.4 | 4.10.4.5 | | |

TABLE B-continued

| | | | | | | | | | |
|---|---|---|---|---|---|---|---|---|---|
| 4.10.4.6 | 4.10.4.7 | 4.10.4.8 | 4.10.4.9 | 4.10.4.10 | 4.10.5.1 | 4.10.5.2 | 4.10.5.3 | 4.10.5.4 | 4.10.5.5 | 4.10.5.6 |
| 4.10.5.7 | 4.10.5.8 | 4.10.5.9 | 4.10.5.10 | 4.10.6.1 | 4.10.6.2 | 4.10.6.3 | 4.10.6.4 | 4.10.6.5 | 4.10.6.6 | 4.10.6.7 |
| 4.10.6.8 | 4.10.6.9 | 4.10.6.10 | 4.11.1.1 | 4.11.1.2 | 4.11.1.3 | 4.11.1.4 | 4.11.1.5 | 4.11.1.6 | 4.11.1.7 | 4.11.1.8 |
| 4.11.1.9 | 4.11.1.10 | 4.11.2.1 | 4.11.2.2 | 4.11.2.3 | 4.11.2.4 | 4.11.2.5 | 4.11.2.6 | 4.11.2.7 | 4.11.2.8 | 4.11.2.9 |
| 4.11.2.10 | 4.11.3.1 | 4.11.3.2 | 4.11.3.3 | 4.11.3.4 | 4.11.3.5 | 4.11.3.6 | 4.11.3.7 | 4.11.3.8 | 4.11.3.9 | 4.11.3.10 |
| 4.11.4.1 | 4.11.4.2 | 4.11.4.3 | 4.11.4.4 | 4.11.4.5 | 4.11.4.6 | 4.11.4.7 | 4.11.4.8 | 4.11.4.9 | 4.11.4.10 | 4.11.5.1 |
| 4.11.5.2 | 4.11.5.3 | 4.11.5.4 | 4.11.5.5 | 4.11.5.6 | 4.11.5.7 | 4.11.5.8 | 4.11.5.9 | 4.11.5.10 | 4.11.6.1 | 4.11.6.2 |
| 4.11.6.3 | 4.11.6.4 | 4.11.6.5 | 4.11.6.6 | 4.11.6.7 | 4.11.6.8 | 4.11.6.9 | 4.11.6.10 | 4.12.1.1 | 4.12.1.2 | 4.12.1.3 |
| 4.12.1.4 | 4.12.1.5 | 4.12.1.6 | 4.12.1.7 | 4.12.1.8 | 4.12.1.9 | 4.12.1.10 | 4.12.2.1 | 4.12.2.2 | 4.12.2.3 | 4.12.2.4 |
| 4.12.2.5 | 4.12.2.6 | 4.12.2.7 | 4.12.2.8 | 4.12.2.9 | 4.12.2.10 | 4.12.3.1 | 4.12.3.2 | 4.12.3.3 | 4.12.3.4 | 4.12.3.5 |
| 4.12.3.6 | 4.12.3.7 | 4.12.3.8 | 4.12.3.9 | 4.12.3.10 | 4.12.4.1 | 4.12.4.2 | 4.12.4.3 | 4.12.4.4 | 4.12.4.5 | 4.12.4.6 |
| 4.12.4.7 | 4.12.4.8 | 4.12.4.9 | 4.12.4.10 | 4.12.5.1 | 4.12.5.2 | 4.12.5.3 | 4.12.5.4 | 4.12.5.5 | 4.12.5.6 | 4.12.5.7 |
| 4.12.5.8 | 4.12.5.9 | 4.12.5.10 | 4.12.6.1 | 4.12.6.2 | 4.12.6.3 | 4.12.6.4 | 4.12.6.5 | 4.12.6.6 | 4.12.6.7 | 4.12.6.8 |
| 4.12.6.9 | 4.12.6.10 | 4.13.1.1 | 4.13.1.2 | 4.13.1.3 | 4.13.1.4 | 4.13.1.5 | 4.13.1.6 | 4.13.1.7 | 4.13.1.8 | 4.13.1.9 |
| 4.13.1.10 | 4.13.2.1 | 4.13.2.2 | 4.13.2.3 | 4.13.2.4 | 4.13.2.5 | 4.13.2.6 | 4.13.2.7 | 4.13.2.8 | 4.13.2.9 | 4.13.2.10 |
| 4.13.3.1 | 4.13.3.2 | 4.13.3.3 | 4.13.3.4 | 4.13.3.5 | 4.13.3.6 | 4.13.3.7 | 4.13.3.8 | 4.13.3.9 | 4.13.3.10 | 4.13.4.1 |
| 4.13.4.2 | 4.13.4.3 | 4.13.4.4 | 4.13.4.5 | 4.13.4.6 | 4.13.4.7 | 4.13.4.8 | 4.13.4.9 | 4.13.4.10 | 4.13.5.1 | 4.13.5.2 |
| 4.13.5.3 | 4.13.5.4 | 4.13.5.5 | 4.13.5.6 | 4.13.5.7 | 4.13.5.8 | 4.13.5.9 | 4.13.5.10 | 4.13.6.1 | 4.13.6.2 | 4.13.6.3 |
| 4.13.6.4 | 4.13.6.5 | 4.13.6.6 | 4.13.6.7 | 4.13.6.8 | 4.13.6.9 | 4.13.6.10 | 4.14.1.1 | 4.14.1.2 | 4.14.1.3 | 4.14.1.4 |
| 4.14.1.5 | 4.14.1.6 | 4.14.1.7 | 4.14.1.8 | 4.14.1.9 | 4.14.1.10 | 4.14.2.1 | 4.14.2.2 | 4.14.2.3 | 4.14.2.4 | 4.14.2.5 |
| 4.14.2.6 | 4.14.2.7 | 4.14.2.8 | 4.14.2.9 | 4.14.2.10 | 4.14.3.1 | 4.14.3.2 | 4.14.3.3 | 4.14.3.4 | 4.14.3.5 | 4.14.3.6 |
| 4.14.3.7 | 4.14.3.8 | 4.14.3.9 | 4.14.3.10 | 4.14.4.1 | 4.14.4.2 | 4.14.4.3 | 4.14.4.4 | 4.14.4.5 | 4.14.4.6 | 4.14.4.7 |
| 4.14.4.8 | 4.14.4.9 | 4.14.4.10 | 4.14.5.1 | 4.14.5.2 | 4.14.5.3 | 4.14.5.4 | 4.14.5.5 | 4.14.5.6 | 4.14.5.7 | 4.14.5.8 |
| 4.14.5.9 | 4.14.5.10 | 4.14.6.1 | 4.14.6.2 | 4.14.6.3 | 4.14.6.4 | 4.14.6.5 | 4.14.6.6 | 4.14.6.7 | 4.14.6.8 | 4.14.6.9 |
| 4.14.6.10 | 4.15.1.1 | 4.15.1.2 | 4.15.1.3 | 4.15.1.4 | 4.15.1.5 | 4.15.1.6 | 4.15.1.7 | 4.15.1.8 | 4.15.1.9 | 4.15.1.10 |
| 4.15.2.1 | 4.15.2.2 | 4.15.2.3 | 4.15.2.4 | 4.15.2.5 | 4.15.2.6 | 4.15.2.7 | 4.15.2.8 | 4.15.2.9 | 4.15.2.10 | 4.15.3.1 |
| 4.15.3.2 | 4.15.3.3 | 4.15.3.4 | 4.15.3.5 | 4.15.3.6 | 4.15.3.7 | 4.15.3.8 | 4.15.3.9 | 4.15.3.10 | 4.15.4.1 | 4.15.4.2 |
| 4.15.4.3 | 4.15.4.4 | 4.15.4.5 | 4.15.4.6 | 4.15.4.7 | 4.15.4.8 | 4.15.4.9 | 4.15.4.10 | 4.15.5.1 | 4.15.5.2 | 4.15.5.3 |
| 4.15.5.4 | 4.15.5.5 | 4.15.5.6 | 4.15.5.7 | 4.15.5.8 | 4.15.5.9 | 4.15.5.10 | 4.15.6.1 | 4.15.6.2 | 4.15.6.3 | 4.15.6.4 |
| 4.15.6.5 | 4.15.6.6 | 4.15.6.7 | 4.15.6.8 | 4.15.6.9 | 4.15.6.10 | 4.16.1.1 | 4.16.1.2 | 4.16.1.3 | 4.16.1.4 | 4.16.1.5 |
| 4.16.1.6 | 4.16.1.7 | 4.16.1.8 | 4.16.1.9 | 4.16.1.10 | 4.16.2.1 | 4.16.2.2 | 4.16.2.3 | 4.16.2.4 | 4.16.2.5 | 4.16.2.6 |
| 4.16.2.7 | 4.16.2.8 | 4.16.2.9 | 4.16.2.10 | 4.16.3.1 | 4.16.3.2 | 4.16.3.3 | 4.16.3.4 | 4.16.3.5 | 4.16.3.6 | 4.16.3.7 |
| 4.16.3.8 | 4.16.3.9 | 4.16.3.10 | 4.16.4.1 | 4.16.4.2 | 4.16.4.3 | 4.16.4.4 | 4.16.4.5 | 4.16.4.6 | 4.16.4.7 | 4.16.4.8 |
| 4.16.4.9 | 4.16.4.10 | 4.16.5.1 | 4.16.5.2 | 4.16.5.3 | 4.16.5.4 | 4.16.5.5 | 4.16.5.6 | 4.16.5.7 | 4.16.5.8 | 4.16.5.9 |
| 4.16.5.10 | 4.16.6.1 | 4.16.6.2 | 4.16.6.3 | 4.16.6.4 | 4.16.6.5 | 4.16.6.6 | 4.16.6.7 | 4.16.6.8 | 4.16.6.9 | 4.16.6.10 |
| 4.17.1.1 | 4.17.1.2 | 4.17.1.3 | 4.17.1.4 | 4.17.1.5 | 4.17.1.6 | 4.17.1.7 | 4.17.1.8 | 4.17.1.9 | 4.17.1.10 | 4.17.2.1 |
| 4.17.2.2 | 4.17.2.3 | 4.17.2.4 | 4.17.2.5 | 4.17.2.6 | 4.17.2.7 | 4.17.2.8 | 4.17.2.9 | 4.17.2.10 | 4.17.3.1 | 4.17.3.2 |
| 4.17.3.3 | 4.17.3.4 | 4.17.3.5 | 4.17.3.6 | 4.17.3.7 | 4.17.3.8 | 4.17.3.9 | 4.17.3.10 | 4.17.4.1 | 4.17.4.2 | 4.17.4.3 |
| 4.17.4.4 | 4.17.4.5 | 4.17.4.6 | 4.17.4.7 | 4.17.4.8 | 4.17.4.9 | 4.17.4.10 | 4.17.5.1 | 4.17.5.2 | 4.17.5.3 | 4.17.5.4 |
| 4.17.5.5 | 4.17.5.6 | 4.17.5.7 | 4.17.5.8 | 4.17.5.9 | 4.17.5.10 | 4.17.6.1 | 4.17.6.2 | 4.17.6.3 | 4.17.6.4 | 4.17.6.5 |
| 4.17.6.6 | 4.17.6.7 | 4.17.6.8 | 4.17.6.9 | 4.17.6.10 | 4.18.1.1 | 4.18.1.2 | 4.18.1.3 | 4.18.1.4 | 4.18.1.5 | 4.18.1.6 |
| 4.18.1.7 | 4.18.1.8 | 4.18.1.9 | 4.18.1.10 | 4.18.2.1 | 4.18.2.2 | 4.18.2.3 | 4.18.2.4 | 4.18.2.5 | 4.18.2.6 | 4.18.2.7 |
| 4.18.2.8 | 4.18.2.9 | 4.18.2.10 | 4.18.3.1 | 4.18.3.2 | 4.18.3.3 | 4.18.3.4 | 4.18.3.5 | 4.18.3.6 | 4.18.3.7 | 4.18.3.8 |
| 4.18.3.9 | 4.18.3.10 | 4.18.4.1 | 4.18.4.2 | 4.18.4.3 | 4.18.4.4 | 4.18.4.5 | 4.18.4.6 | 4.18.4.7 | 4.18.4.8 | 4.18.4.9 |
| 4.18.4.10 | 4.18.5.1 | 4.18.5.2 | 4.18.5.3 | 4.18.5.4 | 4.18.5.5 | 4.18.5.6 | 4.18.5.7 | 4.18.5.8 | 4.18.5.9 | 4.18.5.10 |
| 4.18.6.1 | 4.18.6.2 | 4.18.6.3 | 4.18.6.4 | 4.18.6.5 | 4.18.6.6 | 4.18.6.7 | 4.18.6.8 | 4.18.6.9 | 4.18.6.10 | 4.19.1.1 |
| 4.19.1.2 | 4.19.1.3 | 4.19.1.4 | 4.19.1.5 | 4.19.1.6 | 4.19.1.7 | 4.19.1.8 | 4.19.1.9 | 4.19.1.10 | 4.19.2.1 | 4.19.2.2 |
| 4.19.2.3 | 4.19.2.4 | 4.19.2.5 | 4.19.2.6 | 4.19.2.7 | 4.19.2.8 | 4.19.2.9 | 4.19.2.10 | 4.19.3.1 | 4.19.3.2 | 4.19.3.3 |
| 4.19.3.4 | 4.19.3.5 | 4.19.3.6 | 4.19.3.7 | 4.19.3.8 | 4.19.3.9 | 4.19.3.10 | 4.19.4.1 | 4.19.4.2 | 4.19.4.3 | 4.19.4.4 |
| 4.19.4.5 | 4.19.4.6 | 4.19.4.7 | 4.19.4.8 | 4.19.4.9 | 4.19.4.10 | 4.19.5.1 | 4.19.5.2 | 4.19.5.3 | 4.19.5.4 | 4.19.5.5 |
| 4.19.5.6 | 4.19.5.7 | 4.19.5.8 | 4.19.5.9 | 4.19.5.10 | 4.19.6.1 | 4.19.6.2 | 4.19.6.3 | 4.19.6.4 | 4.19.6.5 | 4.19.6.6 |
| 4.19.6.7 | 4.19.6.8 | 4.19.6.9 | 4.19.6.10 | 4.20.1.1 | 4.20.1.2 | 4.20.1.3 | 4.20.1.4 | 4.20.1.5 | 4.20.1.6 | 4.20.1.7 |
| 4.20.1.8 | 4.20.1.9 | 4.20.1.10 | 4.20.2.1 | 4.20.2.2 | 4.20.2.3 | 4.20.2.4 | 4.20.2.5 | 4.20.2.6 | 4.20.2.7 | 4.20.2.8 |
| 4.20.2.9 | 4.20.2.10 | 4.20.3.1 | 4.20.3.2 | 4.20.3.3 | 4.20.3.4 | 4.20.3.5 | 4.20.3.6 | 4.20.3.7 | 4.20.3.8 | 4.20.3.9 |
| 4.20.3.10 | 4.20.4.1 | 4.20.4.2 | 4.20.4.3 | 4.20.4.4 | 4.20.4.5 | 4.20.4.6 | 4.20.4.7 | 4.20.4.8 | 4.20.4.9 | 4.20.4.10 |
| 4.20.5.1 | 4.20.5.2 | 4.20.5.3 | 4.20.5.4 | 4.20.5.5 | 4.20.5.6 | 4.20.5.7 | 4.20.5.8 | 4.20.5.9 | 4.20.5.10 | 4.20.6.1 |
| 4.20.6.2 | 4.20.6.3 | 4.20.6.4 | 4.20.6.5 | 4.20.6.6 | 4.20.6.7 | 4.20.6.8 | 4.20.6.9 | 4.20.6.10 | 4.21.1.1 | 4.21.1.2 |
| 4.21.1.3 | 4.21.1.4 | 4.21.1.5 | 4.21.1.6 | 4.21.1.7 | 4.21.1.8 | 4.21.1.9 | 4.21.1.10 | 4.21.2.1 | 4.21.2.2 | 4.21.2.3 |
| 4.21.2.4 | 4.21.2.5 | 4.21.2.6 | 4.21.2.7 | 4.21.2.8 | 4.21.2.9 | 4.21.2.10 | 4.21.3.1 | 4.21.3.2 | 4.21.3.3 | 4.21.3.4 |
| 4.21.3.5 | 4.21.3.6 | 4.21.3.7 | 4.21.3.8 | 4.21.3.9 | 4.21.3.10 | 4.21.4.1 | 4.21.4.2 | 4.21.4.3 | 4.21.4.4 | 4.21.4.5 |
| 4.21.4.6 | 4.21.4.7 | 4.21.4.8 | 4.21.4.9 | 4.21.4.10 | 4.21.5.1 | 4.21.5.2 | 4.21.5.3 | 4.21.5.4 | 4.21.5.5 | 4.21.5.6 |
| 4.21.5.7 | 4.21.5.8 | 4.21.5.9 | 4.21.5.10 | 4.21.6.1 | 4.21.6.2 | 4.21.6.3 | 4.21.6.4 | 4.21.6.5 | 4.21.6.6 | 4.21.6.7 |
| 4.21.6.8 | 4.21.6.9 | 4.21.6.10 | 4.22.1.1 | 4.22.1.2 | 4.22.1.3 | 4.22.1.4 | 4.22.1.5 | 4.22.1.6 | 4.22.1.7 | 4.22.1.8 |
| 4.22.1.9 | 4.22.1.10 | 4.22.2.1 | 4.22.2.2 | 4.22.2.3 | 4.22.2.4 | 4.22.2.5 | 4.22.2.6 | 4.22.2.7 | 4.22.2.8 | 4.22.2.9 |
| 4.22.2.10 | 4.22.3.1 | 4.22.3.2 | 4.22.3.3 | 4.22.3.4 | 4.22.3.5 | 4.22.3.6 | 4.22.3.7 | 4.22.3.8 | 4.22.3.9 | 4.22.3.10 |
| 4.22.4.1 | 4.22.4.2 | 4.22.4.3 | 4.22.4.4 | 4.22.4.5 | 4.22.4.6 | 4.22.4.7 | 4.22.4.8 | 4.22.4.9 | 4.22.4.10 | 4.22.5.1 |
| 4.22.5.2 | 4.22.5.3 | 4.22.5.4 | 4.22.5.5 | 4.22.5.6 | 4.22.5.7 | 4.22.5.8 | 4.22.5.9 | 4.22.5.10 | 4.22.6.1 | 4.22.6.2 |
| 4.22.6.3 | 4.22.6.4 | 4.22.6.5 | 4.22.6.6 | 4.22.6.7 | 4.22.6.8 | 4.22.6.9 | 4.22.6.10 | 4.23.1.1 | 4.23.1.2 | 4.23.1.3 |
| 4.23.1.4 | 4.23.1.5 | 4.23.1.6 | 4.23.1.7 | 4.23.1.8 | 4.23.1.9 | 4.23.1.10 | 4.23.2.1 | 4.23.2.2 | 4.23.2.3 | 4.23.2.4 |
| 4.23.2.5 | 4.23.2.6 | 4.23.2.7 | 4.23.2.8 | 4.23.2.9 | 4.23.2.10 | 4.23.3.1 | 4.23.3.2 | 4.23.3.3 | 4.23.3.4 | 4.23.3.5 |
| 4.23.3.6 | 4.23.3.7 | 4.23.3.8 | 4.23.3.9 | 4.23.3.10 | 4.23.4.1 | 4.23.4.2 | 4.23.4.3 | 4.23.4.4 | 4.23.4.5 | 4.23.4.6 |
| 4.23.4.7 | 4.23.4.8 | 4.23.4.9 | 4.23.4.10 | 4.23.5.1 | 4.23.5.2 | 4.23.5.3 | 4.23.5.4 | 4.23.5.5 | 4.23.5.6 | 4.23.5.7 |
| 4.23.5.8 | 4.23.5.9 | 4.23.5.10 | 4.23.6.1 | 4.23.6.2 | 4.23.6.3 | 4.23.6.4 | 4.23.6.5 | 4.23.6.6 | 4.23.6.7 | 4.23.6.8 |
| 4.23.6.9 | 4.23.6.10 | 4.24.1.1 | 4.24.1.2 | 4.24.1.3 | 4.24.1.4 | 4.24.1.5 | 4.24.1.6 | 4.24.1.7 | 4.24.1.8 | 4.24.1.9 |
| 4.24.1.10 | 4.24.2.1 | 4.24.2.2 | 4.24.2.3 | 4.24.2.4 | 4.24.2.5 | 4.24.2.6 | 4.24.2.7 | 4.24.2.8 | 4.24.2.9 | 4.24.2.10 |
| 4.24.3.1 | 4.24.3.2 | 4.24.3.3 | 4.24.3.4 | 4.24.3.5 | 4.24.3.6 | 4.24.3.7 | 4.24.3.8 | 4.24.3.9 | 4.24.3.10 | 4.24.4.1 |
| 4.24.4.2 | 4.24.4.3 | 4.24.4.4 | 4.24.4.5 | 4.24.4.6 | 4.24.4.7 | 4.24.4.8 | 4.24.4.9 | 4.24.4.10 | 4.24.5.1 | 4.24.5.2 |
| 4.24.5.3 | 4.24.5.4 | 4.24.5.5 | 4.24.5.6 | 4.24.5.7 | 4.24.5.8 | 4.24.5.9 | 4.24.5.10 | 4.24.6.1 | 4.24.6.2 | 4.24.6.3 |
| 4.24.6.4 | 4.24.6.5 | 4.24.6.6 | 4.24.6.7 | 4.24.6.8 | 4.24.6.9 | 4.24.6.10 | 4.25.1.1 | 4.25.1.2 | 4.25.1.3 | 4.25.1.4 |

TABLE B-continued

| | | | | | | | | | | | |
|---|---|---|---|---|---|---|---|---|---|---|---|
| 4.25.1.5 | 4.25.1.6 | 4.25.1.7 | 4.25.1.8 | 4.25.1.9 | 4.25.1.10 | 4.25.2.1 | 4.25.2.2 | 4.25.2.3 | 4.25.2.4 | 4.25.2.5 | |
| 4.25.2.6 | 4.25.2.7 | 4.25.2.8 | 4.25.2.9 | 4.25.2.10 | 4.25.3.1 | 4.25.3.2 | 4.25.3.3 | 4.25.3.4 | 4.25.3.5 | 4.25.3.6 | |
| 4.25.3.7 | 4.25.3.8 | 4.25.3.9 | 4.25.3.10 | 4.25.4.1 | 4.25.4.2 | 4.25.4.3 | 4.25.4.4 | 4.25.4.5 | 4.25.4.6 | 4.25.4.7 | |
| 4.25.4.8 | 4.25.4.9 | 4.25.4.10 | 4.25.5.1 | 4.25.5.2 | 4.25.5.3 | 4.25.5.4 | 4.25.5.5 | 4.25.5.6 | 4.25.5.7 | 4.25.5.8 | |
| 4.25.5.9 | 4.25.5.10 | 4.25.6.1 | 4.25.6.2 | 4.25.6.3 | 4.25.6.4 | 4.25.6.5 | 4.25.6.6 | 4.25.6.7 | 4.25.6.8 | 4.25.6.9 | |
| 4.25.6.10 | 5.1.1.1 | 5.1.1.2 | 5.1.1.3 | 2.1.1.4 | 5.1.1.5 | 5.1.1.6 | 5.1.1.7 | 5.1.1.8 | 5.1.1.9 | 5.1.1.10 | 5.1.2.1 | 5.1.2.2 |
| 5.1.2.3 | 5.1.2.4 | 5.1.2.5 | 5.1.2.6 | 5.1.2.7 | 5.1.2.8 | 5.1.2.9 | 5.1.2.10 | 5.1.3.1 | 5.1.3.2 | 5.1.3.3 | 5.1.3.4 | 5.1.3.5 |
| 5.1.3.6 | 5.1.3.7 | 5.1.3.8 | 5.1.3.9 | 5.1.3.10 | 5.1.4.1 | 5.1.4.2 | 5.1.4.3 | 5.1.4.4 | 5.1.4.5 | 5.1.4.6 | 5.1.4.7 | 5.1.4.8 |
| 5.1.4.9 | 5.1.4.10 | 5.1.5.1 | 5.1.5.2 | 5.1.5.3 | 5.1.5.4 | 5.1.5.5 | 5.1.5.6 | 5.1.5.7 | 5.1.5.8 | 5.1.5.9 | 5.1.5.10 | 5.1.6.1 |
| 5.1.6.2 | 5.1.6.3 | 5.1.6.4 | 5.1.6.5 | 5.1.6.6 | 5.1.6.7 | 5.1.6.8 | 5.1.6.9 | 5.1.6.10 | 5.2.1.1 | 5.2.1.2 | 5.2.1.3 | 5.2.1.4 |
| 5.2.1.5 | 5.2.1.6 | 5.2.1.7 | 5.2.1.8 | 5.2.1.9 | 5.2.1.10 | 5.2.2.1 | 5.2.2.2 | 5.2.2.3 | 5.2.2.4 | 5.2.2.5 | 5.2.2.6 | 5.2.2.7 |
| 5.2.2.8 | 5.2.2.9 | 5.2.2.10 | 5.2.3.1 | 5.2.3.2 | 5.2.3.3 | 5.2.3.4 | 5.2.3.5 | 5.2.3.6 | 5.2.3.7 | 5.2.3.8 | 5.2.3.9 | 5.2.3.10 |
| 5.2.4.1 | 5.2.4.2 | 5.2.4.3 | 5.2.4.4 | 5.2.4.5 | 5.2.4.6 | 5.2.4.7 | 5.2.4.8 | 5.2.4.9 | 5.2.4.10 | 5.2.5.1 | 5.2.5.2 | 5.2.5.3 |
| 5.2.5.4 | 5.2.5.5 | 5.2.5.6 | 5.2.5.7 | 5.2.5.8 | 5.2.5.9 | 5.2.5.10 | 5.2.6.1 | 5.2.6.2 | 5.2.6.3 | 5.2.6.4 | 5.2.6.5 | 5.2.6.6 |
| 5.2.6.7 | 5.2.6.8 | 5.2.6.9 | 5.2.6.10 | 5.3.1.1 | 5.3.1.2 | 5.3.1.3 | 5.3.1.4 | 5.3.1.5 | 5.3.1.6 | 5.3.1.7 | 5.3.1.8 | 5.3.1.9 |
| 5.3.1.10 | 5.3.2.1 | 5.3.2.2 | 5.3.2.3 | 5.3.2.4 | 5.3.2.5 | 5.3.2.6 | 5.3.2.7 | 5.3.2.8 | 5.3.2.9 | 5.3.2.10 | 5.3.3.1 | 5.3.3.2 |
| 5.3.3.3 | 5.3.3.4 | 5.3.3.5 | 5.3.3.6 | 5.3.3.7 | 5.3.3.8 | 5.3.3.9 | 5.3.3.10 | 5.3.4.1 | 5.3.4.2 | 5.3.4.3 | 5.3.4.4 | 5.3.4.5 |
| 5.3.4.6 | 5.3.4.7 | 5.3.4.8 | 5.3.4.9 | 5.3.4.10 | 5.3.5.1 | 5.3.5.2 | 5.3.5.3 | 5.3.5.4 | 5.3.5.5 | 5.3.5.6 | 5.3.5.7 | 5.3.5.8 |
| 5.3.5.9 | 5.3.5.10 | 5.3.6.1 | 5.3.6.2 | 5.3.6.3 | 5.3.6.4 | 5.3.6.5 | 5.3.6.6 | 5.3.6.7 | 5.3.6.8 | 5.3.6.9 | 5.3.6.10 | 5.4.1.1 |
| 5.4.1.2 | 5.4.1.3 | 5.4.1.4 | 5.4.1.5 | 5.4.1.6 | 5.4.1.7 | 5.4.1.8 | 5.4.1.9 | 5.4.1.10 | 5.4.2.1 | 5.4.2.2 | 5.4.2.3 | 5.4.2.4 |
| 5.4.2.5 | 5.4.2.6 | 5.4.2.7 | 5.4.2.8 | 5.4.2.9 | 5.4.2.10 | 5.4.3.1 | 5.4.3.2 | 5.4.3.3 | 5.4.3.4 | 5.4.3.5 | 5.4.3.6 | 5.4.3.7 |
| 5.4.3.8 | 5.4.3.9 | 5.4.3.10 | 5.4.4.1 | 5.4.4.2 | 5.4.4.3 | 5.4.4.4 | 5.4.4.5 | 5.4.4.6 | 5.4.4.7 | 5.4.4.8 | 5.4.4.9 | 5.4.4.10 |
| 5.4.5.1 | 5.4.5.2 | 5.4.5.3 | 5.4.5.4 | 5.4.5.5 | 5.4.5.6 | 5.4.5.7 | 5.4.5.8 | 5.4.5.9 | 5.4.5.10 | 5.4.6.1 | 5.4.6.2 | 5.4.6.3 |
| 5.4.6.4 | 5.4.6.5 | 5.4.6.6 | 5.4.6.7 | 5.4.6.8 | 5.4.6.9 | 5.4.6.10 | 5.5.1.1 | 5.5.1.2 | 5.5.1.3 | 5.5.1.4 | 5.5.1.5 | 5.5.1.6 |
| 5.5.1.7 | 5.5.1.8 | 5.5.1.9 | 5.5.1.10 | 5.5.2.1 | 5.5.2.2 | 5.5.2.3 | 5.5.2.4 | 5.5.2.5 | 5.5.2.6 | 5.5.2.7 | 5.5.2.8 | 5.5.2.9 |
| 5.5.2.10 | 5.5.3.1 | 5.5.3.2 | 5.5.3.3 | 5.5.3.4 | 5.5.3.5 | 5.5.3.6 | 5.5.3.7 | 5.5.3.8 | 5.5.3.9 | 5.5.3.10 | 5.5.4.1 | 5.5.4.2 |
| 5.5.4.3 | 5.5.4.4 | 5.5.4.5 | 5.5.4.6 | 5.5.4.7 | 5.5.4.8 | 5.5.4.9 | 5.5.4.10 | 5.5.5.1 | 5.5.5.2 | 5.5.5.3 | 5.5.5.4 | 5.5.5.5 |
| 5.5.5.6 | 5.5.5.7 | 5.5.5.8 | 5.5.5.9 | 5.5.5.10 | 5.5.6.1 | 5.5.6.2 | 5.5.6.3 | 5.5.6.4 | 5.5.6.5 | 5.5.6.6 | 5.5.6.7 | 5.5.6.8 |
| 5.5.6.9 | 5.5.6.10 | 5.6.1.1 | 5.6.1.2 | 5.6.1.3 | 5.6.1.4 | 5.6.1.5 | 5.6.1.6 | 5.6.1.7 | 5.6.1.8 | 5.6.1.9 | 5.6.1.10 | 5.6.2.1 |
| 5.6.2.2 | 5.6.2.3 | 5.6.2.4 | 5.6.2.5 | 5.6.2.6 | 5.6.2.7 | 5.6.2.8 | 5.6.2.9 | 5.6.2.10 | 5.6.3.1 | 5.6.3.2 | 5.6.3.3 | 5.6.3.4 |
| 5.6.3.5 | 5.6.3.6 | 5.6.3.7 | 5.6.3.8 | 5.6.3.9 | 5.6.3.10 | 5.6.4.1 | 5.6.4.2 | 5.6.4.3 | 5.6.4.4 | 5.6.4.5 | 5.6.4.6 | 5.6.4.7 |
| 5.6.4.8 | 5.6.4.9 | 5.6.4.10 | 5.6.5.1 | 5.6.5.2 | 5.6.5.3 | 5.6.5.4 | 5.6.5.5 | 5.6.5.6 | 5.6.5.7 | 5.6.5.8 | 5.6.5.9 | 5.6.5.10 |
| 5.6.6.1 | 5.6.6.2 | 5.6.6.3 | 5.6.6.4 | 5.6.6.5 | 5.6.6.6 | 5.6.6.7 | 5.6.6.8 | 5.6.6.9 | 5.6.6.10 | 5.7.1.1 | 5.7.1.2 | 5.7.1.3 |
| 5.7.1.4 | 5.7.1.5 | 5.7.1.6 | 5.7.1.7 | 5.7.1.8 | 5.7.1.9 | 5.7.1.10 | 5.7.2.1 | 5.7.2.2 | 5.7.2.3 | 5.7.2.4 | 5.7.2.5 | 5.7.2.6 |
| 5.7.2.7 | 5.7.2.8 | 5.7.2.9 | 5.7.2.10 | 5.7.3.1 | 5.7.3.2 | 5.7.3.3 | 5.7.3.4 | 5.7.3.5 | 5.7.3.6 | 5.7.3.7 | 5.7.3.8 | 5.7.3.9 |
| 5.7.3.10 | 5.7.4.1 | 5.7.4.2 | 5.7.4.3 | 5.7.4.4 | 5.7.4.5 | 5.7.4.6 | 5.7.4.7 | 5.7.4.8 | 5.7.4.9 | 5.7.4.10 | 5.7.5.1 | 5.7.5.2 |
| 5.7.5.3 | 5.7.5.4 | 5.7.5.5 | 5.7.5.6 | 5.7.5.7 | 5.7.5.8 | 5.7.5.9 | 5.7.5.10 | 5.7.6.1 | 5.7.6.2 | 5.7.6.3 | 5.7.6.4 | 5.7.6.5 |
| 5.7.6.6 | 5.7.6.7 | 5.7.6.8 | 5.7.6.9 | 5.7.6.10 | 5.8.1.1 | 5.8.1.2 | 5.8.1.3 | 5.8.1.4 | 5.8.1.5 | 5.8.1.6 | 5.8.1.7 | 5.8.1.8 |
| 5.8.1.9 | 5.8.1.10 | 5.8.2.1 | 5.8.2.2 | 5.8.2.3 | 5.8.2.4 | 5.8.2.5 | 5.8.2.6 | 5.8.2.7 | 5.8.2.8 | 5.8.2.9 | 5.8.2.10 | 5.8.3.1 |
| 5.8.3.2 | 5.8.3.3 | 5.8.3.4 | 5.8.3.5 | 5.8.3.6 | 5.8.3.7 | 5.8.3.8 | 5.8.3.9 | 5.8.3.10 | 5.8.4.1 | 5.8.4.2 | 5.8.4.3 | 5.8.4.4 |
| 5.8.4.5 | 5.8.4.6 | 5.8.4.7 | 5.8.4.8 | 5.8.4.9 | 5.8.4.10 | 5.8.5.1 | 5.8.5.2 | 5.8.5.3 | 5.8.5.4 | 5.8.5.5 | 5.8.5.6 | 5.8.5.7 |
| 5.8.5.8 | 5.8.5.9 | 5.8.5.10 | 5.8.6.1 | 5.8.6.2 | 5.8.6.3 | 5.8.6.4 | 5.8.6.5 | 5.8.6.6 | 5.8.6.7 | 5.8.6.8 | 5.8.6.9 | 5.8.6.10 |
| 5.9.1.1 | 5.9.1.2 | 5.9.1.3 | 5.9.1.4 | 5.9.1.5 | 5.9.1.6 | 5.9.1.7 | 5.9.1.8 | 5.9.1.9 | 5.9.1.10 | 5.9.2.1 | 5.9.2.2 | 5.9.2.3 |
| 5.9.2.4 | 5.9.2.5 | 5.9.2.6 | 5.9.2.7 | 5.9.2.8 | 5.9.2.9 | 5.9.2.10 | 5.9.3.1 | 5.9.3.2 | 5.9.3.3 | 5.9.3.4 | 5.9.3.5 | 5.9.3.6 |
| 5.9.3.7 | 5.9.3.8 | 5.9.3.9 | 5.9.3.10 | 5.9.4.1 | 5.9.4.2 | 5.9.4.3 | 5.9.4.4 | 5.9.4.5 | 5.9.4.6 | 5.9.4.7 | 5.9.4.8 | 5.9.4.9 |
| 5.9.4.10 | 5.9.5.1 | 5.9.5.2 | 5.9.5.3 | 5.9.5.4 | 5.9.5.5 | 5.9.5.6 | 5.9.5.7 | 5.9.5.8 | 5.9.5.9 | 5.9.5.10 | 5.9.6.1 | 5.9.6.2 |
| 5.9.6.3 | 5.9.6.4 | 5.9.6.5 | 5.9.6.6 | 5.9.6.7 | 5.9.6.8 | 5.9.6.9 | 5.9.6.10 | 5.10.1.1 | 5.10.1.2 | 5.10.1.3 | 5.10.1.4 | |
| 5.10.1.5 | 5.10.1.6 | 5.10.1.7 | 5.10.1.8 | 5.10.1.9 | 5.10.1.10 | 5.10.2.1 | 5.10.2.2 | 5.10.2.3 | 5.10.2.4 | 5.10.2.5 | |
| 5.10.2.6 | 5.10.2.7 | 5.10.2.8 | 5.10.2.9 | 5.10.2.10 | 5.10.3.1 | 5.10.3.2 | 5.10.3.3 | 5.10.3.4 | 5.10.3.5 | 5.10.3.6 | |
| 5.10.3.7 | 5.10.3.8 | 5.10.3.9 | 5.10.3.10 | 5.10.4.1 | 5.10.4.2 | 5.10.4.3 | 5.10.4.4 | 5.10.4.5 | 5.10.4.6 | 5.10.4.7 | |
| 5.10.4.8 | 5.10.4.9 | 5.10.4.10 | 5.10.5.1 | 5.10.5.2 | 5.10.5.3 | 5.10.5.4 | 5.10.5.5 | 5.10.5.6 | 5.10.5.7 | 5.10.5.8 | |
| 5.10.5.9 | 5.10.5.10 | 5.10.6.1 | 5.10.6.2 | 5.10.6.3 | 5.10.6.4 | 5.10.6.5 | 5.10.6.6 | 5.10.6.7 | 5.10.6.8 | 5.10.6.9 | |
| 5.10.6.10 | 5.11.1.1 | 5.11.1.2 | 5.11.1.3 | 5.11.1.4 | 5.11.1.5 | 5.11.1.6 | 5.11.1.7 | 5.11.1.8 | 5.11.1.9 | 5.11.1.10 | |
| 5.11.2.1 | 5.11.2.2 | 5.11.2.3 | 5.11.2.4 | 5.11.2.5 | 5.11.2.6 | 5.11.2.7 | 5.11.2.8 | 5.11.2.9 | 5.11.2.10 | 5.11.3.1 | |
| 5.11.3.2 | 5.11.3.3 | 5.11.3.4 | 5.11.3.5 | 5.11.3.6 | 5.11.3.7 | 5.11.3.8 | 5.11.3.9 | 5.11.3.10 | 5.11.4.1 | 5.11.4.2 | |
| 5.11.4.3 | 5.11.4.4 | 5.11.4.5 | 5.11.4.6 | 5.11.4.7 | 5.11.4.8 | 5.11.4.9 | 5.11.4.10 | 5.11.5.1 | 5.11.5.2 | 5.11.5.3 | |
| 5.11.5.4 | 5.11.5.5 | 5.11.5.6 | 5.11.5.7 | 5.11.5.8 | 5.11.5.9 | 5.11.5.10 | 5.11.6.1 | 5.11.6.2 | 5.11.6.3 | 5.11.6.4 | |
| 5.11.6.5 | 5.11.6.6 | 5.11.6.7 | 5.11.6.8 | 5.11.6.9 | 5.11.6.10 | 5.12.1.1 | 5.12.1.2 | 5.12.1.3 | 5.12.1.4 | 5.12.1.5 | |
| 5.12.1.6 | 5.12.1.7 | 5.12.1.8 | 5.12.1.9 | 5.12.1.10 | 5.12.2.1 | 5.12.2.2 | 5.12.2.3 | 5.12.2.4 | 5.12.2.5 | 5.12.2.6 | |
| 5.12.2.7 | 5.12.2.8 | 5.12.2.9 | 5.12.2.10 | 5.12.3.1 | 5.12.3.2 | 5.12.3.3 | 5.12.3.4 | 5.12.3.5 | 5.12.3.6 | 5.12.3.7 | |
| 5.12.3.8 | 5.12.3.9 | 5.12.3.10 | 5.12.4.1 | 5.12.4.2 | 5.12.4.3 | 5.12.4.4 | 5.12.4.5 | 5.12.4.6 | 5.12.4.7 | 5.12.4.8 | |
| 5.12.4.9 | 5.12.4.10 | 5.12.5.1 | 5.12.5.2 | 5.12.5.3 | 5.12.5.4 | 5.12.5.5 | 5.12.5.6 | 5.12.5.7 | 5.12.5.8 | 5.12.5.9 | |
| 5.12.5.10 | 5.12.6.1 | 5.12.6.2 | 5.12.6.3 | 5.12.6.4 | 5.12.6.5 | 5.12.6.6 | 5.12.6.7 | 5.12.6.8 | 5.12.6.9 | 5.12.6.10 | |
| 5.13.1.1 | 5.13.1.2 | 5.13.1.3 | 5.13.1.4 | 5.13.1.5 | 5.13.1.6 | 5.13.1.7 | 5.13.1.8 | 5.13.1.9 | 5.13.1.10 | 5.13.2.1 | |
| 5.13.2.2 | 5.13.2.3 | 5.13.2.4 | 5.13.2.5 | 5.13.2.6 | 5.13.2.7 | 5.13.2.8 | 5.13.2.9 | 5.13.2.10 | 5.13.3.1 | 5.13.3.2 | |
| 5.13.3.3 | 5.13.3.4 | 5.13.3.5 | 5.13.3.6 | 5.13.3.7 | 5.13.3.8 | 5.13.3.9 | 5.13.3.10 | 5.13.4.1 | 5.13.4.2 | 5.13.4.3 | |
| 5.13.4.4 | 5.13.4.5 | 5.13.4.6 | 5.13.4.7 | 5.13.4.8 | 5.13.4.9 | 5.13.4.10 | 5.13.5.1 | 5.13.5.2 | 5.13.5.3 | 5.13.5.4 | |
| 5.13.5.5 | 5.13.5.6 | 5.13.5.7 | 5.13.5.8 | 5.13.5.9 | 5.13.5.10 | 5.13.6.1 | 5.13.6.2 | 5.13.6.3 | 5.13.6.4 | 5.13.6.5 | |
| 5.13.6.6 | 5.13.6.7 | 5.13.6.8 | 5.13.6.9 | 5.13.6.10 | 5.14.1.1 | 5.14.1.2 | 5.14.1.3 | 5.14.1.4 | 5.14.1.5 | 5.14.1.6 | |
| 5.14.1.7 | 5.14.1.8 | 5.14.1.9 | 5.14.1.10 | 5.14.2.1 | 5.14.2.2 | 5.14.2.3 | 5.14.2.4 | 5.14.2.5 | 5.14.2.6 | 5.14.2.7 | |
| 5.14.2.8 | 5.14.2.9 | 5.14.2.10 | 5.14.3.1 | 5.14.3.2 | 5.14.3.3 | 5.14.3.4 | 5.14.3.5 | 5.14.3.6 | 5.14.3.7 | 5.14.3.8 | |
| 5.14.3.9 | 5.14.3.10 | 5.14.4.1 | 5.14.4.2 | 5.14.4.3 | 5.14.4.4 | 5.14.4.5 | 5.14.4.6 | 5.14.4.7 | 5.14.4.8 | 5.14.4.9 | |
| 5.14.4.10 | 5.14.5.1 | 5.14.5.2 | 5.14.5.3 | 5.14.5.4 | 5.14.5.5 | 5.14.5.6 | 5.14.5.7 | 5.14.5.8 | 5.14.5.9 | 5.14.5.10 | |
| 5.14.6.1 | 5.14.6.2 | 5.14.6.3 | 5.14.6.4 | 5.14.6.5 | 5.14.6.6 | 5.14.6.7 | 5.14.6.8 | 5.14.6.9 | 5.14.6.10 | 5.15.1.1 | |
| 5.15.1.2 | 5.15.1.3 | 5.15.1.4 | 5.15.1.5 | 5.15.1.6 | 5.15.1.7 | 5.15.1.8 | 5.15.1.9 | 5.15.1.10 | 5.15.2.1 | 5.15.2.2 | |
| 5.15.2.3 | 5.15.2.4 | 5.15.2.5 | 5.15.2.6 | 5.15.2.7 | 5.15.2.8 | 5.15.2.9 | 5.15.2.10 | 5.15.3.1 | 5.15.3.2 | 5.15.3.3 | |
| 5.15.3.4 | 5.15.3.5 | 5.15.3.6 | 5.15.3.7 | 5.15.3.8 | 5.15.3.9 | 5.15.3.10 | 5.15.4.1 | 5.15.4.2 | 5.15.4.3 | 5.15.4.4 | |
| 5.15.4.5 | 5.15.4.6 | 5.15.4.7 | 5.15.4.8 | 5.15.4.9 | 5.15.4.10 | 5.15.5.1 | 5.15.5.2 | 5.15.5.3 | 5.15.5.4 | 5.15.5.5 | |
| 5.15.5.6 | 5.15.5.7 | 5.15.5.8 | 5.15.5.9 | 5.15.5.10 | 5.15.6.1 | 5.15.6.2 | 5.15.6.3 | 5.15.6.4 | 5.15.6.5 | 5.15.6.6 | |

TABLE B-continued

| | | | | | | | | | |
|---|---|---|---|---|---|---|---|---|---|
| 5.15.6.7 | 5.15.6.8 | 5.15.6.9 | 5.15.6.10 | 5.16.1.1 | 5.16.1.2 | 5.16.1.3 | 5.16.1.4 | 5.16.1.5 | 5.16.1.6 | 5.16.1.7 |
| 5.16.1.8 | 5.16.1.9 | 5.16.1.10 | 5.16.2.1 | 5.16.2.2 | 5.16.2.3 | 5.16.2.4 | 5.16.2.5 | 5.16.2.6 | 5.16.2.7 | 5.16.2.8 |
| 5.16.2.9 | 5.16.2.10 | 5.16.3.1 | 5.16.3.2 | 5.16.3.3 | 5.16.3.4 | 5.16.3.5 | 5.16.3.6 | 5.16.3.7 | 5.16.3.8 | 5.16.3.9 |
| 5.16.3.10 | 5.16.4.1 | 5.16.4.2 | 5.16.4.3 | 5.16.4.4 | 5.16.4.5 | 5.16.4.6 | 5.16.4.7 | 5.16.4.8 | 5.16.4.9 | 5.16.4.10 |
| 5.16.5.1 | 5.16.5.2 | 5.16.5.3 | 5.16.5.4 | 5.16.5.5 | 5.16.5.6 | 5.16.5.7 | 5.16.5.8 | 5.16.5.9 | 5.16.5.10 | 5.16.6.1 |
| 5.16.6.2 | 5.16.6.3 | 5.16.6.4 | 5.16.6.5 | 5.16.6.6 | 5.16.6.7 | 5.16.6.8 | 5.16.6.9 | 5.16.6.10 | 5.17.1.1 | 5.17.1.2 |
| 5.17.1.3 | 5.17.1.4 | 5.17.1.5 | 5.17.1.6 | 5.17.1.7 | 5.17.1.8 | 5.17.1.9 | 5.17.1.10 | 5.17.2.1 | 5.17.2.2 | 5.17.2.3 |
| 5.17.2.4 | 5.17.2.5 | 5.17.2.6 | 5.17.2.7 | 5.17.2.8 | 5.17.2.9 | 5.17.2.10 | 5.17.3.1 | 5.17.3.2 | 5.17.3.3 | 5.17.3.4 |
| 5.17.3.5 | 5.17.3.6 | 5.17.3.7 | 5.17.3.8 | 5.17.3.9 | 5.17.3.10 | 5.17.4.1 | 5.17.4.2 | 5.17.4.3 | 5.17.4.4 | 5.17.4.5 |
| 5.17.4.6 | 5.17.4.7 | 5.17.4.8 | 5.17.4.9 | 5.17.4.10 | 5.17.5.1 | 5.17.5.2 | 5.17.5.3 | 5.17.5.4 | 5.17.5.5 | 5.17.5.6 |
| 5.17.5.7 | 5.17.5.8 | 5.17.5.9 | 5.17.5.10 | 5.17.6.1 | 5.17.6.2 | 5.17.6.3 | 5.17.6.4 | 5.17.6.5 | 5.17.6.6 | 5.17.6.7 |
| 5.17.6.8 | 5.17.6.9 | 5.17.6.10 | 5.18.1.1 | 5.18.1.2 | 5.18.1.3 | 5.18.1.4 | 5.18.1.5 | 5.18.1.6 | 5.18.1.7 | 5.18.1.8 |
| 5.18.1.9 | 5.18.1.10 | 5.18.2.1 | 5.18.2.2 | 5.18.2.3 | 5.18.2.4 | 5.18.2.5 | 5.18.2.6 | 5.18.2.7 | 5.18.2.8 | 5.18.2.9 |
| 5.18.2.10 | 5.18.3.1 | 5.18.3.2 | 5.18.3.3 | 5.18.3.4 | 5.18.3.5 | 5.18.3.6 | 5.18.3.7 | 5.18.3.8 | 5.18.3.9 | 5.18.3.10 |
| 5.18.4.1 | 5.18.4.2 | 5.18.4.3 | 5.18.4.4 | 5.18.4.5 | 5.18.4.6 | 5.18.4.7 | 5.18.4.8 | 5.18.4.9 | 5.18.4.10 | 5.18.5.1 |
| 5.18.5.2 | 5.18.5.3 | 5.18.5.4 | 5.18.5.5 | 5.18.5.6 | 5.18.5.7 | 5.18.5.8 | 5.18.5.9 | 5.18.5.10 | 5.18.6.1 | 5.18.6.2 |
| 5.18.6.3 | 5.18.6.4 | 5.18.6.5 | 5.18.6.6 | 5.18.6.7 | 5.18.6.8 | 5.18.6.9 | 5.18.6.10 | 5.19.1.1 | 5.19.1.2 | 5.19.1.3 |
| 5.19.1.4 | 5.19.1.5 | 5.19.1.6 | 5.19.1.7 | 5.19.1.8 | 5.19.1.9 | 5.19.1.10 | 5.19.2.1 | 5.19.2.2 | 5.19.2.3 | 5.19.2.4 |
| 5.19.2.5 | 5.19.2.6 | 5.19.2.7 | 5.19.2.8 | 5.19.2.9 | 5.19.2.10 | 5.19.3.1 | 5.19.3.2 | 5.19.3.3 | 5.19.3.4 | 5.19.3.5 |
| 5.19.3.6 | 5.19.3.7 | 5.19.3.8 | 5.19.3.9 | 5.19.3.10 | 5.19.4.1 | 5.19.4.2 | 5.19.4.3 | 5.19.4.4 | 5.19.4.5 | 5.19.4.6 |
| 5.19.4.7 | 5.19.4.8 | 5.19.4.9 | 5.19.4.10 | 5.19.5.1 | 5.19.5.2 | 5.19.5.3 | 5.19.5.4 | 5.19.5.5 | 5.19.5.6 | 5.19.5.7 |
| 5.19.5.8 | 5.19.5.9 | 5.19.5.10 | 5.19.6.1 | 5.19.6.2 | 5.19.6.3 | 5.19.6.4 | 5.19.6.5 | 5.19.6.6 | 5.19.6.7 | 5.19.6.8 |
| 5.19.6.9 | 5.19.6.10 | 5.20.1.1 | 5.20.1.2 | 5.20.1.3 | 5.20.1.4 | 5.20.1.5 | 5.20.1.6 | 5.20.1.7 | 5.20.1.8 | 5.20.1.9 |
| 5.20.1.10 | 5.20.2.1 | 5.20.2.2 | 5.20.2.3 | 5.20.2.4 | 5.20.2.5 | 5.20.2.6 | 5.20.2.7 | 5.20.2.8 | 5.20.2.9 | 5.20.2.10 |
| 5.20.3.1 | 5.20.3.2 | 5.20.3.3 | 5.20.3.4 | 5.20.3.5 | 5.20.3.6 | 5.20.3.7 | 5.20.3.8 | 5.20.3.9 | 5.20.3.10 | 5.20.4.1 |
| 5.20.4.2 | 5.20.4.3 | 5.20.4.4 | 5.20.4.5 | 5.20.4.6 | 5.20.4.7 | 5.20.4.8 | 5.20.4.9 | 5.20.4.10 | 5.20.5.1 | 5.20.5.2 |
| 5.20.5.3 | 5.20.5.4 | 5.20.5.5 | 5.20.5.6 | 5.20.5.7 | 5.20.5.8 | 5.20.5.9 | 5.20.5.10 | 5.20.6.1 | 5.20.6.2 | 5.20.6.3 |
| 5.20.6.4 | 5.20.6.5 | 5.20.6.6 | 5.20.6.7 | 5.20.6.8 | 5.20.6.9 | 5.20.6.10 | 5.21.1.1 | 5.21.1.2 | 5.21.1.3 | 5.21.1.4 |
| 5.21.1.5 | 5.21.1.6 | 5.21.1.7 | 5.21.1.8 | 5.21.1.9 | 5.21.1.10 | 5.21.2.1 | 5.21.2.2 | 5.21.2.3 | 5.21.2.4 | 5.21.2.5 |
| 5.21.2.6 | 5.21.2.7 | 5.21.2.8 | 5.21.2.9 | 5.21.2.10 | 5.21.3.1 | 5.21.3.2 | 5.21.3.3 | 5.21.3.4 | 5.21.3.5 | 5.21.3.6 |
| 5.21.3.7 | 5.21.3.8 | 5.21.3.9 | 5.21.3.10 | 5.21.4.1 | 5.21.4.2 | 5.21.4.3 | 5.21.4.4 | 5.21.4.5 | 5.21.4.6 | 5.21.4.7 |
| 5.21.4.8 | 5.21.4.9 | 5.21.4.10 | 5.21.5.1 | 5.21.5.2 | 5.21.5.3 | 5.21.5.4 | 5.21.5.5 | 5.21.5.6 | 5.21.5.7 | 5.21.5.8 |
| 5.21.5.9 | 5.21.5.10 | 5.21.6.1 | 5.21.6.2 | 5.21.6.3 | 5.21.6.4 | 5.21.6.5 | 5.21.6.6 | 5.21.6.7 | 5.21.6.8 | 5.21.6.9 |
| 5.21.6.10 | 5.22.1.1 | 5.22.1.2 | 5.22.1.3 | 5.22.1.4 | 5.22.1.5 | 5.22.1.6 | 5.22.1.7 | 5.22.1.8 | 5.22.1.9 | 5.22.1.10 |
| 5.22.2.1 | 5.22.2.2 | 5.22.2.3 | 5.22.2.4 | 5.22.2.5 | 5.22.2.6 | 5.22.2.7 | 5.22.2.8 | 5.22.2.9 | 5.22.2.10 | 5.22.3.1 |
| 5.22.3.2 | 5.22.3.3 | 5.22.3.4 | 5.22.3.5 | 5.22.3.6 | 5.22.3.7 | 5.22.3.8 | 5.22.3.9 | 5.22.3.10 | 5.22.4.1 | 5.22.4.2 |
| 5.22.4.3 | 5.22.4.4 | 5.22.4.5 | 5.22.4.6 | 5.22.4.7 | 5.22.4.8 | 5.22.4.9 | 5.22.4.10 | 5.22.5.1 | 5.22.5.2 | 5.22.5.3 |
| 5.22.5.4 | 5.22.5.5 | 5.22.5.6 | 5.22.5.7 | 5.22.5.8 | 5.22.5.9 | 5.22.5.10 | 5.22.6.1 | 5.22.6.2 | 5.22.6.3 | 5.22.6.4 |
| 5.22.6.5 | 5.22.6.6 | 5.22.6.7 | 5.22.6.8 | 5.22.6.9 | 5.22.6.10 | 5.23.1.1 | 5.23.1.2 | 5.23.1.3 | 5.23.1.4 | 5.23.1.5 |
| 5.23.1.6 | 5.23.1.7 | 5.23.1.8 | 5.23.1.9 | 5.23.1.10 | 5.23.2.1 | 5.23.2.2 | 5.23.2.3 | 5.23.2.4 | 5.23.2.5 | 5.23.2.6 |
| 5.23.2.7 | 5.23.2.8 | 5.23.2.9 | 5.23.2.10 | 5.23.3.1 | 5.23.3.2 | 5.23.3.3 | 5.23.3.4 | 5.23.3.5 | 5.23.3.6 | 5.23.3.7 |
| 5.23.3.8 | 5.23.3.9 | 5.23.3.10 | 5.23.4.1 | 5.23.4.2 | 5.23.4.3 | 5.23.4.4 | 5.23.4.5 | 5.23.4.6 | 5.23.4.7 | 5.23.4.8 |
| 5.23.4.9 | 5.23.4.10 | 5.23.5.1 | 5.23.5.2 | 5.23.5.3 | 5.23.5.4 | 5.23.5.5 | 5.23.5.6 | 5.23.5.7 | 5.23.5.8 | 5.23.5.9 |
| 5.23.5.10 | 5.23.6.1 | 5.23.6.2 | 5.23.6.3 | 5.23.6.4 | 5.23.6.5 | 5.23.6.6 | 5.23.6.7 | 5.23.6.8 | 5.23.6.9 | 5.23.6.10 |
| 5.24.1.1 | 5.24.1.2 | 5.24.1.3 | 5.24.1.4 | 5.24.1.5 | 5.24.1.6 | 5.24.1.7 | 5.24.1.8 | 5.24.1.9 | 5.24.1.10 | 5.24.2.1 |
| 5.24.2.2 | 5.24.2.3 | 5.24.2.4 | 5.24.2.5 | 5.24.2.6 | 5.24.2.7 | 5.24.2.8 | 5.24.2.9 | 5.24.2.10 | 5.24.3.1 | 5.24.3.2 |
| 5.24.3.3 | 5.24.3.4 | 5.24.3.5 | 5.24.3.6 | 5.24.3.7 | 5.24.3.8 | 5.24.3.9 | 5.24.3.10 | 5.24.4.1 | 5.24.4.2 | 5.24.4.3 |
| 5.24.4.4 | 5.24.4.5 | 5.24.4.6 | 5.24.4.7 | 5.24.4.8 | 5.24.4.9 | 5.24.4.10 | 5.24.5.1 | 5.24.5.2 | 5.24.5.3 | 5.24.5.4 |
| 5.24.5.5 | 5.24.5.6 | 5.24.5.7 | 5.24.5.8 | 5.24.5.9 | 5.24.5.10 | 5.24.6.1 | 5.24.6.2 | 5.24.6.3 | 5.24.6.4 | 5.24.6.5 |
| 5.24.6.6 | 5.24.6.7 | 5.24.6.8 | 5.24.6.9 | 5.24.6.10 | 5.25.1.1 | 5.25.1.2 | 5.25.1.3 | 5.25.1.4 | 5.25.1.5 | 5.25.1.6 |
| 5.25.1.7 | 5.25.1.8 | 5.25.1.9 | 5.25.1.10 | 5.25.2.1 | 5.25.2.2 | 5.25.2.3 | 5.25.2.4 | 5.25.2.5 | 5.25.2.6 | 5.25.2.7 |
| 5.25.2.8 | 5.25.2.9 | 5.25.2.10 | 5.25.3.1 | 5.25.3.2 | 5.25.3.3 | 5.25.3.4 | 5.25.3.5 | 5.25.3.6 | 5.25.3.7 | 5.25.3.8 |
| 5.25.3.9 | 5.25.3.10 | 5.25.4.1 | 5.25.4.2 | 5.25.4.3 | 5.25.4.4 | 5.25.4.5 | 5.25.4.6 | 5.25.4.7 | 5.25.4.8 | 5.25.4.9 |
| 5.25.4.10 | 5.25.5.1 | 5.25.5.2 | 5.25.5.3 | 5.25.5.4 | 5.25.5.5 | 5.25.5.6 | 5.25.5.7 | 5.25.5.8 | 5.25.5.9 | 5.25.5.10 |
| 5.25.6.1 | 5.25.6.2 | 5.25.6.3 | 5.25.6.4 | 5.25.6.5 | 5.25.6.6 | 5.25.6.7 | 5.25.6.8 | 5.25.6.9 | 5.25.6.10 | |

Exemplary embodiments include the following numbered groups of compounds.

1 Each compound named in Table B having only one carbonate moiety and a hydroxyl group linked to the phosphorus atom in place of the second carbonate moiety, i.e., B—$CH_2$—$CHR^1$—O—$CH_2$—P(O)(OH)—O—$CHR^2$—O—C(O)—OR. Thus, the group 1 compound named 1.4.1.1 in Table B has the structure:
adenin-9-yl-$CH_2$—CH($CH_3$)—O—$CH_2$—P(O)(OH)—O—$CH_2$—O—C(O)—OCH($CH_3$)$_2$.

2 Compounds named in Table B having only one carbonate moiety and having only the $R^1$ moiety, #3 (—$CH_2OH$), which is modified such that $R^8$ of formula (1) compounds is joined with $R^1$ to form —$CH_2$—. Thus, the group 2 compound named 1.4.3.1 in Table B has the structure:
adenin-9-yl-$CH_2$—CH($CH_2$-◊)—O—$CH_2$—P(O)(O-◊)—O—$CH_2$—O—C(O)—OCH($CH_3$)$_2$, where the symbols ◊ indicate a covalent bond that links the oxygen and carbon atoms together.

3 Compounds named in Table B and compounds named by compound groups 1 and 2 where each purine base listed in Table A is the 3-deaza analog, e.g., 3-deazaadenin-9-yl. Thus, the group 3 compound defined in Table A and named 1.4.1.1 in Table B has the structure:
3-deazaadenin-9-yl-$CH_2$—CH($CH_3$)—O—$CH_2$—P(O)(—O—$CH_2$—O—C(O)—OCH($CH_3$)$_2$)$_2$. The group 3 compound defined in Table A and named 1.4.1.1 in compound group 1 has the structure:
3-deazaadenin-9-yl-$CH_2$—CH($CH_3$)—O—$CH_2$—P(O)(OH)—O—$CH_2$—O—C(O)—OCH($CH_3$)$_2$.

4 Compounds named in Table B and compounds named by compound groups 1 and 2 where each purine base listed in Table A is the 1-deaza analog, e.g., 1-deazaadenin-9-yl. Thus, the group 4 compound defined in Table A and named 1.4.1.1 in Table B has the structure:
1-deazaadenin-9-yl-$CH_2$—CH($CH_3$)—O—$CH_2$—P(O)(—O—$CH_2$—O—C(O)—OCH($CH_3$)$_2$)$_2$. The group 3 compound defined in Table A and named 1.4.1.1 in compound group 1 has the structure:
1-deazaadenin-9-yl-$CH_2$—$CH(CH_3)$—O—$CH_2$—P(O)(OH)—O—$CH_2$—O—C(O)—$OCH(CH_3)_2$.

5 Compounds named in Table B and compounds named by compound groups 1 and 2 where each purine base listed in Table A is the 8-aza analog, e.g., 8-azaadenin-9-yl.

6 Compounds named in Table B and compounds named by compound groups 1–5 where R moieties 1–25 listed in Table A are replaced with the following groups:

1 —cyclopropyl (cyclopropyl replaces —$CH_3$, which is R moiety 1 in Table A
2 —$CH_2$-cyclopropyl
3 —$(CH_2)_2$-cyclopropyl
4 —$(CH_2)_3$-cyclopropyl
5 —$(CH_2)_4$-cyclopropyl
6 —cyclobutyl
7 —$CH_2$-cyclobutyl
8 —$(CH_2)_2$-cyclobutyl
9 —$(CH_2)_3$-cyclobutyl
10 —$(CH_2)_4$-cyclobutyl
11 —cyclopentyl
12 —$CH_2$-cyclopentyl
13 —$(CH_2)_2$-cyclopentyl
14 —$(CH_2)_3$-cyclopentyl
15 —$(CH_2)_4$-cyclopentyl
16 —cyclohexyl
17 —$CH_2$-cyclohexyl
18 —$(CH_2)_2$-cyclohexyl
19 —$(CH_2)_3$-cyclohexyl
20 —$(CH_2)_4$-cyclohexyl
21 —$CH(CH_3)CH_2$-cyclopropyl
22 —$CH(CH_3)CH_2$-cyclobutyl
23 —$CH(CH_3)CH_2$-cyclopentyl
24 —$CH(CH_3)CH_2$-cyclohexyl
25 —$(CH_2)_{0-4}$-cyclooctyl.

Thus, the group 6 compound defined in Table A and named 1.16.1.1 in Table B has the structure:
adenin-9-yl-$CH_2$—$CH(CH_3)$—O—$CH_2$—P(O)(—O—$CH_2$—O—C(O)—O-cyclohexyl)$_2$. The group 6 compound defined in Table A and named 1.16.1.1 in compound group 1 has the structure:
adenin-9-yl-$CH_2$—$CH(CH_3)$—O—$CH_2$—P(O)(OH)—O—$CH_2$—O—C(O)—O-cyclohexyl. The group 6 compound defined in Table A and named 1.16.1.1 in compound group 3 has the structure:
3-deazaadenin-9-yl-$CH_2$—$CH(CH_3)$—O—$CH_2$—P(O)(—O—$CH_2$—O—C(O)—O-cyclohexyl)$_2$.

7 Compounds named in Table B and compounds named by compound groups 1–5 where R moieties 1–25 listed in Table A are replaced with the following groups:

| | | | | | | |
|---|---|---|---|---|---|---|
| 1 | 7 carbon alkyl* | 4 | 10 carbon alkyl | 7 | —$(CH_2)_2C_6H_5$ |
| 2 | 8 carbon alkyl | 5 | 11 carbon alkyl | 8 | —$(CH_2)_3C_6H_5$ |
| 3 | 9 carbon alkyl | 6 | 12 carbon alkyl | 9 | —$(CH_2)_4C_6H_5$ |
| 10 | —$C(CH_3)_2CH(CH_3)_2$ | | | | |
| 11 | —$CH(CH_3)C(CH_3)_3$ | | | | |
| 12 | —$(CH_2)_2CH(C_2H_5)CH_2CH_3$ | | | | |
| 13 | —$(CH_2)_2CH(C_2H_5)(CH_2)_2CH_3$ | | | | |
| 14 | —$(CH_2)_2CH(C_2H_5)(CH_2)_3CH_3$ | | | | |
| 15 | —$(CH_2)_3CH(C_2H_5)CH_3$ | | | | |
| 16 | —$(CH_2)_3CH(C_2H_5)CH_2CH_3$ | | | | |
| 17 | —$(CH_2)_3CH(C_2H_5)(CH_2)_2CH_3$ | | | | |
| 18 | —$CH_2CH(C_2H_5)CH_2CH_3$ | | | | |
| 19 | —$CH_2CH(C_2H_5)(CH_2)_2CH_3$ | | | | |
| 20 | —$CH_2CH(C_2H_5)(CH_2)_3CH_3$ | | | | |
| 21 | —$(CH_2)_2CH(C_3H_7)CH_2CH_3$ | | | | |
| 22 | —$(CH_2)_2CH(C_3H_7)(CH_2)_2CH_3$ | | | | |
| 23 | —$(CH_2)_2CH(C_3H_7)(CH_2)_3CH_3$ | | | | |
| 24 | —$CH_2CH=CH_2$ | | | | |
| 25 | —$CH=CHCH_3$. | | | | |

*Alkyl groups are linear, branched, cyclic or monounsaturated (—C=C—).

8 Compounds named in Table B and compounds named by compound groups 1–5 where R moieties 1–25 listed in Table A are replaced with the following groups:

| | | | |
|---|---|---|---|
| 1 | —$(CH_2)_2OCH_3$ | 14 | —$(CH_2)_5O(CH_2)_2CH_3$ |
| 2 | —$(CH_2)_3OCH_3$ | 15 | —$(CH_2)_6O(CH_2)_2CH_3$ |
| 3 | —$(CH_2)_4OCH_3$ | 16 | —$(CH_2)_2OCH(CH_3)_2$ |
| 4 | —$(CH_2)_5OCH_3$ | 17 | —$(CH_2)_3OCH(CH_3)_2$ |
| 5 | —$(CH_2)_6OCH_3$ | 18 | —$(CH_2)_4OCH(CH_3)_2$ |
| 6 | —$(CH_2)_2OCH_2CH_3$ | 19 | —$(CH_2)_5OCH(CH_3)_2$ |
| 7 | —$(CH_2)_3OCH_2CH_3$ | 20 | —$(CH_2)_6OCH(CH_3)_2$ |
| 8 | —$(CH_2)_4O(CH_2)_2CH_3$ | 21 | —$(CH_2)_2O(CH_2)_3CH_3$ |
| 9 | —$(CH_2)_5O(CH_2)_2CH_3$ | 22 | —$(CH_2)_2OCH_2CH(CH_3)_2$ |
| 10 | —$(CH_2)_6O(CH_2)_2CH_3$ | 23 | —$(CH_2)_2OC(CH_3)_3$ |
| 11 | —$(CH_2)_2O(CH_2)_2CH_3$ | 24 | —$(CH_2)_2OC_5H_{11}$ |
| 12 | —$(CH_2)_3O(CH_2)_2CH_3$ | 25 | —$(CH_2)_2OC_6H_{13}$. |
| 13 | —$(CH_2)_4O(CH_2)_2CH_3$ | | |

9 Compounds named in Table B and compounds named by compound groups 1–5 where R moieties 1–25 listed in Table A are replaced with the following groups:

1 —$CH(CH_3)CH_2OCH_3$
2 —$CH(CH_3)(CH_2)_2OCH_3$
3 —$CH(CH_3)(CH_2)_3OCH_3$
4 —$CH(CH_3)(CH_2)_4OCH_3$
5 —$CH(CH_3)CH_2OCH_2CH_3$
6 —$CH(CH_3)(CH_2)_2OCH_2CH_3$
7 —$CH(CH_3)(CH_2)_3OCH_2CH_3$
8 —$CH(CH_3)(CH_2)_4OCH_2CH_3$
9 —$CH(CH_3)CH_2O(CH_2)_2CH_3$
10 —$CH(CH_3)(CH_2)_2O(CH_2)_2CH_3$
11 —$CH(CH_3)(CH_2)_3O(CH_2)_2CH_3$
12 —$CH(CH_3)(CH_2)_4O(CH_2)_2CH_3$
13 —$CH(CH_3)CH_2OCH(CH_3)_2$
14 —$CH(CH_3)(CH_2)_2OCH(CH_3)_2$
15 —$CH(CH_3)(CH_2)_3OCH(CH_3)_2$
16 —$CH(CH_3)(CH_2)_4OCH(CH_3)_2$
17 —$CH(CH_3)CH_2OC_4H_9$
18 —$CH(CH_3)(CH_2)_2OC_4H_9$
19 —$CH(CH_3)(CH_2)_3OC_4H_9$
20 —$CH(CH_3)(CH_2)_4OC_4H_9$
21 —$CH(CH_3)CH_2OC_5H_{11}$
22 —$CH(CH_3)(CH_2)_2OC_5H_{11}$
23 —$CH(CH_3)(CH_2)_3OC_5H_{11}$
24 —$CH(CH_3)(CH_2)_4OC_5H_{11}$
25 —$CH(CH_3)CH_2OC_6H_{13}$.

Compounds named in Table B and compounds named by compound groups 1–5 where R moieties 1–25 listed in Table A are replaced with the following groups:

1 —$CH(CH_3)(CH_2)_2OC_6H_{13}$
2 —$CH(CH_3)(CH_2)_3OC_6H_{13}$

3 —CH(CH$_3$)(CH$_2$)$_4$OC$_6$H$_{13}$
4 —CH$_2$CH(CH$_3$)OCH$_3$
5 —(CH$_2$)$_2$CH(CH$_3$)OCH$_3$
6 —(CH$_2$)$_3$CH(CH$_3$)OCH$_3$
7 —(CH$_2$)$_4$CH(CH$_3$)OCH$_3$
8 —CH$_2$CH(CH$_3$)OCH$_2$CH$_3$
9 —(CH$_2$)$_2$CH(CH$_3$)OCH$_2$CH$_3$
10 —(CH$_2$)$_3$CH(CH$_3$)OCH$_2$CH$_3$
11 —(CH$_2$)$_4$CH(CH$_3$)OCH$_2$CH$_3$
12 —CH$_2$CH(CH$_3$)OCH$_2$CH$_3$
13 —(CH$_2$)$_2$CH(CH$_3$)O(CH$_2$)$_2$CH$_3$
14 —(CH$_2$)$_3$CH(CH$_3$)O(CH$_2$)$_3$CH$_3$
15 —(CH$_2$)$_4$CH(CH$_3$)O(CH$_2$)$_4$CH$_3$
16 —CH$_2$CH(CH$_3$)OCH(CH$_3$)$_2$
17 —(CH$_2$)$_2$CH(CH$_3$)OCH(CH$_3$)$_2$
18 —(CH$_2$)$_3$CH(CH$_3$)OCH(CH$_3$)$_2$
19 —(CH$_2$)$_4$CH(CH$_3$)OCH(CH$_3$)$_2$
20 —CH$_2$CH(CH$_3$)OC$_4$H$_9$
21 —(CH$_2$)$_2$CH(CH$_3$)OC$_4$H$_9$
22 —(CH$_2$)$_3$CH(CH$_3$)OC$_4$H$_9$
23 —(CH$_2$)$_4$CH(CH$_3$)OC$_4$H$_9$
24 —CH$_2$CH(CH$_3$)OC$_5$H$_{11}$
25 —(CH$_2$)$_2$CH(CH$_3$)OC$_5$H$_{11}$

11 Compounds named in Table B and compounds named by compound groups 1–5 where R moieties 1–25 listed in Table A are replaced with the following groups:

1 —(CH$_2$)$_3$CH(CH$_3$)OC$_5$H$_{11}$
2 —(CH$_2$)$_4$CH(CH$_3$)OC$_5$H$_{11}$
3 —CH$_2$CH(CH$_3$)OC$_6$H$_{13}$
4 —(CH$_2$)$_2$CH(CH$_3$)OC$_6$H$_{13}$
5 —(CH$_2$)$_3$CH(CH$_3$)OC$_6$H$_{13}$
6 —(CH$_2$)$_4$CH(CH$_3$)OC$_6$H$_{13}$
7 —(CH$_2$)$_2$OCH(CH$_3$)C$_2$H$_5$
8 —(CH$_2$)$_2$OCH(CH$_3$)(CH$_2$)$_2$CH$_3$
9 —(CH$_2$)$_2$OCH(CH$_3$)CH(CH$_3$)$_2$
10 —(CH$_2$)$_2$OCH(CH$_3$)(CH$_2$)$_3$CH$_3$
11 —(CH$_2$)$_2$OCH(CH$_3$)C(CH$_3$)$_3$
12 —(CH$_2$)$_2$OCH(CH$_3$)CH(CH$_3$)CH$_2$CH$_3$
13 —(CH$_2$)$_2$OCH(CH$_3$)CH$_2$CH(CH$_3$)$_2$
14 —(CH$_2$)$_3$OCH(CH$_3$)C$_2$H$_5$
15 —(CH$_2$)$_3$OCH(CH$_3$)(CH$_2$)$_2$CH$_3$
16 —(CH$_2$)$_3$OCH(CH$_3$)CH(CH$_3$)$_2$
17 —(CH$_2$)$_3$OCH(CH$_3$)(CH$_2$)$_3$CH$_3$
18 —(CH$_2$)$_3$OCH(CH$_3$)C(CH$_3$)$_3$
19 —(CH$_2$)$_3$OCH(CH$_3$)CH(CH$_3$)CH$_2$CH$_3$
20 —(CH$_2$)$_3$OCH(CH$_3$)CH$_2$CH(CH$_3$)$_2$
21 —(CH$_2$)$_4$OCH(CH$_3$)C$_2$H$_5$
22 —(CH$_2$)$_4$OCH(CH$_3$)(CH$_2$)$_2$CH$_3$
23 —(CH$_2$)$_4$OCH(CH$_3$)CH(CH$_3$)$_2$
24 —(CH$_2$)$_4$OCH(CH$_3$)(CH$_2$)$_3$CH$_3$
25 —(CH$_2$)$_4$OCH(CH$_3$)C(CH$_3$)$_3$

12 Compounds named in Table B and compounds named by compound groups 1–5 where R moieties 1–25 listed in Table A are replaced with the following groups:

1 —(CH$_2$)$_2$O(CH$_2$)$_3$CH$_3$
2 —(CH$_2$)$_2$O(CH$_2$)$_4$CH$_3$
3 —(CH$_2$)$_2$O(CH$_2$)$_5$CH$_3$
4 —(CH$_2$)$_3$O(CH$_2$)$_3$CH$_3$
5 —(CH$_2$)$_3$O(CH$_2$)$_4$CH$_3$
6 —(CH$_2$)$_3$O(CH$_2$)$_5$CH$_3$
7 —(CH$_2$)$_2$OC$_6$H$_5$
8 —(CH$_2$)$_2$OC$_6$H$_5$
9 —(CH$_2$)$_2$OC$_6$H$_5$
10 —CH(C$_2$H$_5$)CH$_2$OCH$_3$
11 —CH(C$_2$H$_5$)CH$_2$OC$_2$H$_5$
12 —CH(C$_2$H$_5$)CH$_2$O(CH$_2$)$_2$CH$_3$
13 —CH(C$_2$H$_5$)CH$_2$OCH$_2$(CH$_3$)$_2$
14 —CH(C$_2$H$_5$)CH$_2$O(CH$_2$)$_3$CH$_3$
15 —CH(C$_2$H$_5$)CH$_2$OCH(CH$_3$)C$_2$H$_5$
16 —CH(C$_2$H$_5$)CH$_2$OCH$_2$CH(CH$_3$)$_2$
17 —CH(C$_2$H$_5$)CH$_2$OC(CH$_3$)$_3$
18 —CH(C$_2$H$_5$)CH$_2$O(CH$_2$)$_4$CH$_3$
19 —CH(C$_2$H$_5$)CH$_2$O(CH$_2$)$_2$CH(CH$_3$)$_2$
20 —CH(C$_2$H$_5$)CH$_2$O(CH$_2$)$_5$CH$_3$
21 —CH(C$_2$H$_5$)CH$_2$O(CH$_2$)$_3$CH(CH$_3$)$_2$
22 —CH$_2$CH(C$_2$H$_5$)OCH$_3$
23 —CH$_2$CH(C$_2$H$_5$)OC$_2$H$_5$
24 —CH$_2$CH(C$_2$H$_5$)OC$_3$H$_7$
25 —CH$_2$CH(C$_2$H$_5$)OC$_4$H$_9$.

13 Compounds named in Table B and compounds named by compound groups 1–5 where R moieties 1–25 listed in Table A are replaced with the following groups:

1 —(CH$_2$)$_2$O-cyclopropyl
2 —(CH$_2$)$_2$O-cyclobutyl
3 —(CH$_2$)$_2$O-cyclopentyl
4 —(CH$_2$)$_2$O-cyclohexyl
5 —(CH$_2$)$_2$OCH$_2$-cyclopropyl
6 —(CH$_2$)$_2$OCH$_2$-cyclobutyl
7 —(CH$_2$)$_2$OCH$_2$-cyclopentyl
8 —(CH$_2$)$_2$OCH$_2$-cyclohexyl
9 —(CH$_2$)$_2$O—(CH$_2$)$_2$cyclopropyl
10 —(CH$_2$)$_2$O—(CH$_2$)$_2$cyclobutyl
11 —(CH$_2$)$_2$O—(CH$_2$)$_2$cyclopentyl
12 —(CH$_2$)$_2$O—(CH$_2$)$_2$cyclohexyl
13 —(CH$_2$)$_3$O-cyclopropyl
14 —(CH$_2$)$_3$O-cyclobutyl
15 —(CH$_2$)$_3$O-cyclopentyl
16 —(CH$_2$)$_3$O-cyclohexyl
17 —(CH$_2$)$_3$OCH$_2$-cyclopropyl
18 —(CH$_2$)$_3$OCH$_2$-cyclobutyl
19 —(CH$_2$)$_3$OCH$_2$-cyclopentyl
20 —(CH$_2$)$_3$OCH$_2$-cyclohexyl
21 —CH(CH$_3$)CH$_2$O-cyclopropyl
22 —CH(CH$_3$)CH$_2$O-cyclobutyl
23 —CH(CH$_3$)CH$_2$O-cyclopentyl
24 —CH(CH$_3$)CH$_2$O-cyclohexyl
25 —CH(CH$_3$)CH$_2$OCH$_2$-cyclohexyl.

14 Compounds named in Table B and compounds named by compound groups 1–5 where R moieties 1–25 listed in Table A are replaced with the following groups:

1 —C(CH$_2$OCH$_3$)$_3$
2 —C(C$_2$H$_5$)$_2$(CH$_2$OCH$_3$)
3 —CH(C$_2$H$_5$)CH$_2$OCH$_3$
4 —CH$_2$(CH$_2$OCH$_3$)

5 —C(CH$_3$)$_2$(CH$_2$OCH$_3$)
6 —CH(CH$_3$)(CH$_2$OCH$_3$)
7 —C(CH$_2$OC$_2$H$_5$)$_3$
8 —C(C$_2$H$_5$)$_2$(CH$_2$OC$_2$H$_5$)
9 —CH(C$_2$H$_5$)(CH$_2$OC$_2$H$_5$)
10 —CH(C$_4$H$_9$)(CH$_2$OCH$_3$)
11 —CH$_2$C(CH$_2$OCH$_3$)$_3$
12 —CH$_2$C(C$_2$H$_5$)$_2$(CH$_2$OCH$_3$)
13 —CH$_2$CH(C$_2$H$_5$)(CH$_2$OCH$_3$)
14 —CH(CH$_2$OCH$_3$)$_2$
15 —CH$_2$C(CH$_2$OCH$_3$)$_3$
16 —CH$_2$CH(CH$_2$OCH$_3$)$_2$
17 —C(CH$_2$OC$_2$H$_5$)$_3$
18 —CH(CH$_2$OC$_2$H$_5$)$_2$
19 —CH$_2$C(CH$_2$OC$_2$H$_5$)$_3$
20 —CH$_2$CH(CH$_2$OC$_2$H$_5$)$_2$
21 —C(C$_2$H$_5$)$_2$(CH$_2$OC$_3$H$_7$)
22 —CH(C$_3$H$_7$)(CH$_2$OCH$_3$)
23 —C(C$_3$H$_7$)$_2$(CH$_2$OCH$_3$)
24 —CH(C$_3$H$_7$)(CH$_2$OC$_2$H$_5$)
25 —C(C$_3$H$_7$)$_2$(CH$_2$OC$_2$H$_5$)

15 The following groups of compounds A–J.

A Compounds named in groups 8–14 where the oxygen atom (—O—) in the R moiety is replaced with —NH—.

B Compounds named in groups 8–14 where the oxygen atom in the R moiety is replaced with —N(CH$_3$)—.

C Compounds named in groups 8–14 where the oxygen atom in the R moiety is replaced with —N(C$_2$H$_5$)—.

D Compounds named in groups 8–14 where the oxygen atom in the R moiety is replaced with —N(CH$_2$CH$_2$CH$_3$)—.

E Compounds named in groups 8–14 where the oxygen atom in the R moiety is replaced with —N(CH(CH$_3$)$_2$—.

F Compounds named in groups 8–14 where the oxygen atom in the R moiety is replaced with n-butyl substituted nitrogen (—N(CH$_2$)$_3$CH$_3$)—).

G Compounds named in groups 8–14 where the oxygen atom in the R moiety is replaced with i-butyl substituted nitrogen.

H Compounds named in groups 8–14 where the oxygen atom in the R moiety is replaced with t-butyl substituted nitrogen.

I Compounds named in groups 8–14 where the oxygen atom in the R moiety is replaced with linear, branched or cyclic 5 carbon alkyl substituted nitrogen.

J Compounds named in groups 8–14 where the oxygen atom in the R moiety is replaced with linear, branched or cyclic 6 carbon alkyl substituted nitrogen.

Thus, the group 15B compound defined in Table A and named 1.1.1.1 in compound group 8 has the structure:
adenin-9-yl-CH$_2$—CH(CH$_3$)—O—CH$_2$—P(O)(—O—CH$_2$—O—C(O)—O—(CH$_2$)$_2$N(CH$_3$)$_2$)$_2$. The group 15B compound defined in Table A and named 1.1.1.1 in compound group 1, as named under group 8, has the structure:
adenin-9-yl-CH$_2$—CH(CH$_3$)—O—CH$_2$—P(O)(OH)—O—CH$_2$—O—C(O)—O—(CH$_2$)$_2$N(CH$_3$)$_2$. The group 15B compound defined in Table A and named 1.16.1.1 in compound group 3, as named under group 8, has the structure:
3-deazaadenin-9-yl-CH$_2$—CH(CH$_3$)—O—CH$_2$—P(O)(—O—CH$_2$—O—C(O)—O—(CH$_2$)$_2$N(CH$_3$)$_2$)$_2$.

Compounds named in Table B and compounds named by compound groups 1–5 where R moieties 1–25 listed in Table A are replaced with the following groups:

1 —(CH$_2$)$_2$R$^9$
2 —(CH$_2$)$_3$R$^9$
3 —(CH$_2$)$_4$R$^9$
4 —(CH$_2$)$_5$R$^9$
5 —(CH$_2$)$_6$R$^9$
6 —(CH$_2$)$_7$R$^9$
7 —(CH$_2$)$_8$R$^9$
8 —CH(CH$_3$)CH$_2$R$^9$
9 —CH(CH$_3$)(CH$_2$)$_2$R$^9$
10 —CH(CH$_3$)(CH$_2$)$_3$R$^9$
11 —(CH$_2$)$_2$R$^9$
12 —(CH$_2$)$_3$R$^9$
13 —(CH$_2$)$_4$R$^9$
14 —(CH$_2$)$_5$R$^9$
15 —(CH$_2$)$_6$R$^9$
16 —(CH$_2$)$_7$R$^9$
17 —(CH$_2$)$_8$R$^9$
18 —CH(CH$_3$)CH$_2$R$^9$
19 —CH(CH$_3$)(CH$_2$)$_2$R$^9$
20 —CH(CH$_3$)(CH$_2$)$_3$R$^9$
21 —(CH$_2$)$_2$R$^9$
22 —(CH$_2$)$_3$R$^9$
23 —(CH$_2$)$_4$R$^9$
24 —(CH$_2$)$_5$R$^9$
25 —(CH$_2$)$_6$R$^9$

In moieties 1–10, R$^9$ is N-morpholino, in moieties 11–20, R$^9$ is 2-pyridyl and in moieties 21–25, R$^9$ is 3-pyridyl.

17 Compounds named in Table B and compounds named by compound groups 1–5 where R moieties 1–25 listed in Table A are replaced with the following groups:

1 —(CH$_2$)$_2$R$^9$
2 —(CH$_2$)$_3$R$^9$
3 —(CH$_2$)$_4$R$^9$
4 —(CH$_2$)$_5$R$^9$
5 —(CH$_2$)$_6$R$^9$
6 —(CH$_2$)$_2$CH(CH$_3$)R$^9$
7 —(CH$_2$)$_3$CH(CH$_3$)R$^9$
8 —(CH$_2$)$_4$CH(CH$_3$)R$^9$
9 —(CH$_2$)$_2$R$^9$
9 —(CH$_2$)$_3$R$^9$
11 —(CH$_2$)$_4$R$^9$
12 —(CH$_2$)$_5$R$^9$
13 —(CH$_2$)$_6$R$^9$
14 —(CH$_2$)$_6$CH$_3$
15 —(CH$_2$)$_7$CH$_3$
16 —(CH$_2$)$_8$CH$_3$
17 —(CH$_2$)$_9$CH$_3$
18 —(CH$_2$)$_{10}$CH$_3$
19 —(CH$_2$)$_{11}$CH$_3$
20 —(CH$_2$)$_4$CH(CH$_3$)$_2$
21 —(CH$_2$)$_5$CH(CH$_3$)$_2$
22 —(CH$_2$)$_6$CH(CH$_3$)$_2$
23 —(CH$_2$)$_7$CH(CH$_3$)$_2$
24 —(CH$_2$)$_8$CH(CH$_3$)$_2$
25 —(CH$_2$)$_9$CH(CH$_3$)$_2$.

In moieties 1–5, R$^9$ is 4-pyridyl, in moieties 6–9 R$^9$ is N-morpholino and in moieties 9–13, R$^9$ is N-piperidyl.

18 The following groups of compounds A–J.

A Compounds named in Table B and compounds named by groups 1–17 where compound (8) is replaced with compound (9)

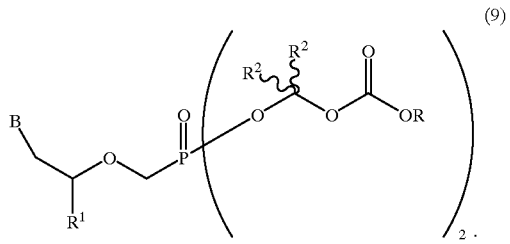

(9)

where one $R^2$ is as specified in Table A and the other $R^2$ is —$CH_3$.

B Compounds named in Table B and compounds named by compound groups 1–17 where compound (8) is replaced with compound (9) where one $R^2$ is as specified in Table A and the other $R^2$ is —$CH_2CH_3$.

C Compounds named in Table B and compounds named by compound groups 1–17 where compound (8) is replaced with compound (9) where one $R^2$ is as specified in Table A and the other $R^2$ is —$(CH_2)_2CH_3$.

D Compounds named in Table B and compounds named by compound groups 1–17 where compound (8) is replaced with compound (9) where one $R^2$ is as specified in Table A and the other $R^2$ is —$CH(CH_3)_2$.

E Compounds named in Table B and compounds named by compound groups 1–17 where compound (8) is replaced with compound (9) where one $R^2$ is as specified in Table A and the other $R^2$ is —$(CH_2)_3CH_3$.

F Compounds named in Table B and compounds named by compound groups 1–17 where compound (8) is replaced with compound (9) where one $R^2$ is as specified in Table A and the other $R^2$ is —$(CH_2)_4CH_3$.

G Compounds named in Table B and compounds named by compound groups 1–17 where compound (8) is replaced with compound (9) where one $R^2$ is as specified in Table A and the other $R^2$ is —$CH_2CH(CH_3)_2$.

H Compounds named in Table B and compounds named by compound groups 1–17 where compound (8) is replaced with compound (9) where one $R^2$ is as specified in Table A and the other $R^2$ is —$C(CH_3)_3$.

I Compounds named in Table B and compounds named by compound groups 1–17 where compound (8) is replaced with compound (9) where one $R^2$ is as specified in Table A and the other $R^2$ is —$C_5H_{11}$.

J Compounds named in Table B and compounds named by compound groups 1–17 where compound (8) is replaced with compound (9) where one $R^2$ is as specified in Table A and the other $R^2$ is —$C_6H_{13}$.

Thus, the group 18A compound defined in Table A and named 1.4.2.3 in Table B has the structure:
adenin-9-yl-$CH_2$—$CH_2$—O—$CH(CH_3$—P(O)(—O—C($C_2H_5$)($CH_3$)—O—C(O)—O—$CH(CH_3)_2)_2$. The group 18A compound defined in Table A and named 1.4.1.1 in compound group 1 has the structure:
adenin-9-yl-$CH_2$—$CH(CH_3)$—O—$CH_2$—P(O)(OH)—O—$CH(CH_3)$—O—C(O)—O—$CH(CH_3)_2$. The group 18A compound defined in Table A and named 1.1.1.1 in compound group 3, as named under compound group 8, has the structure:
3-deazaadenin-9-yl-$CH_2$—$CH(CH_3)$—O—$CH_2$—P(O)(—O—$CH(CH_3)$—O—C(O)—O—$(CH_2)_2OCH_3)_2$.

19 Compounds named in Table B and compounds named by compound groups 1–18 where compound (8) and compound (9) are replaced with compound (10) and (11) respectively

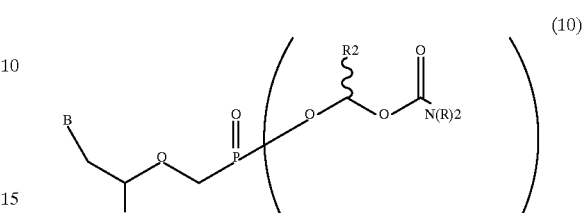

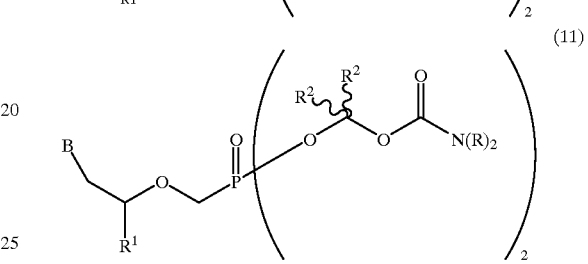

where both R moieties are the same. Thus, the group 19 compound defined in Table A and named 1.4.1.1 in Table B has the structure:
adenin-9-yl-$CH_2$—$CH(CH_3)$—O—$CH(CH_3)$—P(O)(—O—$CH_2$—O—C(O)—N—$CH(CH_3)_2)_2$. The group 19 compound defined in Table A and named 1.4.1.1 in compound group 1 has the structure:
adenin-9-yl-$CH_2$—$CH(CH_3)$—O—$CH_2$—P(O)(OH)—O—$CH_2$—O—C(O)—N—$CH(CH_3)_2$. The group 19 compound defined in Table A and named 1.1.1.1 in compound group 3, as named under compound group 8, has the structure:
3-deazaadenin-9-yl-$CH_2$—$CH(CH_3)$—O—$CH_2$—P(O)(—O—$CH_2$—O—C(O)—N—$(CH_2)_2OCH_3)_2$.

The compounds of this invention are, to varying degrees, chemically stable. It is preferable that the compounds be chemically stable in order to ensure an adequate shelf-life and proper biodistribution upon oral administration. In general, embodiments are selected that have a t ½ at pH 7.4 of greater than 2, 3, 4, 5, 6, 7, 8, 9, 10, 11 or 12 hours and preferably in addition possess a t ½ at pH 2.0 of greater than 1, 10 or 100 hours. For example, the t-butyl carbonate found in Table 1 has a t ½ that is less stable than these parameters and therefor is not preferred. In addition, the optimal compounds of this invention should have bioavailability in beagle dogs (as set forth in more detail below) that exceeds about 20%, preferably, about 30%.

Synthetic Methods

The carbamates and carbonates of this invention are prepared from the diacids of the phosphonomethoxy nucleotide analogs and the synthon $LCH(R^2)OC(O)X(R)_a$. L is a leaving group such as Cl, although it will be appreciated that any of the conventional leaving groups used in organic chemistry in nucleophilic substitution reactions can be successfully employed in place of chloro. In particular, leaving groups include halides, such as Cl, Br and I, and sulfonic acid esters such as methane, benzene or toluene sulfonic acid esters. The synthon is prepared by reacting $LCH(R^2)OC$ (O)L with HOR for preparation of the carbonate synthon or HNR$_2$ for the preparation of the carbamate synthon. The synthon is then reacted with the nucleotide analog of choice, typically PMPA, to form the desired carbamate or carbonate adducts. The carbamates are prepared by reacting the synthon with the nucleotide analog under typical conditions of nucleophilic attack, for example in Et$_3$N/DMF at room temperature. The carbonates are formed by reacting the appropriate synthon with the nucleotide analog in the presence of an organic base, typically an amine base. In addition, masked leaving groups such as thioethers, which may be activated by, for example, oxidation, and coupled directly to the phosphonic acid moiety may be used. Intermediates may be made with other leaving groups in this way, for example diphenylphosphinic acids, and others known in the chemistry of formacetals and glycosylation.

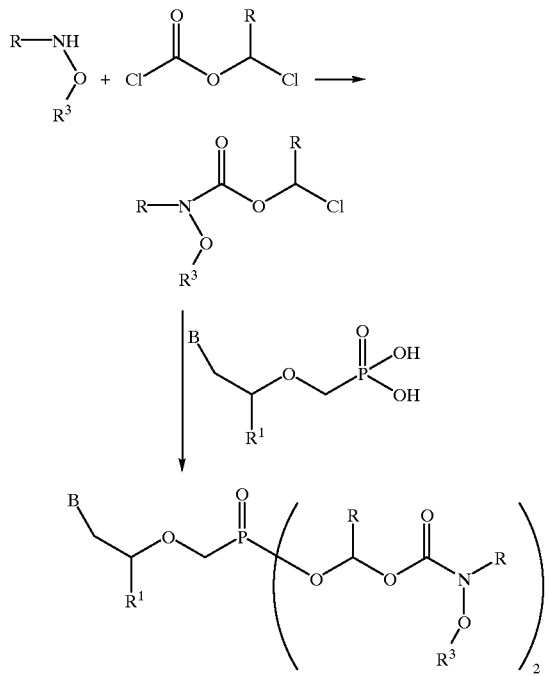

Compounds where X=N and R=OR$^3$ may be prepared by alkylation with the appropriate haloalkyl, O-alkyl carbamate. N, O-dialkylhydroxylamines are known in the literature, and may be prepared by alkylation of hydroxylamine, or by reductive amination of aldehydes or ketones with alkyl hydroxylamines. The dialkylhydroxylamines may be acylated with the appropriately substituted haloalkyl chloroformate under conditions analagous to those used to prepare the unsubstituted chloromethyl carbamates. Phosphonates may then be alkylated with the haloalkyl, O-alkyl carbamates to give the prodrugs under conditions used for the carbonates and carbamates. Leaving groups other than chloride may of course by used throughout.

In a typical method, the carbonate compounds of this invention are prepared by reacting L—CHR$^2$—O—C(O)—OR with (4) to yield a compound of formula (1).

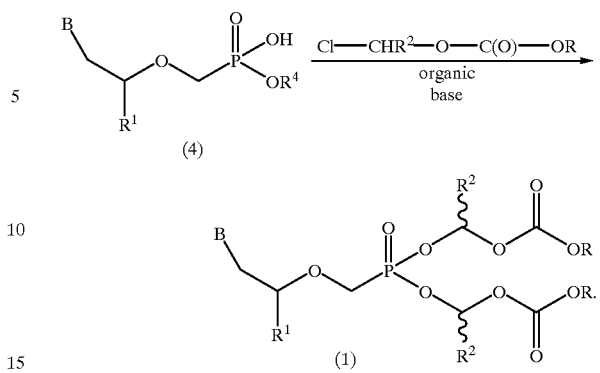

The reaction typically proceeds in two concurrent steps in which the monoester forms first, and then the diester as the reaction proceeds longer. In this situation monoester is not typically isolated as an intermediate.

In order to make a diester that contains different carbonate or carbamate functionalities the monoester intermediate is recovered from the early reaction and the reaction is then completed with for example a second L—CHR$^2$—O—C(O)—OR reagent, thereby resulting in substitution with a second ester different from the first.

One optionally conducts the carbonate synthesis reactions using at least about 1.0 and typically 2 equivalents of L—CHR$^2$—O—C(O)—OR. The reaction is conducted in the presence of an organic base in an organic solvent at a reaction temperature of about 4–100° for about 4–72 hours. Exemplary suitable organic bases include triethylamine or Hunig's base. Exemplary suitable organic solvents include DMF, DMPU, or NMP.

The monoester or diester products are purified by standard methods including flash column chromatography or salting out. Suitable salts for purification and/or formulation will final product include the sulfuric acid, phosphoric acid, lactic acid, fumaric or citric acid salts or complexes of the diester or monoester compounds of structures (1) or (1a).

Utilities

The compounds of this invention are useful in the treatment or prophylaxis of one or more viral infections in man or animals, including infections caused by DNA viruses, RNA viruses, herpesviruses (CMV, HSV 1, HSV 2, VZV, and the like), retroviruses, hepadnaviruses, (e.g. HBV), papillomavirus, hantavirus, adenoviruses and HIV. Other infections to be treated with the compounds herein include MSV, RSV, SIV, FIV, MuLV, and other retroviral infections of rodents and other animals. The prior art describes the antiviral specificity of the nucleotide analogs, and the parental drug specificity is shared by the compounds of this invention. Dosages, viral targets, and suitable administration routes to best attack the site of infection are well known in the art for the parental drugs. Determination of proper doses is a straightforward matter for the clinician, taking into account the molecular weight of the compounds of this invention and, which administering them orally, their bioavailability in animals or as deduced in clinical trials with humans. Oral dosages of the compounds of this invention in humans for antiviral therapy will range about from 0.5 to 60 mg/Kg/day, usually about from 1 to 30 mg/Kg/day and typically about from 1.5 to 10 mg/Kg/day.

The compounds of this invention also are useful as intermediates in the preparation of detectable labels for oligonucleotide probes. The compounds are hydrolyzed to yield the diacid, diphosphorylated and incorporated into an oligonucleotide by conventional enzymatic or chemical means. The incorporated base from the compound of the invention will be capable of participating in base pairing and thus will not interfere substantially with the binding of the oligonucleotide to its complementary sequence (E. De Clercq Rev. Med. Virol. 3:85–96 1993). However, if it does interfere with binding of the oligonucleotide containing the analog to the complementary sequence, the compound of the invention optionally is incorporated into the oligonucleotide as the 3' terminal base, an innocuous position and a conventional site for oligonucleotide labeling. The aglycon donated by the nucleotide analog that is incorporated into the oligonucleotide is detected by any means, such as NMR or by binding to antibodies specific for the nucleotide analog.

Pharmaceutical Formulations

Compounds of the invention and their pharmaceutically, i.e. physiologically, acceptable salts (hereafter collectively referred to as the active ingredients), are administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). Generally, the compounds of this invention are administered orally, but if an embodiment is not sufficiently orally bioavailable it can be administered by any of the other routes noted above.

While it is possible for the active ingredients to be administered as pure compounds it is preferable to present them as pharmaceutical formulations. The formulations of the present invention comprise at least one active ingredient, as above defined, together with one or more acceptable carriers and optionally other therapeutic ingredients. The carrier(s) must be "acceptable" in the sense of being compatible with the other ingredients of the formulation and not deleterious to the patient.

The formulations including those suitable for topical or systemic administration, including oral, rectal, nasal, buccal, sublingual, vaginal or parenteral (including subcutaneous, intramuscular, intravenous, intradermal, intrathecal and epidural) administration. The formulations are in unit dosage form and are prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by moulding in a suitable machine a mixture of the powdered compound moistened with an inert liquid diluent. The tablets may optionally be coated or scored and may be formulated so as to provide slow or controlled release of the active ingredient therein.

For infections of the eye or other external tissues, e.g. mouth and skin, the formulations are preferably applied as a topical ointment or cream containing the active ingredient (s) in an amount of, for example, 0.01 to 10% w/w (including active ingredient(s) in a range between 0.1% and 5% in increments of 0.1% w/w such as 0.6% w/w, 0.7% w/w, etc), preferably 0.2 to 3% w/w and most preferably 0.5 to 2% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as en emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the emulsifying wax, and the wax together with the oil and fat make up the emulsifying ointment base which forms the oily dispersed phase of the cream formulations.

Emulgents and emulsion stabilizers suitable for use in the formulation of the present invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is suitably present in such formulations in a concentration of 0.01 to 20%, in some embodiments 0.1 to 10%, and in others about 1.0% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal or inhalational administration wherein the carrier is a solid include a powder having a particle size for example in the range 1 to 500 microns (including particle sizes in a range between 20 and 500 microns in increments of 5 microns such as 30 microns, 35 microns, etc). Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents. Inhalation therapy is readily administered by metered dose inhalers.

Formulations suitable for vaginal administration may be presented as pessaries, tampons, creams, gels, pastes, foams or spray formulations containing in addition to the active ingredient such carrier as are known in the art to be appropriate.

Formulations suitable for parenteral administration are sterile and include aqueous and non-aqueous injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as recited above, or an appropriate fraction thereof, of an active ingredient.

In addition to the ingredients particularly mentioned above the formulations of this invention may include other agents conventional in the art having regard to the type of formulation in question, for example those suitable for oral administration may include flavoring agents.

The present invention further provides veterinary compositions comprising at least one active ingredient as above defined together with a veterinary carrier therefor.

Veterinary carriers are materials useful for the purpose of administering the composition to cats, dogs, horses, rabbits and other animals and may be solid, liquid or gaseous materials which the otherwise inert or acceptable in the veterinary art and are compatible with the active ingredient. These veterinary compositions may be administered orally, parenterally or by any other desired route.

Compounds of the invention can be used to provide controlled release pharmaceutical formulations containing a matrix or absorbent material and as active ingredient one or more compounds of the invention in which the release of the active ingredient can be controlled and regulated to allow less frequent dosing or to improve the pharmacokinetic or toxicity profile of the compound. Controlled release formulations adapted for oral administration in which discrete units comprising one or more compounds of the invention can be prepared according to conventional methods.

All citations found herein are incorporated by reference.

The following examples further illustrate the invention but are not to be construed as limiting the invention.

EXAMPLES

Example 1

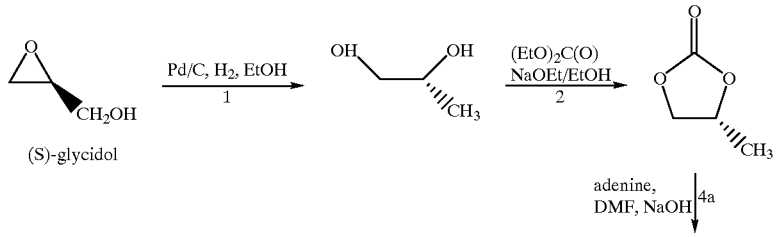

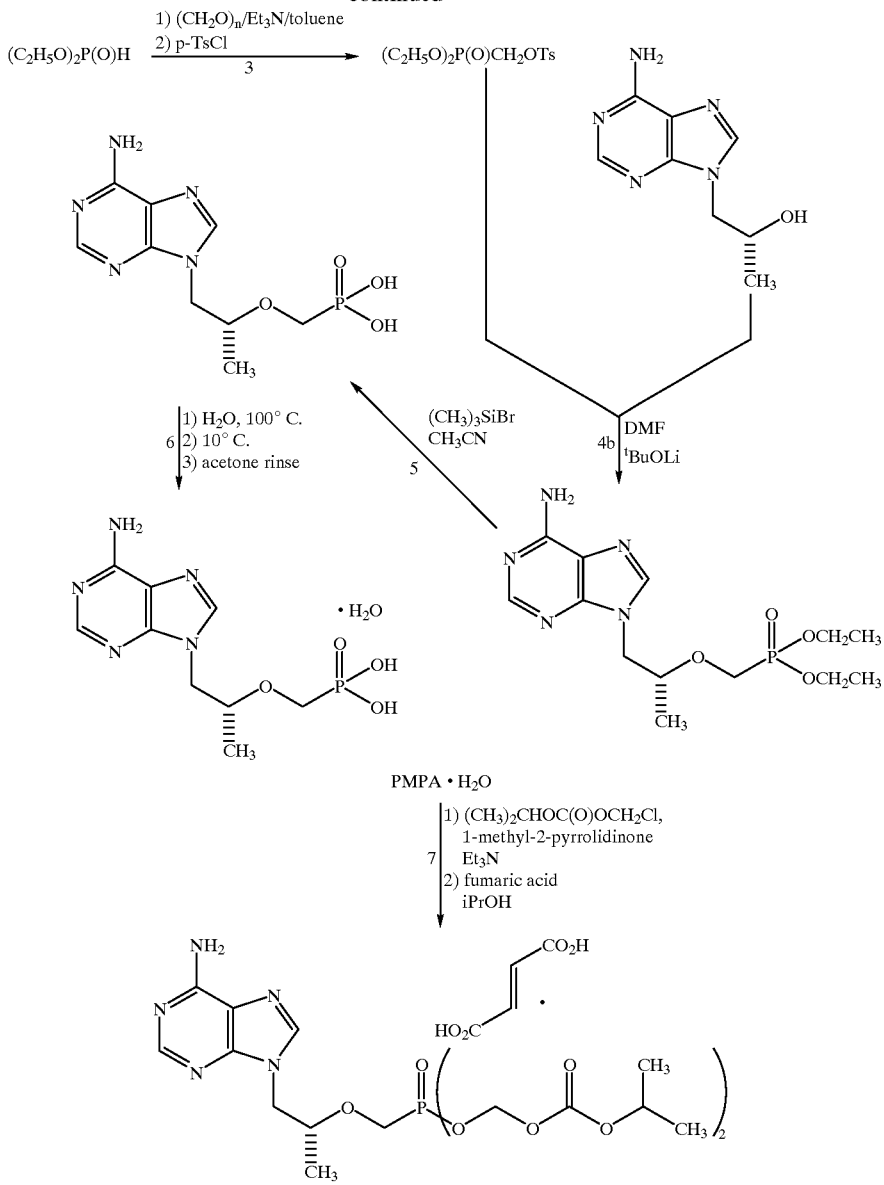

Process Summary

PMPA is prepared as follows: (S)-Glycidol is reduced to (R)-1,2-propanediol by catalytic hydrogenation, which is then reacted with diethyl carbonate to afford (R)-1,2-propylene carbonate. The carbonate is reacted with adenine and catalytic amounts of a base such as sodium hydroxide to give (R)-9-[2-(diethylphosphonomethoxy)propyl]adenine which, without isolation, is reacted with lithium alkoxide (alkyl containing 1, 2, 3, 4, 5 or 6 carbon atoms, e.g., n-hexoxide, n-pentoxide, n-butoxide, i-butoxide, t-butoxide, n-propoxide, i-propoxide, ethoxide, methoxide) and diethyl p-toluenesulfonyloxymethylphosphonate (prepared by reacting diethyl phosphite and paraformaldehyde, and tosylating the product in situ). The resulting (R)-9-[2-diethylphosphonomethoxypropyl]adenine is deesterified with bromotrimethylsilane to give crude PMPA, which is then purified by precipitation from water with pH adjustment. The product is further purified by recrystallization with water to afford PMPA monohydrate.

The process uses a small amount of a base such as NaOH at step 1, which increases the reaction rate about 10-fold compared to the same reaction lacking the base. Step 1 also uses hydrogen gas instead of using a reagent such as $HCO_2NH_4$ to generate hydrogen in situ. The process uses lithium alkoxide at step 4b, which is mildly exothermic on addition to the reaction mixture. The use of a highly reactive base such as NaH, results in an exothermic reaction that generates hydrogen gas in a reaction is difficult to control. The use of NaH thus requires more labor and care to use than lithium alkoxide. Lithium alkoxide bases also give a product that has an improved by-product profile compared to that obtained using NaH, e.g., lower amounts of starting material or overalkylated products usually result from the use of lithium alkoxide.

The scale of the following method is proportionately reduced or increased if desired. The scheme and process steps depict synthesis of (R)-PMPA. One can practice the method using chirally impure starting materials such as (R,S)-glycidol to obtain a chiral mixture of intermediates or of the final product.

One can increase or decrease the scale of the process steps described below if desired. The scheme and process steps depict synthesis of (R)-PMPA and (R)-bis(POC)PMPA. One can practice the method using chirally impure starting materials such as (R,S)-glycidol to obtain a chiral mixture of intermediates, e.g., a chiral mixture of 1,2-propylene carbonate, PMPA or bis(POC)PMPA.

Step 1

(R)-1,2-Propanediol (S)-Glycidol (1.0 kg, 13.5 moles) is added to a reactor containing (i) an inert, e.g., nitrogen, atmosphere and (ii) a stirred suspension of 5% palladium on activated carbon (50% wet) catalyst (100 g) in denatured ethyl alcohol containing 2 mole % sodium hydroxide (7.85 kg EtOH and 54 g of 16.7% NaOH solution). The contents of the inerted reactor containing catalyst and the ethanol solution is usually cooled to about 0° C. (usually about −5 to 5° C.) before the (S)-glycidol is added. Hydrogen gas at no more than 20 psi is then introduced to the inerted reaction vessel containing reactants at a temperature of no more than 25° C. The mixture is agitated for approximately 4–5 hours, until hydrogen consumption stops. Reaction completion is monitored by TLC (trace or no (S)-glycidol remaining). The mixture is then filtered e.g., diatomaceous earth (about 150 g), to remove solids and the filtrate is concentrated in vacuo at no more than 50° C., until volatile collection stops or is very slow, to obtain an oil containing the crude product. The crude product is used directly in the next step. Title compound yield is about 100%.

Step 2

(R)-1,2-Propylene carbonate

Diethyl carbonate (1.78 kg, 15.1 moles) and sodium ethoxide in denatured ethyl alcohol (210 g of 21% w/w sodium ethoxide in ethanol) are added to (R)-1,2-propanediol (1.0 kg theoretical based on the quantity of (S)-glycidol used in step 1 above), and the solution is heated to 80 to 150° C. to distill off the ethanol. If necessary to achieve reaction completion, additional diethyl carbonate (0.16 kg) is added to the reaction mixture, followed by distillation to remove ethanol. Reaction completion is monitored by TLC showing a trace or no detectable (R)-1,2-propanediol. The residue is fractionally distilled at 120° C. and 10–17 mm Hg, to yield the title compound as a colorless liquid. The product purity is typically 96% or greater purity by GC analysis.

Step 3

Diethyl p-toluenesulfonyloxymethylphosphonate

In a reactor containing an inert atmosphere, e.g., nitrogen, a mixture of diethyl phosphite (0.80 kg), paraformaldehyde (0.22 kg), and triethylamine (0.06 kg) in toluene (0.11 kg) is heated at 87° C. for about 2 hours, then refluxed for about 1 hour, until the reaction is complete as monitored by TLC showing a trace or no detectable diethyl phosphite. During the reaction, the inert atmosphere is maintained. Toluene is necessary to moderate the reaction, which may otherwise explode. Reaction completion is optionally confirmed by $^1$H NMR (diethyl phosphite peak at δ 8.4–8.6 ppm no longer detected). The solution is cooled to about 1° C. (typically about −2 to 4° C.) and p-toluenesulfonyl chloride (1.0 kg) is added and then triethylamine (0.82 kg) at about 5° C. is slowly added (exothermic addition) while maintaining the temperature at no more than about 10° C. (typically 0 to 10° C.). The resulting mixture is warmed to 22° C. and stirred for at least about 5 hours (typically about 4.5 to 6.0 hours), until the reaction is complete as shown by TLC (trace or no p-toluenesulfonyl chloride detectable) and optionally confirmed by $^1$H NMR (p-toluenesulfonyl chloride doublet at δ 7.9 ppm no longer detected). The solids are removed by filtration and washed with toluene (0.34 kg). The combined washings and filtrate are washed either twice with water (1.15 kg per wash), or optionally with a sequence of water (1.15 kg), 5% aqueous sodium carbonate (3.38 kg), and then twice with water (1.15 kg). After each wash, the reactor contents are briefly agitated, allowed to settle and the lower aqueous layer is then discarded. If the reaction results in an emulsion, brine (0.23 kg of water containing 0.08 kg NaCl) may be added to the first organic/water mixture, followed by agitating the reactor contents, allowing the solids to settle, discarding the lower aqueous layer, adding 1.15 kg water, agitating, allowing solids to settle and again discarding the lower aqueous layer. The organic phase is distilled in vacuo at no more than 50° C. (to LOD at 110° C. of no more than 10% and water content, by KF titration, no more than 0.3%), affording a yield of about 60–70% of the title compound as an oil of about 85–95% purity, exclusive of toluene.

Step 4

(R)-9-[2-(Diethylphosphonomethoxy)propyl]adenine

In a reactor containing an inert atmosphere, e.g., nitrogen, a mixture of adenine (1.0 kg), sodium hydroxide (11.8 g), (R)-1,2-propylene carbonate (0.83 kg), and N,N-dimethylformamide (6.5 kg) is heated to about 130° C. (typically about 125–138° C.) for about 18–30 hours until the reaction is complete as optionally monitored by area normalized HPLC showing no more than about 0.5% adenine remaining. The resulting mixture is cooled to about 25° C., typically about 20–30° C., and contains the stage I intermediate, (R)-9-(2-hydroxypropyl)adenine, which may precipitate out at this point. After cooling, lithium t-butoxide (3.62 kg), 2.0 M in tetrahydrofuran is added to the stage I intermediate, to produce the lithium salt of (R)-9-(2-hydroxypropyl)adenine in a mildly exothermic addition. The slurry is treated with diethyl p-toluenesulfonyloxymethylphosphonate (1.19 kg) and the mixture is heated to a temperature of about 32° C., typically about 30–45° C., and is stirred for at least about 2 hours (typically about 2–3 hours) during which time the mixture becomes homogeneous. More diethyl p-toluenesulfonyloxymethylphosphonate (1.43 kg) is added and the mixture is stirred at a temperature of about 32° C. (typically about 30–45° C.) for at least about 2 hours (typically about 2–3 hours). Additional lithium t-butoxide (0.66 kg), 2.0 M in tetrahydrofuran and diethyl p-toluenesulfonyloxymethylphosphonate (0.48 kg) are added twice more, each time followed by stirring the mixture, which is at a temperature of about 32° C. for at least about 2 hours. Reaction completion is optionally monitored by area normalized HPLC showing no more than about 10% of stage I intermediate remaining. If the reaction is incomplete, additional lithium t-butoxide (0.33 kg), 2.0 M in tetrahydrofuran and diethyl p-toluenesulfonyloxymethylphosphonate (0.24 kg) are added and the reaction mixture is maintained at a temperature of about 32° C. for at least about 2 hours to achieve reaction completion. The mixture is then cooled to about 25° C. (typically about 20–40° C.) and glacial acetic acid (0.5 kg) is then added. The resulting mixture is concentrated in vacuo at a final maximum mixture temperature of about 80° C. under about 29 in Hg vacuum. The residue is cooled to about 50° C. (typically about 40–60° C.) and water (1.8 kg) is added and the reaction is rinsed forward with additional water (1.8 kg). The solution is continuously extracted with dichloromethane (about 35 kg) for 12–48 hours with periodic additions of glacial acetic acid (0.2 kg) to the aqueous phase after about 5 hours and after about 10 hours of continuous extraction time. Extraction completion is optionally confirmed by area normalized HPLC as shown by no more than about 7% of (R)-9-[2-(diethylphosphonomethoxy)propyl]adenine remaining in the aqueous phase. The combined dichloromethane extracts are concentrated initially at atmospheric pressure then in vacuo at an extract temperature of no more than about 80° C. to give the title compound as a viscous orange oil. The title compound yield is about 40–45% by weight normalized HPLC and its purity is typically 60–65% by area normalized HPLC. The actual weight of the title compound after concentration is approximately 1.6 times the theoretical weight (or 3.8 times the expected yield). The additional observed weight is attributed to impurities and/or solvents remaining after the continuous extraction and concentration.

Step 5

(R)-9-[2-(Phosphonomethoxy)propyl]adenine, crude

Bromotrimethylsilane (1.56 kg) is added to a reactor containing a mixture of crude (R)-9-[2-(diethylphosphonomethoxy)propyl]adenine (1.0 kg calculated based on adenine input from step 4 above) and acetonitrile (0.9 kg) with cooling to maintain a temperature no higher than about 50° C. The lines are rinsed forward with acetonitrile (0.3 kg) and the mixture is refluxed at about 60–75° C. for about 2–4 hours with moderate agitation to avoid splashing the reactor contents. Reaction completion is monitored by area normalized HPLC showing no more than about 3% total of monoethyl PMPA and diethyl PMPA remaining. If the reaction is incomplete, additional bromotrimethylsilane (0.04 kg) is charged into the reactor and the reaction is refluxed for at least about 1 hour with moderate agitation. The volatiles are removed by distillation at no higher than about 70° C. initially at atmospheric pressure and then in vacuo (about 24–27 in Hg) at no higher than about 70° C. The reactor is then cooled to about 20° C. (typically about 15–25° C.) and water (1.9 kg) is added (exothermic addition) to the residue with the temperature maintained at no higher than about 50° C. The mixture is cooled to 20° C. and washed with dichloromethane (1.7 kg) by agitating for about 30 minutes. The isolated aqueous phase is then filtered through a 1 $\mu$m cartridge filter, diluted with water (3.2 kg), heated to about 40° C. (typically about 35–50° C.) and adjusted to pH about 1.1 (typically about 0.9–1.3) with aqueous sodium hydroxide (about 0.15 kg NaOH as a 50% solution) while the temperature is maintained at about 45° C. PMPA seed crystals are added to the mixture and the pH is adjusted to about 2.8 (typically about 2.6–3.0) with a 50% aqueous sodium hydroxide solution (about 0.15 kg NaOH required) while the temperature is maintained at about 45° C. (typically about 35–50° C.). The solution is cooled to about 22° C. (typically about 15–25° C.) over about 3–20 hours with slow to moderate agitation that avoids splashing the contents, during which time the product should precipitate, beginning at about 35° C. The pH of the slurry is adjusted to about 3.2 (typically about 3.1–3.3), usually using 50% aqueous sodium hydroxide or concentrated hydrochloric acid, if necessary. The slurry is cooled to approximately 5° C., typically about 0–10° C., and slowly agitated for at least about 3 hours in that temperature range. The solids are collected by filtration, washed sequentially with cold water (0.35 kg) and acetone (0.3 kg) giving crude PMPA as a damp solid typically of about 97% purity. The product is heated to about 50° C. and dried in vacuo to a water content of less than 10%. The quantity of diethyl PMPA is calculated from the quantity of adenine used in the preceding step of the synthesis (assuming 100% yield) and not from the net weight of the crude diethyl PMPA, which may contain other compounds.

Step 6

(R)-9-[2-(Phosphonomethoxy)propyl]adenine, pure

A suspension of the crude PMPA (1.00 kg corrected for water content) (Step 5 product) in water is heated to about 110° C. (typically about 95–110° C.) with moderate to high agitation until all solids dissolve, and the resulting solution is clarified by filtration while hot, rinsing forward using additional hot water (1 kg, about 95–110° C.). The filtrate is heated to 100° C. prior to cooling, first to about 30° C. (typically about 20–25° C.) over about 3–5 hours with slow agitation, then cooling is continued to about 10° C. (typically about 5–15° C.). After holding at about 10° C. for at least about 3 hours, the solids are collected by filtration and washed sequentially with cold water (1.5 kg, about 0–10° C.) and then acetone (1 kg). The wet cake is dried in vacuo at about 50° C. (typically about 40–60° C.) to a water content of about 5.9% (typically about 3.9–7.9%), affording pure PMPA monohydrate. The product purity is typically 98% or greater by both area normalized and weight normalized HPLC. If the chemical purity is unsatisfactory, the product may be repurified by a repeat of this step.

Optional recrystallization 0.75 g of PMPA (preparation A) was recrystallized from $H_2O$ (11.3 mL, 15:1 wt. ratio) by heating the suspension to 95–100° C. Upon cooling to room temperature, the crystallized PMPA was chilled in a freezer. After 3 h the crystals were filtered on a coarse frit fit with Tyvek™, the filter cake rinsed with ice-cold $H_2O$ and acetone, and air dried to constant weight to give a fluffy white solid (Preparation B). Recovery was 0.64 g (85.3%). HPLC showed 98.5–98.9% pure PMPA. No 14.7 min impurity was observed. Recrystallized liquors (1039-91-23) showed 71.4% pure PMPA with a major impurity at 4.8 min (26.9%), possibly solvent. 14.7 min impurity=0.05%.

Preparation B PMPA was recrystallized again from 9.6 mL (15:1 wt. ratio) $H_2O$ heated to 95–100° C. Upon cooling to room temperature, the crystallized PMPA was chilled in a freezer overnight. The PMPA was filtered through a coarse frit fit with Tyvek™ and the filter cake was rinsed with ice-cold $H_2O$ and acetone, then sucked dry to constant weight to afford a fluffy, white solid (Preparation C). Recovery was 0.52 g (81.3%). HPLC (JH52807, JH52810) showed 99.3–99.5% pure PMPA. The largest impurity at 19 min= 0.22%. Recrystallized liquors showed 64.9% pure PMPA with 0.01% 14.7 min impurity and 0.09% 19 min impurity.

Preparation C PMPA (0.50 g) was recrystallized from approximately 7.5 mL boiling $H_2O$ (15:1 wt. ratio). Upon cooling to room temperature, the PMPA was filtered on a coarse frit fit with Tyvek™. The filter cake was rinsed with ice-cold $H_2O$ and acetone then sucked to dryness to afford a fluffy white solid (Preparation D). The filtrate was also concentrated to afford a white solid (Preparation E). Recovery: Filter cake: 0.41 g (82%), Filtrate: 0.08 g=0.49 g combined (98%). HPLC analysis showed the filtrate (Preparation E) was 99.9% pure. PMPA prepared in this fashion is used to manufacture the compounds of this invention.

Step 7

Bis(POC)PMPA fumarate

In a reactor with an inert atmosphere, e.g., nitrogen, a mixture of 1-methyl-2-pyrrolidinone (4.12 kg), PMPA monohydrate (1.00 kg), triethylamine (0.996 kg), are agitated for about 15–45 min., typically about 30 min, and then chloromethyl-2-propyl carbonate (2.50 kg) is added and the mixture is heated to about 55–65° C., typically about 60° C. and agitated without splashing the contents for about 3–6 hours, typically about 4 hours, until the reaction is complete, as optionally indicated by HPLC (no more than 15% mono (POC)PMPA present). The mixture is diluted with isopropyl acetate (10.72 kg), cooled to about 15–30° C., typically about 25° C., as rapidly as possible, and while holding the reactor contents at a of about 15–30° C., typically at about 25° C., the mixture is agitated for about 20–60 minutes, typically about 30 minutes. The solids are removed by filtration and washed with isopropyl acetate (4.44 kg). The combined organic phases at about 15–30° C., typically about 25° C., are extracted twice with water (3.28 kg) using moderate agitation for about 1–10 min. to avoid forming an emulsion followed by allowing the phases to separate. The combined aqueous phases are back-extracted twice with isopropyl acetate (3.56 kg) (about 15–30° C., typically about 25° C.). All organic phases are combined and washed with water (2.20 kg) (about 15–30° C., typically about 25° C.) using moderate agitation for about 1–10 min. to avoid forming an emulsion, then the combined organic phases, which are at about 25–43° C., but at no more than 45° C., are concentrated in vacuo (about 26.5–28" Hg) to approximately 30% of the original volume (about 10–12 L/kg PMPA monohydrate). After a polishing filtration using an in-line 1 μm filter, the concentration of the organic phase is resumed at about 20–38° C., but no higher than 40° C. under a vacuum (about 28" Hg) until a pale yellow oil remains. The oil is dissolved in a warmed solution (about 45–55° C., typically about 50° C.) of fumaric acid (0.38 kg) in 2-propanol (6.24 kg) with vigorous agitation until solids dissolve, about 0.5–2.0 hours. The warm solution is then optionally filtered using an in-line 1 μm filter while minimizing cooling of the solution. The filtrate at about 34–50° C., typically at about 40° C., is agitated using the minimum agitation needed to obtain a homogenous solution. The resulting solution is cooled to about 30–33° C., typically about 32° C., over about 30 minutes using minimal agitation, optionally seeded with a small quantity of bis(POC)PMPA fumarate (about 100 mg), and cooled to about 12–18° C., typically about 15° C., over about 1–2 hours, typically over about 1 hour. Seed crystals may not be needed if crystal formation begins before seed crystals are added. Crystals may form over a range of about 12–33° C. as the solution is cooled. Crystallization will occur at lower temperatures if the solution is further chilled, e.g., to about –10° to about 11° C. Agitation is discontinued when crystal formation begins. The mixture is allowed to stand at about 15° C. for at least about 12 hours, typically about 12–30 hours. The resulting slurry is filtered (Tyvek) and the filter cake is washed with a premixed solution of isopropyl acetate (0.70 kg) in butyl ether (2.44 kg) (1:4 v/v). The filter cake, which is at no more than 40° C., is dried in vacuo for about 1 to 3 days and the dried product is optionally milled (Fitzmill M5A fitted with a 0.050" screen), affording bis(POC)PMPA fumarate as white, fine, powder-like crystals of about 97.0 to 99.5% purity.

Example 2

Preparation of Alkyl Chloromethylcarbonates

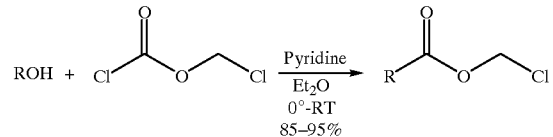

A solution of the alcohol (73 mmol) and chloromethyl chloroformate (Fluka, 6.23 mL, 70 mmol) in diethyl ether was cooled to 0° C. under argon. Pyridine (5.7 mL, 70 mmol) was added dropwise with stirring over 10 minutes. The solution was stirred at 0° C. for one hour, then allowed to warm to room temperature and stirred for three additional hours. The ether solution was filtered, washed with 1 M HCl, dried over MgSO$_4$, filtered, and concentrated on a rotary evaporator. Brief application of 0.1 torr vacuum gave the alkyl chloromethyl carbonates in 85–95% yields. Ethyl chloromethyl carbonate is somewhat volatile, and cannot be left on the rotovap too long, or the yield suffers (87–35%).

Example 3

Preparation of the Bis-ethyl Oxymethyl Carbonate of PMPA

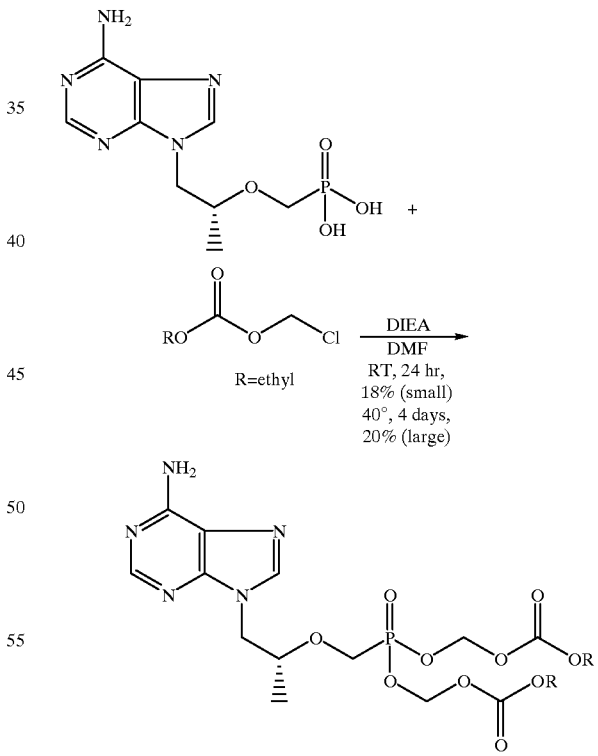

R=Et. Anhydrous PMPA (5 g, 16 mmol) and DIEA (Hunig's base) (11.5 mL, 66 mmol) were placed in anhydrous DMF (50 mL). The chloromethyl carbonate (49 mmol) was then added and the suspension heated to 50° C. under argon with rapid mechanical stirring. After 1 hr the reaction was clear and the temperature was lowered to 35° C. and the reaction stirred for 48 hr. The DMF was removed on a rotary evaporator, and the reaction partitioned between CH₂Cl₂ and water. The CH₂Cl₂ layer was dried over magnesium sulfate, filtered, and concentrated on a rotary evaporator. The residue was taken up in methylene chloride and applied to a silica gel column (150 g SiO₂). It was eluted with 500 mL each 0,3,6,9,2,15,18% (v/v) isopropanol in methylene chloride, and then with 2000 mL 21%. Appropriate fractions were pooled and evaporated to give the desired product.

Example 4

Preparation of the Bis-n-butyl Oxymethyl Carbonate of PMPA

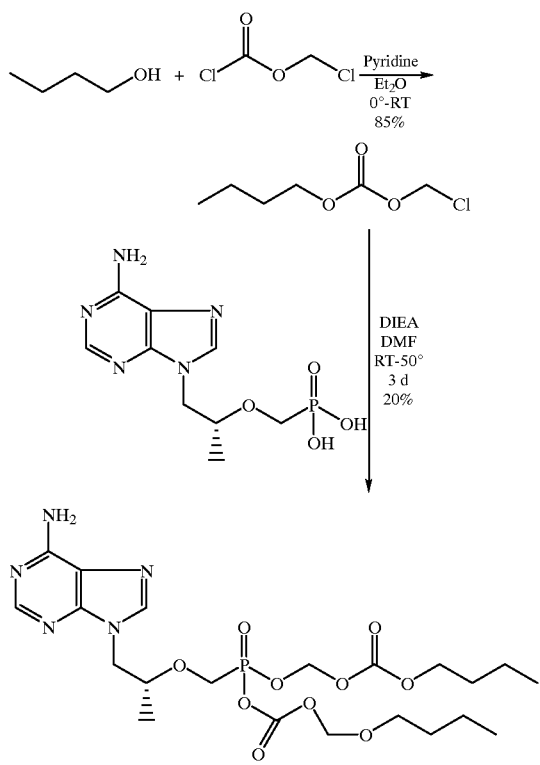

Butyl chloromethyl carbonate

A solution of butyl alcohol (50 mmol) and chloromethyl chloroformate (4.5 mL, 50 mmol) in diethyl ether (200 mL) was cooled to 0° C. under argon. Pyridine (5.7 mL, 50 mmol) was added dropwise with stirring over 5 min. The solution was stirred at 0° C. for 15 min, then allowed to warm to room temperature and stirred for three additional hours. The ether solution was filtered, washed with 1 M HCl, and then twice with water, dried over MgSO₄, filtered, and concentrated on a rotary evaporator to give butyl chloromethyl carbonate (7 g, 85%).

Dibutyl PMPA carbonate

Anhydrous PMPA (4 g, 13 mmol) and DIEA (10.5 mL, 60 mmol) were placed in anhydrous DMF (40 mL). Butyl chloromethyl carbonate (40 mmol) was then added and the suspension stirred at room temperature for 48 hr. The reaction was then heated to 50° C. for 18 hr. The DMF was removed on a rotary evaporator, and the reaction partitioned between CH₂Cl₂ (250 mL) and water (250 mL). The CH₂Cl₂ layer was washed once with saturated aqueous NaHCO₃, dried over magnesium sulfate, filtered, and concentrated on a rotary evaporator. The residue was taken up in methylene chloride and applied to a silica gel column (150 g SiO₂). It was eluted with 1000 mL CH₂Cl₂, 500 mL each 0,3,6,9,12, 15,18% (v/v) isopropanol in methylene chloride, and then with 2000 mL 21% isopropanol in methylene chloride. Appropriate fractions were pooled and evaporated to give the desired product.

Example 5

Synthesis of Bis-n-propyl Oxyethyl Carbonate of PMPA

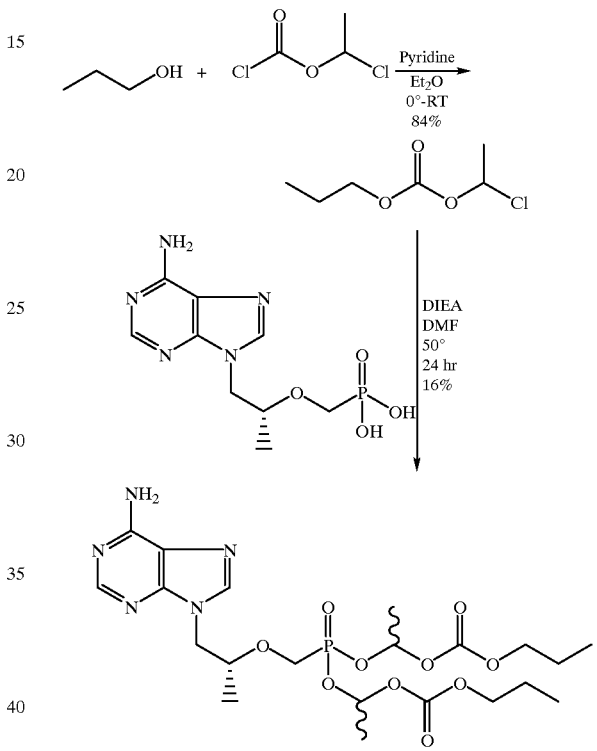

Preparation of propyl-1-chloroethyl carbonate

A solution of propyl alcohol (70 mmol) and 1-chloroethyl chloroformate (7.6 ml, 70 mmol) in diethyl ether (200 mL) was cooled to 0° C. under argon. Pyridine (70 mmol) was added dropwise with stirring over 5 min. The solution was stirred at 0° C. for 15 min, then allowed to warm to room temperature and stirred for 4.5 additional hours. The ether solution was filtered, washed with 1M HCl, and then twice with water, dried over MgSO₄, filtered, and concentrated on a rotary evaporator to give propyl-1-chloroethyl carbonate (9.8 g, 84%). Anhydrous PMPA (0.3 g, 1 mmol) and DIEA (0.7 mL, 4 mmol) were placed in anhydrous DMF (2 mL) under argon. Propyl-1-chloroethyl carbonate (3 mmol) was then added and the suspension stirred at 50° C. for 20 hr. The DMF was removed on a rotary evaporator, and the reaction partitioned between CH₂Cl₂ and water. The CH₂Cl₂ layer was dried over magnesium sulfate, filtered, and concentrated on a rotary evaporator. The residue was taken up in methylene chloride and applied to a silica gel column (25 g SiO₂). It was eluted with 100 mL CH₂Cl₂, 50 mL each 3,6,9,12, 15,18% (v/v) isopropanol in methylene chloride, and then with 200 mL 21% isopropanol in methylene chloride. Appropriate fractions were pooled and evaporated to give the desired product.

Example 6

Synthesis of Chloromethyl Isopropyl Carbonate

To a cold solution (approximately 10° C.) of chloromethylchloroformate (65 mL) in diethyl ether (1.4 L) was added isopropanol (56 mL) followed by a dropwise addition of pyridine (60 mL). After the addition the cold bath was removed and the reaction mixture was stirred for 18 h. The reaction mixture was poured into a separation funnel containing cold water (100 mL). The ether layer was separated and washed with water (100 mL×2) and then dried over $Na_2SO_4$. Evaporation of the solvent furnished the chloromethyl isopropyl carbonate (107 g, 95%). Chloromethyl isobutyl carbonate, chloromethyl neopentyl carbonate, chloromethyl tert butyl carbonate and chloromethyl 3-pentyl carbonate are prepared in a similar manner.

Example 7

Synthesis of Bis Isopropyl Oxymethyl Carbonate of PMPA

To a stirred suspension of PMPA (7.26 g, 0.026 mmol) in DMF (100 mL) at 50° C. was added $Et_3N$ (10.8 mL, 0.0778 mmol). The reaction mixture became homogeneous and chloromethyl isopropyl carbonate (12.1 g, 0.0778 mol) was added to the reaction mixture and stirring continued at 50° C. (oil bath temperature) for 20 h. The solvents were removed under reduced pressure and the crude was chromatographed on a silica gel column. Elution with 10% isopropanol in $CH_2Cl_2$ removed all the non polar impurities. Further elution with the same solvent mixture furnished the prodrug, 1.3 g (approximately 10%).

Example 8

Synthesis of Bis Isopropyl Oxymethyl Carbonate of PMPA

To a stirred suspension of PMPA (1 g, 3.57 mmol) in DMF (5 mL) were added $Et_3N$ (1.5 mL, 10.71 mmol) and chloromethyl isopropyl carbonate (1.67 g, 10.71 mmol). The reaction mixture was then diluted with ethyl acetate (100 mL) and filtered. The filtrate was washed with water (2×50 mL) and finally with brine (10 mL). The crude obtained after removal of the solvent was dried under vacuum. The resulting oil was dissolved in isopropanol (7 mL) and critic acid (260 mg) was added. The mixture was stirred for 16 h at room temperature and then cooled to 0° C. The product was crystallized and crystals were filtered and dried. Mp 76–81° C.

Example 9

Preparation of chloromethylcarbamates

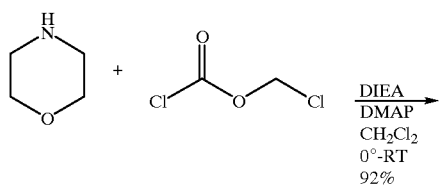

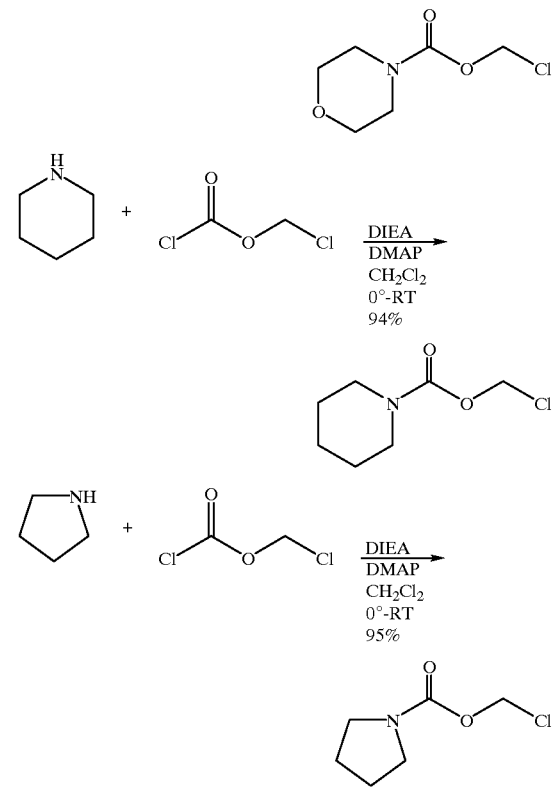

A solution of the amine (24 mmol), DIEA (30 mmol), and DMAP (0.5 mmol) in methylene chloride (5 mL) was added dropwise to a cold (0° C.) solution of chloromethyl chloroformate (25 mmol) in methylene chloride (45 mL) over 5 min. The solution was allowed to warm to room temperature over 1.5 hr. The solution was diluted into ethyl acetate (100 mL), and washed with saturated sodium bicarbonate, 1 M HCl, and saturated sodium chloride. It was then dried over magnesium sulfate, filtered, and evaporated to give the desired chloromethyl carbamate.

Example 10

Synthesis of Bis Morpholino Oxymethyl Carbamate of PMPA

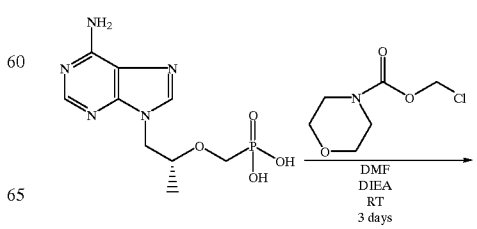

-continued

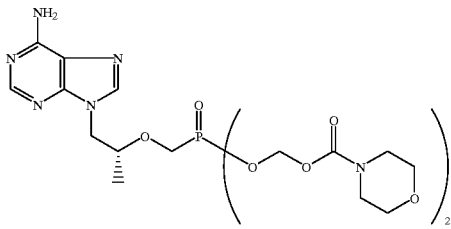

Anhydrous PMPA (0.3 g, 1 mmol) and DIEA (1 mL, 6 mmol) were placed in anhydrous DMF (2 mL). Chloromethyl morpholino carbamate (3 mmol) was then added and the suspension stirred at room temperature for 3 days. The reaction was partitioned between $CH_2Cl_2$/isopropanol and 0.1 M citrate buffer (pH 6). The $CH_2Cl_2$ layer was washed with water, dried over magnesium sulfate, filtered, and concentrated on a rotary evaporator. The residue was taken up in methylene chloride and applied to a silica gel column (5 g $SiO_2$). It was eluted with 25 mL each 0,3,6,9,12,15,18% (v/v) isopropanol in methylene chloride, and then with 100 mL 21% isopropanol in methylene chloride. Appropriate fractions were pooled and evaporated to give the desired product.

Example 11

Synthesis of Bis Piperidino Oxymethyl Carbamate of PMPA

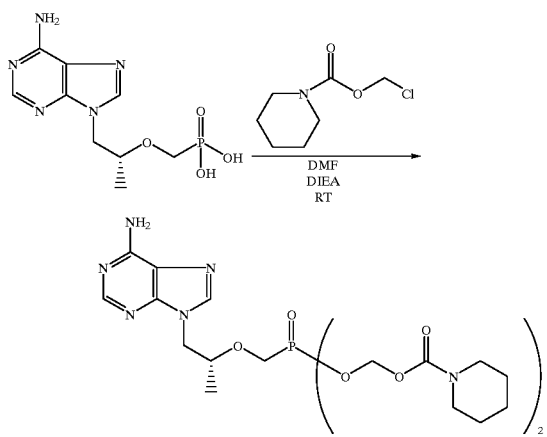

Anhydrous PMPA (0.3 g, 1 mmol) and DIEA (0.7 mL, 4 mmol) were placed in anhydrous DMF (2mL). Chloromethyl piperidino carbamate (3 mmol) was then added and the suspension stirred at room temperature for 3 days. More DIEA (4 mmol) and chloromethyl piperidino carbamate (100 μl) were added, and the reaction stirred for 27 hr. The reaction was partitioned between $CH_2Cl_2$/isopropanol and 0.1 M citrate buffer (pH 6). The $CH_2Cl_2$ layer was dried over magnesium sulfate, filtered, and concentrated on a rotary evaporator. The residue was taken up in methylene chloride and applied to a silica gel column (5 g $SiO_2$). It was eluted with 25 mL each 0,3,6,9,12,15,18% (v/v) isopropanol in methylene chloride, and then with 100 mL 21% isopropanol in methylene chloride. Appropriate fractions were pooled and evaporated to give the desired product.

Example 12

Other Carbamate Intermediates

To a solution of chloromethylchloroformate (4.16 mL) in $CH_2Cl_2$ (30 mL) were added tert butyl amine (4.9 mL) and proton sponge (10 g). The reaction mixture was stirred for 18 h and then it was poured into a separation funnel containing cold 0.5N HCl (100 mL). The $CH_2Cl_2$ layer was separated and washed with water (100 mL×2) and then dried over $Na_2SO_4$. Evaporation of the solvent furnished the chloromethyl tert butyl carbamate (8 g). Chloromethyl n-butyl carbamate (R=n-butyl) and chloromethyl dimethyl carbamate (R=Me) were prepared in the same fashion.

Example 13

Other Oxymethyl Alkyl Carbamate Prodrugs of PMPA

To a stirred suspension of PMPA (4.51 g, 0.016 mmol) in DMF (50 mL) was added $Et_3N$ (6.7 mL, 0.048 mmol). The reaction mixture became homogeneous and chloromethyl tert butyl carbamate (8 g, 0.048 mol) was added to the reaction mixture and stirring continued at room temperature for 3 days. The solvents were removed under reduced pressure and the crude was chromatographed on a silica gel column. Elution with 10% isopropanol in $CH_2Cl_2$ removed all the less polar impurities. Further elution with the same solvent mixture furnished the prodrug (1.25 g). The n-butyl and methyl carbamates were prepared in the same fashion from the intermediates of the preceding example.

Example 14

Chemical Stability of PMPA Carbonates

The solution stability of PMPA carbonates was studied at pH 7.4 at 37° C. in 10 mM buffer ($NaH_2PO_4$ and $Na_2HPO_4$) with the total ionic strength adjusted to 0.15 M with KCl. The assays were performed by adding 200 μl of a PMPA carbonate stock solution (about 1 mg/mL in DMSO) to 10 mL of pre-equilibrated buffer at 37° C. Samples were removed at specific times points and analyzed by HPLC. The chemical t ½ is expressed in terms of the number of hours required to hydrolyze 50% of the carbonate at the specified pH.

Example 15

Oral Bioavailability of PMPA and PMPA Carbonates in Beagle Dogs

PMPA (9-[(R)-2-(phosphonomethoxy)propyl]adenine) and PMPA carbonates were examined to determine the effect of dose on the pharmacokinetics of PMPA in beagle dogs, in particular the bioavailability of PMPA following oral administration to beagle dogs.

PMPA monohydrate was synthesized by Gilead Sciences. Tetrabutylammonium hydrogen phosphate (TBAHP) was obtained from Fluka (Ronkonkoma, N.Y.). Acetonitrile was obtained from Baxter (Muskegon, Mich.). Dibasic potassium phosphate, monobasic potassium phosphate, and sodium acetate trihydrate were obtained from Mallinckrodt (Paris, Ky.). Chloroacetaldehyde and trifluoroacetic acid (TFA) were from Aldrich (Milwaukee, Wis.).

The intravenous formulations used as standards were isotonic aqueous solutions containing 50 mg/mL PMPA. Compound was added to 10 mL of WFI (water for injection from Abbott Laboratory) and 1N NaOH was added to adjust the pH to 7.4. The solutions were diluted to 15 mL with WFI and sterile filtered with a 0.2 μm filter. The PMPA dose was 10 mg/kg (0.2 mL/kg).

The intravenous formulation for a 1 mg/kg dose was prepared as described above except only 75 mg of PMPA was added to WFI and the final concentration was 5 mg/mL. The dose was 1 mg/kg (0.2 mL/kg). Oral formulation of carbonates were prepared in 20–40% PEG 400/50 mM citric acid and were adjusted to pH 2.2. Doses ranged from 6.2–10 mg eq of PMPA/kg and are shown in Table 1.

Two groups of five adult male beagle dogs were used. The mean body weight at the time of the first dose was 9.6±0.4 Kg (range 9.2–10.2). The dogs were fasted 12–18 hours prior to dosing and until 6 hours post-dose. For pentagastrin pretreatment, dogs were given a single intramuscular injection of pentagastrin (Peptavlon 0.25 mg/mL, Ayerst Laboratories, Inc., Philadelphia, Pa.) at a dose of 6 µg/kg, 20 minutes prior to dosing. Water was provided ad lib.

Each formulation was administered as a single dose to five male beagle dogs. Individual vials of each formulation were provided for each animal. The intravenous formulation was administrated via a cephalic vein. The oral suspension was administered by gavage, followed by two 10 mL water washes. At least one week washout period was allowed between administrations.

Blood samples (4.0 mL) were collected by direct jugular access from each animal into heparinized tubes. Animals remained conscious throughout the sample collection period. Blood was processed immediately for plasma by centrifugation at 2000 rpm for 10 minutes. Plasma samples were frozen and maintained at ≦−20° C. until analyzed.

Urine samples were collected over 0–24 and 24–48 hours time periods. Urine samples from 0–24 and 24–48 hours were divided into aliquots and mixed based on the volume collected and analyzed to determine amount of PMPA recovered from urine during 0–48 hours.

PMPA in Plasma and Urine was determined as follows. PMEA (9-(2-phosphono-methoxyethyl)adenine; adefovir) was used as the internal standard for both analyses. The total concentration of PMPA in dog plasma or urine samples was determined by derivatizing PMPA and PMEA with chloroacetaldehyde to yield a highly fluorescent $N^1$, $N^6$-ethenoadenine derivative as described (Russell, J. et al. (1991) Determination of 9-[(2-Phosphonylmethoxy)-ethyl] Adenine in Rat Urine by High-Performance Liquid Chromatography with Fluorescence Detection. *J. Chromatogr. (Netherlands)*, 572, 321–326).

Sample Extraction for PMPA in plasma and urine was performed as follows. Plasma (200 µL) and internal standard (20 µL of 10 µg/mL PMEA providing a final PMEA concentration of 1 µg/mL) were mixed with 400 µL of acetonitrile containing 0.1% TFA to precipitate protein. Samples were then evaporated to dryness under reduced pressure at room temperature (Savant SpeedVac). Urine samples (20 µL) and internal standard (30 µL of 10 µg/mL PMEA providing a final PMEA concentration of 1.5 µg/mL) were used directly for derivatization without drying.

The samples were derivatized for analysis as follows. Dried plasma samples or urine samples were reconstituted or mixed in 200 µL derivatization cocktail (0.34% chloroacetaldehyde in 100 mM sodium acetate, pH 4.5), vortexed, and centrifuged for 10 minutes at 14,000 rpm in an Eppendorf Centrifuge 5402. Supernatant was then transferred to a clean screw capped tube and incubated at 95° C. for 40 minutes. Derivatized samples were quenched on ice and evaporated to dryness under reduced pressure at room temperature. Dried samples were reconstituted in 200 µL Mobile Phase A (see below), vortexed and centrifuged for 10 minutes at 14,000 rpm in an Eppendorf Centrifuge 5402. The supernatant was then transferred to autoinjector vials for HPLC analysis.

The plasma and urine samples were analyzed for HPLC with Fluorescence Detection as follows. The HPLC system comprised a Model P4000 solvent delivery system with a Model AS3000 autoinjector and a Model F2000 Fluorescence detector (Thermo Separation, Jan Jose, Calif.). The column was a Zorbax RX-C18 (5 µm, 150×4.6 mm) (MAC-MOD, Chadds Ford, N.Y.) equipped with a Brownlee RP-18 Newguard guard column (7 µm, 15×3.2 mm) (Alltech, Deerfield, Ill.). The mobile phases used were: A, 2% acetonitrile in 25 mM potassium phosphate buffer with 5 mM TBAHP, pH 6.0; B, 65% acetonitrile in 25 mM potassium phosphate buffer with 5 mM TBAHP, pH 6.0. The flow rate was 1.5 mL/min and the column temperature was maintained at 35° C. by a column oven. The gradient profile was 100% A until 2.0 min, then a linear gradient to 100% B by 13.0 minutes, returning immediately to 100% A. Detection was by fluorescence with excitation at 236 nm and emission at 420 nm, and the injection volume was 50 µL. Total cycle time between injections was 25 min. Data was acquired and stored by a Peak Pro data acquisition system (Beckman, Palo Alto, Calif.).

The pharmacokinetic parameters for intravenous and oral formulations of PMPA and PMPA carbonates were assessed using non-compartmental methods. Intravenous data were analyzed using PCNONLIN Model 201 (5); oral data were analyzed using Model 200. Additional pharmacokinetic parameters were calculated as follows:

CL=Dose/AUC (0–∞); where CL is the total plasma clearance.

Vss=CL×MRT; where Vss is the apparent volume of distribution at steady state. MRT is the mean residence time. The initial plasma concentration (Co) was determined by extrapolation of log transformed data to zero time. Bioavailability was expressed as $$\text{Bioavailability}(\%) = \frac{AUC(0 - \infty) \text{oral or prodrug}}{AUC(0 - \infty) \text{intravenous}} \times 100$$

Urinary recovery was expressed as $$\text{UrinaryRecovery}(\%) = \frac{\text{amount (mg) of } PMPA \text{ in urine (0-48 hr)}}{\text{amount (mg) of } PMPA \text{ dosed}} \times 100$$

Oral bioavailability of t-Bu, 3-pentyl, isopropyl, Et carbonate parameters were compared by unpaired t-tests (StatView® Version 4.0, Software for the Statistical Analysis. Abacus Concepts, Inc., Berkeley, Calif.). A P value of ≦0.05 was considered significant.

Biological t1/2

Dog liver was obtained fresh from Pharmakon USA (Waverly, Pa.). Liver homogenate was prepared following a standard protocol. Dog liver was rinsed three times with ice-cold 50 mM sodium/potassium phosphate buffer and homogenized with a Tekmar Tissumizer homogenizer (VWR 33995-060). The homogenate was centrifuged at 9000 g (11,000 rpm for Eppendorf Centrifuge 5402; Brinkmann Instruments, Westbury, N.Y.) at 4° C. for 20 minutes. The supernatant was designated as the S9 fraction. The concentration of protein in the S9 fraction was determined using a Bio-Rad Protein Assay Kit II, with bovine serum albumin as standard. Esterase activity was determined using o-nitrophenyl butyrate as substrate and activity was calculated based on the increase in absorbance at 420 nm after a 1 min incubation. The homogenates were stored as 1.0 mL aliquots at −70° C.

Intestinal Homogenate

Dog intestinal segments (jejunum/ileum) were obtained fresh from Pharmakon USA (Waverly, Pa.) and intestinal homogenate was prepared as described for liver. The intestinal homogenates were stored as 1.0 mL aliquots at −70° C.

Human intestinal homogenate (S9) was obtained from Keystone Skin Bank (Exton, Pa.) at concentration of 20 mg protein/mL.

Study Design

Enzymatic stability studies involving plasma and intestinal homogenate were performed with 90% biological fluids.

Stability Measurement

One blank (drug free) incubation was performed for each biological fluid. All biological fluid tubes (open) were pre-incubated without PMPA prodrugs in a shaker bath at 37° C. and 100 oscillation/min for 5 minutes. PMPA prodrugs was added to the test incubations (final concentration: 20 μg/mL), mixed and maintained at 37° C. and 100 oscillations/min. Samples (50 μL) were withdrawn at 0, 30, and 60 minutes and the reaction was quenched with 100 μL of 0.1% trifluoroacetic acid (TFA) in acetonitrile. Quenched samples were centrifuged for 5 minutes at 14,000 rpm in an Eppendorf Centrifuge 5402, and the supernatant was used for HPLC analysis.

Calculations

For each incubation, the observed rate constant for degradation was calculated by plotting the log of the peak area of PMPA prodrugs versus time of incubation (min). The slope was the observed rate constant ($k_{obs}$). The half life was calculated according to the following equation:

$$t1/2(\text{min}) = \frac{0.693}{k_{obs}}$$

If the observed rate constant for degradation was less than 0.01 min$^{-1}$, then t1/2 was expressed as stable.

The results of the beagle study are shown below in Table 1.

TABLE 1

PMPA Prodrug Summary

| PRODRUGS CARBONATES (Dose mg e.g. PMPA/Kg) | Chemical t1/2 (hr) pH 7.4 | pH 2.0 | Log PC pH 7.4 | Biological t1/2 (min) (Dog) (Human) Intestine | Plasma | Liver | % of PMPA IV (1 mg/kg) AUC PMPA | Monoester | Prodrug | other | Urinary Recovery (% as PMPA) |
|---|---|---|---|---|---|---|---|---|---|---|---|

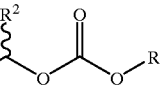

| Bis-t-Bu COM PMPA | 0.4 | 0.4 | 1.93 | 26.6 (<5) | 21.2 | 14.9 | 36.2 ± 6.76 | — | — | — | 34.9 ± 14.0 |

R = ; R² = H (6:45)

| Bis-IBu COM PMPA | 9 | >150 | 2.0 | 15 (<5) | <5 | <5 | 24.5 ± 8.82 | — | — | — | TBD |

R = ; R² = H (7.2)

| Bis-neoPentylCOM PMPA | 6 | >150 | 3.2 | <5 (<5) | <5 | <5 | 18.9 ± 6.57 | — | — | — | TBD |

R = ; R² = H (7.7)

| Bis-nBuCOM PMPA | 6 | >150 | 2.7 | <5 (<5) | <5 | <5 | 17.3 ± 2.57 | — | — | — | TBD |

R = ; R² = H (8.0)

| Bis-3-PentylCOM PMPA | 8 | <150 | 3.2 | 30 (<5) | 15 | <5 | 33.9 ± 9.02 | — | — | — | TBD |

TABLE 1-continued

PMPA Prodrug Summary

| PRODRUGS CARBONATES (Dose mg e.g. PMPA/Kg) | Chemical t1/2 (hr) pH 7.4 | pH 2.0 | Log PC pH 7.4 | Biological t1/2 (min) (Dog) (Human) Intestine | Plasma | Liver | % of PMPA IV (1 mg/kg) AUC PMPA | Monoester | Prodrug | other | Urinary Recovery (% as PMPA) |
|---|---|---|---|---|---|---|---|---|---|---|---|
| R = 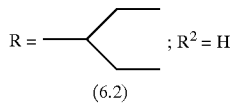 ; R² = H (6.2) | | | | | | | | | | | |
| Bis-EtCOM PMPA | 7 | | 0.6 | 23.3 (<5) | 16.6 | <5 | 29.3 ± 3.4 | −2 | 0 | 0 | TBD |
| R = 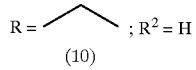 ; R² = H (10) | | | | | | | | | | | |
| Bis-EtCOE PMPA | 4 | | | 62.4 | 42.6 | <5 | NA | NA | NA | NA | NA |
| R = 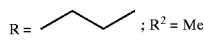 ; R² = Me | | | | | | | | | | | |
| Bis-Methoxy diMeCOM PMPA | 9 | | 1.0 | Stable (30) | 77.6 | 100.8 | NA | NA | NA | NA | NA |
| R = 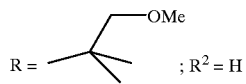 ; R² = H | | | | | | | | | | | |
| Bis-isopropylCOM PMPA | 9 | | 1.25 | 52.6 (<5) | 20.5 | <5 | 35.8 ± 14.7 | 3.1 ± 0.67 | 0 | 0 | TBD |
| R = 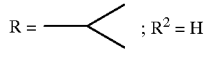 ; R² = H (9) | | | | | | | | | | | |
| 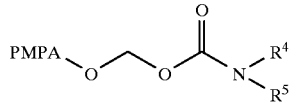 | | | | | | | | | | | |
| Bis-t-BuNCOM PMPA | 0.4 | | | 107.5 | 99.5 | 166.5 | 8.86 ± 2.38 | — | 9.97 ± 2.52 | — | |
| R⁴ = H, R⁵ = 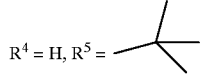 (6.4) | | | | | | | | | | | |
| Bis-n-proCOM PMPA | 13 | | | Stable | Stable | 76 | NA | NA | NA | NA | NA |
| R⁴ = R⁵ = 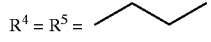 | | | | | | | | | | | |

Example 16

Antiviral Activity of PMPA and PMPA Carbonates in Tissue Culture

PMPA (9-[(R)-2-(phosphonomethoxy)propyl]adenine) and PMPA carbonates were examined to determine their activity against HIV-1. The antiviral activity of the carbonates 5a, 5c–g against HIV-1(IIIB) was determined in MT-2 cells and the $IC_{50}$ (50% inhibitory concentration) and $CC_{50}$ (concentration to kill 50% of the cells) values were measured. The carbonate prodrugs exhibited increased potency (about 2.5–500 fold) compared to PMPA (Table 2). Although cytotoxicity of the prodrugs also increased, the selectivity indices were improved compared to PMPA. The increased activity can be attributed to increased cellular uptake of the prodrugs followed by effective intracellular conversion to PMPA, which undergoes subsequent phosphorylation to the antivirally active diphosphate metabolite. The t-butyl carbonate 5d exhibited only 2.5 fold increased activity over PMPA with reduced selectivity possibly due to chemical instability. The antiviral activity data indicate good permeability of alkyl methyl carbonate prodrugs into cells, possibly due to their increased lipophilicity. The partition coefficient values support this hypothesis, will all prodrugs being more lipophilic (logP=0.6–3.2) compared to PMPA (logP=–2.5).

2

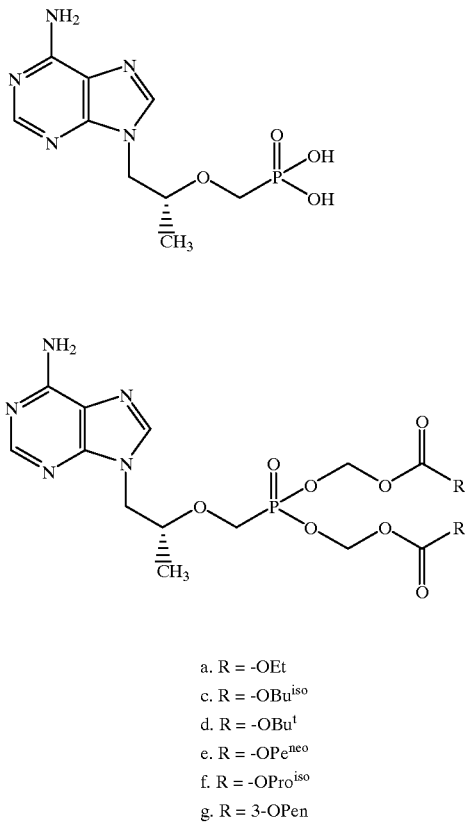

a. R = -OEt
c. R = -OBu$^{iso}$
d. R = -OBu$^t$
e. R = -OPe$^{neo}$
f. R = -OPro$^{iso}$
g. R = 3-OPen

TABLE 2

Antiretroviral activity of PMPA and PMPA prodrugs against HIV-1.

| compound | IC$_{50}$$^a$ ($\mu$M) | CC$_{50}$$^b$ ($\mu$M) | SI$^c$ |
|---|---|---|---|
| 2 | 0.5 | 250 | 500 |
| 5a | 0.002 | 40 | 20000 |
| 5c | <0.001 | 30 | 30000 |
| 5d | 0.2 | 10 | 50 |
| 5e | <0.001 | 3 | 3000 |
| 5f | 0.003 | 50 | 16600 |
| 5g | <0.001 | 40 | 40000 |

$^a$IC$_{50}$ - 50% inhibitory concentration;
$^b$CC$_{50}$ - Concentration to kill 50% of the cells;
$^c$SI -Selectivity Index (CC$_{50}$/IC$_{50}$);
n.d. - not determined;
DMSO used as control.

We claim:
1. A compound having formula (1a)

(1a)

wherein
Z is independently —OC(R$^2$)$_2$OC(O)X(R)$_a$, an ester, an amidate or —H, but at least one Z is —OC(R$^2$)$_2$OC(O)X(R)$_a$;
A is the residue of an antiviral phosphonomethoxy nucleotide analog;
X is N or O;
R$^2$ independently is —H, C$_1$–C$_{12}$ alkyl, C$_5$–C$_{12}$ aryl, C$_2$–C$_{12}$ alkenyl, C$_2$–C$_{12}$ alkynyl, C$_7$–C$_{12}$ alkenylaryl, C$_7$–C$_{12}$ alkynylaryl, or C$_6$–C$_{12}$ alkaryl, any one of which is unsubstituted or is substituted with 1 or 2 halo, cyano, azido, nitro or —OR$^3$ in which R$^3$ is C$_1$–C$_{12}$ alkyl, C$_2$–C$_{12}$ alkenyl, C$_2$–$_{C12}$ alkynyl or C$_5$–C$_{12}$ aryl;
R is independently —H, C$_1$–C$_{12}$ alkyl, C$_5$–C$_{12}$ aryl, C$_2$–C$_{12}$ alkenyl, C$_2$–C$_{12}$ alkynyl, C$_7$–C$_{12}$ alkyenylaryl, C$_7$–C$_{12}$ alkynylaryl, or C$_6$–C$_{12}$ alkaryl, any one of which is unsubstituted or is substituted with 1 or 2 halo, cyano, azido, nitro, —N(R$^4$)$_2$ or —OR$^3$, where R$^4$ independently is —H or C$_1$–C$_8$ alkyl, provided that at least one R is not H; and
a is 1 when X is O, or 1 or 2 when X is N;
with the proviso that when a is 2 and X is N, (a) two N-linked R groups can be taken together to form a carbocycle or oxygen-containing heterocycle, (b) one N-linked R additionally can be —OR$^3$ or (c) both N-linked R groups can be —H;
and the salts, hydrates, tautomers and solvates thereof.
2. The compound of claim 1 having formula (1)

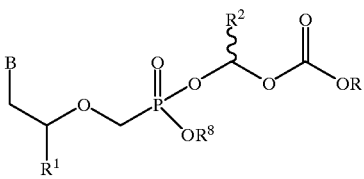

(1)

wherein B is guanin-9-yl, adenin-9-yl, 2,6-diaminopurin-9-yl, 2-aminopurin-9-yl or their 1-deaza, 3-deaza, or 8-aza analogs, or B is cytosin-1-yl;
R is independently —H, C$_1$–C$_{12}$ alkyl, C$_5$–C$_{12}$ aryl, C$_2$–C$_{12}$ alkenyl, C$_2$–C$_{12}$ alkynyl, C$_7$–C$_{12}$ alkenylaryl, C$_7$–C$_{12}$ alkynylaryl, or C$_6$–C$_{12}$ alkaryl, any one of which is unsubstituted or is substituted with 1 or 2 halo, cyano, azido, nitro or —OR$^3$ in which R$^3$ is C$_1$–C$_{12}$ alkyl, C$_2$–C$_{12}$ alkenyl, C$_2$–C$_{12}$ alkynyl or C$_5$–C$_{12}$ aryl;
R$^1$ is hydrogen, —CH$_3$, —CH$_2$OH, —CH$_2$F, —CH=CH$_2$, or —CH$_2$N$_3$, or R$^1$ and R$^8$ are joined to form —CH$_2$—;
R$^2$ independently is hydrogen or C$_1$–C$_6$ alkyl; and
R$^8$ is hydrogen or —CHR$^2$—O—C(O)—OR, or R$^8$ is joined with R$^1$ to form —CH$_2$—;
and the salts, hydrates, tautomers and solvates thereof.
3. The compound of claim 2 wherein R$^2$ is —H.
4. The compound of claim 3 wherein R$^1$ is —CH$_3$.
5. The compound of claim 1 wherein R$^2$ is —H.
6. The compound of claim 1 wherein one R$^2$ is —CH$_3$ and the other R$^2$ is H.

7. The compound of claim 1 wherein $R^3$ is $C_1$–$C_6$ alkyl or phenyl.

8. The compound of claim 1 wherein $R^3$ is —$CH_3$ or —$C_2H_5$.

9. The compound of claim 1 wherein X is O.

10. The compound of claim 1 wherein X is N and one $R^3$ is H.

11. The compound of claim 4 wherein the compound is enriched or resolved at the carbon atom chiral center linked to $R^1$.

12. The compound of claim 4 wherein at least about 90% of the compound is in the (R) configuration at the $R^1$ site.

13. The compound of claim 12 wherein B is adenin-9-yl.

14. The compound of claim 13 wherein each R is ethyl.

15. The compound of claim 13 wherein each R is isopropyl.

16. The compound of claim 13 wherein each R is 3-pentyl or neopentyl.

17. The compound of claim 13 wherein each R is t-butyl or isobutyl.

18. The compound of claim 4 wherein B is 2,6-diaminopurin-9-yl.

19. The compound of claim 3 wherein $R^1$ is H.

20. The compound of claim 19 wherein B is adenin-9-yl.

21. The compound of claim 4 wherein R is $C_1$–$C_{12}$ alkyl.

22. The compound of claim 3 wherein $R^1$ is —$CH_2OH$.

23. The compound of claim 22 wherein B is cytosin-1-yl.

24. The compound of claim 22 wherein at least about 90% of the compound is in the (S) configuration at the $R^1$ site.

25. A method comprising orally administering to a patient infected with virus or at risk to viral infection a therapeutically effective amount of a compound of claim 1.

26. A method for preparing a compound of formula (1a) of claim 1 comprising reacting the diacid of a phosphonomethoxy nucleotide analog with L—$CH(R^2)OC(O)X(R)_n$ wherein L is a leaving group.

27. A method for preparing a compound of formula (1) of claim 2 comprising reacting a compound of formula (6)

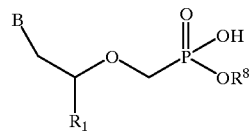

with L—$CHR^2$—O—C(O)—OR and recovering a compound of formula (1), wherein B is guanin-9-yl, adenin-9-yl, 2,6-diaminopurin-9-yl, 2-aminopurin-9-yl or their 1-deaza, 3-deaza, or 8-aza analogs, or B is cytosin-1-yl;

$R^1$ is hydrogen, —$CH_3$, —$CH_2OH$, —$CH_2F$, —CH=$CH_2$, —$CH_2N_3$ or $R^1$ and $R^8$ are joined to form —$CH_2$—; and $R^8$ is hydrogen, —$CHR^2$—O—C(O)—OR or $R^8$ is joined with $R^1$ to form —$CH_2$—; and $R^2$ is H, $C_1$–$C_{12}$ alkyl, aryl, alkenyl, alkynyl, alkyenylaryl, alkynylaryl, alkaryl, arylalkynyl, arylalkenyl or arylalkyl which is unsubstituted or is substituted with halo, azido, nitro or $OR^3$ in which $R^3$ is $C_1$–$C12$ alkyl;

R is independently H, $C_1$–$C_{12}$ alkyl, aryl, alkenyl, alkynyl, alkenylaryl, alkynylaryl, alkaryl, arylalkynyl, arylalkenyl or arylalkyl which is unsubstituted or is substituted with halo, azido, nitro or $OR^3$, provided that at least one R is not H; and L is a leaving group.

28. The method of claim 27 comprising conducting the reaction using at least about 1.0 equivalent of L—$CHR^2$—O—C(O)—OR.

29. The method of claim 27 comprising conducting the reaction in the presence of an organic base in an organic solvent at a reaction temperature of about 4–100° C. for about 4–72 hours.

30. The method of claim 27 wherein the compound of formula (1) is recovered by forming a salt, precipitating the salt and recovering the precipitated salt.

31. The method of claim 30 wherein the salt is formed from sulfuric acid, phosphoric acid, lactic acid, or citric acid.

* * * * *

UNITED STATES PATENT AND TRADEMARK OFFICE
CERTIFICATE OF CORRECTION

PATENT NO. : 5,922,695 C1
APPLICATION NO. : 90/008555
DATED : October 14, 2008
INVENTOR(S) : Arimilli et al.

Page 1 of 2

It is certified that error appears in the above-identified patent and that said Letters Patent is hereby corrected as shown below:

On the title page item (75), left column, line 11, please add --William A. Lee, Los Altos, CA (US)--.

On the title page item (56), under Foreign Patent Documents, left column, line 2, please replace "12/1986" with --7/1992--.

At column 2, line 16, please replace "cloumns" with --columns--.

At column 6, line 13, please replace "2.4.3." with --2.4.3.9--.

At column 6, line 77, please replace "2.16.4.4" with --2.16.5.4--.

At column 20, lines 49-50, please replace "3 as," with --3, as--.

At column 22, line 17, please replace "mL,66" with --mL, 66--.

At column 22, line 35, please replace "Bis –n-butyl" with --Bis–n-butyl--.

At column 23, line 34, please replace "13" with --13.0--.

At column 23, line 45, please replace "[[(R)-2-(phosphonomethoxy)propyl]]adenine" with --[(R)-2-(phosphonomethoxy)propyl]adenine--.

At column 23, line 65, please replace "will" with --with--.

At claim 1, column 24, line 65, please replace "alkenyl, alkenyl" with --alkenyl--.

At claim 1, column 25, line 1, please replace "$N(R^{4)}{}_2$" with --$N(R^4)_2$--.

At claim 27, column 25, line 52, please replace "azido nitro" with --azido, nitro--.

UNITED STATES PATENT AND TRADEMARK OFFICE
CERTIFICATE OF CORRECTION

PATENT NO. : 5,922,695 C1
APPLICATION NO. : 90/008555
DATED : October 14, 2008
INVENTOR(S) : Arimilli et al.

It is certified that error appears in the above-identified patent and that said Letters Patent is hereby corrected as shown below:

At claim 33, column 26, line 37, please replace "cytosin-yl" with --cytosin-l-yl--.

Signed and Sealed this

Eighth Day of December, 2009

David J. Kappos
*Director of the United States Patent and Trademark Office*

UNITED STATES PATENT AND TRADEMARK OFFICE
CERTIFICATE OF CORRECTION

PATENT NO. : 5,922,695 C1  Page 1 of 1
APPLICATION NO. : 90/008555
DATED : October 14, 2008
INVENTOR(S) : Arimilli et al.

It is certified that error appears in the above-identified patent and that said Letters Patent is hereby corrected as shown below:

Claim 32, column 26, line 8, please replace "–$OC(R^2)OC(O)X(R)_a$" with --$OC(R^2)_2OC(O)X(R)_a$--.

Claim 32, column 26, line 9, please replace "–$OC(R^2)OC(O)X(R)_a$" with --$OC(R^2)_2OC(O)X(R)_a$--.

Signed and Sealed this

Second Day of November, 2010

David J. Kappos
*Director of the United States Patent and Trademark Office*

US005922695C1

(12) EX PARTE REEXAMINATION CERTIFICATE (6473rd)
United States Patent
Arimilli et al.

(10) Number: US 5,922,695 C1
(45) Certificate Issued: Oct. 14, 2008

(54) ANTIVIRAL PHOSPHONOMETHYOXY NUCLEOTIDE ANALOGS HAVING INCREASED ORAL BIOAVAILABILITY

(75) Inventors: Murty N. Arimilli, Fremont, CA (US); Kenneth C. Cundy, Belmont, CA (US); Joseph P. Dougherty, New York, NY (US); Choung U. Kim, San Carlos, CA (US); Reza Oliyal, Foster City, CA (US); Valentino J. Stella, Lawrence, KS (US)

(73) Assignee: Gilead Sciences, Inc., Foster City, CA (US)

Reexamination Request:
No. 90/008,555, Apr. 30, 2007

Reexamination Certificate for:
Patent No.: 5,922,695
Issued: Jul. 13, 1999
Appl. No.: 08/900,746
Filed: Jul. 25, 1997

Related U.S. Application Data
(60) Provisional application No. 60/022,708, filed on Jul. 26, 1996.

(51) Int. Cl.
*C07F 9/00* (2006.01)
*C07F 9/6512* (2006.01)
*C07F 9/6561* (2006.01)
*A61K 31/675* (2006.01)

(52) U.S. Cl. .................... 514/81; 514/86; 544/243; 544/244; 546/23

(58) Field of Classification Search ............... None
See application file for complete search history.

(56) References Cited

U.S. PATENT DOCUMENTS

| | | | |
|---|---|---|---|
| 4,003,878 A | 1/1977 | Skaar et al. |
| 4,355,032 A | 10/1982 | Verheyden et al. |
| 4,808,716 A | 2/1989 | Hol et al. |
| 4,957,924 A | 9/1990 | Beauchamp |
| 5,075,445 A | 12/1991 | Jarvest et al. |
| 5,476,938 A | 12/1995 | Vemishetti et al. |
| 5,663,159 A | 9/1997 | Starrett, Jr. et al. |
| 5,798,340 A | 8/1998 | Bischofberger et al. |

FOREIGN PATENT DOCUMENTS

| | | |
|---|---|---|
| EP | 0 182 024 B1 | 5/1986 |
| EP | 0 206 459 B1 | 12/1986 |
| EP | 0 482 657 A2 | 4/1992 |
| EP | 0 206 459 B1 | 7/1992 |
| EP | 0 694 547 B1 | 1/1996 |
| GB | 1 523 865 | 9/1978 |
| GB | 2 111 043 | 6/1983 |
| WO | WO 95/32957 A1 | 12/1995 |

OTHER PUBLICATIONS

Balzarini et al. "Differential Antiherpesvirus and antiretrovirus effects of the (S) and (R) enantiomers of acyclic nucleoside phophonates: potent and selective in vitro and in vivo antiretrovirus activities of (R)–9(2–phosphonomethoxypropyl)–2,6–diaminopurine," Antimicrob. Ag. Chemoth. 37(2):332–8, Feb. 1993.

Bartnof H. "Selected highlights from the 4$^{th}$ conference on retroviruses and opportunistic infections," *Bulletin Exp. Treat. AIDS*, Mar. 1997.

Benzaria et al., "Synthesis in vitro antiviral evaluation, and stability studies of Bis(S–acyl–2–thioethyl) ester derivatives of 9–[2–(phosphonomethoxy)ethyl]adenine (PMEA) as potential PMEA prodrugs with improved oral bioavailability," *J. Med. Chem.* 39(25):4958–65, 1996.

Beauchamp et al., "Amino acid ester prodrugs of acyclovir," *Antivir. Chem. and Chemoth.* 3(3):157–64, 1992.

Colla et al., "Synthesis and antiviral activity of water–soluble esters of acyclovir [9–[(2–Hydroxyethoxy)methyl]guanine]," *J. Med. Chem.* 26:602–04, 1983.

Farquhar et al., "Synthesis and antitumor evaluation of Bis [(pivaloxy)methyl]2'–deoxy–5–fluorouridine 5'–monophosphate (FdUMP): a strategy to introduce nucleotides into cells," *J. Med. Chem.* 37(23):3902–03, 1994.

Fridland et al. "Antiretroviral activity and metabolism of bis(POC)PMPA, an oral bioavailable prodrug of PMPA," *Antiv. Res.* 34(2):A49, 1997.

McIntee et al., "Probing the mechanism of action and decomposition of amino acid phosphomonoester amidates of antiviral nucleoside prodrugs," *J. Med. Chem.* 40(2):3323–31, 1997.

Morris et al., "An integrated approach to the selection of optimal salt form for new drug candidate," *Int'l J. Pharmaceutics* 105:209–17, 1994.

Raic et al., "The Novel 6–(N–Pyrrolyl)Purine Acyclic Nucleosides: 1H and 13C NMR and X–Ray Structural Study," *Nucls. & Nucli.* 15(4):937–960, 1996.

Bischofberger et al., Bis(POC)PMPA, an Orally Bioavailable Prodrug of the Antiretroviral Agent PMPA, Conference on Retroviruses and Opportunistic Infections, 4th:104 (abstract No. 214), Jan. 22–26, 1997.

Notari, Prodrug Design, Pharmaceutical Therapy, 14:25–53, 1981.

Jones et al., Minireview: Nucleotide Prodrugs, Antiviral Research, 27:1–17, 1995.

*Primary Examiner*—Gary L Kunz

(57) ABSTRACT

Novel compounds are provided that comprise esters of antiviral phosphonomethoxy nucleotide analogs with carbonates and/or carbamates having the structure —OC($R^2$)$_2$ OC(O)X (R)$_a$, wherein $R^2$ independently is H, $C_1$–$C_{12}$ alkyl, aryl, alkenyl, alkynyl, alkyenylaryl, alkynylaryl, alkaryl, arylalkynyl, arylalkenyl or arylalkyl which is unsubstituted or is substituted with halo, azido, nitro or $OR^3$ in which $R^3$ is $C_1$–C 12 alkyl; X is N or O; R is independently H, $C_1$–$C_{12}$ alkyl, aryl, alkenyl, alkynyl, alkyenylaryl, alkynylaryl, alkaryl, arylalkynyl, arylalkenyl or arylalkyl which is unsubstituted or is substituted with halo, azido, nitro, —O—, —N=, —$NR^4$—, —N($R^4$)$_2$— or $OR^3$, $R^4$ independently is —H or $C_1$–$C_8$ alkyl, provided that at least one R is not H; and a is 1 or 2, with the proviso that when a is 2 and X is N, (a) two R groups can be taken together to form a carbocycle or oxygen-containing heterocycle, or (b) one R additionally can be $OR^3$. The compounds are useful as intermediates for the preparation of antiviral compounds or oligonucleotides, or are useful for administration directly to patients for antiviral therapy or prophylaxis. Embodiments are particularly useful when administered orally.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, lines 18–31:

Such analogs per se and various technologies for oral delivery of these and other therapeutic compounds are known. See WO 91/19721, WO 94/03467, WO 94/03466, WO 92/13869, U.S. Pat. Nos. 5,208,221, [5,124,051] *5,142,051*, DE 41 38 584 A1, WO 94/10539, WO 94/10467, WO 96/18605, WO 95/07920, WO [95 79/07919] *95/07919*, WO 92/09611, WO 92/01698, WO 91/19721, WO 88/05438, EP 0 632 048, EP 0 481 214, EP 0 369 409, EP 0 269 947, U.S. Pat. Nos. 3,524,846 and 5,386,030, Engel Chem. Rev. 77:349–367 1977, Farquhar et al., J. Pharm. Sci. 72:324 –325 1983, Starrett et al., Antiviral Res. 19:267–273 1992, Safadi et al., Pharmaceutical Research 10(9): 1350–1355 1993, Sakamoto et al., Chem. Pharm. Bull: 32(6):2241–2248 1984, and Davidsen et al., J Med. Chem. 37(26):4423–4429 1994.

Columns 7–8, line 35 to cloumns 23–24, line 49:

TABLE B

| | | | | | | | | | | | | |
|---|---|---|---|---|---|---|---|---|---|---|---|---|
| 1.1.1.1 | 1.1.1.2 | 1.1.1.3 | 1.1.1.4 | 1.1.1.5 | 1.1.1.6 | 1.1.1.7 | 1.1.1.8 | 1.1.1.9 | 1.1.1.10 | 1.1.2.1 | 1.1.2.2 | 1.1.2.3 |
| 1.1.2.4 | 1.1.2.5 | 1.1.2.6 | 1.1.2.7 | 1.1.2.8 | 1.1.2.9 | 1.1.2.10 | 1.1.3.1 | 1.1.3.2 | 1.1.3.3 | 1.1.3.4 | 1.1.3.5 | 1.1.3.6 |
| 1.1.3.7 | 1.1.3.8 | 1.1.3.9 | 1.1.3.10 | 1.1.4.1 | 1.1.4.2 | 1.1.4.3 | 1.1.4.4 | 1.1.4.5 | 1.1.4.6 | 1.1.4.7 | 1.1.4.8 | 1.1.4.9 |
| 1.1.4.10 | 1.1.5.1 | 1.1.5.2 | 1.1.5.3 | 1.1.5.4 | 1.1.5.5 | 1.1.5.6 | 1.1.5.7 | 1.1.5.8 | 1.1.5.9 | 1.1.5.10 | 1.1.6.1 | 1.1.6.2 |
| 1.1.6.3 | 1.1.6.4 | 1.1.6.5 | 1.1.6.6 | 1.1.6.7 | 1.1.6.8 | 1.1.6.9 | 1.1.6.10 | 1.2.1.1 | 1.2.1.2 | 1.2.1.3 | 1.2.1.4 | 1.2.1.5 |
| 1.2.1.6 | 1.2.1.7 | 1.2.1.8 | 1.2.1.9 | 1.2.1.10 | 1.2.2.1 | 1.2.2.2 | 1.2.2.3 | 1.2.2.4 | 1.2.2.5 | 1.2.2.6 | 1.2.2.7 | 1.2.2.8 |
| 1.2.2.9 | 1.2.2.10 | 1.2.3.1 | 1.2.3.2 | 1.2.3.3 | 1.2.3.4 | 1.2.3.5 | 1.2.3.6 | 1.2.3.7 | 1.2.3.8 | 1.2.3.9 | 1.2.3.10 | 1.2.4.1 |
| 1.2.4.2 | 1.2.4.3 | 1.2.4.4 | 1.2.4.5 | 1.2.4.6 | 1.2.4.7 | 1.2.4.8 | 1.2.4.9 | 1.2.4.10 | 1.2.5.1 | 1.2.5.2 | 1.2.5.3 | 1.2.5.4 |
| 1.2.5.5 | 1.2.5.6 | 1.2.5.7 | 1.2.5.8 | 1.2.5.9 | 1.2.5.10 | 1.2.6.1 | 1.2.6.2 | 1.2.6.3 | 1.2.6.4 | 1.2.6.5 | 1.2.6.6 | 1.2.6.7 |
| 1.2.6.8 | 1.2.6.9 | 1.2.6.10 | 1.3.1.1 | 1.3.1.2 | 1.3.1.3 | 1.3.1.4 | 1.3.1.5 | 1.3.1.6 | 1.3.1.7 | 1.3.1.8 | 1.3.1.9 | 1.3.1.10 |
| 1.3.2.1 | 1.3.2.2 | 1.3.2.3 | 1.3.2.4 | 1.3.2.5 | 1.3.2.6 | 1.3.2.7 | 1.3.2.8 | 1.3.2.9 | 1.3.2.10 | 1.3.3.1 | 1.3.3.2 | 1.3.3.3 |
| 1.3.3.4 | 1.3.3.5 | 1.3.3.6 | 1.3.3.7 | 1.3.3.8 | 1.3.3.9 | 1.3.3.10 | 1.3.4.1 | 1.3.4.2 | 1.3.4.3 | 1.3.4.4 | 1.3.4.5 | 1.3.4.6 |
| 1.3.4.7 | 1.3.4.8 | 1.3.4.9 | 1.3.4.10 | 1.3.5.1 | 1.3.5.2 | 1.3.5.3 | 1.3.5.4 | 1.3.5.5 | 1.3.5.6 | 1.3.5.7 | 1.3.5.8 | 1.3.5.9 |
| 1.3.5.10 | 1.3.6.1 | 1.3.6.2 | 1.3.6.3 | 1.3.6.4 | 1.3.6.5 | 1.3.6.6 | 1.3.6.7 | 1.3.6.8 | 1.3.6.9 | 1.3.6.10 | 1.4.1.1 | 1.4.1.2 |
| 1.4.1.3 | 1.4.1.4 | 1.4.1.5 | 1.4.1.6 | 1.4.1.7 | 1.4.1.8 | 1.4.1.9 | 1.4.1.10 | 1.4.2.1 | 1.4.2.2 | 1.4.2.3 | 1.4.2.4 | 1.4.2.5 |
| 1.4.2.6 | 1.4.2.7 | 1.4.2.8 | 1.4.2.9 | 1.4.2.10 | 1.4.3.1 | 1.4.3.2 | 1.4.3.3 | 1.4.3.4 | 1.4.3.5 | 1.4.3.6 | 1.4.3.7 | 1.4.3.8 |
| 1.4.3.9 | 1.4.3.10 | 1.4.4.1 | 1.4.4.2 | 1.4.4.3 | 1.4.4.4 | 1.4.4.5 | 1.4.4.6 | 1.4.4.7 | 1.4.4.8 | 1.4.4.9 | 1.4.4.10 | 1.4.5.1 |
| 1.4.5.2 | 1.4.5.3 | 1.4.5.4 | 1.4.5.5 | 1.4.5.6 | 1.4.5.7 | 1.4.5.8 | 1.4.5.9 | 1.4.5.10 | 1.4.6.1 | 1.4.6.2 | 1.4.6.3 | 1.4.6.4 |
| 1.4.6.5 | 1.4.6.6 | 1.4.6.7 | 1.4.6.8 | 1.4.6.9 | 1.4.6.10 | 1.5.1.1 | 1.5.1.2 | 1.5.1.3 | 1.5.1.4 | 1.5.1.5 | 1.5.1.6 | 1.5.1.7 |
| 1.5.1.8 | 1.5.1.9 | 1.5.1.10 | 1.5.2.1 | 1.5.2.2 | 1.5.2.3 | 1.5.2.4 | 1.5.2.5 | 1.5.2.6 | 1.5.2.7 | 1.5.2.8 | 1.5.2.9 | 1.5.2.10 |
| 1.5.3.1 | 1.5.3.2 | 1.5.3.3 | 1.5.3.4 | 1.5.3.5 | 1.5.3.6 | 1.5.3.7 | 1.5.3.8 | 1.5.3.9 | 1.5.3.10 | 1.5.4.1 | 1.5.4.2 | 1.5.4.3 |
| 1.5.4.4 | 1.5.4.5 | 1.5.4.6 | 1.5.4.7 | 1.5.4.8 | 1.5.4.9 | 1.5.4.10 | 1.5.5.1 | 1.5.5.2 | 1.5.5.3 | 1.5.5.4 | 1.5.5.5 | 1.5.5.6 |
| 1.5.5.7 | 1.5.5.8 | 1.5.5.9 | 1.5.5.10 | 1.5.6.1 | 1.5.6.2 | 1.5.6.3 | 1.5.6.4 | 1.5.6.5 | 1.5.6.6 | 1.5.6.7 | 1.5.6.8 | 1.5.6.9 |
| 1.5.6.10 | 1.6.1.1 | 1.6.1.2 | 1.6.1.3 | 1.6.1.4 | 1.6.1.5 | 1.6.1.6 | 1.6.1.7 | 1.6.1.8 | 1.6.1.9 | 1.6.1.10 | 1.6.2.1 | 1.6.2.2 |
| 1.6.2.3 | 1.6.2.4 | 1.6.2.5 | 1.6.2.6 | 1.6.2.7 | 1.6.2.8 | 1.6.2.9 | 1.6.2.10 | 1.6.3.1 | 1.6.3.2 | 1.6.3.3 | 1.6.3.4 | 1.6.3.5 |
| 1.6.3.6 | 1.6.3.7 | 1.6.3.8 | 1.6.3.9 | 1.6.3.10 | 1.6.4.1 | 1.6.4.2 | 1.6.4.3 | 1.6.4.4 | 1.6.4.5 | 1.6.4.6 | 1.6.4.7 | 1.6.4.8 |
| 1.6.4.9 | 1.6.4.10 | 1.6.5.1 | 1.6.5.2 | 1.6.5.3 | 1.6.5.4 | 1.6.5.5 | 1.6.5.6 | 1.6.5.7 | 1.6.5.8 | 1.6.5.9 | 1.6.5.10 | 1.6.6.1 |
| 1.6.6.2 | 1.6.6.3 | 1.6.6.4 | 1.6.6.5 | 1.6.6.6 | 1.6.6.7 | 1.6.6.8 | 1.6.6.9 | 1.6.6.10 | 1.7.1.1 | 1.7.1.2 | 1.7.1.3 | 1.7.1.4 |
| 1.7.1.5 | 1.7.1.6 | 1.7.1.7 | 1.7.1.8 | 1.7.1.9 | 1.7.1.10 | 1.7.2.1 | 1.7.2.2 | 1.7.2.3 | 1.7.2.4 | 1.7.2.5 | 1.7.2.6 | 1.7.2.7 |
| 1.7.2.8 | 1.7.2.9 | 1.7.2.10 | 1.7.3.1 | 1.7.3.2 | 1.7.3.3 | 1.7.3.4 | 1.7.3.5 | 1.7.3.6 | 1.7.3.7 | 1.7.3.8 | 1.7.3.9 | 1.7.3.10 |
| 1.7.4.1 | 1.7.4.2 | 1.7.4.3 | 1.7.4.4 | 1.7.4.5 | 1.7.4.6 | 1.7.4.7 | 1.7.4.8 | 1.7.4.9 | 1.7.4.10 | 1.7.5.1 | 1.7.5.2 | 1.7.5.3 |
| 1.7.5.4 | 1.7.5.5 | 1.7.5.6 | 1.7.5.7 | 1.7.5.8 | 1.7.5.9 | 1.7.5.10 | 1.7.6.1 | 1.7.6.2 | 1.7.6.3 | 1.7.6.4 | 1.7.6.5 | 1.7.6.6 |
| 1.7.6.7 | 1.7.6.8 | 1.7.6.9 | 1.7.6.10 | 1.8.1.1 | 1.8.1.2 | 1.8.1.3 | 1.8.1.4 | 1.8.1.5 | 1.8.1.6 | 1.8.1.7 | 1.8.1.8 | 1.8.1.9 |
| 1.8.1.10 | 1.8.2.1 | 1.8.2.2 | 1.8.2.3 | 1.8.2.4 | 1.8.2.5 | 1.8.2.6 | 1.8.2.7 | 1.8.2.8 | 1.8.2.9 | 1.8.2.10 | 1.8.3.1 | 1.8.3.2 |
| 1.8.3.3 | 1.8.3.4 | 1.8.3.5 | 1.8.3.6 | 1.8.3.7 | 1.8.3.8 | 1.8.3.9 | 1.8.3.10 | 1.8.4.1 | 1.8.4.2 | 1.8.4.3 | 1.8.4.4 | 1.8.4.5 |
| 1.8.4.6 | 1.8.4.7 | 1.8.4.8 | 1.8.4.9 | 1.8.4.10 | 1.8.5.1 | 1.8.5.2 | 1.8.5.3 | 1.8.5.4 | 1.8.5.5 | 1.8.5.6 | 1.8.5.7 | 1.8.5.8 |
| 1.8.5.9 | 1.8.5.10 | 1.8.6.1 | 1.8.6.2 | 1.8.6.3 | 1.8.6.4 | 1.8.6.5 | 1.8.6.6 | 1.8.6.7 | 1.8.6.8 | 1.8.6.9 | 1.8.6.10 | 1.9.1.1 |
| 1.9.1.2 | 1.9.1.3 | 1.9.1.4 | 1.9.1.5 | 1.9.1.6 | 1.9.1.7 | 1.9.1.8 | 1.9.1.9 | 1.9.1.10 | 1.9.2.1 | 1.9.2.2 | 1.9.2.3 | 1.9.2.4 |
| 1.9.2.5 | 1.9.2.6 | 1.9.2.7 | 1.9.2.8 | 1.9.2.9 | 1.9.2.10 | 1.9.3.1 | 1.9.3.2 | 1.9.3.3 | 1.9.3.4 | 1.9.3.5 | 1.9.3.6 | 1.9.3.7 |
| 1.9.3.8 | 1.9.3.9 | 1.9.3.10 | 1.9.4.1 | 1.9.4.2 | 1.9.4.3 | 1.9.4.4 | 1.9.4.5 | 1.9.4.6 | 1.9.4.7 | 1.9.4.8 | 1.9.4.9 | 1.9.4.10 |
| 1.9.5.1 | 1.9.5.2 | 1.9.5.3 | 1.9.5.4 | 1.9.5.5 | 1.9.5.6 | 1.9.5.7 | 1.9.5.8 | 1.9.5.9 | 1.9.5.10 | 1.9.6.1 | 1.9.6.2 | 1.9.6.3 |
| 1.9.6.4 | 1.9.6.5 | 1.9.6.6 | 1.9.6.7 | 1.9.6.8 | 1.9.6.9 | 1.9.6.10 | 1.10.1.1 | 1.10.1.2 | 1.10.1.3 | 1.10.1.4 | 1.10.1.5 | |
| 1.10.1.6 | 1.10.1.7 | 1.10.1.8 | 1.10.1.9 | 1.10.1.10 | 1.10.2.1 | 1.10.2.2 | 1.10.2.3 | 1.10.2.4 | 1.10.2.5 | 1.10.2.6 | | |
| 1.10.2.7 | 1.10.2.8 | 1.10.2.9 | 1.10.2.10 | 1.10.3.1 | 1.10.3.2 | 1.10.3.3 | 1.10.3.4 | 1.10.3.5 | 1.10.3.6 | 1.10.3.7 | | |
| 1.10.3.8 | 1.10.3.9 | 1.10.3.10 | 1.10.4.1 | 1.10.4.2 | 1.10.4.3 | 1.10.4.4 | 1.10.4.5 | 1.10.4.6 | 1.10.4.7 | 1.10.4.8 | | |
| 1.10.4.9 | 1.10.4.10 | 1.10.5.1 | 1.10.5.2 | 1.10.5.3 | 1.10.5.4 | 1.10.5.5 | 1.10.5.6 | 1.10.5.7 | 1.10.5.8 | 1.10.5.9 | | |
| 1.10.5.10 | 1.10.6.1 | 1.10.6.2 | 1.10.6.3 | 1.10.6.4 | 1.10.6.5 | 1.10.6.6 | 1.10.6.7 | 1.10.6.8 | 1.10.6.9 | 1.10.6.10 | | |
| 1.11.1.1 | 1.11.1.2 | 1.11.1.3 | 1.11.1.4 | 1.11.1.5 | 1.11.1.6 | 1.11.1.7 | 1.11.1.8 | 1.11.1.9 | 1.11.1.10 | 1.11.2.1 | | |
| 1.11.2.2 | 1.11.2.3 | 1.11.2.4 | 1.11.2.5 | 1.11.2.6 | 1.11.2.7 | 1.11.2.8 | 1.11.2.9 | 1.11.2.10 | 1.11.3.1 | 1.11.3.2 | | |
| 1.11.3.3 | 1.11.3.4 | 1.11.3.5 | 1.11.3.6 | 1.11.3.7 | 1.11.3.8 | 1.11.3.9 | 1.11.3.10 | 1.11.4.1 | 1.11.4.2 | 1.11.4.3 | | |
| 1.11.4.4 | 1.11.4.5 | 1.11.4.6 | 1.11.4.7 | 1.11.4.8 | 1.11.4.9 | 1.11.4.10 | 1.11.5.1 | 1.11.5.2 | 1.11.5.3 | 1.11.5.4 | | |
| 1.11.5.5 | 1.11.5.6 | 1.11.5.7 | 1.11.5.8 | 1.11.5.9 | 1.11.5.10 | 1.11.6.1 | 1.11.6.2 | 1.11.6.3 | 1.11.6.4 | 1.11.6.5 | | |
| 1.11.6.6 | 1.11.6.7 | 1.11.6.8 | 1.11.6.9 | 1.11.6.10 | 1.12.1.1 | 1.12.1.2 | 1.12.1.3 | 1.12.1.4 | 1.12.1.5 | 1.12.1.6 | | |
| 1.12.1.7 | 1.12.1.8 | 1.12.1.9 | 1.12.1.10 | 1.12.2.1 | 1.12.2.2 | 1.12.2.3 | 1.12.2.4 | 1.12.2.5 | 1.12.2.6 | 1.12.2.7 | | |
| 1.12.2.8 | 1.12.2.9 | 1.12.2.10 | 1.12.3.1 | 1.12.3.2 | 1.12.3.3 | 1.12.3.4 | 1.12.3.5 | 1.12.3.6 | 1.12.3.7 | 1.12.3.8 | | |

TABLE B-continued

| | | | | | | | | | | | |
|---|---|---|---|---|---|---|---|---|---|---|---|
| 1.12.3.9 | 1.12.3.10 | 1.12.4.1 | 1.12.4.2 | 1.12.4.3 | 1.12.4.4 | 1.12.4.5 | 1.12.4.6 | 1.12.4.7 | 1.12.4.8 | 1.12.4.9 | |
| 1.12.4.10 | 1.12.5.1 | 1.12.5.2 | 1.12.5.3 | 1.12.5.4 | 1.12.5.5 | 1.12.5.6 | 1.12.5.7 | 1.12.5.8 | 1.12.5.9 | 1.12.5.10 | |
| 1.12.6.1 | 1.12.6.2 | 1.12.6.3 | 1.12.6.4 | 1.12.6.5 | 1.12.6.6 | 1.12.6.7 | 1.12.6.8 | 1.12.6.9 | 1.12.6.10 | 1.13.1.1 | |
| 1.13.1.2 | 1.13.1.3 | 1.13.1.4 | 1.13.1.5 | 1.13.1.6 | 1.13.1.7 | 1.13.1.8 | 1.13.1.9 | 1.13.1.10 | 1.13.2.1 | 1.13.2.2 | |
| 1.13.2.3 | 1.13.2.4 | 1.13.2.5 | 1.13.2.6 | 1.13.2.7 | 1.13.2.8 | 1.13.2.9 | 1.13.2.10 | 1.13.3.1 | 1.13.3.2 | 1.13.3.3 | |
| 1.13.3.4 | 1.13.3.5 | 1.13.3.6 | 1.13.3.7 | 1.13.3.8 | 1.13.3.9 | 1.13.3.10 | 1.13.4.1 | 1.13.4.2 | 1.13.4.3 | 1.13.4.4 | |
| 1.13.4.5 | 1.13.4.6 | 1.13.4.7 | 1.13.4.8 | 1.13.4.9 | 1.13.4.10 | 1.13.5.1 | 1.13.5.2 | 1.13.5.3 | 1.13.5.4 | 1.13.5.5 | |
| 1.13.5.6 | 1.13.5.7 | 1.13.5.8 | 1.13.5.9 | 1.13.5.10 | 1.13.6.1 | 1.13.6.2 | 1.13.6.3 | 1.13.6.4 | 1.13.6.5 | 1.13.6.6 | |
| 1.13.6.7 | 1.13.6.8 | 1.13.6.9 | 1.13.6.10 | 1.14.1.1 | 1.14.1.2 | 1.14.1.3 | 1.14.1.4 | 1.14.1.5 | 1.14.1.6 | 1.14.1.7 | |
| 1.14.1.8 | 1.14.1.9 | 1.14.1.10 | 1.14.2.1 | 1.14.2.2 | 1.14.2.3 | 1.14.2.4 | 1.14.2.5 | 1.14.2.6 | 1.14.2.7 | 1.14.2.8 | |
| 1.14.2.9 | 1.14.2.10 | 1.14.3.1 | 1.14.3.2 | 1.14.3.3 | 1.14.3.4 | 1.14.3.5 | 1.14.3.6 | 1.14.3.7 | 1.14.3.8 | 1.14.3.9 | |
| 1.14.3.10 | 1.14.4.1 | 1.14.4.2 | 1.14.4.3 | 1.14.4.4 | 1.14.4.5 | 1.14.4.6 | 1.14.4.7 | 1.14.4.8 | 1.14.4.9 | 1.14.4.10 | |
| 1.14.5.1 | 1.14.5.2 | 1.14.5.3 | 1.14.5.4 | 1.14.5.5 | 1.14.5.6 | 1.14.5.7 | 1.14.5.8 | 1.14.5.9 | 1.14.5.10 | 1.14.6.1 | |
| 1.14.6.2 | 1.14.6.3 | 1.14.6.4 | 1.14.6.5 | 1.14.6.6 | 1.14.6.7 | 1.14.6.8 | 1.14.6.9 | 1.14.6.10 | 1.15.1.1 | 1.15.1.2 | |
| 1.15.1.3 | 1.15.1.4 | 1.15.1.5 | 1.15.1.6 | 1.15.1.7 | 1.15.1.8 | 1.15.1.9 | 1.15.1.10 | 1.15.2.1 | 1.15.2.2 | 1.15.2.3 | |
| 1.15.2.4 | 1.15.2.5 | 1.15.2.6 | 1.15.2.7 | 1.15.2.8 | 1.15.2.9 | 1.15.2.10 | 1.15.3.1 | 1.15.3.2 | 1.15.3.3 | 1.15.3.4 | |
| 1.15.3.5 | 1.15.3.6 | 1.15.3.7 | 1.15.3.8 | 1.15.3.9 | 1.15.3.10 | 1.15.4.1 | 1.15.4.2 | 1.15.4.3 | 1.15.4.4 | 1.15.4.5 | |
| 1.15.4.6 | 1.15.4.7 | 1.15.4.8 | 1.15.4.9 | 1.15.4.10 | 1.15.5.1 | 1.15.5.2 | 1.15.5.3 | 1.15.5.4 | 1.15.5.5 | 1.15.5.6 | |
| 1.15.5.7 | 1.15.5.8 | 1.15.5.9 | 1.15.5.10 | 1.15.6.1 | 1.15.6.2 | 1.15.6.3 | 1.15.6.4 | 1.15.6.5 | 1.15.6.6 | 1.15.6.7 | |
| 1.15.6.8 | 1.15.6.9 | 1.15.6.10 | 1.16.1.1 | 1.16.1.2 | 1.16.1.3 | 1.16.1.4 | 1.16.1.5 | 1.16.1.6 | 1.16.1.7 | 1.16.1.8 | |
| 1.16.1.9 | 1.16.1.10 | 1.16.2.1 | 1.16.2.2 | 1.16.2.3 | 1.16.2.4 | 1.16.2.5 | 1.16.2.6 | 1.16.2.7 | 1.16.2.8 | 1.16.2.9 | |
| 1.16.2.10 | 1.16.3.1 | 1.16.3.2 | 1.16.3.3 | 1.16.3.4 | 1.16.3.5 | 1.16.3.6 | 1.16.3.7 | 1.16.3.8 | 1.16.3.9 | 1.16.3.10 | |
| 1.16.4.1 | 1.16.4.2 | 1.16.4.3 | 1.16.4.4 | 1.16.4.5 | 1.16.4.6 | 1.16.4.7 | 1.16.4.8 | 1.16.4.9 | 1.16.4.10 | 1.16.5.1 | |
| 1.16.5.2 | 1.16.5.3 | 1.16.5.4 | 1.16.5.5 | 1.16.5.6 | 1.16.5.7 | 1.16.5.8 | 1.16.5.9 | 1.16.5.10 | 1.16.6.1 | 1.16.6.2 | |
| 1.16.6.3 | 1.16.6.4 | 1.16.6.5 | 1.16.6.6 | 1.16.6.7 | 1.16.6.8 | 1.16.6.9 | 1.16.6.10 | 1.17.1.1 | 1.17.1.2 | 1.17.1.3 | |
| 1.17.1.4 | 1.17.1.5 | 1.17.1.6 | 1.17.1.7 | 1.17.1.8 | 1.17.1.9 | 1.17.1.10 | 1.17.2.1 | 1.17.2.2 | 1.17.2.3 | 1.17.2.4 | |
| 1.17.2.5 | 1.17.2.6 | 1.17.2.7 | 1.17.2.8 | 1.17.2.9 | 1.17.2.10 | 1.17.3.1 | 1.17.3.2 | 1.17.3.3 | 1.17.3.4 | 1.17.3.5 | |
| 1.17.3.6 | 1.17.3.7 | 1.17.3.8 | 1.17.3.9 | 1.17.3.10 | 1.17.4.1 | 1.17.4.2 | 1.17.4.3 | 1.17.4.4 | 1.17.4.5 | 1.17.4.6 | |
| 1.17.4.7 | 1.17.4.8 | 1.17.4.9 | 1.17.4.10 | 1.17.5.1 | 1.17.5.2 | 1.17.5.3 | 1.17.5.4 | 1.17.5.5 | 1.17.5.6 | 1.17.5.7 | |
| 1.17.5.8 | 1.17.5.9 | 1.17.5.10 | 1.17.6.1 | 1.17.6.2 | 1.17.6.3 | 1.17.6.4 | 1.17.6.5 | 1.17.6.6 | 1.17.6.7 | 1.17.6.8 | |
| 1.17.6.9 | 1.17.6.10 | 1.18.1.1 | 1.18.1.2 | 1.18.1.3 | 1.18.1.4 | 1.18.1.5 | 1.18.1.6 | 1.18.1.7 | 1.18.1.8 | 1.18.1.9 | |
| 1.18.1.10 | 1.18.2.1 | 1.18.2.2 | 1.18.2.3 | 1.18.2.4 | 1.18.2.5 | 1.18.2.6 | 1.18.2.7 | 1.18.2.8 | 1.18.2.9 | 1.18.2.10 | |
| 1.18.3.1 | 1.18.3.2 | 1.18.3.3 | 1.18.3.4 | 1.18.3.5 | 1.18.3.6 | 1.18.3.7 | 1.18.3.8 | 1.18.3.9 | 1.18.3.10 | 1.18.4.1 | |
| 1.18.4.2 | 1.18.4.3 | 1.18.4.4 | 1.18.4.5 | 1.18.4.6 | 1.18.4.7 | 1.18.4.8 | 1.18.4.9 | 1.18.4.10 | 1.18.5.1 | 1.18.5.2 | |
| 1.18.5.3 | 1.18.5.4 | 1.18.5.5 | 1.18.5.6 | 1.18.5.7 | 1.18.5.8 | 1.18.5.9 | 1.18.5.10 | 1.18.6.1 | 1.18.6.2 | 1.18.6.3 | |
| 1.18.6.4 | 1.18.6.5 | 1.18.6.6 | 1.18.6.7 | 1.18.6.8 | 1.18.6.9 | 1.18.6.10 | 1.19.1.1 | 1.19.1.2 | 1.19.1.3 | 1.19.1.4 | |
| 1.19.1.5 | 1.19.1.6 | 1.19.1.7 | 1.19.1.8 | 1.19.1.9 | 1.19.1.10 | 1.19.2.1 | 1.19.2.2 | 1.19.2.3 | 1.19.2.4 | 1.19.2.5 | |
| 1.19.2.6 | 1.19.2.7 | 1.19.2.8 | 1.19.2.9 | 1.19.2.10 | 1.19.3.1 | 1.19.3.2 | 1.19.3.3 | 1.19.3.4 | 1.19.3.5 | 1.19.3.6 | |
| 1.19.3.7 | 1.19.3.8 | 1.19.3.9 | 1.19.3.10 | 1.19.4.1 | 1.19.4.2 | 1.19.4.3 | 1.19.4.4 | 1.19.4.5 | 1.19.4.6 | 1.19.4.7 | |
| 1.19.4.8 | 1.19.4.9 | 1.19.4.10 | 1.19.5.1 | 1.19.5.2 | 1.19.5.3 | 1.19.5.4 | 1.19.5.5 | 1.19.5.6 | 1.19.5.7 | 1.19.5.8 | |
| 1.19.5.9 | 1.19.5.10 | 1.19.6.1 | 1.19.6.2 | 1.19.6.3 | 1.19.6.4 | 1.19.6.5 | 1.19.6.6 | 1.19.6.7 | 1.19.6.8 | 1.19.6.9 | |
| 1.19.6.10 | 1.20.1.1 | 1.20.1.2 | 1.20.1.3 | 1.20.1.4 | 1.20.1.5 | 1.20.1.6 | 1.20.1.7 | 1.20.1.8 | 1.20.1.9 | 1.20.1.10 | |
| 1.20.2.1 | 1.20.2.2 | 1.20.2.3 | 1.20.2.4 | 1.20.2.5 | 1.20.2.6 | 1.20.2.7 | 1.20.2.8 | 1.20.2.9 | 1.20.2.10 | 1.20.3.1 | |
| 1.20.3.2 | 1.20.3.3 | 1.20.3.4 | 1.20.3.5 | 1.20.3.6 | 1.20.3.7 | 1.20.3.8 | 1.20.3.9 | 1.20.3.10 | 1.20.4.1 | 1.20.4.2 | |
| 1.20.4.3 | 1.20.4.4 | 1.20.4.5 | 1.20.4.6 | 1.20.4.7 | 1.20.4.8 | 1.20.4.9 | 1.20.4.10 | 1.20.5.1 | 1.20.5.2 | 1.20.5.3 | |
| 1.20.5.4 | 1.20.5.5 | 1.20.5.6 | 1.20.5.7 | 1.20.5.8 | 1.20.5.9 | 1.20.5.10 | 1.20.6.1 | 1.20.6.2 | 1.20.6.3 | 1.20.6.4 | |
| 1.20.6.5 | 1.20.6.6 | 1.20.6.7 | 1.20.6.8 | 1.20.6.9 | 1.20.6.10 | 1.21.1.1 | 1.21.1.2 | 1.21.1.3 | 1.21.1.4 | 1.21.1.5 | |
| 1.21.1.6 | 1.21.1.7 | 1.21.1.8 | 1.21.1.9 | 1.21.1.10 | 1.21.2.1 | 1.21.2.2 | 1.21.2.3 | 1.21.2.4 | 1.21.2.5 | 1.21.2.6 | |
| 1.21.2.7 | 1.21.2.8 | 1.21.2.9 | 1.21.2.10 | 1.21.3.1 | 1.21.3.2 | 1.21.3.3 | 1.21.3.4 | 1.21.3.5 | 1.21.3.6 | 1.21.3.7 | |
| 1.21.3.8 | 1.21.3.9 | 1.21.3.10 | 1.21.4.1 | 1.21.4.2 | 1.21.4.3 | 1.21.4.4 | 1.21.4.5 | 1.21.4.6 | 1.21.4.7 | 1.21.4.8 | |
| 1.21.4.9 | 1.21.4.10 | 1.21.5.1 | 1.21.5.2 | 1.21.5.3 | 1.21.5.4 | 1.21.5.5 | 1.21.5.6 | 1.21.5.7 | 1.21.5.8 | 1.21.5.9 | |
| 1.21.5.10 | 1.21.6.1 | 1.21.6.2 | 1.21.6.3 | 1.21.6.4 | 1.21.6.5 | 1.21.6.6 | 1.21.6.7 | 1.21.6.8 | 1.21.6.9 | 1.21.6.10 | |
| 1.22.1.1 | 1.22.1.2 | 1.22.1.3 | 1.22.1.4 | 1.22.1.5 | 1.22.1.6 | 1.22.1.7 | 1.22.1.8 | 1.22.1.9 | 1.22.1.10 | 1.22.2.1 | |
| 1.22.2.2 | 1.22.2.3 | 1.22.2.4 | 1.22.2.5 | 1.22.2.6 | 1.22.2.7 | 1.22.2.8 | 1.22.2.9 | 1.22.2.10 | 1.22.3.1 | 1.22.3.2 | |
| 1.22.3.3 | 1.22.3.4 | 1.22.3.5 | 1.22.3.6 | 1.22.3.7 | 1.22.3.8 | 1.22.3.9 | 1.22.3.10 | 1.22.4.1 | 1.22.4.2 | 1.22.4.3 | |
| 1.22.4.4 | 1.22.4.5 | 1.22.4.6 | 1.22.4.7 | 1.22.4.8 | 1.22.4.9 | 1.22.4.10 | 1.22.5.1 | 1.22.5.2 | 1.22.5.3 | 1.22.5.4 | |
| 1.22.5.5 | 1.22.5.6 | 1.22.5.7 | 1.22.5.8 | 1.22.5.9 | 1.22.5.10 | 1.22.6.1 | 1.22.6.2 | 1.22.6.3 | 1.22.6.4 | 1.22.6.5 | |
| 1.22.6.6 | 1.22.6.7 | 1.22.6.8 | 1.22.6.9 | 1.22.6.10 | 1.23.1.1 | 1.23.1.2 | 1.23.1.3 | 1.23.1.4 | 1.23.1.5 | 1.23.1.6 | |
| 1.23.1.7 | 1.23.1.8 | 1.23.1.9 | 1.23.1.10 | 1.23.2.1 | 1.23.2.2 | 1.23.2.3 | 1.23.2.4 | 1.23.2.5 | 1.23.2.6 | 1.23.2.7 | |
| 1.23.2.8 | 1.23.2.9 | 1.23.2.10 | 1.23.3.1 | 1.23.3.2 | 1.23.3.3 | 1.23.3.4 | 1.23.3.5 | 1.23.3.6 | 1.23.3.7 | 1.23.3.8 | |
| 1.23.3.9 | 1.23.3.10 | 1.23.4.1 | 1.23.4.2 | 1.23.4.3 | 1.23.4.4 | 1.23.4.5 | 1.23.4.6 | 1.23.4.7 | 1.23.4.8 | 1.23.4.9 | |
| 1.23.4.10 | 1.23.5.1 | 1.23.5.2 | 1.23.5.3 | 1.23.5.4 | 1.23.5.5 | 1.23.5.6 | 1.23.5.7 | 1.23.5.8 | 1.23.5.9 | 1.23.5.10 | |
| 1.23.6.1 | 1.23.6.2 | 1.23.6.3 | 1.23.6.4 | 1.23.6.5 | 1.23.6.6 | 1.23.6.7 | 1.23.6.8 | 1.23.6.9 | 1.23.6.10 | 1.24.1.1 | |
| 1.24.1.2 | 1.24.1.3 | 1.24.1.4 | 1.24.1.5 | 1.24.1.6 | 1.24.1.7 | 1.24.1.8 | 1.24.1.9 | 1.24.1.10 | 1.24.2.1 | 1.24.2.2 | |
| 1.24.2.3 | 1.24.2.4 | 1.24.2.5 | 1.24.2.6 | 1.24.2.7 | 1.24.2.8 | 1.24.2.9 | 1.24.2.10 | 1.24.3.1 | 1.24.3.2 | 1.24.3.3 | |
| 1.24.3.4 | 1.24.3.5 | 1.24.3.6 | 1.24.3.7 | 1.24.3.8 | 1.24.3.9 | 1.24.3.10 | 1.24.4.1 | 1.24.4.2 | 1.24.4.3 | 1.24.4.4 | |
| 1.24.4.5 | 1.24.4.6 | 1.24.4.7 | 1.24.4.8 | 1.24.4.9 | 1.24.4.10 | 1.24.5.1 | 1.24.5.2 | 1.24.5.3 | 1.24.5.4 | 1.24.5.5 | |
| 1.24.5.6 | 1.24.5.7 | 1.24.5.8 | 1.24.5.9 | 1.24.5.10 | 1.24.6.1 | 1.24.6.2 | 1.24.6.3 | 1.24.6.4 | 1.24.6.5 | 1.24.6.6 | |
| 1.24.6.7 | 1.24.6.8 | 1.24.6.9 | 1.24.6.10 | 1.25.1.1 | 1.25.1.2 | 1.25.1.3 | 1.25.1.4 | 1.25.1.5 | 1.25.1.6 | 1.25.1.7 | |
| 1.25.1.8 | 1.25.1.9 | 1.25.1.10 | 1.25.2.1 | 1.25.2.2 | 1.25.2.3 | 1.25.2.4 | 1.25.2.5 | 1.25.2.6 | 1.25.2.7 | 1.25.2.8 | |
| 1.25.2.9 | 1.25.2.10 | 1.25.3.1 | 1.25.3.2 | 1.25.3.3 | 1.25.3.4 | 1.25.3.5 | 1.25.3.6 | 1.25.3.7 | 1.25.3.8 | 1.25.3.9 | |
| 1.25.3.10 | 1.25.4.1 | 1.25.4.2 | 1.25.4.3 | 1.25.4.4 | 1.25.4.5 | 1.25.4.6 | 1.25.4.7 | 1.25.4.8 | 1.25.4.9 | 1.25.4.10 | |
| 1.25.5.1 | 1.25.5.2 | 1.25.5.3 | 1.25.5.4 | 1.25.5.5 | 1.25.5.6 | 1.25.5.7 | 1.25.5.8 | 1.25.5.9 | 1.25.5.10 | 1.25.6.1 | |
| 1.25.6.2 | 1.25.6.3 | 1.25.6.4 | 1.25.6.5 | 1.25.6.6 | 1.25.6.7 | 1.25.6.8 | 1.25.6.9 | 1.25.6.10 | 2.1.1.1 | 2.1.1.2 | 2.1.1.3 |
| 2.1.1.4 | 2.1.1.5 | 2.1.1.6 | 2.1.1.7 | 2.1.1.8 | 2.1.1.9 | 2.1.1.10 | 2.1.2.1 | 2.1.2.2 | 2.1.2.3 | 2.1.2.4 | 2.1.2.5 | 2.1.2.6 |
| 2.1.2.7 | 2.1.2.8 | 2.1.2.9 | 2.1.2.10 | 2.1.3.1 | 2.1.3.2 | 2.1.3.3 | 2.1.3.4 | 2.1.3.5 | 2.1.3.6 | 2.1.3.7 | 2.1.3.8 | 2.1.3.9 |
| 2.1.3.10 | 2.1.4.1 | 2.1.4.2 | 2.1.4.3 | 2.1.4.4 | 2.1.4.5 | 2.1.4.6 | 2.1.4.7 | 2.1.4.8 | 2.1.4.9 | 2.1.4.10 | 2.1.5.1 | 2.1.5.2 |
| 2.1.5.3 | 2.1.5.4 | 2.1.5.5 | 2.1.5.6 | 2.1.5.7 | 2.1.5.8 | 2.1.5.9 | 2.1.5.10 | 2.1.6.1 | 2.1.6.2 | 2.1.6.3 | 2.1.6.4 | 2.1.6.5 |
| 2.1.6.6 | 2.1.6.7 | 2.1.6.8 | 2.1.6.9 | 2.1.6.10 | 2.2.1.1 | 2.2.1.2 | 2.2.1.3 | 2.2.1.4 | 2.2.1.5 | 2.2.1.6 | 2.2.1.7 | 2.2.1.8 |

TABLE B-continued

| | | | | | | | | | | | |
|---|---|---|---|---|---|---|---|---|---|---|---|
| 2.2.1.9 | 2.2.1.10 | 2.2.2.1 | 2.2.2.2 | 2.2.2.3 | 2.2.2.4 | 2.2.2.5 | 2.2.2.6 | 2.2.2.7 | 2.2.2.8 | 2.2.2.9 | 2.2.2.10 | 2.2.3.1 |
| 2.2.3.2 | 2.2.3.3 | 2.2.3.4 | 2.2.3.5 | 2.2.3.6 | 2.2.3.7 | 2.2.3.8 | 2.2.3.9 | 2.2.3.10 | 2.2.4.1 | 2.2.4.2 | 2.2.4.3 | 2.2.4.4 |
| 2.2.4.5 | 2.2.4.6 | 2.2.4.7 | 2.2.4.8 | 2.2.4.9 | 2.2.4.10 | 2.2.5.1 | 2.2.5.2 | 2.2.5.3 | 2.2.5.4 | 2.2.5.5 | 2.2.5.6 | 2.2.5.7 |
| 2.2.5.8 | 2.2.5.9 | 2.2.5.10 | 2.2.6.1 | 2.2.6.2 | 2.2.6.3 | 2.2.6.4 | 2.2.6.5 | 2.2.6.6 | 2.2.6.7 | 2.2.6.8 | 2.2.6.9 | 2.2.6.10 |
| 2.3.1.1 | 2.3.1.2 | 2.3.1.3 | 2.3.1.4 | 2.3.1.5 | 2.3.1.6 | 2.3.1.7 | 2.3.1.8 | 2.3.1.9 | 2.3.1.10 | 2.3.2.1 | 2.3.2.2 | 2.3.2.3 |
| 2.3.2.4 | 2.3.2.5 | 2.3.2.6 | 2.3.2.7 | 2.3.2.8 | 2.3.2.9 | 2.3.2.10 | 2.3.3.1 | 2.3.3.2 | 2.3.3.3 | 2.3.3.4 | 2.3.3.5 | 2.3.3.6 |
| 2.3.3.7 | 2.3.3.8 | 2.3.3.9 | 2.3.3.10 | 2.3.4.1 | 2.3.4.2 | 2.3.4.3 | 2.3.4.4 | 2.3.4.5 | 2.3.4.6 | 2.3.4.7 | 2.3.4.8 | 2.3.4.9 |
| 2.3.4.10 | 2.3.5.1 | 2.3.5.2 | 2.3.5.3 | 2.3.5.4 | 2.3.5.5 | 2.3.5.6 | 2.3.5.7 | 2.3.5.8 | 2.3.5.9 | 2.3.5.10 | 2.3.6.1 | 2.3.6.2 |
| 2.3.6.3 | 2.3.6.4 | 2.3.6.5 | 2.3.6.6 | 2.3.6.7 | 2.3.6.8 | 2.3.6.9 | 2.3.6.10 | 2.4.1.1 | 2.4.1.2 | 2.4.1.3 | 2.4.1.4 | 2.4.1.5 |
| 2.4.1.6 | 2.4.1.7 | 2.4.1.8 | 2.4.1.9 | 2.4.1.10 | 2.4.2.1 | 2.4.2.2 | 2.4.2.3 | 2.4.2.4 | 2.4.2.5 | 2.4.2.6 | 2.4.2.7 | 2.4.2.8 |
| 2.4.2.9 | 2.4.2.10 | 2.4.3.1 | [1.4.3.2] *2.4.3.2* | 2.4.3.3 | 2.4.3.4 | 2.4.3.5 | 2.4.3.6 | 2.4.3.7 | 2.4.3.8 | 2.4.3. | [1.4.3.10] *2.4.3.10* | 2.4.4.1 |
| 2.4.4.2 | 2.4.4.3 | 2.4.4.4 | 2.4.4.5 | 2.4.4.6 | 2.4.4.7 | 2.4.4.8 | 2.4.4.9 | 2.4.4.10 | 2.4.5.1 | 2.4.5.2 | 2.4.5.3 | 2.4.5.4 |
| 2.4.5.5 | 2.4.5.6 | 2.4.5.7 | 2.4.5.8 | 2.4.5.9 | 2.4.5.10 | 2.4.6.1 | 2.4.6.2 | 2.4.6.3 | 2.4.6.4 | 2.4.6.5 | 2.4.6.6 | 2.4.6.7 |
| 2.4.6.8 | 2.4.6.9 | 2.4.6.10 | 2.5.1.1 | 2.5.1.2 | 2.5.1.3 | 2.5.1.4 | 2.5.1.5 | 2.5.1.6 | 2.5.1.7 | 2.5.1.8 | 2.5.1.9 | 2.5.1.10 |
| 2.5.2.1 | 2.5.2.2 | 2.5.2.3 | 2.5.2.4 | 2.5.2.5 | 2.5.2.6 | 2.5.2.7 | 2.5.2.8 | 2.5.2.9 | 2.5.2.10 | 2.5.3.1 | 2.5.3.2 | 2.5.3.3 |
| 2.5.3.4 | 2.5.3.5 | 2.5.3.6 | 2.5.3.7 | 2.5.3.8 | 2.5.3.9 | 2.5.3.10 | 2.5.4.1 | 2.5.4.2 | 2.5.4.3 | 2.5.4.4 | 2.5.4.5 | 2.5.4.6 |
| 2.5.4.7 | 2.5.4.8 | 2.5.4.9 | 2.5.4.10 | 2.5.5.1 | 2.5.5.2 | 2.5.5.3 | 2.5.5.4 | 2.5.5.5 | 2.5.5.6 | 2.5.5.7 | 2.5.5.8 | 2.5.5.9 |
| 2.5.5.10 | 2.5.6.1 | 2.5.6.2 | 2.5.6.3 | 2.5.6.4 | 2.5.6.5 | 2.5.6.6 | 2.5.6.7 | 2.5.6.8 | 2.5.6.9 | 2.5.6.10 | 2.6.1.1 | 2.6.1.2 |
| 2.6.1.3 | 2.6.1.4 | 2.6.1.5 | 2.6.1.6 | 2.6.1.7 | 2.6.1.8 | 2.6.1.9 | [1.6.1.10] *2.6.1.10* | 2.6.2.1 | 2.6.2.2 | 2.6.2.3 | 2.6.2.4 | 2.6.2.5 |
| 2.6.2.6 | 2.6.2.7 | 2.6.2.8 | 2.6.2.9 | 2.6.2.10 | 2.6.3.1 | 2.6.3.2 | 2.6.3.3 | 2.6.3.4 | 2.6.3.5 | 2.6.3.6 | 2.6.3.7 | 2.6.3.8 |
| 2.6.3.9 | 2.6.3.10 | 2.6.4.1 | 2.6.4.2 | 2.6.4.3 | 2.6.4.4 | 2.6.4.5 | 2.6.4.6 | 2.6.4.7 | 2.6.4.8 | 2.6.4.9 | 2.6.4.10 | 2.6.5.1 |
| 2.6.5.2 | 2.6.5.3 | 2.6.5.4 | 2.6.5.5 | 2.6.5.6 | 2.6.5.7 | 2.6.5.8 | 2.6.5.9 | 2.6.5.10 | 2.6.6.1 | 2.6.6.2 | 2.6.6.3 | 2.6.6.4 |
| 2.6.6.5 | 2.6.6.6 | 2.6.6.7 | 2.6.6.8 | 2.6.6.9 | 2.6.6.10 | 2.7.1.1 | 2.7.1.2 | 2.7.1.3 | 2.7.1.4 | 2.7.1.5 | 2.7.1.6 | 2.7.1.7 |
| 2.7.1.8 | 2.7.1.9 | 2.7.1.10 | 2.7.2.1 | 2.7.2.2 | 2.7.2.3 | 2.7.2.4 | 2.7.2.5 | 2.7.2.6 | 2.7.2.7 | 2.7.2.8 | 2.7.2.9 | 2.7.2.10 |
| 2.7.3.1 | 2.7.3.2 | 2.7.3.3 | 2.7.3.4 | 2.7.3.5 | 2.7.3.6 | 2.7.3.7 | 2.7.3.8 | 2.7.3.9 | 2.7.3.10 | 2.7.4.1 | 2.7.4.2 | 2.7.4.3 |
| 2.7.4.4 | 2.7.4.5 | 2.7.4.6 | 2.7.4.7 | 2.7.4.8 | 2.7.4.9 | 2.7.4.10 | 2.7.5.1 | 2.7.5.2 | 2.7.5.3 | 2.7.5.4 | 2.7.5.5 | 2.7.5.6 |
| 2.7.5.7 | 2.7.5.8 | 2.7.5.9 | 2.7.5.10 | 2.7.6.1 | 2.7.6.2 | 2.7.6.3 | 2.7.6.4 | 2.7.6.5 | 2.7.6.6 | 2.7.6.7 | 2.7.6.8 | 2.7.6.9 |
| 2.7.6.10 | 2.8.1.1 | 2.8.1.2 | 2.8.1.3 | 2.8.1.4 | 2.8.1.5 | 2.8.1.6 | 2.8.1.7 | 2.8.1.8 | 2.8.1.9 | 2.8.1.10 | 2.8.2.1 | 2.8.2.2 |
| 2.8.2.3 | 2.8.2.4 | 2.8.2.5 | 2.8.2.6 | 2.8.2.7 | 2.8.2.8 | 2.8.2.9 | 2.8.2.10 | 2.8.3.1 | 2.8.3.2 | 2.8.3.3 | 2.8.3.4 | 2.8.3.5 |
| 2.8.3.6 | 2.8.3.7 | 2.8.3.8 | 2.8.3.9 | 2.8.3.10 | 2.8.4.1 | 2.8.4.2 | 2.8.4.3 | 2.8.4.4 | 2.8.4.5 | 2.8.4.6 | 2.8.4.7 | 2.8.4.8 |
| 2.8.4.9 | 2.8.4.10 | 2.8.5.1 | 2.8.5.2 | 2.8.5.3 | 2.8.5.4 | 2.8.5.5 | 2.8.5.6 | 2.8.5.7 | 2.8.5.8 | 2.8.5.9 | 2.8.5.10 | 2.8.6.1 |
| 2.8.6.2 | 2.8.6.3 | 2.8.6.4 | 2.8.6.5 | 2.8.6.6 | 2.8.6.7 | 2.8.6.8 | 2.8.6.9 | 2.8.6.10 | 2.9.1.1 | 2.9.1.2 | 2.9.1.3 | 2.9.1.4 |
| 2.9.1.5 | 2.9.1.6 | 2.9.1.7 | 2.9.1.8 | 2.9.1.9 | 2.9.1.10 | 2.9.2.1 | 2.9.2.2 | 2.9.2.3 | 2.9.2.4 | 2.9.2.5 | 2.9.2.6 | 2.9.2.7 |
| 2.9.2.8 | 2.9.2.9 | 2.9.2.10 | 2.9.3.1 | 2.9.3.2 | 2.9.3.3 | 2.9.3.4 | 2.9.3.5 | 2.9.3.6 | 2.9.3.7 | 2.9.3.8 | 2.9.3.9 | 2.9.3.10 |
| 2.9.4.1 | 2.9.4.2 | 2.9.4.3 | 2.9.4.4 | 2.9.4.5 | 2.9.4.6 | 2.9.4.7 | 2.9.4.8 | 2.9.4.9 | 2.9.4.10 | 2.9.5.1 | 2.9.5.2 | 2.9.5.3 |
| 2.9.5.4 | 2.9.5.5 | 2.9.5.6 | 2.9.5.7 | 2.9.5.8 | 2.9.5.9 | 2.9.5.10 | 2.9.6.1 | 2.9.6.2 | 2.9.6.3 | 2.9.6.4 | 2.9.6.5 | 2.9.6.6 |
| 2.9.6.7 | 2.9.6.8 | 2.9.6.9 | 2.9.6.10 | 2.10.1.1 | 2.10.1.2 | 2.10.1.3 | 2.10.1.4 | 2.10.1.5 | 2.10.1.6 | 2.10.1.7 | 2.10.1.8 | |
| 2.10.1.9 | 2.10.1.10 | 2.10.2.1 | 2.10.2.2 | 2.10.2.3 | 2.10.2.4 | 2.10.2.5 | 2.10.2.6 | 2.10.2.7 | 2.10.2.8 | 2.10.2.9 | | |
| 2.10.2.10 | 2.10.3.1 | 2.10.3.2 | 2.10.3.3 | 2.10.3.4 | 2.10.3.5 | 2.10.3.6 | 2.10.3.7 | 2.10.3.8 | 2.10.3.9 | 2.10.3.10 | | |
| 2.10.4.1 | 2.10.4.2 | 2.10.4.3 | 2.10.4.4 | 2.10.4.5 | 2.10.4.6 | 2.10.4.7 | 2.10.4.8 | 2.10.4.9 | 2.10.4.10 | 2.10.5.1 | | |
| 2.10.5.2 | 2.10.5.3 | 2.10.5.4 | 2.10.5.5 | 2.10.5.6 | 2.10.5.7 | 2.10.5.8 | 2.10.5.9 | 2.10.5.10 | 2.10.6.1 | 2.10.6.2 | | |
| 2.10.6.3 | 2.10.6.4 | 2.10.6.5 | 2.10.6.6 | 2.10.6.7 | 2.10.6.8 | 2.10.6.9 | 2.10.6.10 | 2.11.1.1 | 2.11.1.2 | 2.11.1.3 | | |
| 2.11.1.4 | 2.11.1.5 | 2.11.1.6 | 2.11.1.7 | 2.11.1.8 | 2.11.1.9 | 2.11.1.10 | 2.11.2.1 | 2.11.2.2 | 2.11.2.3 | 2.11.2.4 | | |
| 2.11.2.5 | 2.11.2.6 | 2.11.2.7 | 2.11.2.8 | 2.11.2.9 | 2.11.2.10 | 2.11.3.1 | 2.11.3.2 | 2.11.3.3 | 2.11.3.4 | 2.11.3.5 | | |
| 2.11.3.6 | 2.11.3.7 | 2.11.3.8 | 2.11.3.9 | 2.11.3.10 | 2.11.4.1 | 2.11.4.2 | 2.11.4.3 | 2.11.4.4 | 2.11.4.5 | 2.11.4.6 | | |
| 2.11.4.7 | 2.11.4.8 | 2.11.4.9 | 2.11.4.10 | 2.11.5.1 | 2.11.5.2 | 2.11.5.3 | 2.11.5.4 | 2.11.5.5 | 2.11.5.6 | 2.11.5.7 | | |
| 2.11.5.8 | 2.11.5.9 | 2.11.5.10 | 2.11.6.1 | 2.11.6.2 | 2.11.6.3 | 2.11.6.4 | 2.11.6.5 | 2.11.6.6 | 2.11.6.7 | 2.11.6.8 | | |
| 2.11.6.9 | 2.11.6.10 | 2.12.1.1 | 2.12.1.2 | 2.12.1.3 | 2.12.1.4 | 2.12.1.5 | 2.12.1.6 | 2.12.1.7 | 2.12.1.8 | 2.12.1.9 | | |
| 2.12.1.10 | 2.12.2.1 | 2.12.2.2 | 2.12.2.3 | 2.12.2.4 | 2.12.2.5 | 2.12.2.6 | 2.12.2.7 | 2.12.2.8 | 2.12.2.9 | 2.12.2.10 | | |
| 2.12.3.1 | 2.12.3.2 | 2.12.3.3 | 2.12.3.4 | 2.12.3.5 | 2.12.3.6 | 2.12.3.7 | 2.12.3.8 | 2.12.3.9 | 2.12.3.10 | 2.12.4.1 | | |
| 2.12.4.2 | 2.12.4.3 | 2.12.4.4 | 2.12.4.5 | 2.12.4.6 | 2.12.4.7 | 2.12.4.8 | 2.12.4.9 | 2.12.4.10 | 2.12.5.1 | 2.12.5.2 | | |
| 2.12.5.3 | 2.12.5.4 | 2.12.5.5 | 2.12.5.6 | 2.12.5.7 | 2.12.5.8 | 2.12.5.9 | 2.12.5.10 | 2.12.6.1 | 2.12.6.2 | 2.12.6.3 | | |
| 2.12.6.4 | 2.12.6.5 | 2.12.6.6 | 2.12.6.7 | 2.12.6.8 | 2.12.6.9 | 2.12.6.10 | 2.13.1.1 | 2.13.1.2 | 2.13.1.3 | 2.13.1.4 | | |
| 2.13.1.5 | 2.13.1.6 | 2.13.1.7 | 2.13.1.8 | 2.13.1.9 | 2.13.1.10 | 2.13.2.1 | 2.13.2.2 | 2.13.2.3 | 2.13.2.4 | 2.13.2.5 | | |
| 2.13.2.6 | 2.13.2.7 | 2.13.2.8 | 2.13.2.9 | 2.13.2.10 | 2.13.3.1 | 2.13.3.2 | 2.13.3.3 | 2.13.3.4 | 2.13.3.5 | 2.13.3.6 | | |
| 2.13.3.7 | 2.13.3.8 | 2.13.3.9 | 2.13.3.10 | 2.13.4.1 | 2.13.4.2 | 2.13.4.3 | 2.13.4.4 | 2.13.4.5 | 2.13.4.6 | 2.13.4.7 | | |
| 2.13.4.8 | 2.13.4.9 | 2.13.4.10 | 2.13.5.1 | 2.13.5.2 | 2.13.5.3 | 2.13.5.4 | 2.13.5.5 | 2.13.5.6 | 2.13.5.7 | 2.13.5.8 | | |
| 2.13.5.9 | 2.13.5.10 | 2.13.6.1 | 2.13.6.2 | 2.13.6.3 | 2.13.6.4 | 2.13.6.5 | 2.13.6.6 | 2.13.6.7 | 2.13.6.8 | 2.13.6.9 | | |
| 2.13.6.10 | 2.14.1.1 | 2.14.1.2 | 2.14.1.3 | 2.14.1.4 | 2.14.1.5 | 2.14.1.6 | 2.14.1.7 | 2.14.1.8 | 2.14.1.9 | 2.14.1.10 | | |
| 2.14.2.1 | 2.14.2.2 | 2.14.2.3 | 2.14.2.4 | 2.14.2.5 | 2.14.2.6 | 2.14.2.7 | 2.14.2.8 | 2.14.2.9 | 2.14.2.10 | 2.14.3.1 | | |
| 2.14.3.2 | 2.14.3.3 | 2.14.3.4 | 2.14.3.5 | 2.14.3.6 | 2.14.3.7 | 2.14.3.8 | 2.14.3.9 | 2.14.3.10 | 2.14.4.1 | 2.14.4.2 | | |
| 2.14.4.3 | 2.14.4.4 | 2.14.4.5 | 2.14.4.6 | 2.14.4.7 | 2.14.4.8 | 2.14.4.9 | 2.14.4.10 | 2.14.5.1 | 2.14.5.2 | 2.14.5.3 | | |
| 2.14.5.4 | 2.14.5.5 | 2.14.5.6 | 2.14.5.7 | 2.14.5.8 | 2.14.5.9 | 2.14.5.10 | 2.14.6.1 | 2.14.6.2 | 2.14.6.3 | 2.14.6.4 | | |
| 2.14.6.5 | 2.14.6.6 | 2.14.6.7 | 2.14.6.8 | 2.14.6.9 | 2.14.6.10 | 2.15.1.1 | 2.15.1.2 | 2.15.1.3 | 2.15.1.4 | 2.15.1.5 | | |
| 2.15.1.6 | 2.15.1.7 | 2.15.1.8 | 2.15.1.9 | 2.15.1.10 | 2.15.2.1 | 2.15.2.2 | 2.15.2.3 | 2.15.2.4 | 2.15.2.5 | 2.15.2.6 | | |
| 2.15.2.7 | 2.15.2.8 | 2.15.2.9 | 2.15.2.10 | 2.15.3.1 | 2.15.3.2 | 2.15.3.3 | 2.15.3.4 | 2.15.3.5 | 2.15.3.6 | 2.15.3.7 | | |
| 2.15.3.8 | 2.15.3.9 | 2.15.3.10 | 2.15.4.1 | 2.15.4.2 | 2.15.4.3 | 2.15.4.4 | 2.15.4.5 | 2.15.4.6 | 2.15.4.7 | 2.15.4.8 | | |
| 2.15.4.9 | 2.15.4.10 | 2.15.5.1 | 2.15.5.2 | 2.15.5.3 | 2.15.5.4 | 2.15.5.5 | 2.15.5.6 | 2.15.5.7 | 2.15.5.8 | 2.15.5.9 | | |
| 2.15.5.10 | 2.15.6.1 | 2.15.6.2 | 2.15.6.3 | 2.15.6.4 | 2.15.6.5 | 2.15.6.6 | 2.15.6.7 | 2.15.6.8 | 2.15.6.9 | 2.15.6.10 | | |
| 2.16.1.1 | 2.16.1.2 | 2.16.1.3 | 2.16.1.4 | 2.16.1.5 | 2.16.1.6 | 2.16.1.7 | 2.16.1.8 | 2.16.1.9 | 2.16.1.10 | 2.16.2.1 | | |
| 2.16.2.2 | 2.16.2.3 | 2.16.2.4 | 2.16.2.5 | 2.16.2.6 | 2.16.2.7 | 2.16.2.8 | 2.16.2.9 | 2.16.2.10 | 2.16.3.1 | 2.16.3.2 | | |
| 2.16.3.3 | 2.16.3.4 | 2.16.3.5 | 2.16.3.6 | 2.16.3.7 | 2.16.3.8 | 2.16.3.9 | 2.16.3.10 | 2.16.4.1 | 2.16.4.2 | 2.16.4.3 | | |
| 2.16.4.4 | 2.16.4.5 | 2.16.4.6 | 2.16.4.7 | 2.16.4.8 | 2.16.4.9 | 2.16.4.10 | 2.16.5.1 | 2.16.5.2 | 2.16.5.3 | 2.16.5.4 | | |
| 2.16.5.5 | 2.16.5.6 | 2.16.5.7 | 2.16.5.8 | 2.16.5.9 | 2.16.5.10 | 2.16.6.1 | 2.16.6.2 | 2.16.6.3 | 2.16.6.4 | 2.16.6.5 | | |
| 2.16.6.6 | 2.16.6.7 | 2.16.6.8 | 2.16.6.9 | 2.16.6.10 | 2.17.1.1 | 2.17.1.2 | 2.17.1.3 | 2.17.1.4 | 2.17.1.5 | 2.17.1.6 | | |
| 2.17.1.7 | 2.17.1.8 | 2.17.1.9 | 2.17.1.10 | 2.17.2.1 | 2.17.2.2 | 2.17.2.3 | 2.17.2.4 | 2.17.2.5 | 2.17.2.6 | 2.17.2.7 | | |
| 2.17.2.8 | 2.17.2.9 | 2.17.2.10 | 2.17.3.1 | 2.17.3.2 | 2.17.3.3 | 2.17.3.4 | 2.17.3.5 | 2.17.3.6 | 2.17.3.7 | 2.17.3.8 | | |

TABLE B-continued

| | | | | | | | | | | | |
|---|---|---|---|---|---|---|---|---|---|---|---|
| 2.17.3.9 | 2.17.3.10 | 2.17.4.1 | 2.17.4.2 | 2.17.4.3 | 2.17.4.4 | 2.17.4.5 | 2.17.4.6 | 2.17.4.7 | 2.17.4.8 | 2.17.4.9 | |
| 2.17.4.10 | 2.17.5.1 | 2.17.5.2 | 2.17.5.3 | 2.17.5.4 | 2.17.5.5 | 2.17.5.6 | 2.17.5.7 | 2.17.5.8 | 2.17.5.9 | 2.17.5.10 | |
| 2.17.6.1 | 2.17.6.2 | 2.17.6.3 | 2.17.6.4 | 2.17.6.5 | 2.17.6.6 | 2.17.6.7 | 2.17.6.8 | 2.17.6.9 | 2.17.6.10 | 2.18.1.1 | |
| 2.18.1.2 | 2.18.1.3 | 2.18.1.4 | 2.18.1.5 | 2.18.1.6 | 2.18.1.7 | 2.18.1.8 | 2.18.1.9 | 2.18.1.10 | 2.18.2.1 | 2.18.2.2 | |
| 2.18.2.3 | 2.18.2.4 | 2.18.2.5 | 2.18.2.6 | 2.18.2.7 | 2.18.2.8 | 2.18.2.9 | 2.18.2.10 | 2.18.3.1 | 2.18.3.2 | 2.18.3.3 | |
| 2.18.3.4 | 2.18.3.5 | 2.18.3.6 | 2.18.3.7 | 2.18.3.8 | 2.18.3.9 | 2.18.3.10 | 2.18.4.1 | 2.18.4.2 | 2.18.4.3 | 2.18.4.4 | |
| 2.18.4.5 | 2.18.4.6 | 2.18.4.7 | 2.18.4.8 | 2.18.4.9 | 2.18.4.10 | 2.18.5.1 | 2.18.5.2 | 2.18.5.3 | 2.18.5.4 | 2.18.5.5 | |
| 2.18.5.6 | 2.18.5.7 | 2.18.5.8 | 2.18.5.9 | 2.18.5.10 | 2.18.6.1 | 2.18.6.2 | 2.18.6.3 | 2.18.6.4 | 2.18.6.5 | 2.18.6.6 | |
| 2.18.6.7 | 2.18.6.8 | 2.18.6.9 | 2.18.6.10 | 2.19.1.1 | 2.19.1.2 | 2.19.1.3 | 2.19.1.4 | 2.19.1.5 | 2.19.1.6 | 2.19.1.7 | |
| 2.19.1.8 | 2.19.1.9 | 2.19.1.10 | 2.19.2.1 | 2.19.2.2 | 2.19.2.3 | 2.19.2.4 | 2.19.2.5 | 2.19.2.6 | 2.19.2.7 | 2.19.2.8 | |
| 2.19.2.9 | 2.19.2.10 | 2.19.3.1 | 2.19.3.2 | 2.19.3.3 | 2.19.3.4 | 2.19.3.5 | 2.19.3.6 | 2.19.3.7 | 2.19.3.8 | 2.19.3.9 | |
| 2.19.3.10 | 2.19.4.1 | 2.19.4.2 | 2.19.4.3 | 2.19.4.4 | 2.19.4.5 | 2.19.4.6 | 2.19.4.7 | 2.19.4.8 | 2.19.4.9 | 2.19.4.10 | |
| 2.19.5.1 | 2.19.5.2 | 2.19.5.3 | 2.19.5.4 | 2.19.5.5 | 2.19.5.6 | 2.19.5.7 | 2.19.5.8 | 2.19.5.9 | 2.19.5.10 | 2.19.6.1 | |
| 2.19.6.2 | 2.19.6.3 | 2.19.6.4 | 2.19.6.5 | 2.19.6.6 | 2.19.6.7 | 2.19.6.8 | 2.19.6.9 | 2.19.6.10 | 2.20.1.1 | 2.20.1.2 | |
| 2.20.1.3 | 2.20.1.4 | 2.20.1.5 | 2.20.1.6 | 2.20.1.7 | 2.20.1.8 | 2.20.1.9 | 2.20.1.10 | 2.20.2.1 | 2.20.2.2 | 2.20.2.3 | |
| 2.20.2.4 | 2.20.2.5 | 2.20.2.6 | 2.20.2.7 | 2.20.2.8 | 2.20.2.9 | 2.20.2.10 | 2.20.3.1 | 2.20.3.2 | 2.20.3.3 | 2.20.3.4 | |
| 2.20.3.5 | 2.20.3.6 | 2.20.3.7 | 2.20.3.8 | 2.20.3.9 | 2.20.3.10 | 2.20.4.1 | 2.20.4.2 | 2.20.4.3 | 2.20.4.4 | 2.20.4.5 | |
| 2.20.4.6 | 2.20.4.7 | 2.20.4.8 | 2.20.4.9 | 2.20.4.10 | 2.20.5.1 | 2.20.5.2 | 2.20.5.3 | 2.20.5.4 | 2.20.5.5 | 2.20.5.6 | |
| 2.20.5.7 | 2.20.5.8 | 2.20.5.9 | 2.20.5.10 | 2.20.6.1 | 2.20.6.2 | 2.20.6.3 | 2.20.6.4 | 2.20.6.5 | 2.20.6.6 | 2.20.6.7 | |
| 2.20.6.8 | 2.20.6.9 | 2.20.6.10 | 2.21.1.1 | 2.21.1.2 | 2.21.1.3 | 2.21.1.4 | 2.21.1.5 | 2.21.1.6 | 2.21.1.7 | 2.21.1.8 | |
| 2.21.1.9 | 2.21.1.10 | 2.21.2.1 | 2.21.2.2 | 2.21.2.3 | 2.21.2.4 | 2.21.2.5 | 2.21.2.6 | 2.21.2.7 | 2.21.2.8 | 2.21.2.9 | |
| 2.21.2.10 | 2.21.3.1 | 2.21.3.2 | 2.21.3.3 | 2.21.3.4 | 2.21.3.5 | 2.21.3.6 | 2.21.3.7 | 2.21.3.8 | 2.21.3.9 | 2.21.3.10 | |
| 2.21.4.1 | 2.21.4.2 | 2.21.4.3 | 2.21.4.4 | 2.21.4.5 | 2.21.4.6 | 2.21.4.7 | 2.21.4.8 | 2.21.4.9 | 2.21.4.10 | 2.21.5.1 | |
| 2.21.5.2 | 2.21.5.3 | 2.21.5.4 | 2.21.5.5 | 2.21.5.6 | 2.21.5.7 | 2.21.5.8 | 2.21.5.9 | 2.21.5.10 | 2.21.6.1 | 2.21.6.2 | |
| 2.21.6.3 | 2.21.6.4 | 2.21.6.5 | 2.21.6.6 | 2.21.6.7 | 2.21.6.8 | 2.21.6.9 | 2.21.6.10 | 2.22.1.1 | 2.22.1.2 | 2.22.1.3 | |
| 2.22.1.4 | 2.22.1.5 | 2.22.1.6 | 2.22.1.7 | 2.22.1.8 | 2.22.1.9 | 2.22.1.10 | 2.22.2.1 | 2.22.2.2 | 2.22.2.3 | 2.22.2.4 | |
| 2.22.2.5 | 2.22.2.6 | 2.22.2.7 | 2.22.2.8 | 2.22.2.9 | 2.22.2.10 | 2.22.3.1 | 2.22.3.2 | 2.22.3.3 | 2.22.3.4 | 2.22.3.5 | |
| 2.22.3.6 | 2.22.3.7 | 2.22.3.8 | 2.22.3.9 | 2.22.3.10 | 2.22.4.1 | 2.22.4.2 | 2.22.4.3 | 2.22.4.4 | 2.22.4.5 | 2.22.4.6 | |
| 2.22.4.7 | 2.22.4.8 | 2.22.4.9 | 2.22.4.10 | 2.22.5.1 | 2.22.5.2 | 2.22.5.3 | 2.22.5.4 | 2.22.5.5 | 2.22.5.6 | 2.22.5.7 | |
| 2.22.5.8 | 2.22.5.9 | 2.22.5.10 | 2.22.6.1 | 2.22.6.2 | 2.22.6.3 | 2.22.6.4 | 2.22.6.5 | 2.22.6.6 | 2.22.6.7 | 2.22.6.8 | |
| 2.22.6.9 | 2.22.6.10 | 2.23.1.1 | 2.23.1.2 | 2.23.1.3 | 2.23.1.4 | 2.23.1.5 | 2.23.1.6 | 2.23.1.7 | 2.23.1.8 | 2.23.1.9 | |
| 2.23.1.10 | 2.23.2.1 | 2.23.2.2 | 2.23.2.3 | 2.23.2.4 | 2.23.2.5 | 2.23.2.6 | 2.23.2.7 | 2.23.2.8 | 2.23.2.9 | 2.23.2.10 | |
| 2.23.3.1 | 2.23.3.2 | 2.23.3.3 | 2.23.3.4 | 2.23.3.5 | 2.23.3.6 | 2.23.3.7 | 2.23.3.8 | 2.23.3.9 | 2.23.3.10 | 2.23.4.1 | |
| 2.23.4.2 | 2.23.4.3 | 2.23.4.4 | 2.23.4.5 | 2.23.4.6 | 2.23.4.7 | 2.23.4.8 | 2.23.4.9 | 2.23.4.10 | 2.23.5.1 | 2.23.5.2 | |
| 2.23.5.3 | 2.23.5.4 | 2.23.5.5 | 2.23.5.6 | 2.23.5.7 | 2.23.5.8 | 2.23.5.9 | 2.23.5.10 | 2.23.6.1 | 2.23.6.2 | 2.23.6.3 | |
| 2.23.6.4 | 2.23.6.5 | 2.23.6.6 | 2.23.6.7 | 2.23.6.8 | 2.23.6.9 | 2.23.6.10 | 2.24.1.1 | 2.24.1.2 | 2.24.1.3 | 2.24.1.4 | |
| 2.24.1.5 | 2.24.1.6 | 2.24.1.7 | 2.24.1.8 | 2.24.1.9 | 2.24.1.10 | 2.24.2.1 | 2.24.2.2 | 2.24.2.3 | 2.24.2.4 | 2.24.2.5 | |
| 2.24.2.6 | 2.24.2.7 | 2.24.2.8 | 2.24.2.9 | 2.24.2.10 | 2.24.3.1 | 2.24.3.2 | 2.24.3.3 | 2.24.3.4 | 2.24.3.5 | 2.24.3.6 | |
| 2.24.3.7 | 2.24.3.8 | 2.24.3.9 | 2.24.3.10 | 2.24.4.1 | 2.24.4.2 | 2.24.4.3 | 2.24.4.4 | 2.24.4.5 | 2.24.4.6 | 2.24.4.7 | |
| 2.24.4.8 | 2.24.4.9 | 2.24.4.10 | 2.24.5.1 | 2.24.5.2 | 2.24.5.3 | 2.24.5.4 | 2.24.5.5 | 2.24.5.6 | 2.24.5.7 | 2.24.5.8 | |
| 2.24.5.9 | 2.24.5.10 | 2.24.6.1 | 2.24.6.2 | 2.24.6.3 | 2.24.6.4 | 2.24.6.5 | 2.24.6.6 | 2.24.6.7 | 2.24.6.8 | 2.24.6.9 | |
| 2.24.6.10 | 2.25.1.1 | 2.25.1.2 | 2.25.1.3 | 2.25.1.4 | 2.25.1.5 | 2.25.1.6 | 2.25.1.7 | 2.25.1.8 | 2.25.1.9 | 2.25.1.10 | |
| 2.25.2.1 | 2.25.2.2 | 2.25.2.3 | 2.25.2.4 | 2.25.2.5 | 2.25.2.6 | 2.25.2.7 | 2.25.2.8 | 2.25.2.9 | 2.25.2.10 | 2.25.3.1 | |
| 2.25.3.2 | 2.25.3.3 | 2.25.3.4 | 2.25.3.5 | 2.25.3.6 | 2.25.3.7 | 2.25.3.8 | 2.25.3.9 | 2.25.3.10 | 2.25.4.1 | 2.25.4.2 | |
| 2.25.4.3 | 2.25.4.4 | 2.25.4.5 | 2.25.4.6 | 2.25.4.7 | 2.25.4.8 | 2.25.4.9 | 2.25.4.10 | 2.25.5.1 | 2.25.5.2 | 2.25.5.3 | |
| 2.25.5.4 | 2.25.5.5 | 2.25.5.6 | 2.25.5.7 | 2.25.5.8 | 2.25.5.9 | 2.25.5.10 | 2.25.6.1 | 2.25.6.2 | 2.25.6.3 | 2.25.6.4 | |
| 2.25.6.5 | 2.25.6.6 | 2.25.6.7 | 2.25.6.8 | 2.25.6.9 | 2.25.6.10 | 3.1.1.1 | 3.1.1.2 | 3.1.1.3 | [2.1.1.4]<br>*3.1.1.4* | 3.1.1.5 | 3.1.1.6 |
| 3.1.1.7 | 3.1.1.8 | 3.1.1.9 | 3.1.1.10 | 3.1.2.1 | 3.1.2.2 | 3.1.2.3 | 3.1.2.4 | 3.1.2.5 | 3.1.2.6 | 3.1.2.7 | 3.1.2.8 | 3.1.2.9 |
| 3.1.2.10 | 3.1.3.1 | 3.1.3.2 | 3.1.3.3 | 3.1.3.4 | 3.1.3.5 | 3.1.3.6 | 3.1.3.7 | 3.1.3.8 | 3.1.3.9 | 3.1.3.10 | 3.1.4.1 | 3.1.4.2 |
| 3.1.4.3 | 3.1.4.4 | 3.1.4.5 | 3.1.4.6 | 3.1.4.7 | 3.1.4.8 | 3.1.4.9 | 3.1.4.10 | 3.1.5.1 | 3.1.5.2 | 3.1.5.3 | 3.1.5.4 | 3.1.5.5 |
| 3.1.5.6 | 3.1.5.7 | 3.1.5.8 | 3.1.5.9 | 3.1.5.10 | 3.1.6.1 | 3.1.6.2 | 3.1.6.3 | 3.1.6.4 | 3.1.6.5 | 3.1.6.6 | 3.1.6.7 | 3.1.6.8 |
| 3.1.6.9 | 3.1.6.10 | 3.2.1.1 | 3.2.1.2 | 3.2.1.3 | 3.2.1.4 | 3.2.1.5 | 3.2.1.6 | 3.2.1.7 | 3.2.1.8 | 3.2.1.9 | 3.2.1.10 | 3.2.2.1 |
| 3.2.2.2 | 3.2.2.3 | 3.2.2.4 | 3.2.2.5 | 3.2.2.6 | 3.2.2.7 | 3.2.2.8 | 3.2.2.9 | 3.2.2.10 | 3.2.3.1 | 3.2.3.2 | 3.2.3.3 | 3.2.3.4 |
| 3.2.3.5 | 3.2.3.6 | 3.2.3.7 | 3.2.3.8 | 3.2.3.9 | 3.2.3.10 | 3.2.4.1 | 3.2.4.2 | 3.2.4.3 | 3.2.4.4 | 3.2.4.5 | 3.2.4.6 | 3.2.4.7 |
| 3.2.4.8 | 3.2.4.9 | 3.2.4.10 | 3.2.5.1 | 3.2.5.2 | 3.2.5.3 | 3.2.5.4 | 3.2.5.5 | 3.2.5.6 | 3.2.5.7 | 3.2.5.8 | 3.2.5.9 | 3.2.5.10 |
| 3.2.6.1 | 3.2.6.2 | 3.2.6.3 | 3.2.6.4 | 3.2.6.5 | 3.2.6.6 | 3.2.6.7 | 3.2.6.8 | 3.2.6.9 | 3.2.6.10 | 3.3.1.1 | 3.3.1.2 | 3.3.1.3 |
| 3.3.1.4 | 3.3.1.5 | 3.3.1.6 | 3.3.1.7 | 3.3.1.8 | 3.3.1.9 | 3.3.1.10 | 3.3.2.1 | 3.3.2.2 | 3.3.2.3 | 3.3.2.4 | 3.3.2.5 | 3.3.2.6 |
| 3.3.2.7 | 3.3.2.8 | 3.3.2.9 | 3.3.2.10 | 3.3.3.1 | 3.3.3.2 | 3.3.3.3 | 3.3.3.4 | 3.3.3.5 | 3.3.3.6 | 3.3.3.7 | 3.3.3.8 | 3.3.3.9 |
| 3.3.3.10 | 3.3.4.1 | 3.3.4.2 | 3.3.4.3 | 3.3.4.4 | 3.3.4.5 | 3.3.4.6 | 3.3.4.7 | 3.3.4.8 | 3.3.4.9 | 3.3.4.10 | 3.3.5.1 | 3.3.5.2 |
| 3.3.5.3 | 3.3.5.4 | 3.3.5.5 | 3.3.5.6 | 3.3.5.7 | 3.3.5.8 | 3.3.5.9 | 3.3.5.10 | 3.3.6.1 | 3.3.6.2 | 3.3.6.3 | 3.3.6.4 | 3.3.6.5 |
| 3.3.6.6 | 3.3.6.7 | 3.3.6.8 | 3.3.6.9 | 3.3.6.10 | 3.4.1.1 | 3.4.1.2 | 3.4.1.3 | 3.4.1.4 | 3.4.1.5 | 3.4.1.6 | 3.4.1.7 | 3.4.1.8 |
| 3.4.1.9 | 3.4.1.10 | 3.4.2.1 | 3.4.2.2 | 3.4.2.3 | 3.4.2.4 | 3.4.2.5 | 3.4.2.6 | 3.4.2.7 | 3.4.2.8 | 3.4.2.9 | 3.4.2.10 | 3.4.3.1 |
| 3.4.3.2 | 3.4.3.3 | 3.4.3.4 | 3.4.3.5 | 3.4.3.6 | 3.4.3.7 | 3.4.3.8 | 3.4.3.9 | 3.4.3.10 | 3.4.4.1 | 3.4.4.2 | 3.4.4.3 | 3.4.4.4 |
| 3.4.4.5 | 3.4.4.6 | 3.4.4.7 | 3.4.4.8 | 3.4.4.9 | 3.4.4.10 | 3.4.5.1 | 3.4.5.2 | 3.4.5.3 | 3.4.5.4 | 3.4.5.5 | 3.4.5.6 | 3.4.5.7 |
| 3.4.5.8 | 3.4.5.9 | 3.4.5.10 | 3.4.6.1 | 3.4.6.2 | 3.4.6.3 | 3.4.6.4 | 3.4.6.5 | 3.4.6.6 | 3.4.6.7 | 3.4.6.8 | 3.4.6.9 | 3.4.6.10 |
| 3.5.1.1 | 3.5.1.2 | 3.5.1.3 | 3.5.1.4 | 3.5.1.5 | 3.5.1.6 | 3.5.1.7 | 3.5.1.8 | 3.5.1.9 | 3.5.1.10 | 3.5.2.1 | 3.5.2.2 | 3.5.2.3 |
| 3.5.2.4 | 3.5.2.5 | 3.5.2.6 | 3.5.2.7 | 3.5.2.8 | 3.5.2.9 | 3.5.2.10 | 3.5.3.1 | 3.5.3.2 | 3.5.3.3 | 3.5.3.4 | 3.5.3.5 | 3.5.3.6 |
| 3.5.3.7 | 3.5.3.8 | 3.5.3.9 | 3.5.3.10 | 3.5.4.1 | 3.5.4.2 | 3.5.4.3 | 3.5.4.4 | 3.5.4.5 | 3.5.4.6 | 3.5.4.7 | 3.5.4.8 | 3.5.4.9 |
| 3.5.4.10 | 3.5.5.1 | 3.5.5.2 | 3.5.5.3 | 3.5.5.4 | 3.5.5.5 | 3.5.5.6 | 3.5.5.7 | 3.5.5.8 | 3.5.5.9 | 3.5.5.10 | 3.5.6.1 | 3.5.6.2 |
| 3.5.6.3 | 3.5.6.4 | 3.5.6.5 | 3.5.6.6 | 3.5.6.7 | 3.5.6.8 | 3.5.6.9 | 3.5.6.10 | 3.6.1.1 | 3.6.1.2 | 3.6.1.3 | 3.6.1.4 | 3.6.1.5 |
| 3.6.1.6 | 3.6.1.7 | 3.6.1.8 | 3.6.1.9 | 3.6.1.10 | 3.6.2.1 | 3.6.2.2 | 3.6.2.3 | 3.6.2.4 | 3.6.2.5 | 3.6.2.6 | 3.6.2.7 | 3.6.2.8 |
| 3.6.2.9 | 3.6.2.10 | 3.6.3.1 | 3.6.3.2 | 3.6.3.3 | 3.6.3.4 | 3.6.3.5 | 3.6.3.6 | 3.6.3.7 | 3.6.3.8 | 3.6.3.9 | 3.6.3.10 | 3.6.4.1 |
| 3.6.4.2 | 3.6.4.3 | 3.6.4.4 | 3.6.4.5 | 3.6.4.6 | 3.6.4.7 | 3.6.4.8 | 3.6.4.9 | 3.6.4.10 | 3.6.5.1 | 3.6.5.2 | 3.6.5.3 | 3.6.5.4 |
| 3.6.5.5 | 3.6.5.6 | 3.6.5.7 | 3.6.5.8 | 3.6.5.9 | 3.6.5.10 | 3.6.6.1 | 3.6.6.2 | 3.6.6.3 | 3.6.6.4 | 3.6.6.5 | 3.6.6.6 | 3.6.6.7 |
| 3.6.6.8 | 3.6.6.9 | 3.6.6.10 | 3.7.1.1 | 3.7.1.2 | 3.7.1.3 | 3.7.1.4 | 3.7.1.5 | 3.7.1.6 | 3.7.1.7 | 3.7.1.8 | 3.7.1.9 | 3.7.1.10 |
| 3.7.2.1 | 3.7.2.2 | 3.7.2.3 | 3.7.2.4 | 3.7.2.5 | 3.7.2.6 | 3.7.2.7 | 3.7.2.8 | 3.7.2.9 | 3.7.2.10 | 3.7.3.1 | 3.7.3.2 | 3.7.3.3 |
| 3.7.3.4 | 3.7.3.5 | 3.7.3.6 | 3.7.3.7 | 3.7.3.8 | 3.7.3.9 | 3.7.3.10 | 3.7.4.1 | 3.7.4.2 | 3.7.4.3 | 3.7.4.4 | 3.7.4.5 | 3.7.4.6 |
| 3.7.4.7 | 3.7.4.8 | 3.7.4.9 | 3.7.4.10 | 3.7.5.1 | 3.7.5.2 | 3.7.5.3 | 3.7.5.4 | 3.7.5.5 | 3.7.5.6 | 3.7.5.7 | 3.7.5.8 | 3.7.5.9 |

TABLE B-continued

| | | | | | | | | | | | |
|---|---|---|---|---|---|---|---|---|---|---|---|
| 3.7.5.10 | 3.7.6.1 | 3.7.6.2 | 3.7.6.3 | 3.7.6.4 | 3.7.6.5 | 3.7.6.6 | 3.7.6.7 | 3.7.6.8 | 3.7.6.9 | 3.7.6.10 | 3.8.1.1 | 3.8.1.2 |
| 3.8.1.3 | 3.8.1.4 | 3.8.1.5 | 3.8.1.6 | 3.8.1.7 | 3.8.1.8 | 3.8.1.9 | 3.8.1.10 | 3.8.2.1 | 3.8.2.2 | 3.8.2.3 | 3.8.2.4 | 3.8.2.5 |
| 3.8.2.6 | 3.8.2.7 | 3.8.2.8 | 3.8.2.9 | 3.8.2.10 | 3.8.3.1 | 3.8.3.2 | 3.8.3.3 | 3.8.3.4 | 3.8.3.5 | 3.8.3.6 | 3.8.3.7 | 3.8.3.8 |
| 3.8.3.9 | 3.8.3.10 | 3.8.4.1 | 3.8.4.2 | 3.8.4.3 | 3.8.4.4 | 3.8.4.5 | 3.8.4.6 | 3.8.4.7 | 3.8.4.8 | 3.8.4.9 | 3.8.4.10 | 3.8.5.1 |
| 3.8.5.2 | 3.8.5.3 | 3.8.5.4 | 3.8.5.5 | 3.8.5.6 | 3.8.5.7 | 3.8.5.8 | 3.8.5.9 | 3.8.5.10 | 3.8.6.1 | 3.8.6.2 | 3.8.6.3 | 3.8.6.4 |
| 3.8.6.5 | 3.8.6.6 | 3.8.6.7 | 3.8.6.8 | 3.8.6.9 | 3.8.6.10 | 3.9.1.1 | 3.9.1.2 | 3.9.1.3 | 3.9.1.4 | 3.9.1.5 | 3.9.1.6 | 3.9.1.7 |
| 3.9.1.8 | 3.9.1.9 | 3.9.1.10 | 3.9.2.1 | 3.9.2.2 | 3.9.2.3 | 3.9.2.4 | 3.9.2.5 | 3.9.2.6 | 3.9.2.7 | 3.9.2.8 | 3.9.2.9 | 3.9.2.10 |
| 3.9.3.1 | 3.9.3.2 | 3.9.3.3 | 3.9.3.4 | 3.9.3.5 | 3.9.3.6 | 3.9.3.7 | 3.9.3.8 | 3.9.3.9 | 3.9.3.10 | 3.9.4.1 | 3.9.4.2 | 3.9.4.3 |
| 3.9.4.4 | 3.9.4.5 | 3.9.4.6 | 3.9.4.7 | 3.9.4.8 | 3.9.4.9 | 3.9.4.10 | 3.9.5.1 | 3.9.5.2 | 3.9.5.3 | 3.9.5.4 | 3.9.5.5 | 3.9.5.6 |
| 3.9.5.7 | 3.9.5.8 | 3.9.5.9 | 3.9.5.10 | 3.9.6.1 | 3.9.6.2 | 3.9.6.3 | 3.9.6.4 | 3.9.6.5 | 3.9.6.6 | 3.9.6.7 | 3.9.6.8 | 3.9.6.9 |
| 3.9.6.10 | 3.10.1.1 | 3.10.1.2 | 3.10.1.3 | 3.10.1.4 | 3.10.1.5 | 3.10.1.6 | 3.10.1.7 | 3.10.1.8 | 3.10.1.9 | 3.10.1.10 | | |
| 3.10.2.1 | 3.10.2.2 | 3.10.2.3 | 3.10.2.4 | 3.10.2.5 | 3.10.2.6 | 3.10.2.7 | 3.10.2.8 | 3.10.2.9 | 3.10.2.10 | 3.10.3.1 | | |
| 3.10.3.2 | 3.10.3.3 | 3.10.3.4 | 3.10.3.5 | 3.10.3.6 | 3.10.3.7 | 3.10.3.8 | 3.10.3.9 | 3.10.3.10 | 3.10.4.1 | 3.10.4.2 | | |
| 3.10.4.3 | 3.10.4.4 | 3.10.4.5 | 3.10.4.6 | 3.10.4.7 | 3.10.4.8 | 3.10.4.9 | 3.10.4.10 | 3.10.5.1 | 3.10.5.2 | 3.10.5.3 | | |
| 3.10.5.4 | 3.10.5.5 | 3.10.5.6 | 3.10.5.7 | 3.10.5.8 | 3.10.5.9 | 3.10.5.10 | 3.10.6.1 | 3.10.6.2 | 3.10.6.3 | 3.10.6.4 | | |
| 3.10.6.5 | 3.10.6.6 | 3.10.6.7 | 3.10.6.8 | 3.10.6.9 | 3.10.6.10 | 3.11.1.1 | 3.11.1.2 | 3.11.1.3 | 3.11.1.4 | 3.11.1.5 | | |
| 3.11.1.6 | 3.11.1.7 | 3.11.1.8 | 3.11.1.9 | 3.11.1.10 | 3.11.2.1 | 3.11.2.2 | 3.11.2.3 | 3.11.2.4 | 3.11.2.5 | 3.11.2.6 | | |
| 3.11.2.7 | 3.11.2.8 | 3.11.2.9 | 3.11.2.10 | 3.11.3.1 | 3.11.3.2 | 3.11.3.3 | 3.11.3.4 | 3.11.3.5 | 3.11.3.6 | 3.11.3.7 | | |
| 3.11.3.8 | 3.11.3.9 | 3.11.3.10 | 3.11.4.1 | 3.11.4.2 | 3.11.4.3 | 3.11.4.4 | 3.11.4.5 | 3.11.4.6 | 3.11.4.7 | 3.11.4.8 | | |
| 3.11.4.9 | 3.11.4.10 | 3.11.5.1 | 3.11.5.2 | 3.11.5.3 | 3.11.5.4 | 3.11.5.5 | 3.11.5.6 | 3.11.5.7 | 3.11.5.8 | 3.11.5.9 | | |
| 3.11.5.10 | 3.11.6.1 | 3.11.6.2 | 3.11.6.3 | 3.11.6.4 | 3.11.6.5 | 3.11.6.6 | 3.11.6.7 | 3.11.6.8 | 3.11.6.9 | 3.11.6.10 | | |
| 3.12.1.1 | 3.12.1.2 | 3.12.1.3 | 3.12.1.4 | 3.12.1.5 | 3.12.1.6 | 3.12.1.7 | 3.12.1.8 | 3.12.1.9 | 3.12.1.10 | 3.12.2.1 | | |
| 3.12.2.2 | 3.12.2.3 | 3.12.2.4 | 3.12.2.5 | 3.12.2.6 | 3.12.2.7 | 3.12.2.8 | 3.12.2.9 | 3.12.2.10 | 3.12.3.1 | 3.12.3.2 | | |
| 3.12.3.3 | 3.12.3.4 | 3.12.3.5 | 3.12.3.6 | 3.12.3.7 | 3.12.3.8 | 3.12.3.9 | 3.12.3.10 | 3.12.4.1 | 3.12.4.2 | 3.12.4.3 | | |
| 3.12.4.4 | 3.12.4.5 | 3.12.4.6 | 3.12.4.7 | 3.12.4.8 | 3.12.4.9 | 3.12.4.10 | 3.12.5.1 | 3.12.5.2 | 3.12.5.3 | 3.12.5.4 | | |
| 3.12.5.5 | 3.12.5.6 | 3.12.5.7 | 3.12.5.8 | 3.12.5.9 | 3.12.5.10 | 3.12.6.1 | 3.12.6.2 | 3.12.6.3 | 3.12.6.4 | 3.12.6.5 | | |
| 3.12.6.6 | 3.12.6.7 | 3.12.6.8 | 3.12.6.9 | 3.12.6.10 | 3.13.1.1 | 3.13.1.2 | 3.13.1.3 | 3.13.1.4 | 3.13.1.5 | 3.13.1.6 | | |
| 3.13.1.7 | 3.13.1.8 | 3.13.1.9 | 3.13.1.10 | 3.13.2.1 | 3.13.2.2 | 3.13.2.3 | 3.13.2.4 | 3.13.2.5 | 3.13.2.6 | 3.13.2.7 | | |
| 3.13.2.8 | 3.13.2.9 | 3.13.2.10 | 3.13.3.1 | 3.13.3.2 | 3.13.3.3 | 3.13.3.4 | 3.13.3.5 | 3.13.3.6 | 3.13.3.7 | 3.13.3.8 | | |
| 3.13.3.9 | 3.13.3.10 | 3.13.4.1 | 3.13.4.2 | 3.13.4.3 | 3.13.4.4 | 3.13.4.5 | 3.13.4.6 | 3.13.4.7 | 3.13.4.8 | 3.13.4.9 | | |
| 3.13.4.10 | 3.13.5.1 | 3.13.5.2 | 3.13.5.3 | 3.13.5.4 | 3.13.5.5 | 3.13.5.6 | 3.13.5.7 | 3.13.5.8 | 3.13.5.9 | 3.13.5.10 | | |
| 3.13.6.1 | 3.13.6.2 | 3.13.6.3 | 3.13.6.4 | 3.13.6.5 | 3.13.6.6 | 3.13.6.7 | 3.13.6.8 | 3.13.6.9 | 3.13.6.10 | 3.14.1.1 | | |
| 3.14.1.2 | 3.14.1.3 | 3.14.1.4 | 3.14.1.5 | 3.14.1.6 | 3.14.1.7 | 3.14.1.8 | 3.14.1.9 | 3.14.1.10 | 3.14.2.1 | 3.14.2.2 | | |
| 3.14.2.3 | 3.14.2.4 | 3.14.2.5 | 3.14.2.6 | 3.14.2.7 | 3.14.2.8 | 3.14.2.9 | 3.14.2.10 | 3.14.3.1 | 3.14.3.2 | 3.14.3.3 | | |
| 3.14.3.4 | 3.14.3.5 | 3.14.3.6 | 3.14.3.7 | 3.14.3.8 | 3.14.3.9 | 3.14.3.10 | 3.14.4.1 | 3.14.4.2 | 3.14.4.3 | 3.14.4.4 | | |
| 3.14.4.5 | 3.14.4.6 | 3.14.4.7 | 3.14.4.8 | 3.14.4.9 | 3.14.4.10 | 3.14.5.1 | 3.14.5.2 | 3.14.5.3 | 3.14.5.4 | 3.14.5.5 | | |
| 3.14.5.6 | 3.14.5.7 | 3.14.5.8 | 3.14.5.9 | 3.14.5.10 | 3.14.6.1 | 3.14.6.2 | 3.14.6.3 | 3.14.6.4 | 3.14.6.5 | 3.14.6.6 | | |
| 3.14.6.7 | 3.14.6.8 | 3.14.6.9 | 3.14.6.10 | 3.15.1.1 | 3.15.1.2 | 3.15.1.3 | 3.15.1.4 | 3.15.1.5 | 3.15.1.6 | 3.15.1.7 | | |
| 3.15.1.8 | 3.15.1.9 | 3.15.1.10 | 3.15.2.1 | 3.15.2.2 | 3.15.2.3 | 3.15.2.4 | 3.15.2.5 | 3.15.2.6 | 3.15.2.7 | 3.15.2.8 | | |
| 3.15.2.9 | 3.15.2.10 | 3.15.3.1 | 3.15.3.2 | 3.15.3.3 | 3.15.3.4 | 3.15.3.5 | 3.15.3.6 | 3.15.3.7 | 3.15.3.8 | 3.15.3.9 | | |
| 3.15.3.10 | 3.15.4.1 | 3.15.4.2 | 3.15.4.3 | 3.15.4.4 | 3.15.4.5 | 3.15.4.6 | 3.15.4.7 | 3.15.4.8 | 3.15.4.9 | 3.15.4.10 | | |
| 3.15.5.1 | 3.15.5.2 | 3.15.5.3 | 3.15.5.4 | 3.15.5.5 | 3.15.5.6 | 3.15.5.7 | 3.15.5.8 | 3.15.5.9 | 3.15.5.10 | 3.15.6.1 | | |
| 3.15.6.2 | 3.15.6.3 | 3.15.6.4 | 3.15.6.5 | 3.15.6.6 | 3.15.6.7 | 3.15.6.8 | 3.15.6.9 | 3.15.6.10 | 3.16.1.1 | 3.16.1.2 | | |
| 3.16.1.3 | 3.16.1.4 | 3.16.1.5 | 3.16.1.6 | 3.16.1.7 | 3.16.1.8 | 3.16.1.9 | 3.16.1.10 | 3.16.2.1 | 3.16.2.2 | 3.16.2.3 | | |
| 3.16.2.4 | 3.16.2.5 | 3.16.2.6 | 3.16.2.7 | 3.16.2.8 | 3.16.2.9 | 3.16.2.10 | 3.16.3.1 | 3.16.3.2 | 3.16.3.3 | 3.16.3.4 | | |
| 3.16.3.5 | 3.16.3.6 | 3.16.3.7 | 3.16.3.8 | 3.16.3.9 | 3.16.3.10 | 3.16.4.1 | 3.16.4.2 | 3.16.4.3 | 3.16.4.4 | 3.16.4.5 | | |
| 3.16.4.6 | 3.16.4.7 | 3.16.4.8 | 3.16.4.9 | 3.16.4.10 | 3.16.5.1 | 3.16.5.2 | 3.16.5.3 | 3.16.5.4 | 3.16.5.5 | 3.16.5.6 | | |
| 3.16.5.7 | 3.16.5.8 | 3.16.5.9 | 3.16.5.10 | 3.16.6.1 | 3.16.6.2 | 3.16.6.3 | 3.16.6.4 | 3.16.6.5 | 3.16.6.6 | 3.16.6.7 | | |
| 3.16.6.8 | 3.16.6.9 | 3.16.6.10 | 3.17.1.1 | 3.17.1.2 | 3.17.1.3 | 3.17.1.4 | 3.17.1.5 | 3.17.1.6 | 3.17.1.7 | 3.17.1.8 | | |
| 3.17.1.9 | 3.17.1.10 | 3.17.2.1 | 3.17.2.2 | 3.17.2.3 | 3.17.2.4 | 3.17.2.5 | 3.17.2.6 | 3.17.2.7 | 3.17.2.8 | 3.17.2.9 | | |
| 3.17.2.10 | 3.17.3.1 | 3.17.3.2 | 3.17.3.3 | 3.17.3.4 | 3.17.3.5 | 3.17.3.6 | 3.17.3.7 | 3.17.3.8 | 3.17.3.9 | 3.17.3.10 | | |
| 3.17.4.1 | 3.17.4.2 | 3.17.4.3 | 3.17.4.4 | 3.17.4.5 | 3.17.4.6 | 3.17.4.7 | 3.17.4.8 | 3.17.4.9 | 3.17.4.10 | 3.17.5.1 | | |
| 3.17.5.2 | 3.17.5.3 | 3.17.5.4 | 3.17.5.5 | 3.17.5.6 | 3.17.5.7 | 3.17.5.8 | 3.17.5.9 | 3.17.5.10 | 3.17.6.1 | 3.17.6.2 | | |
| 3.17.6.3 | 3.17.6.4 | 3.17.6.5 | 3.17.6.6 | 3.17.6.7 | 3.17.6.8 | 3.17.6.9 | 3.17.6.10 | 3.18.1.1 | 3.18.1.2 | 3.18.1.3 | | |
| 3.18.1.4 | 3.18.1.5 | 3.18.1.6 | 3.18.1.7 | 3.18.1.8 | 3.18.1.9 | 3.18.1.10 | 3.18.2.1 | 3.18.2.2 | 3.18.2.3 | 3.18.2.4 | | |
| 3.18.2.5 | 3.18.2.6 | 3.18.2.7 | 3.18.2.8 | 3.18.2.9 | 3.18.2.10 | 3.18.3.1 | 3.18.3.2 | 3.18.3.3 | 3.18.3.4 | 3.18.3.5 | | |
| 3.18.3.6 | 3.18.3.7 | 3.18.3.8 | 3.18.3.9 | 3.18.3.10 | 3.18.4.1 | 3.18.4.2 | 3.18.4.3 | 3.18.4.4 | 3.18.4.5 | 3.18.4.6 | | |
| 3.18.4.7 | 3.18.4.8 | 3.18.4.9 | 3.18.4.10 | 3.18.5.1 | 3.18.5.2 | 3.18.5.3 | 3.18.5.4 | 3.18.5.5 | 3.18.5.6 | 3.18.5.7 | | |
| 3.18.5.8 | 3.18.5.9 | 3.18.5.10 | 3.18.6.1 | 3.18.6.2 | 3.18.6.3 | 3.18.6.4 | 3.18.6.5 | 3.18.6.6 | 3.18.6.7 | 3.18.6.8 | | |
| 3.18.6.9 | 3.18.6.10 | 3.19.1.1 | 3.19.1.2 | 3.19.1.3 | 3.19.1.4 | 3.19.1.5 | 3.19.1.6 | 3.19.1.7 | 3.19.1.8 | 3.19.1.9 | | |
| 3.19.1.10 | 3.19.2.1 | 3.19.2.2 | 3.19.2.3 | 3.19.2.4 | 3.19.2.5 | 3.19.2.6 | 3.19.2.7 | 3.19.2.8 | 3.19.2.9 | 3.19.2.10 | | |
| 3.19.3.1 | 3.19.3.2 | 3.19.3.3 | 3.19.3.4 | 3.19.3.5 | 3.19.3.6 | 3.19.3.7 | 3.19.3.8 | 3.19.3.9 | 3.19.3.10 | 3.19.4.1 | | |
| 3.19.4.2 | 3.19.4.3 | 3.19.4.4 | 3.19.4.5 | 3.19.4.6 | 3.19.4.7 | 3.19.4.8 | 3.19.4.9 | 3.19.4.10 | 3.19.5.1 | 3.19.5.2 | | |
| 3.19.5.3 | 3.19.5.4 | 3.19.5.5 | 3.19.5.6 | 3.19.5.7 | 3.19.5.8 | 3.19.5.9 | 3.19.5.10 | 3.19.6.1 | 3.19.6.2 | 3.19.6.3 | | |
| 3.19.6.4 | 3.19.6.5 | 3.19.6.6 | 3.19.6.7 | 3.19.6.8 | 3.19.6.9 | 3.19.6.10 | 3.20.1.1 | 3.20.1.2 | 3.20.1.3 | 3.20.1.4 | | |
| 3.20.1.5 | 3.20.1.6 | 3.20.1.7 | 3.20.1.8 | 3.20.1.9 | 3.20.1.10 | 3.20.2.1 | 3.20.2.2 | 3.20.2.3 | 3.20.2.4 | 3.20.2.5 | | |
| 3.20.2.6 | 3.20.2.7 | 3.20.2.8 | 3.20.2.9 | 3.20.2.10 | 3.20.3.1 | 3.20.3.2 | 3.20.3.3 | 3.20.3.4 | 3.20.3.5 | 3.20.3.6 | | |
| 3.20.3.7 | 3.20.3.8 | 3.20.3.9 | 3.20.3.10 | 3.20.4.1 | 3.20.4.2 | 3.20.4.3 | 3.20.4.4 | 3.20.4.5 | 3.20.4.6 | 3.20.4.7 | | |
| 3.20.4.8 | 3.20.4.9 | 3.20.4.10 | 3.20.5.1 | 3.20.5.2 | 3.20.5.3 | 3.20.5.4 | 3.20.5.5 | 3.20.5.6 | 3.20.5.7 | 3.20.5.8 | | |
| 3.20.5.9 | 3.20.5.10 | 3.20.6.1 | 3.20.6.2 | 3.20.6.3 | 3.20.6.4 | 3.20.6.5 | 3.20.6.6 | 3.20.6.7 | 3.20.6.8 | 3.20.6.9 | | |
| 3.20.6.10 | 3.21.1.1 | 3.21.1.2 | 3.21.1.3 | 3.21.1.4 | 3.21.1.5 | 3.21.1.6 | 3.21.1.7 | 3.21.1.8 | 3.21.1.9 | 3.21.1.10 | | |
| 3.21.2.1 | 3.21.2.2 | 3.21.2.3 | 3.21.2.4 | 3.21.2.5 | 3.21.2.6 | 3.21.2.7 | 3.21.2.8 | 3.21.2.9 | 3.21.2.10 | 3.21.3.1 | | |
| 3.21.3.2 | 3.21.3.3 | 3.21.3.4 | 3.21.3.5 | 3.21.3.6 | 3.21.3.7 | 3.21.3.8 | 3.21.3.9 | 3.21.3.10 | 3.21.4.1 | 3.21.4.2 | | |
| 3.21.4.3 | 3.21.4.4 | 3.21.4.5 | 3.21.4.6 | 3.21.4.7 | 3.21.4.8 | 3.21.4.9 | 3.21.4.10 | 3.21.5.1 | 3.21.5.2 | 3.21.5.3 | | |
| 3.21.5.4 | 3.21.5.5 | 3.21.5.6 | 3.21.5.7 | 3.21.5.8 | 3.21.5.9 | 3.21.5.10 | 3.21.6.1 | 3.21.6.2 | 3.21.6.3 | 3.21.6.4 | | |
| 3.21.6.5 | 3.21.6.6 | 3.21.6.7 | 3.21.6.8 | 3.21.6.9 | 3.21.6.10 | 3.22.1.1 | 3.22.1.2 | 3.22.1.3 | 3.22.1.4 | 3.22.1.5 | | |
| 3.22.1.6 | 3.22.1.7 | 3.22.1.8 | 3.22.1.9 | 3.22.1.10 | 3.22.2.1 | 3.22.2.2 | 3.22.2.3 | 3.22.2.4 | 3.22.2.5 | 3.22.2.6 | | |
| 3.22.2.7 | 3.22.2.8 | 3.22.2.9 | 3.22.2.10 | 3.22.3.1 | 3.22.3.2 | 3.22.3.3 | 3.22.3.4 | 3.22.3.5 | 3.22.3.6 | 3.22.3.7 | | |
| 3.22.3.8 | 3.22.3.9 | 3.22.3.10 | 3.22.4.1 | 3.22.4.2 | 3.22.4.3 | 3.22.4.4 | 3.22.4.5 | 3.22.4.6 | 3.22.4.7 | 3.22.4.8 | | |

TABLE B-continued

| | | | | | | | | | | | |
|---|---|---|---|---|---|---|---|---|---|---|---|
| 3.22.4.9 | 3.22.4.10 | 3.22.5.1 | 3.22.5.2 | 3.22.5.3 | 3.22.5.4 | 3.22.5.5 | 3.22.5.6 | 3.22.5.7 | 3.22.5.8 | 3.22.5.9 | |
| 3.22.5.10 | 3.22.6.1 | 3.22.6.2 | 3.22.6.3 | 3.22.6.4 | 3.22.6.5 | 3.22.6.6 | 3.22.6.7 | 3.22.6.8 | 3.22.6.9 | 3.22.6.10 | |
| 3.23.1.1 | 3.23.1.2 | 3.23.1.3 | 3.23.1.4 | 3.23.1.5 | 3.23.1.6 | 3.23.1.7 | 3.23.1.8 | 3.23.1.9 | 3.23.1.10 | 3.23.2.1 | |
| 3.23.2.2 | 3.23.2.3 | 3.23.2.4 | 3.23.2.5 | 3.23.2.6 | 3.23.2.7 | 3.23.2.8 | 3.23.2.9 | 3.23.2.10 | 3.23.3.1 | 3.23.3.2 | |
| 3.23.3.3 | 3.23.3.4 | 3.23.3.5 | 3.23.3.6 | 3.23.3.7 | 3.23.3.8 | 3.23.3.9 | 3.23.3.10 | 3.23.4.1 | 3.23.4.2 | 3.23.4.3 | |
| 3.23.4.4 | 3.23.4.5 | 3.23.4.6 | 3.23.4.7 | 3.23.4.8 | 3.23.4.9 | 3.23.4.10 | 3.23.5.1 | 3.23.5.2 | 3.23.5.3 | 3.23.5.4 | |
| 3.23.5.5 | 3.23.5.6 | 3.23.5.7 | 3.23.5.8 | 3.23.5.9 | 3.23.5.10 | 3.23.6.1 | 3.23.6.2 | 3.23.6.3 | 3.23.6.4 | 3.23.6.5 | |
| 3.23.6.6 | 3.23.6.7 | 3.23.6.8 | 3.23.6.9 | 3.23.6.10 | 3.24.1.1 | 3.24.1.2 | 3.24.1.3 | 3.24.1.4 | 3.24.1.5 | 3.24.1.6 | |
| 3.24.1.7 | 3.24.1.8 | 3.24.1.9 | 3.24.1.10 | 3.24.2.1 | 3.24.2.2 | 3.24.2.3 | 3.24.2.4 | 3.24.2.5 | 3.24.2.6 | 3.24.2.7 | |
| 3.24.2.8 | 3.24.2.9 | 3.24.2.10 | 3.24.3.1 | 3.24.3.2 | 3.24.3.3 | 3.24.3.4 | 3.24.3.5 | 3.24.3.6 | 3.24.3.7 | 3.24.3.8 | |
| 3.24.3.9 | 3.24.3.10 | 3.24.4.1 | 3.24.4.2 | 3.24.4.3 | 3.24.4.4 | 3.24.4.5 | 3.24.4.6 | 3.24.4.7 | 3.24.4.8 | 3.24.4.9 | |
| 3.24.4.10 | 3.24.5.1 | 3.24.5.2 | 3.24.5.3 | 3.24.5.4 | 3.24.5.5 | 3.24.5.6 | 3.24.5.7 | 3.24.5.8 | 3.24.5.9 | 3.24.5.10 | |
| 3.24.6.1 | 3.24.6.2 | 3.24.6.3 | 3.24.6.4 | 3.24.6.5 | 3.24.6.6 | 3.24.6.7 | 3.24.6.8 | 3.24.6.9 | 3.24.6.10 | 3.25.1.1 | |
| 3.25.1.2 | 3.25.1.3 | 3.25.1.4 | 3.25.1.5 | 3.25.1.6 | 3.25.1.7 | 3.25.1.8 | 3.25.1.9 | 3.25.1.10 | 3.25.2.1 | 3.25.2.2 | |
| 3.25.2.3 | 3.25.2.4 | 3.25.2.5 | 3.25.2.6 | 3.25.2.7 | 3.25.2.8 | 3.25.2.9 | 3.25.2.10 | 3.25.3.1 | 3.25.3.2 | 3.25.3.3 | |
| 3.25.3.4 | 3.25.3.5 | 3.25.3.6 | 3.25.3.7 | 3.25.3.8 | 3.25.3.9 | 3.25.3.10 | 3.25.4.1 | 3.25.4.2 | 3.25.4.3 | 3.25.4.4 | |
| 3.25.4.5 | 3.25.4.6 | 3.25.4.7 | 3.25.4.8 | 3.25.4.9 | 3.25.4.10 | 3.25.5.1 | 3.25.5.2 | 3.25.5.3 | 3.25.5.4 | 3.25.5.5 | |
| 3.25.5.6 | 3.25.5.7 | 3.25.5.8 | 3.25.5.9 | 3.25.5.10 | 3.25.6.1 | 3.25.6.2 | 3.25.6.3 | 3.25.6.4 | 3.25.6.5 | 3.25.6.6 | |
| 3.25.6.7 | 3.25.6.8 | 3.25.6.9 | 3.25.6.10 | 4.1.1.1 | 4.1.1.2 | 4.1.1.3 | [2.1.1.4] 4.1.1.4 | 4.1.1.5 | 4.1.1.6 | 4.1.1.7 | 4.1.1.8 | 4.1.1.9 |
| 4.1.1.10 | 4.1.2.1 | 4.1.2.2 | 4.1.2.3 | 4.1.2.4 | 4.1.2.5 | 4.1.2.6 | 4.1.2.7 | 4.1.2.8 | 4.1.2.9 | 4.1.2.10 | 4.1.3.1 | 4.1.3.2 |
| 4.1.3.3 | 4.1.3.4 | 4.1.3.5 | 4.1.3.6 | 4.1.3.7 | 4.1.3.8 | 4.1.3.9 | 4.1.3.10 | 4.1.4.1 | 4.1.4.2 | 4.1.4.3 | 4.1.4.4 | 4.1.4.5 |
| 4.1.4.6 | 4.1.4.7 | 4.1.4.8 | 4.1.4.9 | 4.1.4.10 | 4.1.5.1 | 4.1.5.2 | 4.1.5.3 | 4.1.5.4 | 4.1.5.5 | 4.1.5.6 | 4.1.5.7 | 4.1.5.8 |
| 4.1.5.9 | 4.1.5.10 | 4.1.6.1 | 4.1.6.2 | 4.1.6.3 | 4.1.6.4 | 4.1.6.5 | 4.1.6.6 | 4.1.6.7 | 4.1.6.8 | 4.1.6.9 | 4.1.6.10 | 4.2.1.1 |
| 4.2.1.2 | 4.2.1.3 | 4.2.1.4 | 4.2.1.5 | 4.2.1.6 | 4.2.1.7 | 4.2.1.8 | 4.2.1.9 | 4.2.1.10 | 4.2.2.1 | 4.2.2.2 | 4.2.2.3 | 4.2.2.4 |
| 4.2.2.5 | 4.2.2.6 | 4.2.2.7 | 4.2.2.8 | 4.2.2.9 | 4.2.2.10 | 4.2.3.1 | 4.2.3.2 | 4.2.3.3 | 4.2.3.4 | 4.2.3.5 | 4.2.3.6 | 4.2.3.7 |
| 4.2.3.8 | 4.2.3.9 | 4.2.3.10 | 4.2.4.1 | 4.2.4.2 | 4.2.4.3 | 4.2.4.4 | 4.2.4.5 | 4.2.4.6 | 4.2.4.7 | 4.2.4.8 | 4.2.4.9 | 4.2.4.10 |
| 4.2.5.1 | 4.2.5.2 | 4.2.5.3 | 4.2.5.4 | 4.2.5.5 | 4.2.5.6 | 4.2.5.7 | 4.2.5.8 | 4.2.5.9 | 4.2.5.10 | 4.2.6.1 | 4.2.6.2 | 4.2.6.3 |
| 4.2.6.4 | 4.2.6.5 | 4.2.6.6 | 4.2.6.7 | 4.2.6.8 | 4.2.6.9 | 4.2.6.10 | 4.3.1.1 | 4.3.1.2 | 4.3.1.3 | 4.3.1.4 | 4.3.1.5 | 4.3.1.6 |
| 4.3.1.7 | 4.3.1.8 | 4.3.1.9 | 4.3.1.10 | 4.3.2.1 | 4.3.2.2 | 4.3.2.3 | 4.3.2.4 | 4.3.2.5 | 4.3.2.6 | 4.3.2.7 | 4.3.2.8 | 4.3.2.9 |
| 4.3.2.10 | 4.3.3.1 | 4.3.3.2 | 4.3.3.3 | 4.3.3.4 | 4.3.3.5 | 4.3.3.6 | 4.3.3.7 | 4.3.3.8 | 4.3.3.9 | 4.3.3.10 | 4.3.4.1 | 4.3.4.2 |
| 4.3.4.3 | 4.3.4.4 | 4.3.4.5 | 4.3.4.6 | 4.3.4.7 | 4.3.4.8 | 4.3.4.9 | 4.3.4.10 | 4.3.5.1 | 4.3.5.2 | 4.3.5.3 | 4.3.5.4 | 4.3.5.5 |
| 4.3.5.6 | 4.3.5.7 | 4.3.5.8 | 4.3.5.9 | 4.3.5.10 | 4.3.6.1 | 4.3.6.2 | 4.3.6.3 | 4.3.6.4 | 4.3.6.5 | 4.3.6.6 | 4.3.6.7 | 4.3.6.8 |
| 4.3.6.9 | 4.3.6.10 | 4.4.1.1 | 4.4.1.2 | 4.4.1.3 | 4.4.1.4 | 4.4.1.5 | 4.4.1.6 | 4.4.1.7 | 4.4.1.8 | 4.4.1.9 | 4.4.1.10 | 4.4.2.1 |
| 4.4.2.2 | 4.4.2.3 | 4.4.2.4 | 4.4.2.5 | 4.4.2.6 | 4.4.2.7 | 4.4.2.8 | 4.4.2.9 | 4.4.2.10 | 4.4.3.1 | 4.4.3.2 | 4.4.3.3 | 4.4.3.4 |
| 4.4.3.5 | 4.4.3.6 | 4.4.3.7 | 4.4.3.8 | 4.4.3.9 | 4.4.3.10 | 4.4.4.1 | 4.4.4.2 | 4.4.4.3 | 4.4.4.4 | 4.4.4.5 | 4.4.4.6 | 4.4.4.7 |
| 4.4.4.8 | 4.4.4.9 | 4.4.4.10 | 4.4.5.1 | 4.4.5.2 | 4.4.5.3 | 4.4.5.4 | 4.4.5.5 | 4.4.5.6 | 4.4.5.7 | 4.4.5.8 | 4.4.5.9 | 4.4.5.10 |
| 4.4.6.1 | 4.4.6.2 | 4.4.6.3 | 4.4.6.4 | 4.4.6.5 | 4.4.6.6 | 4.4.6.7 | 4.4.6.8 | 4.4.6.9 | 4.4.6.10 | 4.5.1.1 | 4.5.1.2 | 4.5.1.3 |
| 4.5.1.4 | 4.5.1.5 | 4.5.1.6 | 4.5.1.7 | 4.5.1.8 | 4.5.1.9 | 4.5.1.10 | 4.5.2.1 | 4.5.2.2 | 4.5.2.3 | 4.5.2.4 | 4.5.2.5 | 4.5.2.6 |
| 4.5.2.7 | 4.5.2.8 | 4.5.2.9 | 4.5.2.10 | 4.5.3.1 | 4.5.3.2 | 4.5.3.3 | 4.5.3.4 | 4.5.3.5 | 4.5.3.6 | 4.5.3.7 | 4.5.3.8 | 4.5.3.9 |
| 4.5.3.10 | 4.5.4.1 | 4.5.4.2 | 4.5.4.3 | 4.5.4.4 | 4.5.4.5 | 4.5.4.6 | 4.5.4.7 | 4.5.4.8 | 4.5.4.9 | 4.5.4.10 | 4.5.5.1 | 4.5.5.2 |
| 4.5.5.3 | 4.5.5.4 | 4.5.5.5 | 4.5.5.6 | 4.5.5.7 | 4.5.5.8 | 4.5.5.9 | 4.5.5.10 | 4.5.6.1 | 4.5.6.2 | 4.5.6.3 | 4.5.6.4 | 4.5.6.5 |
| 4.5.6.6 | 4.5.6.7 | 4.5.6.8 | 4.5.6.9 | 4.5.6.10 | 4.6.1.1 | 4.6.1.2 | 4.6.1.3 | 4.6.1.4 | 4.6.1.5 | 4.6.1.6 | 4.6.1.7 | 4.6.1.8 |
| 4.6.1.9 | 4.6.1.10 | 4.6.2.1 | 4.6.2.2 | 4.6.2.3 | 4.6.2.4 | 4.6.2.5 | 4.6.2.6 | 4.6.2.7 | 4.6.2.8 | 4.6.2.9 | 4.6.2.10 | 4.6.3.1 |
| 4.6.3.2 | 4.6.3.3 | 4.6.3.4 | 4.6.3.5 | 4.6.3.6 | 4.6.3.7 | 4.6.3.8 | 4.6.3.9 | 4.6.3.10 | 4.6.4.1 | 4.6.4.2 | 4.6.4.3 | 4.6.4.4 |
| 4.6.4.5 | 4.6.4.6 | 4.6.4.7 | 4.6.4.8 | 4.6.4.9 | 4.6.4.10 | 4.6.5.1 | 4.6.5.2 | 4.6.5.3 | 4.6.5.4 | 4.6.5.5 | 4.6.5.6 | 4.6.5.7 |
| 4.6.5.8 | 4.6.5.9 | 4.6.5.10 | 4.6.6.1 | 4.6.6.2 | 4.6.6.3 | 4.6.6.4 | 4.6.6.5 | 4.6.6.6 | 4.6.6.7 | 4.6.6.8 | 4.6.6.9 | 4.6.6.10 |
| 4.7.1.1 | 4.7.1.2 | 4.7.1.3 | 4.7.1.4 | 4.7.1.5 | 4.7.1.6 | 4.7.1.7 | 4.7.1.8 | 4.7.1.9 | 4.7.1.10 | 4.7.2.1 | 4.7.2.2 | 4.7.2.3 |
| 4.7.2.4 | 4.7.2.5 | 4.7.2.6 | 4.7.2.7 | 4.7.2.8 | 4.7.2.9 | 4.7.2.10 | 4.7.3.1 | 4.7.3.2 | 4.7.3.3 | 4.7.3.4 | 4.7.3.5 | 4.7.3.6 |
| 4.7.3.7 | 4.7.3.8 | 4.7.3.9 | 4.7.3.10 | 4.7.4.1 | 4.7.4.2 | 4.7.4.3 | 4.7.4.4 | 4.7.4.5 | 4.7.4.6 | 4.7.4.7 | 4.7.4.8 | 4.7.4.9 |
| 4.7.4.10 | 4.7.5.1 | 4.7.5.2 | 4.7.5.3 | 4.7.5.4 | 4.7.5.5 | 4.7.5.6 | 4.7.5.7 | 4.7.5.8 | 4.7.5.9 | 4.7.5.10 | 4.7.6.1 | 4.7.6.2 |
| 4.7.6.3 | 4.7.6.4 | 4.7.6.5 | 4.7.6.6 | 4.7.6.7 | 4.7.6.8 | 4.7.6.9 | 4.7.6.10 | 4.8.1.1 | 4.8.1.2 | 4.8.1.3 | 4.8.1.4 | 4.8.1.5 |
| 4.8.1.6 | 4.8.1.7 | 4.8.1.8 | 4.8.1.9 | 4.8.1.10 | 4.8.2.1 | 4.8.2.2 | 4.8.2.3 | 4.8.2.4 | 4.8.2.5 | 4.8.2.6 | 4.8.2.7 | 4.8.2.8 |
| 4.8.2.9 | 4.8.2.10 | 4.8.3.1 | 4.8.3.2 | 4.8.3.3 | 4.8.3.4 | 4.8.3.5 | 4.8.3.6 | 4.8.3.7 | 4.8.3.8 | 4.8.3.9 | 4.8.3.10 | 4.8.4.1 |
| 4.8.4.2 | 4.8.4.3 | 4.8.4.4 | 4.8.4.5 | 4.8.4.6 | 4.8.4.7 | 4.8.4.8 | 4.8.4.9 | 4.8.4.10 | 4.8.5.1 | 4.8.5.2 | 4.8.5.3 | 4.8.5.4 |
| 4.8.5.5 | 4.8.5.6 | 4.8.5.7 | 4.8.5.8 | 4.8.5.9 | 4.8.5.10 | 4.8.6.1 | 4.8.6.2 | 4.8.6.3 | 4.8.6.4 | 4.8.6.5 | 4.8.6.6 | 4.8.6.7 |
| 4.8.6.8 | 4.8.6.9 | 4.8.6.10 | 4.9.1.1 | 4.9.1.2 | 4.9.1.3 | 4.9.1.4 | 4.9.1.5 | 4.9.1.6 | 4.9.1.7 | 4.9.1.8 | 4.9.1.9 | 4.9.1.10 |
| 4.9.2.1 | 4.9.2.2 | 4.9.2.3 | 4.9.2.4 | 4.9.2.5 | 4.9.2.6 | 4.9.2.7 | 4.9.2.8 | 4.9.2.9 | 4.9.2.10 | 4.9.3.1 | 4.9.3.2 | 4.9.3.3 |
| 4.9.3.4 | 4.9.3.5 | 4.9.3.6 | 4.9.3.7 | 4.9.3.8 | 4.9.3.9 | 4.9.3.10 | 4.9.4.1 | 4.9.4.2 | 4.9.4.3 | 4.9.4.4 | 4.9.4.5 | 4.9.4.6 |
| 4.9.4.7 | 4.9.4.8 | 4.9.4.9 | 4.9.4.10 | 3.9.5.1 | 3.9.5.2 | 3.9.5.3 | 3.9.5.4 | 3.9.5.5 | 3.9.5.6 | 3.9.5.7 | 3.9.5.8 | 3.9.5.9 |
| 3.9.5.10 | 4.9.6.1 | 4.9.6.2 | 4.9.6.3 | 4.9.6.4 | 4.9.6.5 | 4.9.6.6 | 4.9.6.7 | 4.9.6.8 | 4.9.6.9 | 4.9.6.10 | 4.10.1.1 | 4.10.1.2 |
| 4.10.1.3 | 4.10.1.4 | 4.10.1.5 | 4.10.1.6 | 4.10.1.7 | 4.10.1.8 | 4.10.1.9 | 4.10.1.10 | 4.10.2.1 | 4.10.2.2 | 4.10.2.3 | | |
| 4.10.2.4 | 4.10.2.5 | 4.10.2.6 | 4.10.2.7 | 4.10.2.8 | 4.10.2.9 | 4.10.2.10 | 4.10.3.1 | 4.10.3.2 | 4.10.3.3 | 4.10.3.4 | | |
| 4.10.3.5 | 4.10.3.6 | 4.10.3.7 | 4.10.3.8 | 4.10.3.9 | 4.10.3.10 | 4.10.4.1 | 4.10.4.2 | 4.10.4.3 | 4.10.4.4 | 4.10.4.5 | | |
| 4.10.4.6 | 4.10.4.7 | 4.10.4.8 | 4.10.4.9 | 4.10.4.10 | 4.10.5.1 | 4.10.5.2 | 4.10.5.3 | 4.10.5.4 | 4.10.5.5 | 4.10.5.6 | | |
| 4.10.5.7 | 4.10.5.8 | 4.10.5.9 | 4.10.5.10 | 4.10.6.1 | 4.10.6.2 | 4.10.6.3 | 4.10.6.4 | 4.10.6.5 | 4.10.6.6 | 4.10.6.7 | | |
| 4.10.6.8 | 4.10.6.9 | 4.10.6.10 | 4.11.1.1 | 4.11.1.2 | 4.11.1.3 | 4.11.1.4 | 4.11.1.5 | 4.11.1.6 | 4.11.1.7 | 4.11.1.8 | | |
| 4.11.1.9 | 4.11.1.10 | 4.11.2.1 | 4.11.2.2 | 4.11.2.3 | 4.11.2.4 | 4.11.2.5 | 4.11.2.6 | 4.11.2.7 | 4.11.2.8 | 4.11.2.9 | | |
| 4.11.2.10 | 4.11.3.1 | 4.11.3.2 | 4.11.3.3 | 4.11.3.4 | 4.11.3.5 | 4.11.3.6 | 4.11.3.7 | 4.11.3.8 | 4.11.3.9 | 4.11.3.10 | | |
| 4.11.4.1 | 4.11.4.2 | 4.11.4.3 | 4.11.4.4 | 4.11.4.5 | 4.11.4.6 | 4.11.4.7 | 4.11.4.8 | 4.11.4.9 | 4.11.4.10 | 4.11.5.1 | | |
| 4.11.5.2 | 4.11.5.3 | 4.11.5.4 | 4.11.5.5 | 4.11.5.6 | 4.11.5.7 | 4.11.5.8 | 4.11.5.9 | 4.11.5.10 | 4.11.6.1 | 4.11.6.2 | | |
| 4.11.6.3 | 4.11.6.4 | 4.11.6.5 | 4.11.6.6 | 4.11.6.7 | 4.11.6.8 | 4.11.6.9 | 4.11.6.10 | 4.12.1.1 | 4.12.1.2 | 4.12.1.3 | | |
| 4.12.1.4 | 4.12.1.5 | 4.12.1.6 | 4.12.1.7 | 4.12.1.8 | 4.12.1.9 | 4.12.1.10 | 4.12.2.1 | 4.12.2.2 | 4.12.2.3 | 4.12.2.4 | | |
| 4.12.2.5 | 4.12.2.6 | 4.12.2.7 | 4.12.2.8 | 4.12.2.9 | 4.12.2.10 | 4.12.3.1 | 4.12.3.2 | 4.12.3.3 | 4.12.3.4 | 4.12.3.5 | | |
| 4.12.3.6 | 4.12.3.7 | 4.12.3.8 | 4.12.3.9 | 4.12.3.10 | 4.12.4.1 | 4.12.4.2 | 4.12.4.3 | 4.12.4.4 | 4.12.4.5 | 4.12.4.6 | | |
| 4.12.4.7 | 4.12.4.8 | 4.12.4.9 | 4.12.4.10 | 4.12.5.1 | 4.12.5.2 | 4.12.5.3 | 4.12.5.4 | 4.12.5.5 | 4.12.5.6 | 4.12.5.7 | | |
| 4.12.5.8 | 4.12.5.9 | 4.12.5.10 | 4.12.6.1 | 4.12.6.2 | 4.12.6.3 | 4.12.6.4 | 4.12.6.5 | 4.12.6.6 | 4.12.6.7 | 4.12.6.8 | | |
| 4.12.6.9 | 4.12.6.10 | 4.13.1.1 | 4.13.1.2 | 4.13.1.3 | 4.13.1.4 | 4.13.1.5 | 4.13.1.6 | 4.13.1.7 | 4.13.1.8 | 4.13.1.9 | | |
| 4.13.1.10 | 4.13.2.1 | 4.13.2.2 | 4.13.2.3 | 4.13.2.4 | 4.13.2.5 | 4.13.2.6 | 4.13.2.7 | 4.13.2.8 | 4.13.2.9 | 4.13.2.10 | | |

TABLE B-continued

| | | | | | | | | | | | |
|---|---|---|---|---|---|---|---|---|---|---|---|
| 4.13.3.1 | 4.13.3.2 | 4.13.3.3 | 4.13.3.4 | 4.13.3.5 | 4.13.3.6 | 4.13.3.7 | 4.13.3.8 | 4.13.3.9 | 4.13.3.10 | 4.13.4.1 | |
| 4.13.4.2 | 4.13.4.3 | 4.13.4.4 | 4.13.4.5 | 4.13.4.6 | 4.13.4.7 | 4.13.4.8 | 4.13.4.9 | 4.13.4.10 | 4.13.5.1 | 4.13.5.2 | |
| 4.13.5.3 | 4.13.5.4 | 4.13.5.5 | 4.13.5.6 | 4.13.5.7 | 4.13.5.8 | 4.13.5.9 | 4.13.5.10 | 4.13.6.1 | 4.13.6.2 | 4.13.6.3 | |
| 4.13.6.4 | 4.13.6.5 | 4.13.6.6 | 4.13.6.7 | 4.13.6.8 | 4.13.6.9 | 4.13.6.10 | 4.14.1.1 | 4.14.1.2 | 4.14.1.3 | 4.14.1.4 | |
| 4.14.1.5 | 4.14.1.6 | 4.14.1.7 | 4.14.1.8 | 4.14.1.9 | 4.14.1.10 | 4.14.2.1 | 4.14.2.2 | 4.14.2.3 | 4.14.2.4 | 4.14.2.5 | |
| 4.14.2.6 | 4.14.2.7 | 4.14.2.8 | 4.14.2.9 | 4.14.2.10 | 4.14.3.1 | 4.14.3.2 | 4.14.3.3 | 4.14.3.4 | 4.14.3.5 | 4.14.3.6 | |
| 4.14.3.7 | 4.14.3.8 | 4.14.3.9 | 4.14.3.10 | 4.14.4.1 | 4.14.4.2 | 4.14.4.3 | 4.14.4.4 | 4.14.4.5 | 4.14.4.6 | 4.14.4.7 | |
| 4.14.4.8 | 4.14.4.9 | 4.14.4.10 | 4.14.5.1 | 4.14.5.2 | 4.14.5.3 | 4.14.5.4 | 4.14.5.5 | 4.14.5.6 | 4.14.5.7 | 4.14.5.8 | |
| 4.14.5.9 | 4.14.5.10 | 4.14.6.1 | 4.14.6.2 | 4.14.6.3 | 4.14.6.4 | 4.14.6.5 | 4.14.6.6 | 4.14.6.7 | 4.14.6.8 | 4.14.6.9 | |
| 4.14.6.10 | 4.15.1.1 | 4.15.1.2 | 4.15.1.3 | 4.15.1.4 | 4.15.1.5 | 4.15.1.6 | 4.15.1.7 | 4.15.1.8 | 4.15.1.9 | 4.15.1.10 | |
| 4.15.2.1 | 4.15.2.2 | 4.15.2.3 | 4.15.2.4 | 4.15.2.5 | 4.15.2.6 | 4.15.2.7 | 4.15.2.8 | 4.15.2.9 | 4.15.2.10 | 4.15.3.1 | |
| 4.15.3.2 | 4.15.3.3 | 4.15.3.4 | 4.15.3.5 | 4.15.3.6 | 4.15.3.7 | 4.15.3.8 | 4.15.3.9 | 4.15.3.10 | 4.15.4.1 | 4.15.4.2 | |
| 4.15.4.3 | 4.15.4.4 | 4.15.4.5 | 4.15.4.6 | 4.15.4.7 | 4.15.4.8 | 4.15.4.9 | 4.15.4.10 | 4.15.5.1 | 4.15.5.2 | 4.15.5.3 | |
| 4.15.5.4 | 4.15.5.5 | 4.15.5.6 | 4.15.5.7 | 4.15.5.8 | 4.15.5.9 | 4.15.5.10 | 4.15.6.1 | 4.15.6.2 | 4.15.6.3 | 4.15.6.4 | |
| 4.15.6.5 | 4.15.6.6 | 4.15.6.7 | 4.15.6.8 | 4.15.6.9 | 4.15.6.10 | 4.16.1.1 | 4.16.1.2 | 4.16.1.3 | 4.16.1.4 | 4.16.1.5 | |
| 4.16.1.6 | 4.16.1.7 | 4.16.1.8 | 4.16.1.9 | 4.16.1.10 | 4.16.2.1 | 4.16.2.2 | 4.16.2.3 | 4.16.2.4 | 4.16.2.5 | 4.16.2.6 | |
| 4.16.2.7 | 4.16.2.8 | 4.16.2.9 | 4.16.2.10 | 4.16.3.1 | 4.16.3.2 | 4.16.3.3 | 4.16.3.4 | 4.16.3.5 | 4.16.3.6 | 4.16.3.7 | |
| 4.16.3.8 | 4.16.3.9 | 4.16.3.10 | 4.16.4.1 | 4.16.4.2 | 4.16.4.3 | 4.16.4.4 | 4.16.4.5 | 4.16.4.6 | 4.16.4.7 | 4.16.4.8 | |
| 4.16.4.9 | 4.16.4.10 | 4.16.5.1 | 4.16.5.2 | 4.16.5.3 | 4.16.5.4 | 4.16.5.5 | 4.16.5.6 | 4.16.5.7 | 4.16.5.8 | 4.16.5.9 | |
| 4.16.5.10 | 4.16.6.1 | 4.16.6.2 | 4.16.6.3 | 4.16.6.4 | 4.16.6.5 | 4.16.6.6 | 4.16.6.7 | 4.16.6.8 | 4.16.6.9 | 4.16.6.10 | |
| 4.17.1.1 | 4.17.1.2 | 4.17.1.3 | 4.17.1.4 | 4.17.1.5 | 4.17.1.6 | 4.17.1.7 | 4.17.1.8 | 4.17.1.9 | 4.17.1.10 | 4.17.2.1 | |
| 4.17.2.2 | 4.17.2.3 | 4.17.2.4 | 4.17.2.5 | 4.17.2.6 | 4.17.2.7 | 4.17.2.8 | 4.17.2.9 | 4.17.2.10 | 4.17.3.1 | 4.17.3.2 | |
| 4.17.3.3 | 4.17.3.4 | 4.17.3.5 | 4.17.3.6 | 4.17.3.7 | 4.17.3.8 | 4.17.3.9 | 4.17.3.10 | 4.17.4.1 | 4.17.4.2 | 4.17.4.3 | |
| 4.17.4.4 | 4.17.4.5 | 4.17.4.6 | 4.17.4.7 | 4.17.4.8 | 4.17.4.9 | 4.17.4.10 | 4.17.5.1 | 4.17.5.2 | 4.17.5.3 | 4.17.5.4 | |
| 4.17.5.5 | 4.17.5.6 | 4.17.5.7 | 4.17.5.8 | 4.17.5.9 | 4.17.5.10 | 4.17.6.1 | 4.17.6.2 | 4.17.6.3 | 4.17.6.4 | 4.17.6.5 | |
| 4.17.6.6 | 4.17.6.7 | 4.17.6.8 | 4.17.6.9 | 4.17.6.10 | 4.18.1.1 | 4.18.1.2 | 4.18.1.3 | 4.18.1.4 | 4.18.1.5 | 4.18.1.6 | |
| 4.18.1.7 | 4.18.1.8 | 4.18.1.9 | 4.18.1.10 | 4.18.2.1 | 4.18.2.2 | 4.18.2.3 | 4.18.2.4 | 4.18.2.5 | 4.18.2.6 | 4.18.2.7 | |
| 4.18.2.8 | 4.18.2.9 | 4.18.2.10 | 4.18.3.1 | 4.18.3.2 | 4.18.3.3 | 4.18.3.4 | 4.18.3.5 | 4.18.3.6 | 4.18.3.7 | 4.18.3.8 | |
| 4.18.3.9 | 4.18.3.10 | 4.18.4.1 | 4.18.4.2 | 4.18.4.3 | 4.18.4.4 | 4.18.4.5 | 4.18.4.6 | 4.18.4.7 | 4.18.4.8 | 4.18.4.9 | |
| 4.18.4.10 | 4.18.5.1 | 4.18.5.2 | 4.18.5.3 | 4.18.5.4 | 4.18.5.5 | 4.18.5.6 | 4.18.5.7 | 4.18.5.8 | 4.18.5.9 | 4.18.5.10 | |
| 4.18.6.1 | 4.18.6.2 | 4.18.6.3 | 4.18.6.4 | 4.18.6.5 | 4.18.6.6 | 4.18.6.7 | 4.18.6.8 | 4.18.6.9 | 4.18.6.10 | 4.19.1.1 | |
| 4.19.1.2 | 4.19.1.3 | 4.19.1.4 | 4.19.1.5 | 4.19.1.6 | 4.19.1.7 | 4.19.1.8 | 4.19.1.9 | 4.19.1.10 | 4.19.2.1 | 4.19.2.2 | |
| 4.19.2.3 | 4.19.2.4 | 4.19.2.5 | 4.19.2.6 | 4.19.2.7 | 4.19.2.8 | 4.19.2.9 | 4.19.2.10 | 4.19.3.1 | 4.19.3.2 | 4.19.3.3 | |
| 4.19.3.4 | 4.19.3.5 | 4.19.3.6 | 4.19.3.7 | 4.19.3.8 | 4.19.3.9 | 4.19.3.10 | 4.19.4.1 | 4.19.4.2 | 4.19.4.3 | 4.19.4.4 | |
| 4.19.4.5 | 4.19.4.6 | 4.19.4.7 | 4.19.4.8 | 4.19.4.9 | 4.19.4.10 | 4.19.5.1 | 4.19.5.2 | 4.19.5.3 | 4.19.5.4 | 4.19.5.5 | |
| 4.19.5.6 | 4.19.5.7 | 4.19.5.8 | 4.19.5.9 | 4.19.5.10 | 4.19.6.1 | 4.19.6.2 | 4.19.6.3 | 4.19.6.4 | 4.19.6.5 | 4.19.6.6 | |
| 4.19.6.7 | 4.19.6.8 | 4.19.6.9 | 4.19.6.10 | 4.20.1.1 | 4.20.1.2 | 4.20.1.3 | 4.20.1.4 | 4.20.1.5 | 4.20.1.6 | 4.20.1.7 | |
| 4.20.1.8 | 4.20.1.9 | 4.20.1.10 | 4.20.2.1 | 4.20.2.2 | 4.20.2.3 | 4.20.2.4 | 4.20.2.5 | 4.20.2.6 | 4.20.2.7 | 4.20.2.8 | |
| 4.20.2.9 | 4.20.2.10 | 4.20.3.1 | 4.20.3.2 | 4.20.3.3 | 4.20.3.4 | 4.20.3.5 | 4.20.3.6 | 4.20.3.7 | 4.20.3.8 | 4.20.3.9 | |
| 4.20.3.10 | 4.20.4.1 | 4.20.4.2 | 4.20.4.3 | 4.20.4.4 | 4.20.4.5 | 4.20.4.6 | 4.20.4.7 | 4.20.4.8 | 4.20.4.9 | 4.20.4.10 | |
| 4.20.5.1 | 4.20.5.2 | 4.20.5.3 | 4.20.5.4 | 4.20.5.5 | 4.20.5.6 | 4.20.5.7 | 4.20.5.8 | 4.20.5.9 | 4.20.5.10 | 4.20.6.1 | |
| 4.20.6.2 | 4.20.6.3 | 4.20.6.4 | 4.20.6.5 | 4.20.6.6 | 4.20.6.7 | 4.20.6.8 | 4.20.6.9 | 4.20.6.10 | 4.21.1.1 | 4.21.1.2 | |
| 4.21.1.3 | 4.21.1.4 | 4.21.1.5 | 4.21.1.6 | 4.21.1.7 | 4.21.1.8 | 4.21.1.9 | 4.21.1.10 | 4.21.2.1 | 4.21.2.2 | 4.21.2.3 | |
| 4.21.2.4 | 4.21.2.5 | 4.21.2.6 | 4.21.2.7 | 4.21.2.8 | 4.21.2.9 | 4.21.2.10 | 4.21.3.1 | 4.21.3.2 | 4.21.3.3 | 4.21.3.4 | |
| 4.21.3.5 | 4.21.3.6 | 4.21.3.7 | 4.21.3.8 | 4.21.3.9 | 4.21.3.10 | 4.21.4.1 | 4.21.4.2 | 4.21.4.3 | 4.21.4.4 | 4.21.4.5 | |
| 4.21.4.6 | 4.21.4.7 | 4.21.4.8 | 4.21.4.9 | 4.21.4.10 | 4.21.5.1 | 4.21.5.2 | 4.21.5.3 | 4.21.5.4 | 4.21.5.5 | 4.21.5.6 | |
| 4.21.5.7 | 4.21.5.8 | 4.21.5.9 | 4.21.5.10 | 4.21.6.1 | 4.21.6.2 | 4.21.6.3 | 4.21.6.4 | 4.21.6.5 | 4.21.6.6 | 4.21.6.7 | |
| 4.21.6.8 | 4.21.6.9 | 4.21.6.10 | 4.22.1.1 | 4.22.1.2 | 4.22.1.3 | 4.22.1.4 | 4.22.1.5 | 4.22.1.6 | 4.22.1.7 | 4.22.1.8 | |
| 4.22.1.9 | 4.22.1.10 | 4.22.2.1 | 4.22.2.2 | 4.22.2.3 | 4.22.2.4 | 4.22.2.5 | 4.22.2.6 | 4.22.2.7 | 4.22.2.8 | 4.22.2.9 | |
| 4.22.2.10 | 4.22.3.1 | 4.22.3.2 | 4.22.3.3 | 4.22.3.4 | 4.22.3.5 | 4.22.3.6 | 4.22.3.7 | 4.22.3.8 | 4.22.3.9 | 4.22.3.10 | |
| 4.22.4.1 | 4.22.4.2 | 4.22.4.3 | 4.22.4.4 | 4.22.4.5 | 4.22.4.6 | 4.22.4.7 | 4.22.4.8 | 4.22.4.9 | 4.22.4.10 | 4.22.5.1 | |
| 4.22.5.2 | 4.22.5.3 | 4.22.5.4 | 4.22.5.5 | 4.22.5.6 | 4.22.5.7 | 4.22.5.8 | 4.22.5.9 | 4.22.5.10 | 4.22.6.1 | 4.22.6.2 | |
| 4.22.6.3 | 4.22.6.4 | 4.22.6.5 | 4.22.6.6 | 4.22.6.7 | 4.22.6.8 | 4.22.6.9 | 4.22.6.10 | 4.23.1.1 | 4.23.1.2 | 4.23.1.3 | |
| 4.23.1.4 | 4.23.1.5 | 4.23.1.6 | 4.23.1.7 | 4.23.1.8 | 4.23.1.9 | 4.23.1.10 | 4.23.2.1 | 4.23.2.2 | 4.23.2.3 | 4.23.2.4 | |
| 4.23.2.5 | 4.23.2.6 | 4.23.2.7 | 4.23.2.8 | 4.23.2.9 | 4.23.2.10 | 4.23.3.1 | 4.23.3.2 | 4.23.3.3 | 4.23.3.4 | 4.23.3.5 | |
| 4.23.3.6 | 4.23.3.7 | 4.23.3.8 | 4.23.3.9 | 4.23.3.10 | 4.23.4.1 | 4.23.4.2 | 4.23.4.3 | 4.23.4.4 | 4.23.4.5 | 4.23.4.6 | |
| 4.23.4.7 | 4.23.4.8 | 4.23.4.9 | 4.23.4.10 | 4.23.5.1 | 4.23.5.2 | 4.23.5.3 | 4.23.5.4 | 4.23.5.5 | 4.23.5.6 | 4.23.5.7 | |
| 4.23.5.8 | 4.23.5.9 | 4.23.5.10 | 4.23.6.1 | 4.23.6.2 | 4.23.6.3 | 4.23.6.4 | 4.23.6.5 | 4.23.6.6 | 4.23.6.7 | 4.23.6.8 | |
| 4.23.6.9 | 4.23.6.10 | 4.24.1.1 | 4.24.1.2 | 4.24.1.3 | 4.24.1.4 | 4.24.1.5 | 4.24.1.6 | 4.24.1.7 | 4.24.1.8 | 4.24.1.9 | |
| 4.24.1.10 | 4.24.2.1 | 4.24.2.2 | 4.24.2.3 | 4.24.2.4 | 4.24.2.5 | 4.24.2.6 | 4.24.2.7 | 4.24.2.8 | 4.24.2.9 | 4.24.2.10 | |
| 4.24.3.1 | 4.24.3.2 | 4.24.3.3 | 4.24.3.4 | 4.24.3.5 | 4.24.3.6 | 4.24.3.7 | 4.24.3.8 | 4.24.3.9 | 4.24.3.10 | 4.24.4.1 | |
| 4.24.4.2 | 4.24.4.3 | 4.24.4.4 | 4.24.4.5 | 4.24.4.6 | 4.24.4.7 | 4.24.4.8 | 4.24.4.9 | 4.24.4.10 | 4.24.5.1 | 4.24.5.2 | |
| 4.24.5.3 | 4.24.5.4 | 4.24.5.5 | 4.24.5.6 | 4.24.5.7 | 4.24.5.8 | 4.24.5.9 | 4.24.5.10 | 4.24.6.1 | 4.24.6.2 | 4.24.6.3 | |
| 4.24.6.4 | 4.24.6.5 | 4.24.6.6 | 4.24.6.7 | 4.24.6.8 | 4.24.6.9 | 4.24.6.10 | 4.25.1.1 | 4.25.1.2 | 4.25.1.3 | 4.25.1.4 | |
| 4.25.1.5 | 4.25.1.6 | 4.25.1.7 | 4.25.1.8 | 4.25.1.9 | 4.25.1.10 | 4.25.2.1 | 4.25.2.2 | 4.25.2.3 | 4.25.2.4 | 4.25.2.5 | |
| 4.25.2.6 | 4.25.2.7 | 4.25.2.8 | 4.25.2.9 | 4.25.2.10 | 4.25.3.1 | 4.25.3.2 | 4.25.3.3 | 4.25.3.4 | 4.25.3.5 | 4.25.3.6 | |
| 4.25.3.7 | 4.25.3.8 | 4.25.3.9 | 4.25.3.10 | 4.25.4.1 | 4.25.4.2 | 4.25.4.3 | 4.25.4.4 | 4.25.4.5 | 4.25.4.6 | 4.25.4.7 | |
| 4.25.4.8 | 4.25.4.9 | 4.25.4.10 | 4.25.5.1 | 4.25.5.2 | 4.25.5.3 | 4.25.5.4 | 4.25.5.5 | 4.25.5.6 | 4.25.5.7 | 4.25.5.8 | |
| 4.25.5.9 | 4.25.5.10 | 4.25.6.1 | 4.25.6.2 | 4.25.6.3 | 4.25.6.4 | 4.25.6.5 | 4.25.6.6 | 4.25.6.7 | 4.25.6.8 | 4.25.6.9 | |
| 4.25.6.10 | 5.1.1.1 | 5.1.1.2 | 5.1.1.3 | [2.1.1.4] *5.1.1.4* | 5.1.1.5 | 5.1.1.6 | 5.1.1.7 | 5.1.1.8 | 5.1.1.9 | 5.1.1.10 | 5.1.2.1 | 5.1.2.2 |
| 5.1.2.3 | 5.1.2.4 | 5.1.2.5 | 5.1.2.6 | 5.1.2.7 | 5.1.2.8 | 5.1.2.9 | 5.1.2.10 | 5.1.3.1 | 5.1.3.2 | 5.1.3.3 | 5.1.3.4 | 5.1.3.5 |
| 5.1.3.6 | 5.1.3.7 | 5.1.3.8 | 5.1.3.9 | 5.1.3.10 | 5.1.4.1 | 5.1.4.2 | 5.1.4.3 | 5.1.4.4 | 5.1.4.5 | 5.1.4.6 | 5.1.4.7 | 5.1.4.8 |
| 5.1.4.9 | 5.1.4.10 | 5.1.5.1 | 5.1.5.2 | 5.1.5.3 | 5.1.5.4 | 5.1.5.5 | 5.1.5.6 | 5.1.5.7 | 5.1.5.8 | 5.1.5.9 | 5.1.5.10 | 5.1.6.1 |
| 5.1.6.2 | 5.1.6.3 | 5.1.6.4 | 5.1.6.5 | 5.1.6.6 | 5.1.6.7 | 5.1.6.8 | 5.1.6.9 | 5.1.6.10 | 5.2.1.1 | 5.2.1.2 | 5.2.1.3 | 5.2.1.4 |
| 5.2.1.5 | 5.2.1.6 | 5.2.1.7 | 5.2.1.8 | 5.2.1.9 | 5.2.1.10 | 5.2.2.1 | 5.2.2.2 | 5.2.2.3 | 5.2.2.4 | 5.2.2.5 | 5.2.2.6 | 5.2.2.7 |
| 5.2.2.8 | 5.2.2.9 | 5.2.2.10 | 5.2.3.1 | 5.2.3.2 | 5.2.3.3 | 5.2.3.4 | 5.2.3.5 | 5.2.3.6 | 5.2.3.7 | 5.2.3.8 | 5.2.3.9 | 5.2.3.10 |
| 5.2.4.1 | 5.2.4.2 | 5.2.4.3 | 5.2.4.4 | 5.2.4.5 | 5.2.4.6 | 5.2.4.7 | 5.2.4.8 | 5.2.4.9 | 5.2.4.10 | 5.2.5.1 | 5.2.5.2 | 5.2.5.3 |
| 5.2.5.4 | 5.2.5.5 | 5.2.5.6 | 5.2.5.7 | 5.2.5.8 | 5.2.5.9 | 5.2.5.10 | 5.2.6.1 | 5.2.6.2 | 5.2.6.3 | 5.2.6.4 | 5.2.6.5 | 5.2.6.6 |

TABLE B-continued

| | | | | | | | | | | | |
|---|---|---|---|---|---|---|---|---|---|---|---|
| 5.2.6.7 | 5.2.6.8 | 5.2.6.9 | 5.2.6.10 | 5.3.1.1 | 5.3.1.2 | 5.3.1.3 | 5.3.1.4 | 5.3.1.5 | 5.3.1.6 | 5.3.1.7 | 5.3.1.8 | 5.3.1.9 |
| 5.3.1.10 | 5.3.2.1 | 5.3.2.2 | 5.3.2.3 | 5.3.2.4 | 5.3.2.5 | 5.3.2.6 | 5.3.2.7 | 5.3.2.8 | 5.3.2.9 | 5.3.2.10 | 5.3.3.1 | 5.3.3.2 |
| 5.3.3.3 | 5.3.3.4 | 5.3.3.5 | 5.3.3.6 | 5.3.3.7 | 5.3.3.8 | 5.3.3.9 | 5.3.3.10 | 5.3.4.1 | 5.3.4.2 | 5.3.4.3 | 5.3.4.4 | 5.3.4.5 |
| 5.3.4.6 | 5.3.4.7 | 5.3.4.8 | 5.3.4.9 | 5.3.4.10 | 5.3.5.1 | 5.3.5.2 | 5.3.5.3 | 5.3.5.4 | 5.3.5.5 | 5.3.5.6 | 5.3.5.7 | 5.3.5.8 |
| 5.3.5.9 | 5.3.5.10 | 5.3.6.1 | 5.3.6.2 | 5.3.6.3 | 5.3.6.4 | 5.3.6.5 | 5.3.6.6 | 5.3.6.7 | 5.3.6.8 | 5.3.6.9 | 5.3.6.10 | 5.4.1.1 |
| 5.4.1.2 | 5.4.1.3 | 5.4.1.4 | 5.4.1.5 | 5.4.1.6 | 5.4.1.7 | 5.4.1.8 | 5.4.1.9 | 5.4.1.10 | 5.4.2.1 | 5.4.2.2 | 5.4.2.3 | 5.4.2.4 |
| 5.4.2.5 | 5.4.2.6 | 5.4.2.7 | 5.4.2.8 | 5.4.2.9 | 5.4.2.10 | 5.4.3.1 | 5.4.3.2 | 5.4.3.3 | 5.4.3.4 | 5.4.3.5 | 5.4.3.6 | 5.4.3.7 |
| 5.4.3.8 | 5.4.3.9 | 5.4.3.10 | 5.4.4.1 | 5.4.4.2 | 5.4.4.3 | 5.4.4.4 | 5.4.4.5 | 5.4.4.6 | 5.4.4.7 | 5.4.4.8 | 5.4.4.9 | 5.4.4.10 |
| 5.4.5.1 | 5.4.5.2 | 5.4.5.3 | 5.4.5.4 | 5.4.5.5 | 5.4.5.6 | 5.4.5.7 | 5.4.5.8 | 5.4.5.9 | 5.4.5.10 | 5.4.6.1 | 5.4.6.2 | 5.4.6.3 |
| 5.4.6.4 | 5.4.6.5 | 5.4.6.6 | 5.4.6.7 | 5.4.6.8 | 5.4.6.9 | 5.4.6.10 | 5.5.1.1 | 5.5.1.2 | 5.5.1.3 | 5.5.1.4 | 5.5.1.5 | 5.5.1.6 |
| 5.5.1.7 | 5.5.1.8 | 5.5.1.9 | 5.5.1.10 | 5.5.2.1 | 5.5.2.2 | 5.5.2.3 | 5.5.2.4 | 5.5.2.5 | 5.5.2.6 | 5.5.2.7 | 5.5.2.8 | 5.5.2.9 |
| 5.5.2.10 | 5.5.3.1 | 5.5.3.2 | 5.5.3.3 | 5.5.3.4 | 5.5.3.5 | 5.5.3.6 | 5.5.3.7 | 5.5.3.8 | 5.5.3.9 | 5.5.3.10 | 5.5.4.1 | 5.5.4.2 |
| 5.5.4.3 | 5.5.4.4 | 5.5.4.5 | 5.5.4.6 | 5.5.4.7 | 5.5.4.8 | 5.5.4.9 | 5.5.4.10 | 5.5.5.1 | 5.5.5.2 | 5.5.5.3 | 5.5.5.4 | 5.5.5.5 |
| 5.5.5.6 | 5.5.5.7 | 5.5.5.8 | 5.5.5.9 | 5.5.5.10 | 5.5.6.1 | 5.5.6.2 | 5.5.6.3 | 5.5.6.4 | 5.5.6.5 | 5.5.6.6 | 5.5.6.7 | 5.5.6.8 |
| 5.5.6.9 | 5.5.6.10 | 5.6.1.1 | 5.6.1.2 | 5.6.1.3 | 5.6.1.4 | 5.6.1.5 | 5.6.1.6 | 5.6.1.7 | 5.6.1.8 | 5.6.1.9 | 5.6.1.10 | 5.6.2.1 |
| 5.6.2.2 | 5.6.2.3 | 5.6.2.4 | 5.6.2.5 | 5.6.2.6 | 5.6.2.7 | 5.6.2.8 | 5.6.2.9 | 5.6.2.10 | 5.6.3.1 | 5.6.3.2 | 5.6.3.3 | 5.6.3.4 |
| 5.6.3.5 | 5.6.3.6 | 5.6.3.7 | 5.6.3.8 | 5.6.3.9 | 5.6.3.10 | 5.6.4.1 | 5.6.4.2 | 5.6.4.3 | 5.6.4.4 | 5.6.4.5 | 5.6.4.6 | 5.6.4.7 |
| 5.6.4.8 | 5.6.4.9 | 5.6.4.10 | 5.6.5.1 | 5.6.5.2 | 5.6.5.3 | 5.6.5.4 | 5.6.5.5 | 5.6.5.6 | 5.6.5.7 | 5.6.5.8 | 5.6.5.9 | 5.6.5.10 |
| 5.6.6.1 | 5.6.6.2 | 5.6.6.3 | 5.6.6.4 | 5.6.6.5 | 5.6.6.6 | 5.6.6.7 | 5.6.6.8 | 5.6.6.9 | 5.6.6.10 | 5.7.1.1 | 5.7.1.2 | 5.7.1.3 |
| 5.7.1.4 | 5.7.1.5 | 5.7.1.6 | 5.7.1.7 | 5.7.1.8 | 5.7.1.9 | 5.7.1.10 | 5.7.2.1 | 5.7.2.2 | 5.7.2.3 | 5.7.2.4 | 5.7.2.5 | 5.7.2.6 |
| 5.7.2.7 | 5.7.2.8 | 5.7.2.9 | 5.7.2.10 | 5.7.3.1 | 5.7.3.2 | 5.7.3.3 | 5.7.3.4 | 5.7.3.5 | 5.7.3.6 | 5.7.3.7 | 5.7.3.8 | 5.7.3.9 |
| 5.7.3.10 | 5.7.4.1 | 5.7.4.2 | 5.7.4.3 | 5.7.4.4 | 5.7.4.5 | 5.7.4.6 | 5.7.4.7 | 5.7.4.8 | 5.7.4.9 | 5.7.4.10 | 5.7.5.1 | 5.7.5.2 |
| 5.7.5.3 | 5.7.5.4 | 5.7.5.5 | 5.7.5.6 | 5.7.5.7 | 5.7.5.8 | 5.7.5.9 | 5.7.5.10 | 5.7.6.1 | 5.7.6.2 | 5.7.6.3 | 5.7.6.4 | 5.7.6.5 |
| 5.7.6.6 | 5.7.6.7 | 5.7.6.8 | 5.7.6.9 | 5.7.6.10 | 5.8.1.1 | 5.8.1.2 | 5.8.1.3 | 5.8.1.4 | 5.8.1.5 | 5.8.1.6 | 5.8.1.7 | 5.8.1.8 |
| 5.8.1.9 | 5.8.1.10 | 5.8.2.1 | 5.8.2.2 | 5.8.2.3 | 5.8.2.4 | 5.8.2.5 | 5.8.2.6 | 5.8.2.7 | 5.8.2.8 | 5.8.2.9 | 5.8.2.10 | 5.8.3.1 |
| 5.8.3.2 | 5.8.3.3 | 5.8.3.4 | 5.8.3.5 | 5.8.3.6 | 5.8.3.7 | 5.8.3.8 | 5.8.3.9 | 5.8.3.10 | 5.8.4.1 | 5.8.4.2 | 5.8.4.3 | 5.8.4.4 |
| 5.8.4.5 | 5.8.4.6 | 5.8.4.7 | 5.8.4.8 | 5.8.4.9 | 5.8.4.10 | 5.8.5.1 | 5.8.5.2 | 5.8.5.3 | 5.8.5.4 | 5.8.5.5 | 5.8.5.6 | 5.8.5.7 |
| 5.8.5.8 | 5.8.5.9 | 5.8.5.10 | 5.8.6.1 | 5.8.6.2 | 5.8.6.3 | 5.8.6.4 | 5.8.6.5 | 5.8.6.6 | 5.8.6.7 | 5.8.6.8 | 5.8.6.9 | 5.8.6.10 |
| 5.9.1.1 | 5.9.1.2 | 5.9.1.3 | 5.9.1.4 | 5.9.1.5 | 5.9.1.6 | 5.9.1.7 | 5.9.1.8 | 5.9.1.9 | 5.9.1.10 | 5.9.2.1 | 5.9.2.2 | 5.9.2.3 |
| 5.9.2.4 | 5.9.2.5 | 5.9.2.6 | 5.9.2.7 | 5.9.2.8 | 5.9.2.9 | 5.9.2.10 | 5.9.3.1 | 5.9.3.2 | 5.9.3.3 | 5.9.3.4 | 5.9.3.5 | 5.9.3.6 |
| 5.9.3.7 | 5.9.3.8 | 5.9.3.9 | 5.9.3.10 | 5.9.4.1 | 5.9.4.2 | 5.9.4.3 | 5.9.4.4 | 5.9.4.5 | 5.9.4.6 | 5.9.4.7 | 5.9.4.8 | 5.9.4.9 |
| 5.9.4.10 | 5.9.5.1 | 5.9.5.2 | 5.9.5.3 | 5.9.5.4 | 5.9.5.5 | 5.9.5.6 | 5.9.5.7 | 5.9.5.8 | 5.9.5.9 | 5.9.5.10 | 5.9.6.1 | 5.9.6.2 |
| 5.9.6.3 | 5.9.6.4 | 5.9.6.5 | 5.9.6.6 | 5.9.6.7 | 5.9.6.8 | 5.9.6.9 | 5.10.1.1 | 5.10.1.2 | 5.10.1.3 | 5.10.1.4 | | |
| 5.10.1.5 | 5.10.1.6 | 5.10.1.7 | 5.10.1.8 | 5.10.1.9 | 5.10.1.10 | 5.10.2.1 | 5.10.2.2 | 5.10.2.3 | 5.10.2.4 | 5.10.2.5 | | |
| 5.10.2.6 | 5.10.2.7 | 5.10.2.8 | 5.10.2.9 | 5.10.2.10 | 5.10.3.1 | 5.10.3.2 | 5.10.3.3 | 5.10.3.4 | 5.10.3.5 | 5.10.3.6 | | |
| 5.10.3.7 | 5.10.3.8 | 5.10.3.9 | 5.10.3.10 | 5.10.4.1 | 5.10.4.2 | 5.10.4.3 | 5.10.4.4 | 5.10.4.5 | 5.10.4.6 | 5.10.4.7 | | |
| 5.10.4.8 | 5.10.4.9 | 5.10.4.10 | 5.10.5.1 | 5.10.5.2 | 5.10.5.3 | 5.10.5.4 | 5.10.5.5 | 5.10.5.6 | 5.10.5.7 | 5.10.5.8 | | |
| 5.10.5.9 | 5.10.5.10 | 5.10.6.1 | 5.10.6.2 | 5.10.6.3 | 5.10.6.4 | 5.10.6.5 | 5.10.6.6 | 5.10.6.7 | 5.10.6.8 | 5.10.6.9 | | |
| 5.10.6.10 | 5.11.1.1 | 5.11.1.2 | 5.11.1.3 | 5.11.1.4 | 5.11.1.5 | 5.11.1.6 | 5.11.1.7 | 5.11.1.8 | 5.11.1.9 | 5.11.1.10 | | |
| 5.11.2.1 | 5.11.2.2 | 5.11.2.3 | 5.11.2.4 | 5.11.2.5 | 5.11.2.6 | 5.11.2.7 | 5.11.2.8 | 5.11.2.9 | 5.11.2.10 | 5.11.3.1 | | |
| 5.11.3.2 | 5.11.3.3 | 5.11.3.4 | 5.11.3.5 | 5.11.3.6 | 5.11.3.7 | 5.11.3.8 | 5.11.3.9 | 5.11.3.10 | 5.11.4.1 | 5.11.4.2 | | |
| 5.11.4.3 | 5.11.4.4 | 5.11.4.5 | 5.11.4.6 | 5.11.4.7 | 5.11.4.8 | 5.11.4.9 | 5.11.4.10 | 5.11.5.1 | 5.11.5.2 | 5.11.5.3 | | |
| 5.11.5.4 | 5.11.5.5 | 5.11.5.6 | 5.11.5.7 | 5.11.5.8 | 5.11.5.9 | 5.11.5.10 | 5.11.6.1 | 5.11.6.2 | 5.11.6.3 | 5.11.6.4 | | |
| 5.11.6.5 | 5.11.6.6 | 5.11.6.7 | 5.11.6.8 | 5.11.6.9 | 5.11.6.10 | 5.12.1.1 | 5.12.1.2 | 5.12.1.3 | 5.12.1.4 | 5.12.1.5 | | |
| 5.12.1.6 | 5.12.1.7 | 5.12.1.8 | 5.12.1.9 | 5.12.1.10 | 5.12.2.1 | 5.12.2.2 | 5.12.2.3 | 5.12.2.4 | 5.12.2.5 | 5.12.2.6 | | |
| 5.12.2.7 | 5.12.2.8 | 5.12.2.9 | 5.12.2.10 | 5.12.3.1 | 5.12.3.2 | 5.12.3.3 | 5.12.3.4 | 5.12.3.5 | 5.12.3.6 | 5.12.3.7 | | |
| 5.12.3.8 | 5.12.3.9 | 5.12.3.10 | 5.12.4.1 | 5.12.4.2 | 5.12.4.3 | 5.12.4.4 | 5.12.4.5 | 5.12.4.6 | 5.12.4.7 | 5.12.4.8 | | |
| 5.12.4.9 | 5.12.4.10 | 5.12.5.1 | 5.12.5.2 | 5.12.5.3 | 5.12.5.4 | 5.12.5.5 | 5.12.5.6 | 5.12.5.7 | 5.12.5.8 | 5.12.5.9 | | |
| 5.12.5.10 | 5.12.6.1 | 5.12.6.2 | 5.12.6.3 | 5.12.6.4 | 5.12.6.5 | 5.12.6.6 | 5.12.6.7 | 5.12.6.8 | 5.12.6.9 | 5.12.6.10 | | |
| 5.13.1.1 | 5.13.1.2 | 5.13.1.3 | 5.13.1.4 | 5.13.1.5 | 5.13.1.6 | 5.13.1.7 | 5.13.1.8 | 5.13.1.9 | 5.13.1.10 | 5.13.2.1 | | |
| 5.13.2.2 | 5.13.2.3 | 5.13.2.4 | 5.13.2.5 | 5.13.2.6 | 5.13.2.7 | 5.13.2.8 | 5.13.2.9 | 5.13.2.10 | 5.13.3.1 | 5.13.3.2 | | |
| 5.13.3.3 | 5.13.3.4 | 5.13.3.5 | 5.13.3.6 | 5.13.3.7 | 5.13.3.8 | 5.13.3.9 | 5.13.3.10 | 5.13.4.1 | 5.13.4.2 | 5.13.4.3 | | |
| 5.13.4.4 | 5.13.4.5 | 5.13.4.6 | 5.13.4.7 | 5.13.4.8 | 5.13.4.9 | 5.13.4.10 | 5.13.5.1 | 5.13.5.2 | 5.13.5.3 | 5.13.5.4 | | |
| 5.13.5.5 | 5.13.5.6 | 5.13.5.7 | 5.13.5.8 | 5.13.5.9 | 5.13.5.10 | 5.13.6.1 | 5.13.6.2 | 5.13.6.3 | 5.13.6.4 | 5.13.6.5 | | |
| 5.13.6.6 | 5.13.6.7 | 5.13.6.8 | 5.13.6.9 | 5.13.6.10 | 5.14.1.1 | 5.14.1.2 | 5.14.1.3 | 5.14.1.4 | 5.14.1.5 | 5.14.1.6 | | |
| 5.14.1.7 | 5.14.1.8 | 5.14.1.9 | 5.14.1.10 | 5.14.2.1 | 5.14.2.2 | 5.14.2.3 | 5.14.2.4 | 5.14.2.5 | 5.14.2.6 | 5.14.2.7 | | |
| 5.14.2.8 | 5.14.2.9 | 5.14.2.10 | 5.14.3.1 | 5.14.3.2 | 5.14.3.3 | 5.14.3.4 | 5.14.3.5 | 5.14.3.6 | 5.14.3.7 | 5.14.3.8 | | |
| 5.14.3.9 | 5.14.3.10 | 5.14.4.1 | 5.14.4.2 | 5.14.4.3 | 5.14.4.4 | 5.14.4.5 | 5.14.4.6 | 5.14.4.7 | 5.14.4.8 | 5.14.4.9 | | |
| 5.14.4.10 | 5.14.5.1 | 5.14.5.2 | 5.14.5.3 | 5.14.5.4 | 5.14.5.5 | 5.14.5.6 | 5.14.5.7 | 5.14.5.8 | 5.14.5.9 | 5.14.5.10 | | |
| 5.14.6.1 | 5.14.6.2 | 5.14.6.3 | 5.14.6.4 | 5.14.6.5 | 5.14.6.6 | 5.14.6.7 | 5.14.6.8 | 5.14.6.9 | 5.14.6.10 | 5.15.1.1 | | |
| 5.15.1.2 | 5.15.1.3 | 5.15.1.4 | 5.15.1.5 | 5.15.1.6 | 5.15.1.7 | 5.15.1.8 | 5.15.1.9 | 5.15.1.10 | 5.15.2.1 | 5.15.2.2 | | |
| 5.15.2.3 | 5.15.2.4 | 5.15.2.5 | 5.15.2.6 | 5.15.2.7 | 5.15.2.8 | 5.15.2.9 | 5.15.2.10 | 5.15.3.1 | 5.15.3.2 | 5.15.3.3 | | |
| 5.15.3.4 | 5.15.3.5 | 5.15.3.6 | 5.15.3.7 | 5.15.3.8 | 5.15.3.9 | 5.15.3.10 | 5.15.4.1 | 5.15.4.2 | 5.15.4.3 | 5.15.4.4 | | |
| 5.15.4.5 | 5.15.4.6 | 5.15.4.7 | 5.15.4.8 | 5.15.4.9 | 5.15.4.10 | 5.15.5.1 | 5.15.5.2 | 5.15.5.3 | 5.15.5.4 | 5.15.5.5 | | |
| 5.15.5.6 | 5.15.5.7 | 5.15.5.8 | 5.15.5.9 | 5.15.5.10 | 5.15.6.1 | 5.15.6.2 | 5.15.6.3 | 5.15.6.4 | 5.15.6.5 | 5.15.6.6 | | |
| 5.15.6.7 | 5.15.6.8 | 5.15.6.9 | 5.15.6.10 | 5.16.1.1 | 5.16.1.2 | 5.16.1.3 | 5.16.1.4 | 5.16.1.5 | 5.16.1.6 | 5.16.1.7 | | |
| 5.16.1.8 | 5.16.1.9 | 5.16.1.10 | 5.16.2.1 | 5.16.2.2 | 5.16.2.3 | 5.16.2.4 | 5.16.2.5 | 5.16.2.6 | 5.16.2.7 | 5.16.2.8 | | |
| 5.16.2.9 | 5.16.2.10 | 5.16.3.1 | 5.16.3.2 | 5.16.3.3 | 5.16.3.4 | 5.16.3.5 | 5.16.3.6 | 5.16.3.7 | 5.16.3.8 | 5.16.3.9 | | |
| 5.16.3.10 | 5.16.4.1 | 5.16.4.2 | 5.16.4.3 | 5.16.4.4 | 5.16.4.5 | 5.16.4.6 | 5.16.4.7 | 5.16.4.8 | 5.16.4.9 | 5.16.4.10 | | |
| 5.16.5.1 | 5.16.5.2 | 5.16.5.3 | 5.16.5.4 | 5.16.5.5 | 5.16.5.6 | 5.16.5.7 | 5.16.5.8 | 5.16.5.9 | 5.16.5.10 | 5.16.6.1 | | |
| 5.16.6.2 | 5.16.6.3 | 5.16.6.4 | 5.16.6.5 | 5.16.6.6 | 5.16.6.7 | 5.16.6.8 | 5.16.6.9 | 5.16.6.10 | 5.17.1.1 | 5.17.1.2 | | |
| 5.17.1.3 | 5.17.1.4 | 5.17.1.5 | 5.17.1.6 | 5.17.1.7 | 5.17.1.8 | 5.17.1.9 | 5.17.1.10 | 5.17.2.1 | 5.17.2.2 | 5.17.2.3 | | |
| 5.17.2.4 | 5.17.2.5 | 5.17.2.6 | 5.17.2.7 | 5.17.2.8 | 5.17.2.9 | 5.17.2.10 | 5.17.3.1 | 5.17.3.2 | 5.17.3.3 | 5.17.3.4 | | |
| 5.17.3.5 | 5.17.3.6 | 5.17.3.7 | 5.17.3.8 | 5.17.3.9 | 5.17.3.10 | 5.17.4.1 | 5.17.4.2 | 5.17.4.3 | 5.17.4.4 | 5.17.4.5 | | |
| 5.17.4.6 | 5.17.4.7 | 5.17.4.8 | 5.17.4.9 | 5.17.4.10 | 5.17.5.1 | 5.17.5.2 | 5.17.5.3 | 5.17.5.4 | 5.17.5.5 | 5.17.5.6 | | |
| 5.17.5.7 | 5.17.5.8 | 5.17.5.9 | 5.17.5.10 | 5.17.6.1 | 5.17.6.2 | 5.17.6.3 | 5.17.6.4 | 5.17.6.5 | 5.17.6.6 | 5.17.6.7 | | |
| 5.17.6.8 | 5.17.6.9 | 5.17.6.10 | 5.18.1.1 | 5.18.1.2 | 5.18.1.3 | 5.18.1.4 | 5.18.1.5 | 5.18.1.6 | 5.18.1.7 | 5.18.1.8 | | |
| 5.18.1.9 | 5.18.1.10 | 5.18.2.1 | 5.18.2.2 | 5.18.2.3 | 5.18.2.4 | 5.18.2.5 | 5.18.2.6 | 5.18.2.7 | 5.18.2.8 | 5.18.2.9 | | |
| 5.18.2.10 | 5.18.3.1 | 5.18.3.2 | 5.18.3.3 | 5.18.3.4 | 5.18.3.5 | 5.18.3.6 | 5.18.3.7 | 5.18.3.8 | 5.18.3.9 | 5.18.3.10 | | |

TABLE B-continued

| | | | | | | | | | |
|---|---|---|---|---|---|---|---|---|---|
| 5.18.4.1 | 5.18.4.2 | 5.18.4.3 | 5.18.4.4 | 5.18.4.5 | 5.18.4.6 | 5.18.4.7 | 5.18.4.8 | 5.18.4.9 | 5.18.4.10 | 5.18.5.1 |
| 5.18.5.2 | 5.18.5.3 | 5.18.5.4 | 5.18.5.5 | 5.18.5.6 | 5.18.5.7 | 5.18.5.8 | 5.18.5.9 | 5.18.5.10 | 5.18.6.1 | 5.18.6.2 |
| 5.18.6.3 | 5.18.6.4 | 5.18.6.5 | 5.18.6.6 | 5.18.6.7 | 5.18.6.8 | 5.18.6.9 | 5.18.6.10 | 5.19.1.1 | 5.19.1.2 | 5.19.1.3 |
| 5.19.1.4 | 5.19.1.5 | 5.19.1.6 | 5.19.1.7 | 5.19.1.8 | 5.19.1.9 | 5.19.1.10 | 5.19.2.1 | 5.19.2.2 | 5.19.2.3 | 5.19.2.4 |
| 5.19.2.5 | 5.19.2.6 | 5.19.2.7 | 5.19.2.8 | 5.19.2.9 | 5.19.2.10 | 5.19.3.1 | 5.19.3.2 | 5.19.3.3 | 5.19.3.4 | 5.19.3.5 |
| 5.19.3.6 | 5.19.3.7 | 5.19.3.8 | 5.19.3.9 | 5.19.3.10 | 5.19.4.1 | 5.19.4.2 | 5.19.4.3 | 5.19.4.4 | 5.19.4.5 | 5.19.4.6 |
| 5.19.4.7 | 5.19.4.8 | 5.19.4.9 | 5.19.4.10 | 5.19.5.1 | 5.19.5.2 | 5.19.5.3 | 5.19.5.4 | 5.19.5.5 | 5.19.5.6 | 5.19.5.7 |
| 5.19.5.8 | 5.19.5.9 | 5.19.5.10 | 5.19.6.1 | 5.19.6.2 | 5.19.6.3 | 5.19.6.4 | 5.19.6.5 | 5.19.6.6 | 5.19.6.7 | 5.19.6.8 |
| 5.19.6.9 | 5.19.6.10 | 5.20.1.1 | 5.20.1.2 | 5.20.1.3 | 5.20.1.4 | 5.20.1.5 | 5.20.1.6 | 5.20.1.7 | 5.20.1.8 | 5.20.1.9 |
| 5.20.1.10 | 5.20.2.1 | 5.20.2.2 | 5.20.2.3 | 5.20.2.4 | 5.20.2.5 | 5.20.2.6 | 5.20.2.7 | 5.20.2.8 | 5.20.2.9 | 5.20.2.10 |
| 5.20.3.1 | 5.20.3.2 | 5.20.3.3 | 5.20.3.4 | 5.20.3.5 | 5.20.3.6 | 5.20.3.7 | 5.20.3.8 | 5.20.3.9 | 5.20.3.10 | 5.20.4.1 |
| 5.20.4.2 | 5.20.4.3 | 5.20.4.4 | 5.20.4.5 | 5.20.4.6 | 5.20.4.7 | 5.20.4.8 | 5.20.4.9 | 5.20.4.10 | 5.20.5.1 | 5.20.5.2 |
| 5.20.5.3 | 5.20.5.4 | 5.20.5.5 | 5.20.5.6 | 5.20.5.7 | 5.20.5.8 | 5.20.5.9 | 5.20.5.10 | 5.20.6.1 | 5.20.6.2 | 5.20.6.3 |
| 5.20.6.4 | 5.20.6.5 | 5.20.6.6 | 5.20.6.7 | 5.20.6.8 | 5.20.6.9 | 5.20.6.10 | 5.21.1.1 | 5.21.1.2 | 5.21.1.3 | 5.21.1.4 |
| 5.21.1.5 | 5.21.1.6 | 5.21.1.7 | 5.21.1.8 | 5.21.1.9 | 5.21.1.10 | 5.21.2.1 | 5.21.2.2 | 5.21.2.3 | 5.21.2.4 | 5.21.2.5 |
| 5.21.2.6 | 5.21.2.7 | 5.21.2.8 | 5.21.2.9 | 5.21.2.10 | 5.21.3.1 | 5.21.3.2 | 5.21.3.3 | 5.21.3.4 | 5.21.3.5 | 5.21.3.6 |
| 5.21.3.7 | 5.21.3.8 | 5.21.3.9 | 5.21.3.10 | 5.21.4.1 | 5.21.4.2 | 5.21.4.3 | 5.21.4.4 | 5.21.4.5 | 5.21.4.6 | 5.21.4.7 |
| 5.21.4.8 | 5.21.4.9 | 5.21.4.10 | 5.21.5.1 | 5.21.5.2 | 5.21.5.3 | 5.21.5.4 | 5.21.5.5 | 5.21.5.6 | 5.21.5.7 | 5.21.5.8 |
| 5.21.5.9 | 5.21.5.10 | 5.21.6.1 | 5.21.6.2 | 5.21.6.3 | 5.21.6.4 | 5.21.6.5 | 5.21.6.6 | 5.21.6.7 | 5.21.6.8 | 5.21.6.9 |
| 5.21.6.10 | 5.22.1.1 | 5.22.1.2 | 5.22.1.3 | 5.22.1.4 | 5.22.1.5 | 5.22.1.6 | 5.22.1.7 | 5.22.1.8 | 5.22.1.9 | 5.22.1.10 |
| 5.22.2.1 | 5.22.2.2 | 5.22.2.3 | 5.22.2.4 | 5.22.2.5 | 5.22.2.6 | 5.22.2.7 | 5.22.2.8 | 5.22.2.9 | 5.22.2.10 | 5.22.3.1 |
| 5.22.3.2 | 5.22.3.3 | 5.22.3.4 | 5.22.3.5 | 5.22.3.6 | 5.22.3.7 | 5.22.3.8 | 5.22.3.9 | 5.22.3.10 | 5.22.4.1 | 5.22.4.2 |
| 5.22.4.3 | 5.22.4.4 | 5.22.4.5 | 5.22.4.6 | 5.22.4.7 | 5.22.4.8 | 5.22.4.9 | 5.22.4.10 | 5.22.5.1 | 5.22.5.2 | 5.22.5.3 |
| 5.22.5.4 | 5.22.5.5 | 5.22.5.6 | 5.22.5.7 | 5.22.5.8 | 5.22.5.9 | 5.22.5.10 | 5.22.6.1 | 5.22.6.2 | 5.22.6.3 | 5.22.6.4 |
| 5.22.6.5 | 5.22.6.6 | 5.22.6.7 | 5.22.6.8 | 5.22.6.9 | 5.22.6.10 | 5.23.1.1 | 5.23.1.2 | 5.23.1.3 | 5.23.1.4 | 5.23.1.5 |
| 5.23.1.6 | 5.23.1.7 | 5.23.1.8 | 5.23.1.9 | 5.23.1.10 | 5.23.2.1 | 5.23.2.2 | 5.23.2.3 | 5.23.2.4 | 5.23.2.5 | 5.23.2.6 |
| 5.23.2.7 | 5.23.2.8 | 5.23.2.9 | 5.23.2.10 | 5.23.3.1 | 5.23.3.2 | 5.23.3.3 | 5.23.3.4 | 5.23.3.5 | 5.23.3.6 | 5.23.3.7 |
| 5.23.3.8 | 5.23.3.9 | 5.23.3.10 | 5.23.4.1 | 5.23.4.2 | 5.23.4.3 | 5.23.4.4 | 5.23.4.5 | 5.23.4.6 | 5.23.4.7 | 5.23.4.8 |
| 5.23.4.9 | 5.23.4.10 | 5.23.5.1 | 5.23.5.2 | 5.23.5.3 | 5.23.5.4 | 5.23.5.5 | 5.23.5.6 | 5.23.5.7 | 5.23.5.8 | 5.23.5.9 |
| 5.23.5.10 | 5.23.6.1 | 5.23.6.2 | 5.23.6.3 | 5.23.6.4 | 5.23.6.5 | 5.23.6.6 | 5.23.6.7 | 5.23.6.8 | 5.23.6.9 | 5.23.6.10 |
| 5.24.1.1 | 5.24.1.2 | 5.24.1.3 | 5.24.1.4 | 5.24.1.5 | 5.24.1.6 | 5.24.1.7 | 5.24.1.8 | 5.24.1.9 | 5.24.1.10 | 5.24.2.1 |
| 5.24.2.2 | 5.24.2.3 | 5.24.2.4 | 5.24.2.5 | 5.24.2.6 | 5.24.2.7 | 5.24.2.8 | 5.24.2.9 | 5.24.2.10 | 5.24.3.1 | 5.24.3.2 |
| 5.24.3.3 | 5.24.3.4 | 5.24.3.5 | 5.24.3.6 | 5.24.3.7 | 5.24.3.8 | 5.24.3.9 | 5.24.3.10 | 5.24.4.1 | 5.24.4.2 | 5.24.4.3 |
| 5.24.4.4 | 5.24.4.5 | 5.24.4.6 | 5.24.4.7 | 5.24.4.8 | 5.24.4.9 | 5.24.4.10 | 5.24.5.1 | 5.24.5.2 | 5.24.5.3 | 5.24.5.4 |
| 5.24.5.5 | 5.24.5.6 | 5.24.5.7 | 5.24.5.8 | 5.24.5.9 | 5.24.5.10 | 5.24.6.1 | 5.24.6.2 | 5.24.6.3 | 5.24.6.4 | 5.24.6.5 |
| 5.24.6.6 | 5.24.6.7 | 5.24.6.8 | 5.24.6.9 | 5.24.6.10 | 5.25.1.1 | 5.25.1.2 | 5.25.1.3 | 5.25.1.4 | 5.25.1.5 | 5.25.1.6 |
| 5.25.1.7 | 5.25.1.8 | 5.25.1.9 | 5.25.1.10 | 5.25.2.1 | 5.25.2.2 | 5.25.2.3 | 5.25.2.4 | 5.25.2.5 | 5.25.2.6 | 5.25.2.7 |
| 5.25.2.8 | 5.25.2.9 | 5.25.2.10 | 5.25.3.1 | 5.25.3.2 | 5.25.3.3 | 5.25.3.4 | 5.25.3.5 | 5.25.3.6 | 5.25.3.7 | 5.25.3.8 |
| 5.25.3.9 | 5.25.3.10 | 5.25.4.1 | 5.25.4.2 | 5.25.4.3 | 5.25.4.4 | 5.25.4.5 | 5.25.4.6 | 5.25.4.7 | 5.25.4.8 | 5.25.4.9 |
| 5.25.4.10 | 5.25.5.1 | 5.25.5.2 | 5.25.5.3 | 5.25.5.4 | 5.25.5.5 | 5.25.5.6 | 5.25.5.7 | 5.25.5.8 | 5.25.5.9 | 5.25.5.10 |
| 5.25.6.1 | 5.25.6.2 | 5.25.6.3 | 5.25.6.4 | 5.25.6.5 | 5.25.6.6 | 5.25.6.7 | 5.25.6.8 | 5.25.6.9 | 5.25.6.10 | |

Column 25, lines 8–41:

*6* Compounds named in Table B and compounds named by compound groups 1–5 where R moieties 1–25 listed in Table A are replaced with the following groups:

1 —cyclopropyl (cyclopropyl replaces —$CH_3$, which is R moiety 1 in Table A)
2 —$CH_2$-cyclopropyl
3 —$(CH_2)_2$-cyclopropyl
4 —$(CH_2)_3$-cyclopropyl
5 —$(CH_2)_4$-cyclopropyl
6 —cyclobutyl
7 —$CH_2$-cyclobutyl
8 —$(CH_2)_2$-cyclobutyl
9 —$(CH_2)_3$-cyclobutyl
10 —$(CH_2)_4$-cyclobutyl
11 —cyclopentyl
12 —$CH_2$-cyclopentyl
13 —$(CH_2)_2$-cyclopentyl
14 —$(CH_2)_3$-cyclopentyl
15 —$(CH_2)_4$-cyclopentyl
16 —cyclohexyl
17 —$CH_2$-cyclohexyl
18 —$(CH_2)_2$-cyclohexyl
19 —$(CH_2)_3$-cyclohexyl
20 —$(CH_2)_4$-cyclohexyl
21 —$CH(CH_3)CH_2$-cyclopropyl
22 —$CH(CH_3)CH_2$-cyclobutyl
23 —$CH(CH_3)CH_2$-cyclopentyl
24 —$CH(CH_3)CH_2$-cyclohexyl
25 —$(CH_2)_{0-4}$-cyclooctyl.

Column 26, line 63 to column 27, line 27:

*10* Compounds named in Table B and compounds named by compound groups 1–5 where R moieties 1–25 listed in Table A are replaced with the following groups:

1 —$CH(CH_3)(CH_2)_2OC_6H_{13}$
2 —$CH(CH_3)(CH_2)_3OC_6H_{13}$
3 —$CH(CH_3)(CH_2)_4OC_6H_{13}$
4 —$CH_2CH(CH_3)OCH_3$
5 —$(CH_2)_2CH(CH_3)OCH_3$
6 —$(CH_2)_3CH(CH_3)OCH_3$
7 —$(CH_2)_4CH(CH_3)OCH_3$
8 —$CH_2CH(CH_3)OCH_2CH_3$
9 —$(CH_2)_2CH(CH_3)OCH_2CH_3$
10 —$(CH_2)_3CH(CH_3)OCH_2CH_3$
11 —$(CH_2)_4CH(CH_3)OCH_2CH_3$
12 —$CH_2CH(CH_3)OCH_2 CH_3$
13 —$(CH_2)_2CH(CH_3)O(CH_2)_2CH_3$
14 —$(CH_2)_3CH(CH_3)O(CH_2)_3CH_3$
15 —$(CH_2)_4CH(CH_3)O(CH_2)_4CH_3$
16 —$CH_2CH(CH_3)OCH(CH_3)_2$
17 —$(CH_2)_2CH(CH_3)OCH(CH_3)_2$

18 —(CH$_2$)$_3$CH(CH$_3$)OCH(CH$_3$)$_2$
19 —(CH$_2$)$_4$CH(CH$_3$)OCH(CH$_3$)$_2$
20 —CH$_2$CH(CH$_3$)OC$_4$H$_9$
21 —(CH$_2$)$_2$CH(CH$_3$)OC$_4$H$_9$
22 —(CH$_2$)$_3$CH(CH$_3$)OC$_4$H$_9$
23 —(CH$_2$)$_4$CH(CH$_3$)OC$_4$H$_9$
24 —CH$_2$CH(CH$_3$)OC$_5$H$_{11}$
25 —(CH$_2$)$_2$CH(CH$_3$)OC$_5$H$_{11}$

Column 28, line 60 to column 29, line 25:

14 Compounds named in Table B and compounds named by compound groups 1–5 where R moieties 1–25 listed in Table A are replaced with the following groups:

1 —C(CH$_2$OCH$_3$)$_3$
2 —C(C$_2$H$_5$)$_2$(CH$_2$OCH$_3$)
3 —CH(C$_2$H$_5$)[CH$_2$OCH$_3$](CH$_2$OCH$_3$)
4 —CH$_2$(CH$_2$OCH$_3$)
5 —C(CH$_3$)$_2$(CH$_2$OCH$_3$)
6 —CH(CH$_3$)(CH$_2$OCH$_3$)
7 —C(CH$_2$OC$_2$H$_5$)$_3$
8 —C(C$_2$H$_5$)$_2$(CH$_2$OC$_2$H$_5$)
9 —CH(C$_2$H$_5$)(CH$_2$OC$_2$H$_5$)
10 —CH(C$_4$H$_9$)(CH$_2$OCH$_3$)
11 —CH$_2$C(CH$_2$OCH$_3$)$_3$
12 —CH$_2$C(C$_2$H$_5$)$_2$(CH$_2$OCH$_3$)
13 —CH$_2$CH(C$_2$H$_5$)(CH$_2$OCH$_3$)
14 —CH(CH$_2$OCH$_3$)$_2$
15 —CH$_2$C(CH$_2$OCH$_3$)$_3$
16 —CH$_2$CH(CH$_2$OCH$_3$)$_2$
17 —C(CH$_2$OC$_2$H$_5$)$_3$
18 —CH(CH$_2$OC$_2$H$_5$)$_2$
19 —CH$_2$C(CH$_2$OC$_2$H$_5$)$_3$
20 —CH$_2$CH(CH$_2$OC$_2$H$_5$)$_2$
21 —C(C$_2$H$_5$)$_2$(CH$_2$OC$_3$H$_7$)
22 —CH(C$_3$H$_7$)(CH$_2$OCH$_3$)
23 —C(C$_3$H$_7$)$_2$(CH$_2$OCH$_3$)
24 —CH(C$_3$H$_7$)(CH$_2$OC$_2$H$_5$)
25 —C(C$_3$H$_7$)$_2$(CH$_2$OC$_2$H$_5$)

Column 29, line 65 to column 30 line 30:

16 Compounds named in Table B and compounds named by compound groups 1–5 where R moieties 1–25 listed in Table A are replaced with the following groups:

1 —(CH$_2$)$_2$R$^9$
2 —(CH$_2$)$_3$R$^9$
3 —(CH$_2$)$_4$R$^9$
4 —(CH$_2$)$_5$R$^9$
5 —(CH$_2$)$_6$R$^9$
6 —(CH$_2$)$_7$R$^9$
7 —(CH$_2$)$_8$R$^9$
8 —CH(CH$_3$)CH$_2$R$^9$
9 —CH(CH$_3$)(CH$_2$)$_2$R$^9$
10 —CH(CH$_3$)(CH$_2$)$_3$R$^9$
11 —(CH$_2$)$_2$R$^9$
12 —(CH$_2$)$_3$R$^9$
13 —(CH$_2$)$_4$R$^9$
14 —(CH$_2$)$_5$R$^9$
15 —(CH$_2$)$_6$R$^9$
16 —(CH$_2$)$_7$R$^9$
17 —(CH$_2$)$_8$R$^9$
18 —CH(CH$_3$)CH$_2$R$^9$
19 —CH(CH$_3$)(CH$_2$)$_2$R$^9$
20 —CH(CH$_3$)(CH$_2$)$_3$R$^9$
21 —(CH$_2$)$_2$R$^9$
22 —(CH$_2$)$_3$R$^9$
23 —(CH$_2$)$_4$R$^9$
24 —(CH$_2$)$_5$R$^9$
25 —(CH$_2$)$_6$R$^9$

Column 32, lines 3–40:

19 Compounds named in Table B and compounds named by compound groups 1–18 where compound (8) and compound (9) are replaced with compound (10) and (11) respectively

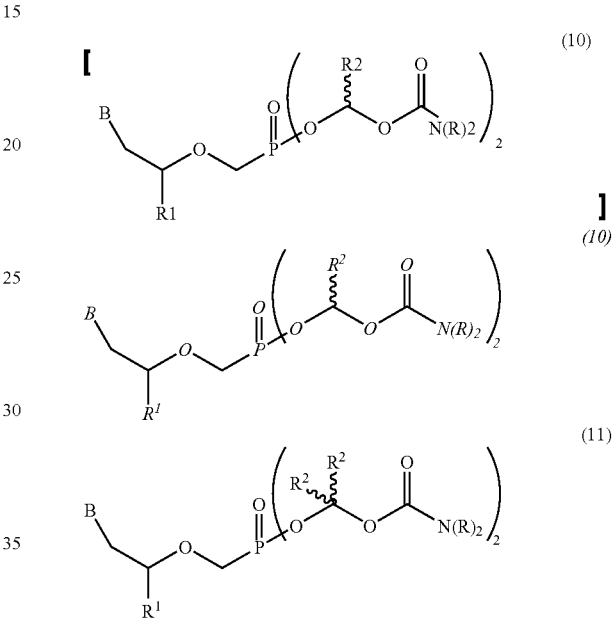

where both R moieties are the same. Thus, the group 19 compound defined in Table A and named 1.4.1.1 in Table B has the structure:
adenin-9-yl-CH$_2$—CH(CH$_3$)—O—CH(CH$_3$)—P(O)(—O—CH$_2$—O—C(O)—N—CH(CH$_3$)$_2$)$_2$. The group 19 compound defined in Table A and named 1.4.1.1 in compound group 1 has the structure:
adenin-9-yl-CH$_2$—CH(CH$_3$)—O—CH$_2$—P(O)(OH)—O—CH$_2$—O—C(O)—N—CH(CH$_3$)$_2$. The group 19 compound defined in Table A and named 1.1.1.1 in compound group 3 as, named under compound group 8, has the structure:
3-deazaadenin-9-yl-CH$_2$—CH(CH$_3$)—O—CH$_2$—P(O)(—O—CH$_2$—O—C(O)—N—(CH$_2$)$_2$OCH$_3$)$_2$.

Column 44, lines 8–26:

A suspension of the crude PMPA (1.00 kg corrected for water content) (Step 5 product) in water is heated to about [110°] *100°* C. (typically about 95–110° C.) with moderate to high agitation until all solids dissolve, and the resulting solution is clarified by filtration while hot, rinsing forward using additional hot water (1 kg, about 95–110° C.). The filtrate is heated to 100° C. prior to cooling, first to about 30° C. (typically about 20–25° C. ) over about 3–5 hours with slow agitation, then cooling is continued to about 10° C. (typically about 5–15° C.). After holding at about 10° C. for at least about 3 hours, the solids are collected by filtration and washed sequentially with cold water (1.5 kg, about 0–10° C.) and then acetone (1 kg). The wet cake is dried in vacuo at about 50° C. (typically about 40–60° C.) to a water content of about 5.9% (typically about 3.9–7.9%), affording pure PMPA monohydrate. The product purity is typically 98% or greater by both area normalized and weight normalized HPLC. If the chemical purity is unsatisfactory, the product may be repurified by a repeat of this step.

Column 44, line 66 to column 45 line 66:

In a reactor with an inert atmosphere, e.g., nitrogen, a mixture of 1-methyl-2-pyrrolidinone (4.12 kg), PMPA monohydrate (1.00 kg), triethylamine (0.996 kg), are agitated for about 15–45 min., typically about 30 min, and then chloromethyl-2-propyl carbonate (2.50 kg) is added and the mixture is heated to about 55–65° C., typically about 60° C. and agitated without splashing the contents for about 3–6 hours, typically about 4 hours, until the reaction is complete, as optionally indicated by HPLC (no more than 15% mono (POC)PMPA present). The mixture is diluted with isopropyl acetate (10.72 kg), cooled to about 15–30° C., typically about 25° C., as rapidly as possible, and while holding the reactor contents at a *temperature* of about 15–30° C., typically at about 25° C., the mixture is agitated for about 20–60 minutes, typically about 30 minutes. The solids are removed by filtration and washed with isopropyl acetate (4.44 kg). The combined organic phases at about 15–30° C., typically about 25° C., are extracted twice with water (3.28 kg) using moderate agitation for about 1–10 min. to avoid forming an emulsion followed by allowing the phases to separate. The combined aqueous phases are back-extracted twice with isopropyl acetate (3.56 kg) (about 15–30° C., typically about 25° C.). All organic phases are combined and washed with water (2.20 kg) (about 15–30° C., typically about 25° C.) using moderate agitation for about 1–10 min. to avoid forming an emulsion, then the combined organic phases, which are at about 25–43° C., but at no more than 45° C., are concentrated in vacuo (about 26.5–28" Hg) to approximately 30% of the original volume (about 10–12 L/kg PMPA monohydrate). After a polishing filtration using an in-line 1 µm filter, the concentration of the organic phase is resumed at about 20–38° C., but no higher than 40° C. under a vacuum (about 28" Hg) until a pale yellow oil remains. The oil is dissolved in a warmed solution (about 45–55° C., typically about 50° C.) of fumaric acid (0.38 kg) in 2-propanol (6.24 kg) with vigorous agitation until solids dissolve, about 0.5–2.0 hours. The warm solution is then optionally filtered using an in-line 1 µm filter while minimizing cooling of the solution. The filtrate at about 34–50° C., typically at about 40° C., is agitated using the minimum agitation needed to obtain a homogenous solution. The resulting solution is cooled to about 30–33° C., typically about 32° C., over about 30 minutes using minimal agitation, optionally seeded with a small quantity of bis(POC)PMPA fumarate (about 100 mg), and cooled to about 12–18° C., typically about 15° C., over about 1–2 hours, typically over about 1 hour. Seed crystals may not be needed if crystal formation begins before seed crystals are added. Crystals may form over a range of about 12–33° C. as the solution is cooled. Crystallization will occur at lower temperatures if the solution is further chilled, e.g., to about −10° to about 11° C. Agitation is discontinued when crystal formation begins. The mixture is allowed to stand at about 15° C. for at least about 12 hours, typically about 12–30 hours. The resulting slurry is filtered (Tyvek) and the filter cake is washed with a premixed solution of isopropyl acetate (0.70 kg) in butyl ether (2.44 kg) (1:4 v/v). The filter cake, which is at no more than 40° C., is dried in vacuo for about 1 to 3 days and the dried product is optionally milled (Fitzmill M5A fitted with a 0.050" screen), affording bis(POC)PMPA fumarate as white, fine, powder-like crystals of about 97.0 to 99.5% purity.

Column 46, lines 3–13:

Preparation of Alkyl Chloromethylcarbonates

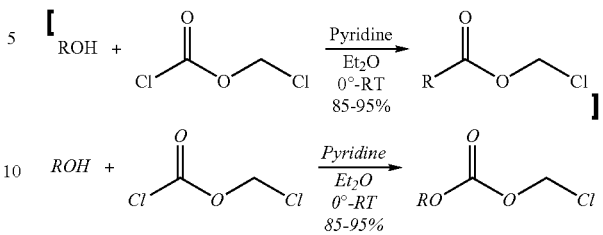

Column 46, line 62 to column 47 line 11:

R=Et. Anhydrous PMPA (5 g, 16 mmol) and DIEA (Hunig's base) (11.5 mL,66 mmol) were placed in anyhydrous DMF (50 mL). The chloromethyl carbonate (49 mmol) was then added and the suspension heated to 50° C. under argon with rapid mechanical stirring. After 1 hr the reaction was clear and the temperature was lowered to 35° C. and the reaction stirred for 48 hr. The DMF was removed on a rotary evaporator, and the reaction partitioned between $CH_2Cl_2$ and water. The $CH_2Cl_2$ layer was dried over magnesium sulfate, filtered, and concentrated on a rotary evaporator. The residue was taken up in methylene chloride and applied to a silica gel column (150 g $SiO_2$). It was eluted with 500 mL each [0,3,6,9,2,15,18%] *0, 3, 6, 9, 12, 15, 18%* (v/v) isopropanol in methylene chloride, and then with 2000 mL 21%. Appropriate fractions were pooled and evaporated to give the desired product.

Column 47, lines 14–45:

Preparation of the Bis -n-butyl Oxymethyl Carbonate of PMPA

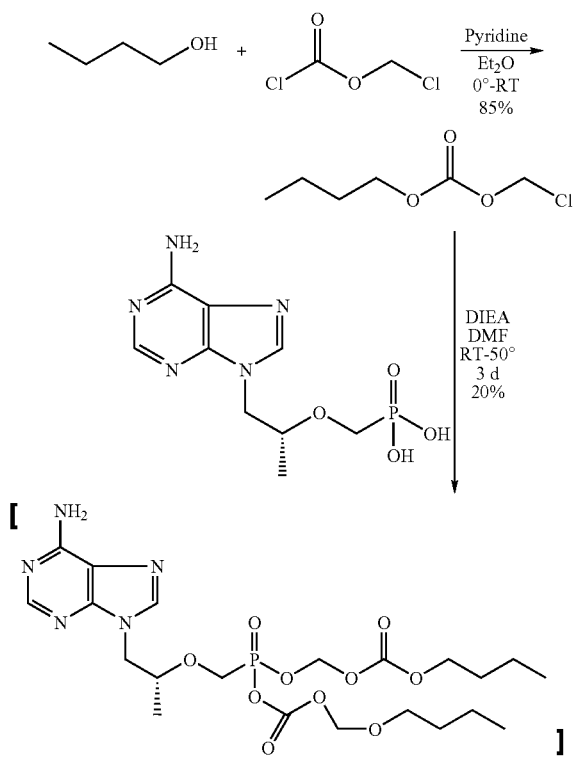

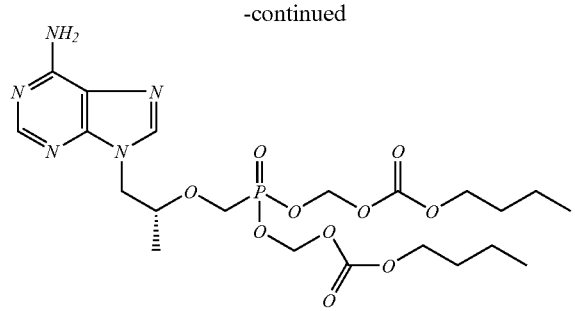

Column 54, lines 1–20:

The plasma and urine samples were analyzed for HPLC with Fluorescence Detection as follows. The HPLC system comprised a Model P4000 solvent delivery system with a Model AS3000 autoinjector and a Model F2000 Fluorescence detector (Thermo Separation, [Jan ] San Jose, Calif.). The column was a Zorbax RX-C18 (5 μm, 150×4.6 mm) (MAC-MOD, Chadds Ford, N.Y.) equipped with a Brownlee RP-18 Newguard guard column (7 μm, 15×3.2 mm) (Alltech, Deerfield, Ill.). The mobile phases used were: A, 2% acetonitrile in 25 mM potassium phosphate buffer with 5 mM TBAHP, pH 6.0; B, 65% acetonitrile in 25 mM potassium phosphate buffer with 5 mM TBAHP, pH 6.0. The flow rate was 1.5 mL/min and the column temperature was maintained at 35° C. by a column oven. The gradient profile was 100% A until 2.0 min, then a linear gradient to 100% B by 13 minutes, returning immediately to 100% A. Detection was by fluorescence with excitation at 236 nm and emission at 420 nm, and the injection volume was 50 μL. Total cycle time between injections was 25 min. Data was acquired and stored by a Peak Pro data acquisition system (Beckman, Palo Alto, Calif.).

Column 57, line 63 to column 59 line 41:

PMPA (9-[[(R)-2-(phosphonomethoxy)propyl]]adenine) and PMPA carbonates were examined to determine their activity against HIV-1. The antiviral activity of the carbonates 5a, 5c–g against HIV-1(IIIB) was determined in MT-2 cells and the $IC_{50}$ (50% inhibitory concentration) and $CC_{50}$ (concentration to kill 50% of the cells) values were measured. The carbonate prodrugs exhibited increased potency (about 2.5–500 fold) compared to PMPA (Table 2). Although cytotoxicity of the prodrugs also increased, the selectivity indices were improved compared to PMPA. The increased activity can be attributed to increased cellular uptake of the prodrugs followed by effective intracellular conversion to PMPA, which undergoes subsequent phosphorylation to the antivirally active diphosphate metabolite. The t-butyl carbonate 5d exhibited only 2.5 fold increased activity over PMPA with reduced selectivity possibly due to chemical instability. The antiviral activity data indicate good permeability of alkyl methyl carbonate prodrugs into cells, possibly due to their increased lipophilicity. The partition coefficient values support this hypothesis, will all prodrugs being more lipophilic (logP=0.6–3.2) compared to PMPA (logP=−2.5).

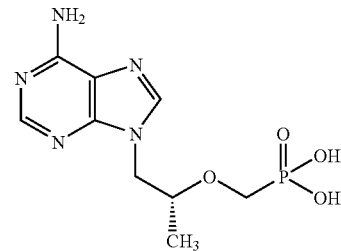

2

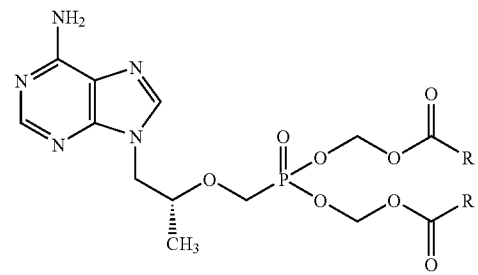

5 a. $R = -OEt$
c. $R = -OBu^{iso}$
d. $R = -OBu^{t}$
e. $R = $ [ $-OPe^{neo}$ ] $-OPen^{neo}$
f. $R = -OPro^{iso}$
g. $R = 3-OPen$

AS A RESULT OF REEXAMINATION, IT HAS BEEN DETERMINED THAT:

Claims 1 and 27 are determined to be patentable as amended.

Claims 2–26 and 28–31, dependent on an amended claim, are determined to be patentable.

New claims 32–34 are added and determined to be patentable.

1. A compound having formula (1a)

(1a)

wherein
Z is independently $-OC(R^2)_2OC(O)X(R)_a$, an ester, an amidate or —H, but at least one Z is $-OC(R^2)_2OC(O)X(R)_a$;
A is the residue of an antiviral phosphonomethoxy nucleotide analog;
X is N or O;
$R^2$ independently is —H, $C_1$–$C_{12}$ alkyl, $C_5$–$C_{12}$ aryl, $C_2$–$C_{12}$ alkenyl, $C_2$–$C_{12}$ alkynyl, $C_7$–$C_{12}$ alkenylaryl, $C_7$–$C_{12}$ alkynylaryl, or $C_6$–$C_{12}$ alkaryl, any one of which is unsubstituted or is substituted with 1 or 2 halo, cyano, azido, nitro or —$OR^3$ in which $R^3$ is $C_1$–$C_{12}$ alkyl, $C_2$–$C_{12}$ alkenyl, [$C_{2-C\ 12}$] $C_2$–$C_{12}$ alkynyl or $C_5$–$C_{12}$ aryl;
R is independently —H, $C_1$–$C_{12}$ alkyl, $C_5$–$C_{12}$ aryl, $C_2$–$C_{12}$ alkenyl, alkenyl, $C_2$–$C_{12}$ alkynyl, $C_7$–$C_{12}$ alkyenylaryl, $C_7$–$C_{12}$ alkynylaryl, or $C_6$–$C_{12}$ alkaryl, any one of which is unsubstituted or is substituted with 1 or 2 halo, cyano, azido, nitro, —N(R$^4$)$_2$ or —OR$^3$, where R$^4$ independently is —H or C$_1$–C$_8$ alkyl, provided that at least one R is not H; and a is 1 when X is O, or 1 or 2 when X is N;

with the proviso that when a is 2 and X is N, (a) two N-linked R groups can be taken together to form a carbocycle or oxygen-containing heterocycle, (b) one N-linked R additionally can be —OR$^3$ or (c) both N-linked R groups can be —H;

and the salts, hydrates, tautomers and solvates thereof.

27. A method for preparing a compound of formula (1) of claim 2 comprising reacting a compound of formula (6)

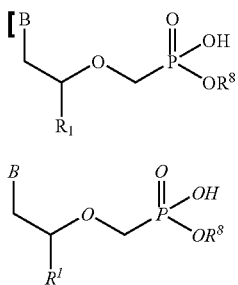

with L—CHR$^2$—O—C(O)—OR and recovering a compound of formula (1), wherein B is guanin-9-yl, adenin-9-yl, 2,6-diaminopurin-9-yl, 2-aminopurin-9-yl or their 1-deaza, 3-deaza, or 8-aza analogs, or B is cytosin-1-yl;

R$^1$ is hydrogen, —CH$_3$, —CH$_2$OH, —CH$_2$F, —CH=CH$_2$, —CH$_2$N$_3$ or R$^1$ and R$^8$ are joined to form —CH$_2$—; and R$^8$ is hydrogen, —CHR$^2$—O—C(O)—OR or R$^8$ is joined with R$^1$ to form —CH$_2$—; and R$^2$ is H, C$_1$–C$_{12}$ alkyl, aryl, alkenyl, alkynyl, alkyenylaryl, alkynylaryl, alkaryl, arylalkynyl, arylalkenyl or arylalkyl which is unsubstituted or is substituted with halo, azido, nitro or OR$^3$ in which R$^3$ is [C$_1$–C12] C$_1$–C$_{12}$ alkyl;

R is independently H, C$_1$–C$_{12}$ alkyl, aryl, alkenyl, alkynyl, alkenylaryl, alkynylaryl, alkaryl, arylalkynyl, arylalkenyl or arylalkyl which is unsubstituted or is substituted with halo, azido nitro or OR$^3$, provided that at least one R is not H; and L is a leaving group.

32. A compound having a formula (1a)

(1a)

wherein

Z is independently —OC(R$^2$)OC(O)X(R)$_a$-or —H, but at least one Z is —OC(R$^2$)OC(O)X(R)$_a$;

A is the residue of an antiviral phosphonomethoxy nucleotide analog;

X is N or O;

R$^2$ independently is —H, —C$_1$–C$_{12}$ alkyl, C$_2$–C$_{12}$ alkenyl, or C$_2$–C$_{12}$ alkynyl, any one of which is unsubstituted or is substituted with azido, nitro or —OR$^3$ in which R$^3$ is C$_1$–C$_{12}$ alkyl, C$_2$–C$_{12}$ alkenyl, or C$_2$–C$_{12}$ alkynyl;

R is independently —H, C$_1$–C$_{12}$ alkyl, C$_2$–C$_{12}$ alkenyl, or C$_2$–C$_{12}$ alkynyl, any one of which is unsubstituted or is substituted with azido, nitro, or —OR$^3$; and a is 1 when X is O, or 1 or 2 when X is N;

with the proviso that when a is 2 and X is N, (a) two N-linked R groups can be taken together to form a carbocycle or oxygen-containing heterocycle, or (b) one N-linked R additionally can be —OR$^3$;

and the salts, hydrates, tautomers and solvates thereof.

33. A compound of claim 32, having formula (1)

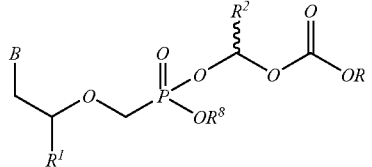

(1)

wherein B is guanin-9-yl, adenin-9-yl, 2,6-diaminopurin-9-yl, 2-aminopurin-9-yl or their 1-deaza, 3-deaza, or 8-aza analogs, or B is cytosin-yl;

R is independently —H, C$_1$–C$_{12}$ alkyl, C$_2$–C$_{12}$ alkenyl, or C$_2$–C$_{12}$ alkynyl, any one of which is unsubstituted or is substituted with azido, nitro or —OR$^3$ in which R$^3$ is C$_1$–C$_{12}$ alkyl, C$_2$–C$_{12}$ alkenyl, or C$_2$–C$_{12}$ alkynyl;

R$^1$ is hydrogen, —CH$_3$, —CH$_2$OH, —CH$_2$F, —CH=CH$_2$, or —CH$_2$N$_3$, or R$^1$ and R$^8$ are joined to form —CH$_2$—;

R$^2$ independently is hydrogen or C$_1$–C$_6$ alkyl; and

R$^8$ is hydrogen or —CHR$^2$—O—C(O)—OR, or R$^8$ is joined with R$^1$ to form —CH$_2$—; and the salts, hydrates, tautomers and solvates thereof.

34. The compound of claim 33, wherein

B is adenin-9-yl;

R$^1$ is –CH$_3$;

R$^2$ is H;

R is isopropyl; and

R$^8$ is CHR$^2$—O—C(O)—OR.

* * * * *